US012383249B2

(12) United States Patent
Josse

(10) Patent No.: US 12,383,249 B2
(45) Date of Patent: Aug. 12, 2025

(54) TISSUE RETRACTOR, RETRACTION MODULES, AND ASSOCIATED METHODS

(71) Applicant: Warsaw Orthopedic, Inc., Warsaw, IN (US)

(72) Inventor: Loic Josse, Palm Beach Gardens, FL (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 835 days.

(21) Appl. No.: 17/683,925

(22) Filed: Mar. 1, 2022

(65) Prior Publication Data

US 2022/0387013 A1     Dec. 8, 2022

Related U.S. Application Data

(63) Continuation-in-part of application No. 17/336,860, filed on Jun. 2, 2021, now Pat. No. 12,096,923, which
(Continued)

(51) Int. Cl.
*A61B 17/02* (2006.01)
*A61B 17/00* (2006.01)

(52) U.S. Cl.
CPC ............... *A61B 17/0206* (2013.01); *A61B 2017/00473* (2013.01)

(58) Field of Classification Search
CPC ... A61B 17/02; A61B 17/025; A61B 17/0206; A61B 17/0218; A61B 17/0293; A61B 2017/00367; A61B 2017/0046
(Continued)

(56) References Cited

U.S. PATENT DOCUMENTS 4,034,746 A     7/1977 Williams
5,681,265 A    10/1997 Maeda et al.
(Continued)

FOREIGN PATENT DOCUMENTS

EP         3270792 B1      5/2020
WO     2012040206 A1      3/2012

OTHER PUBLICATIONS

International Search Report and Written Opinion, PCT/US2021/040225 Dated Nov. 11, 2021, (16 PP).
(Continued)

*Primary Examiner* — Eduardo C Robert
*Assistant Examiner* — Christina NegrelliRodriguez
(74) *Attorney, Agent, or Firm* — FOX ROTHSCHILD LLP

(57) ABSTRACT

A modular retractor may include a first body portion that houses a distraction mechanism for opening and closing a first arm and a second arm. A first pivoting member may be coupled to a distal end of the first arm and a second pivoting member may be coupled to a distal end of the second arm, for example. A first blade attachment mechanism may be coupled to the first pivoting member and a second blade attachment mechanism may be coupled to the second pivoting member. The first and second blade attachment mechanisms may be configured to couple to first and second blades and be independently inclinable. Various embodiments may include at least one connection point for connecting to at least one additional retractor module. Various embodiments may include at least one quick connect coupler for connecting to a snap on table mount.

22 Claims, 163 Drawing Sheets

Related U.S. Application Data is a continuation-in-part of application No. 16/926,173, filed on Jul. 10, 2020, now Pat. No. 11,224,415.

(60) Provisional application No. 63/254,929, filed on Oct. 12, 2021.

(58) Field of Classification Search
USPC .................................. 600/201, 214, 219
See application file for complete search history.

(56) References Cited

U.S. PATENT DOCUMENTS

| | | | |
|---|---|---|---|
| 5,931,777 | A | 8/1999 | Sava |
| 5,993,385 | A | 11/1999 | Johnston et al. |
| 6,074,343 | A | 6/2000 | Nathanson et al. |
| 6,193,651 | B1 | 2/2001 | DeFonzo |
| 6,712,795 | B1 | 3/2004 | Cohen |
| 6,945,933 | B2 | 9/2005 | Branch et al. |
| 7,141,015 | B2 | 11/2006 | Ruane |
| 7,407,483 | B2 | 8/2008 | Perez-Cruet et al. |
| 7,481,766 | B2 | 1/2009 | Lee et al. |
| 7,491,168 | B2 | 2/2009 | Raymond et al. |
| 7,537,565 | B2 | 5/2009 | Bass |
| 7,780,594 | B2 | 8/2010 | Hutton |
| 7,819,801 | B2 | 10/2010 | Miles et al. |
| 7,850,608 | B2 | 12/2010 | Hamada |
| 7,892,173 | B2 | 2/2011 | Miles et al. |
| 7,981,031 | B2 | 7/2011 | Frasier et al. |
| 8,062,217 | B2 | 11/2011 | Boucher et al. |
| 8,262,570 | B2 | 9/2012 | White et al. |
| 8,303,498 | B2 | 11/2012 | Miles et al. |
| 8,323,185 | B2 | 12/2012 | Perez-Cruet et al. |
| 8,343,048 | B2 | 1/2013 | Warren, Jr. |
| 8,353,826 | B2 | 1/2013 | Weiman |
| 8,355,780 | B2 | 1/2013 | Miles et al. |
| 8,388,527 | B2 | 3/2013 | Miles et al. |
| 8,480,576 | B2 | 7/2013 | Sandhu |
| 8,500,634 | B2 | 8/2013 | Miles et al. |
| 8,517,935 | B2 | 8/2013 | Marchek et al. |
| 8,550,994 | B2 | 10/2013 | Miles et al. |
| 8,556,808 | B2 | 10/2013 | Miles et al. |
| 8,579,809 | B2 | 11/2013 | Parker |
| 8,602,984 | B2 | 12/2013 | Raymond et al. |
| 8,668,715 | B2 | 3/2014 | Sandhu |
| 8,696,559 | B2 | 4/2014 | Miles et al. |
| 8,753,271 | B1 | 6/2014 | Miles et al. |
| 8,764,649 | B2 | 7/2014 | Miles et al. |
| 8,827,902 | B2 | 9/2014 | Dietze, Jr. et al. |
| 8,968,363 | B2 | 3/2015 | Weiman et al. |
| 8,986,344 | B2 | 3/2015 | Sandhu |
| 8,992,425 | B2 | 3/2015 | Karpowicz et al. |
| 9,050,146 | B2 | 6/2015 | Woolley et al. |
| 9,084,591 | B2 | 7/2015 | Reglos et al. |
| 9,113,854 | B2 | 8/2015 | Ellman |
| 9,138,217 | B2 | 9/2015 | Smith et al. |
| 9,179,903 | B2 | 11/2015 | Cianfrani et al. |
| 9,357,909 | B2 | 6/2016 | Perez-Cruet et al. |
| 9,381,008 | B2 | 7/2016 | Thornburg |
| 9,386,916 | B2 | 7/2016 | Predick et al. |
| 9,408,596 | B2 | 8/2016 | Blain |
| 9,414,828 | B2 | 8/2016 | Abidin et al. |
| 9,468,405 | B2 | 10/2016 | Miles et al. |
| 9,486,133 | B2 | 11/2016 | Lee et al. |
| 9,549,723 | B2 | 1/2017 | Hynes et al. |
| 9,572,560 | B2 | 2/2017 | Mast et al. |
| 9,585,649 | B2 | 3/2017 | Blain et al. |
| 9,615,818 | B2 | 4/2017 | Baudouin et al. |
| 9,622,732 | B2 | 4/2017 | Martinelli et al. |
| 9,636,097 | B2 | 5/2017 | Bass |
| 9,649,101 | B2 | 5/2017 | Karpowicz et al. |
| 9,730,683 | B2 | 8/2017 | Reimels |
| 9,737,288 | B2 | 8/2017 | Karpowicz et al. |
| 9,795,370 | B2 | 10/2017 | O'Connell et al. |
| 9,795,371 | B2 | 10/2017 | Miles et al. |
| 9,826,966 | B2 | 11/2017 | Mast et al. |
| 9,918,709 | B2 | 3/2018 | Sandhu |
| 9,924,859 | B2 | 3/2018 | Lee et al. |
| 9,937,060 | B2 | 4/2018 | Fuhrer et al. |
| 9,974,531 | B2 | 5/2018 | Miles et al. |
| 9,993,239 | B2 | 6/2018 | Karpowicz et al. |
| 10,039,539 | B2 | 8/2018 | Friedrich et al. |
| 10,070,852 | B2 | 9/2018 | Mast et al. |
| 10,076,320 | B2 | 9/2018 | Mast et al. |
| 10,149,671 | B2 | 12/2018 | Predick et al. |
| 10,154,781 | B2 | 12/2018 | Weiman |
| 10,172,515 | B2 | 1/2019 | Lee et al. |
| 10,172,652 | B2 | 1/2019 | Woolley et al. |
| 10,178,987 | B2 | 1/2019 | Predick et al. |
| 10,213,192 | B2 | 2/2019 | Capote |
| 10,213,193 | B2 | 2/2019 | Karpowicz et al. |
| 10,219,798 | B2 | 3/2019 | Capote |
| 10,238,375 | B2 | 3/2019 | O'Connell et al. |
| 10,245,015 | B2 | 4/2019 | Predick et al. |
| 10,278,686 | B2 | 5/2019 | Baudouin et al. |
| 10,278,786 | B2 | 5/2019 | Friedrich et al. |
| 10,285,680 | B2 | 5/2019 | Friedrich et al. |
| 10,299,777 | B2 | 5/2019 | Mast et al. |
| 10,357,233 | B2 | 7/2019 | Miles et al. |
| 10,426,450 | B2 | 10/2019 | Vogel et al. |
| 10,898,239 | B2 | 1/2021 | Olea et al. |
| 10,959,760 | B2 | 3/2021 | Bobbitt et al. |
| 10,980,528 | B2 | 4/2021 | Cryder et al. |
| 10,980,576 | B2 | 4/2021 | Woolley et al. |
| 11,013,616 | B2 | 5/2021 | LaMarca et al. |
| 11,020,102 | B2 | 6/2021 | McClymont et al. |
| 11,051,796 | B2 | 7/2021 | Serokosz et al. |
| 11,051,859 | B2 | 7/2021 | Bobbitt et al. |
| 11,116,489 | B2 | 9/2021 | Kim |
| 11,154,288 | B1 | 10/2021 | Lovell et al. |
| 11,154,336 | B2 | 10/2021 | Levine |
| 11,172,918 | B2 | 11/2021 | Ponmudi et al. |
| 11,185,319 | B2 | 11/2021 | Wilson et al. |
| 11,219,477 | B2 | 1/2022 | Biedermann et al. |
| 11,224,415 | B1* | 1/2022 | Josse .................. A61B 17/0206 |
| 11,350,922 | B1 | 6/2022 | Italiaie |
| 11,357,490 | B2 | 6/2022 | Gasser |
| 11,399,816 | B2 | 8/2022 | O'Connell et al. |
| 11,413,028 | B2 | 8/2022 | Serokosz et al. |
| 11,432,810 | B2 | 9/2022 | Gregersen et al. |
| 11,432,852 | B1 | 9/2022 | Melkent et al. |
| 11,484,349 | B2 | 11/2022 | Peultier et al. |
| 11,490,933 | B2 | 11/2022 | Peultier et al. |
| 12,096,923 | B2* | 9/2024 | Josse .................. A61B 17/0206 |
| 2005/0215863 | A1 | 9/2005 | Ravikumar et al. |
| 2006/0224044 | A1 | 10/2006 | Marchek et al. |
| 2007/0100212 | A1 | 5/2007 | Pimenta et al. |
| 2009/0024158 | A1 | 1/2009 | Viker |
| 2010/0174148 | A1 | 7/2010 | Miles et al. |
| 2012/0283521 | A1 | 11/2012 | Smith et al. |
| 2013/0317312 | A1 | 11/2013 | Eastlack et al. |
| 2014/0114137 | A1 | 4/2014 | Reglos et al. |
| 2016/0081681 | A1 | 3/2016 | Waugh et al. |
| 2016/0345952 | A1 | 12/2016 | Kucharzyk et al. |
| 2017/0035406 | A1 | 2/2017 | Abidin et al. |
| 2017/0215856 | A1 | 8/2017 | Martinelli et al. |
| 2018/0085105 | A1 | 3/2018 | Kim |
| 2018/0303473 | A1 | 10/2018 | Spann et al. |
| 2018/0344307 | A1 | 12/2018 | Hynes et al. |
| 2019/0021716 | A1 | 1/2019 | Waugh et al. |
| 2019/0082949 | A1 | 3/2019 | Weiman |
| 2019/0083081 | A1 | 3/2019 | Ortiz et al. |
| 2019/0125328 | A1 | 5/2019 | Blain |
| 2019/0133434 | A1 | 5/2019 | Lee et al. |
| 2019/0142480 | A1 | 5/2019 | Woolley et al. |
| 2019/0209155 | A1 | 7/2019 | Mast et al. |
| 2019/0216453 | A1 | 7/2019 | Predick et al. |
| 2019/0254650 | A1 | 8/2019 | Martinelli et al. |
| 2019/0274670 | A1 | 9/2019 | O'Connell et al. |
| 2019/0274671 | A1 | 9/2019 | Lauf et al. |
| 2019/0321022 | A1* | 10/2019 | Karpowicz .......... A61K 9/0019 |
| 2019/0350573 | A1 | 11/2019 | Vogel et al. |
| 2020/0315602 | A1 | 10/2020 | Melton et al. |
| 2021/0128204 | A1 | 5/2021 | Olea et al. |
| 2021/0186567 | A1 | 6/2021 | Bobbitt et al. |

(56) References Cited

U.S. PATENT DOCUMENTS

| | | |
|---|---|---|
| 2021/0186576 A1 | 6/2021 | Woolley et al. |
| 2021/0204927 A1 | 7/2021 | Cryder et al. |
| 2021/0267645 A1 | 9/2021 | Wooley et al. |
| 2021/0307790 A1 | 10/2021 | Woolley et al. |
| 2021/0322066 A1 | 10/2021 | Bobbitt et al. |
| 2021/0330312 A1 | 10/2021 | Lovell et al. |
| 2021/0401423 A1 | 12/2021 | Eckhof et al. |
| 2022/0008055 A1 | 1/2022 | Ponmudi et al. |
| 2022/0008057 A1 | 1/2022 | Josse |
| 2022/0039836 A1 | 2/2022 | Levine |
| 2022/0175362 A1 | 6/2022 | Considine et al. |
| 2022/0192645 A1 | 6/2022 | Peultier et al. |
| 2022/0192647 A1 | 6/2022 | Josse et al. |
| 2022/0202450 A1 | 6/2022 | Josse et al. |
| 2022/0218325 A1* | 7/2022 | Josse ................. A61B 17/0206 |
| 2022/0218395 A1 | 7/2022 | Josse et al. |
| 2022/0218417 A1 | 7/2022 | Josse et al. |
| 2022/0249136 A1 | 8/2022 | Boesel et al. |
| 2022/0296228 A1 | 9/2022 | O'Connell et al. |
| 2022/0387013 A1* | 12/2022 | Josse ................. A61B 17/0206 |
| 2023/0035781 A1 | 2/2023 | Jaye |
| 2023/0059813 A1 | 2/2023 | Josse et al. |

OTHER PUBLICATIONS

International Search Report and Written Opinion in Application No. PCT/US2022/035720 dated Dec. 19, 2022.

* cited by examiner

200

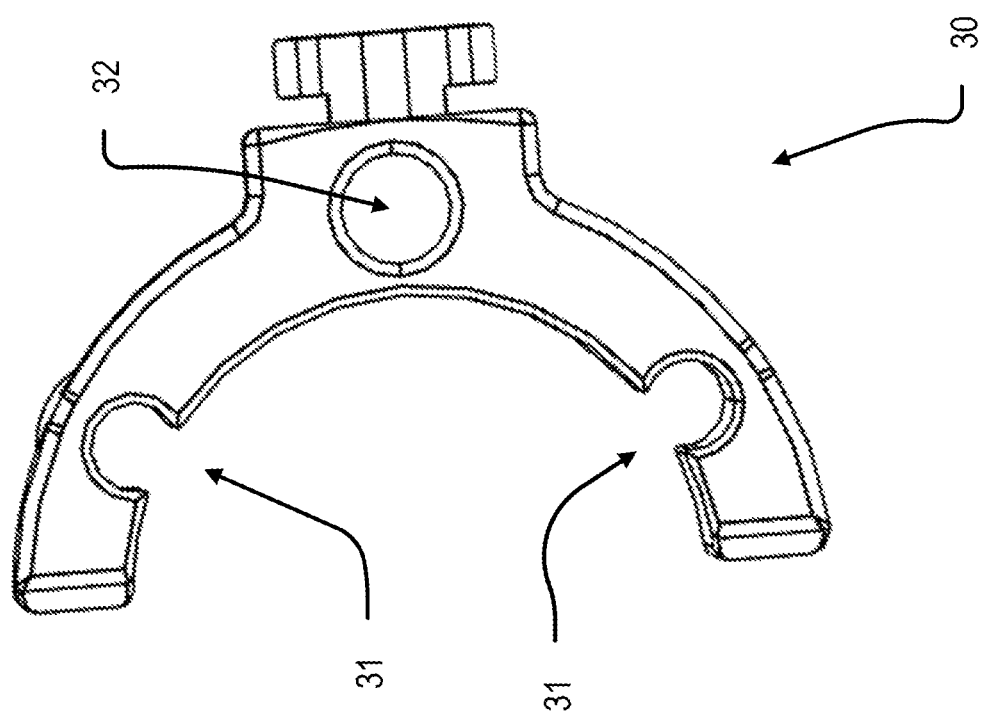
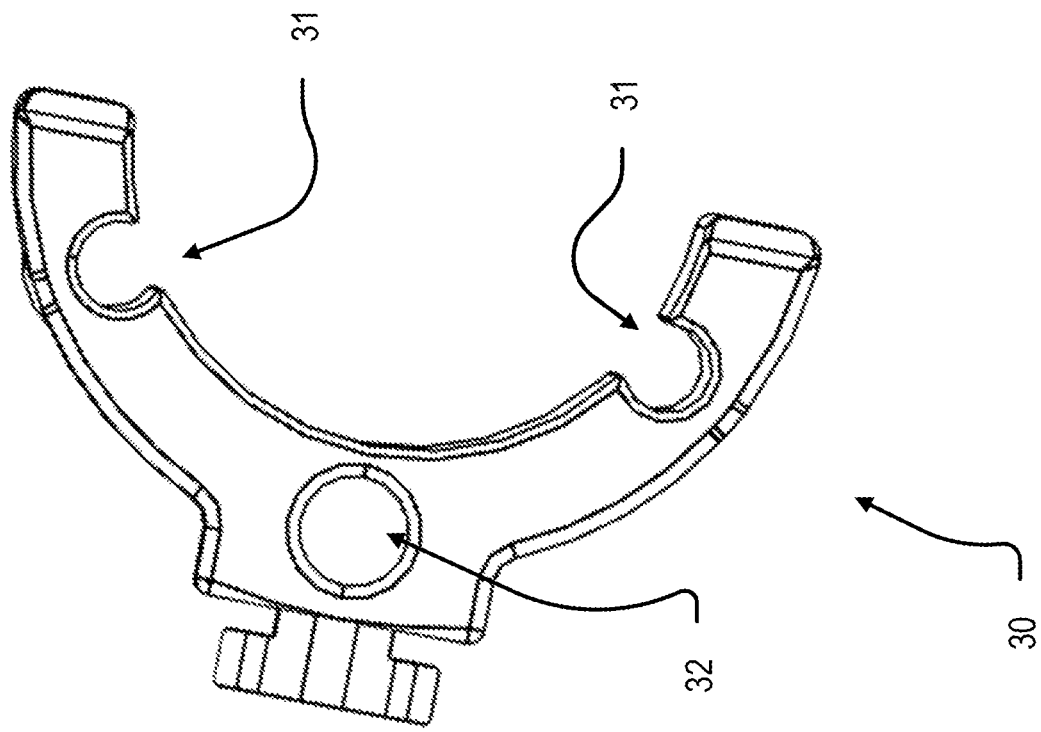
FIG. 66

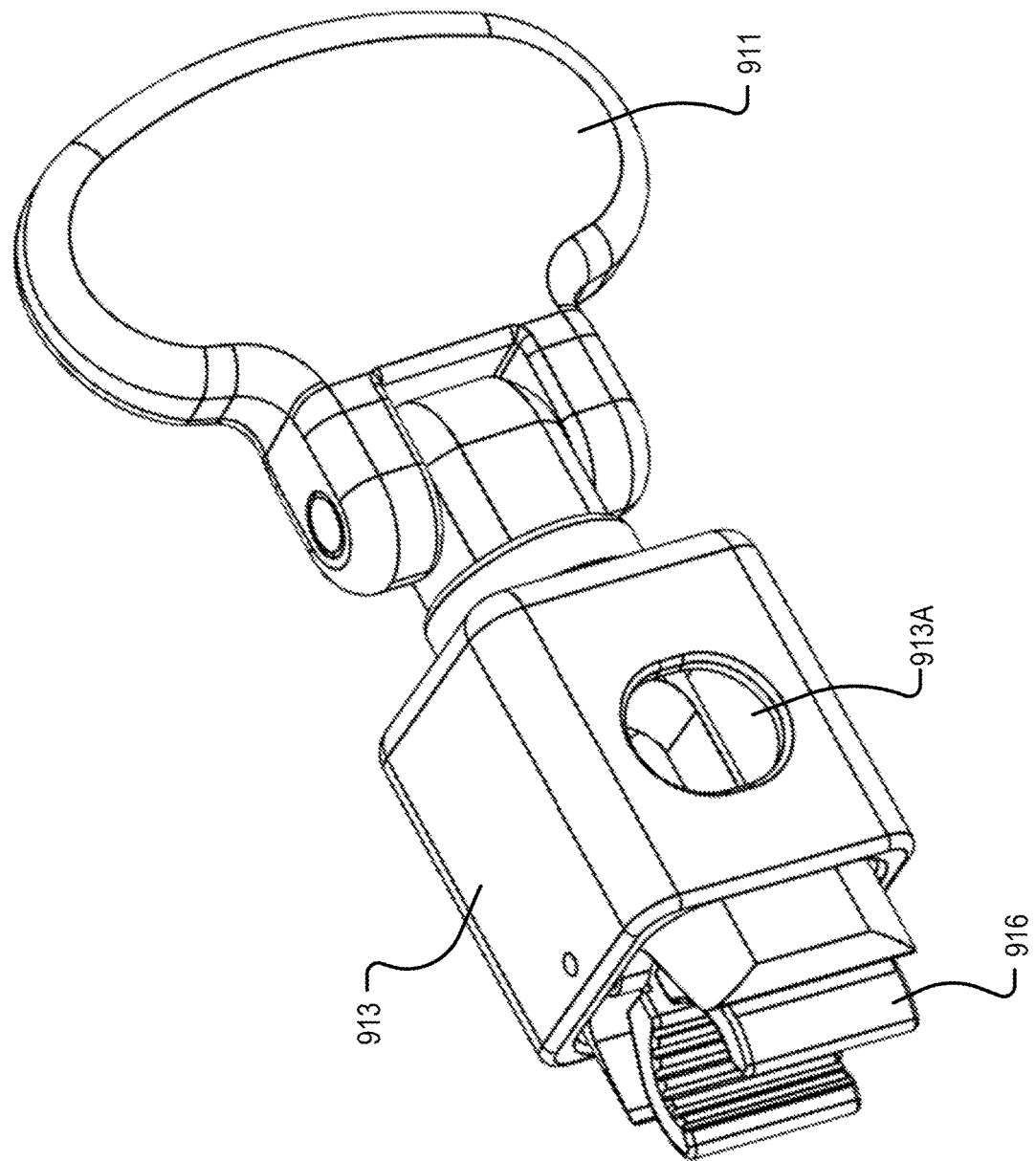

360 ically, the present disclosure is directed to a

TISSUE RETRACTOR, RETRACTION MODULES, AND ASSOCIATED METHODS

CROSS-REFERENCE TO RELATED U.S. PATENT APPLICATION

This application is a continuation in part of: U.S. Nonprovisional patent application Ser. No. 17/336,860 entitled "Tissue Retractor, Retraction Modules, and Associated Methods," filed Jun. 2, 2021 which is a continuation in part of U.S. Nonprovisional patent application Ser. No. 16/926,173 entitled "Tissue Retractor," filed Jul. 10, 2020. This application also claims priority to U.S. Provisional Application Ser. No. 63/254,929 filed Oct. 12, 2021. The entire disclosure of each of the above applications is incorporated by reference in its entirety.

FIELD

The present technology is generally related to medical devices to assist a surgeon during treatment of musculoskeletal disorders, and more particularly to a surgical system and method for accessing a surgical site to facilitate treatment. More particularly, the present disclosure is directed to a surgical retractor system including a primary retractor assembly and a secondary retractor assembly that are configured for various approaches to the spine, including for example, anterior, lateral, and oblique surgical techniques.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, how-ever, may fail to relieve the symptoms associated with these disorders. Surgical treatment of these spinal disorders includes fusion, fixation, discectomy, laminectomy and implantable prosthetics. Surgical retractors may be employed during a surgical treatment to provide access and visualization of a surgical site. Such retractors space apart and support tissue and/or other anatomical structures to expose anatomical structures at the surgical site and/or provide a surgical pathway for the surgeon to the surgical site.

SUMMARY

This disclosure describes a plurality of different embodiments and modules for use as a modular retractor system. The system may use any of the variously disclosed blades, extendable blades, and dilators. Additionally, this disclosure describes a quick connect and release coupler for securing the modular retractor system to a table mount.

In an aspect, this disclosure describes a modular surgical retractor system including a modular retractor configured to couple and uncouple from a plurality of different add on modules. The retractor system may be designed for enabling access to a surgical site and/or forming an operative corridor, for example. In various embodiments, the retractor system may include a modular retractor having a longitudinal axis extending in a longitudinal direction and a lateral axis extending from a first lateral end to a second lateral end in a lateral direction, for example. In various embodiments, the modular retractor may include a first body portion that houses a distraction mechanism, a first arm and a second arm pivotally coupled together, and a first handle coupled to the first arm and a second handle coupled to the second arm, for example. In various embodiments, a first pivoting member may be coupled to a distal end of the first arm and a second pivoting member may be coupled to a distal end of the second arm, for example. In various embodiments, a first blade attachment mechanism coupled to the first pivoting member and a second blade attachment mechanism coupled to the second pivoting member, the first and second blade attachment mechanisms being configured to couple to first and second blades, respectively. In various embodiments, a first actuator may be operably coupled to the distraction mechanism for opening and closing the first arm and the second arm, for example. In various embodiments, a second actuator for adjusting the angulation of the first pivoting member, and a third actuator for adjusting the angulation of the second pivoting member may be provided, for example. In various embodiments, the modular retractor may include at least one table mount quick release coupler.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 66 is a top view of a pair of blades for use with disclosed modular retractor embodiments.

FIG. 100 is a perspective view of a modular blade.

FIG. 101 is a perspective view of a modular blade.

FIG. 102 is a perspective view of an extendable blade for coupling to the modular blade of FIGS. 100-101.

FIG. 103 is a perspective view of an extendable blade for coupling to the modular blade of FIGS. 100-101.

FIG. 104 is a perspective view of an extendable blade for coupling to the modular blade of FIGS. 100-101.

FIG. 105 is a front view of the extendable blades of FIGS. 103-105.

FIG. 106 is a perspective view of the outside surfaces of a modular blade and an extendable blade having a pointed end.

FIG. 107 is a perspective view of the inside surfaces of the modular blade and the extendable blade of FIG. 106.

FIG. 108A is a first exploded parts view of the modular blade and extendable blade of FIGS. 106-107.

FIG. 108B is a second exploded parts view of the modular blade and extendable blade of FIGS. 106-107.

FIG. 108C is a perspective view of the modular blade of FIGS. 106-107.

FIG. 108D is a top down view of the modular blade of FIGS. 106-107.

Figure 106:
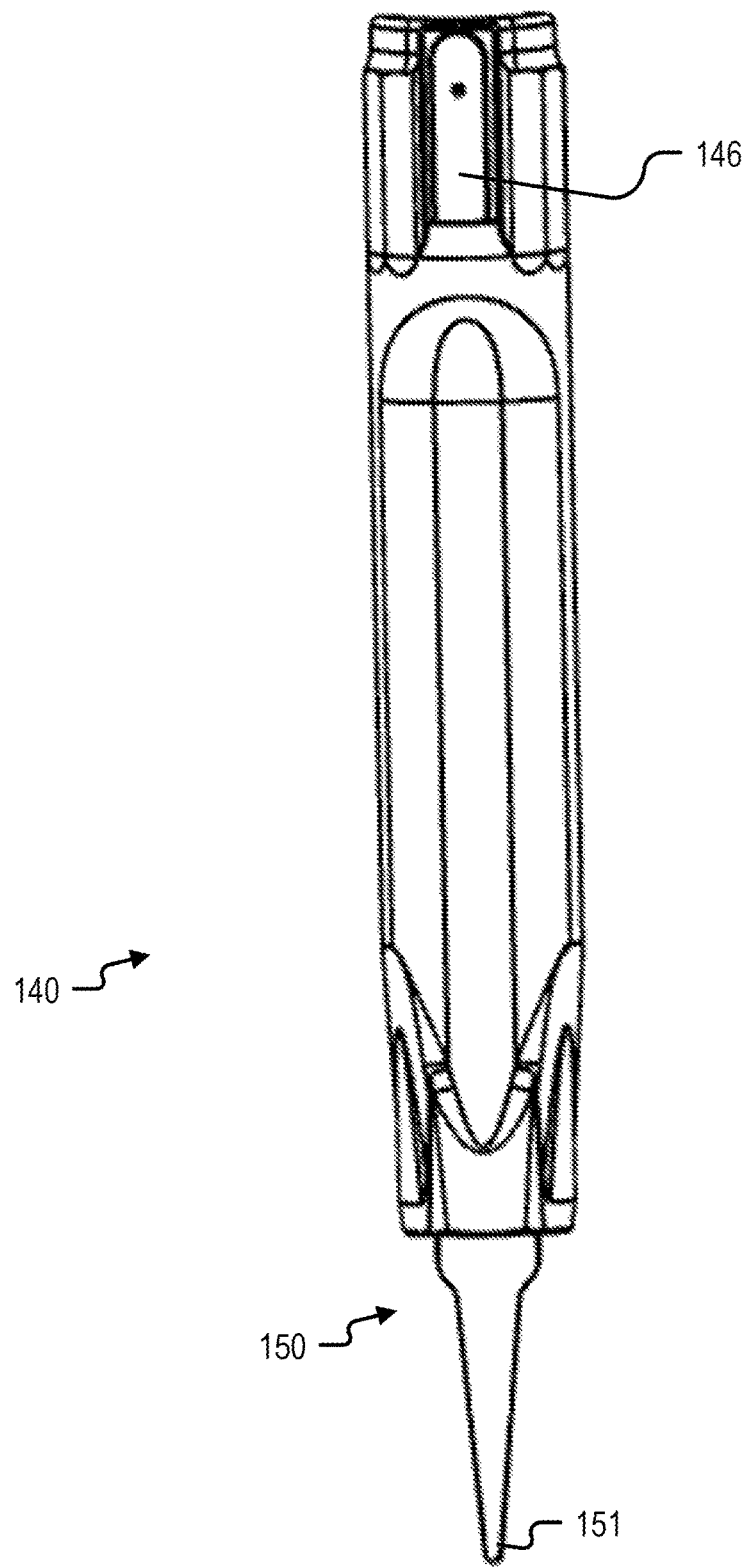
Figure 107:
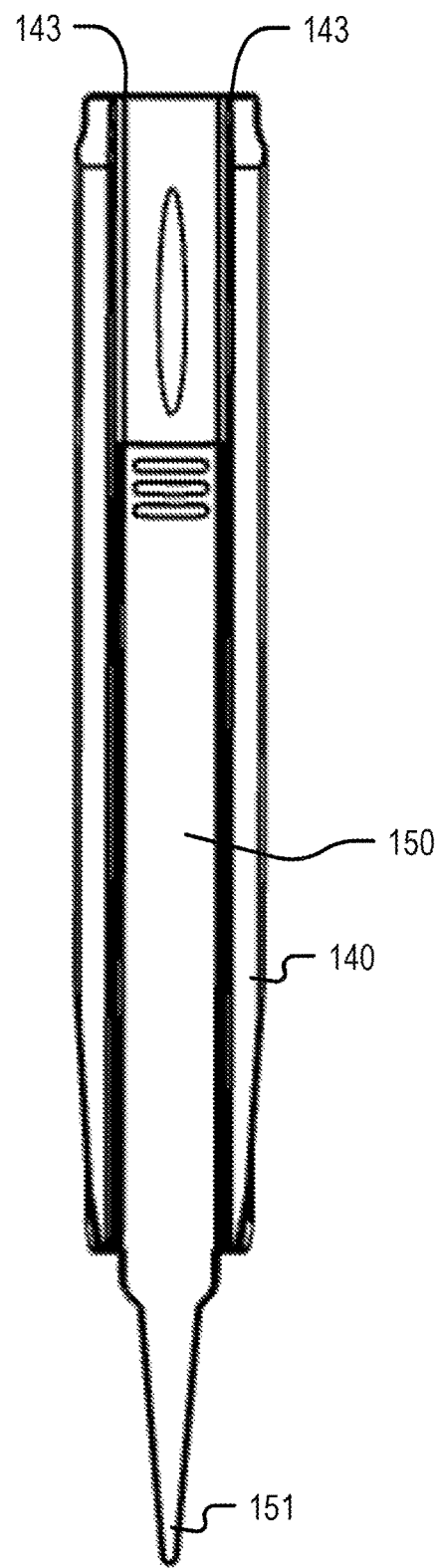
Figure 108A:
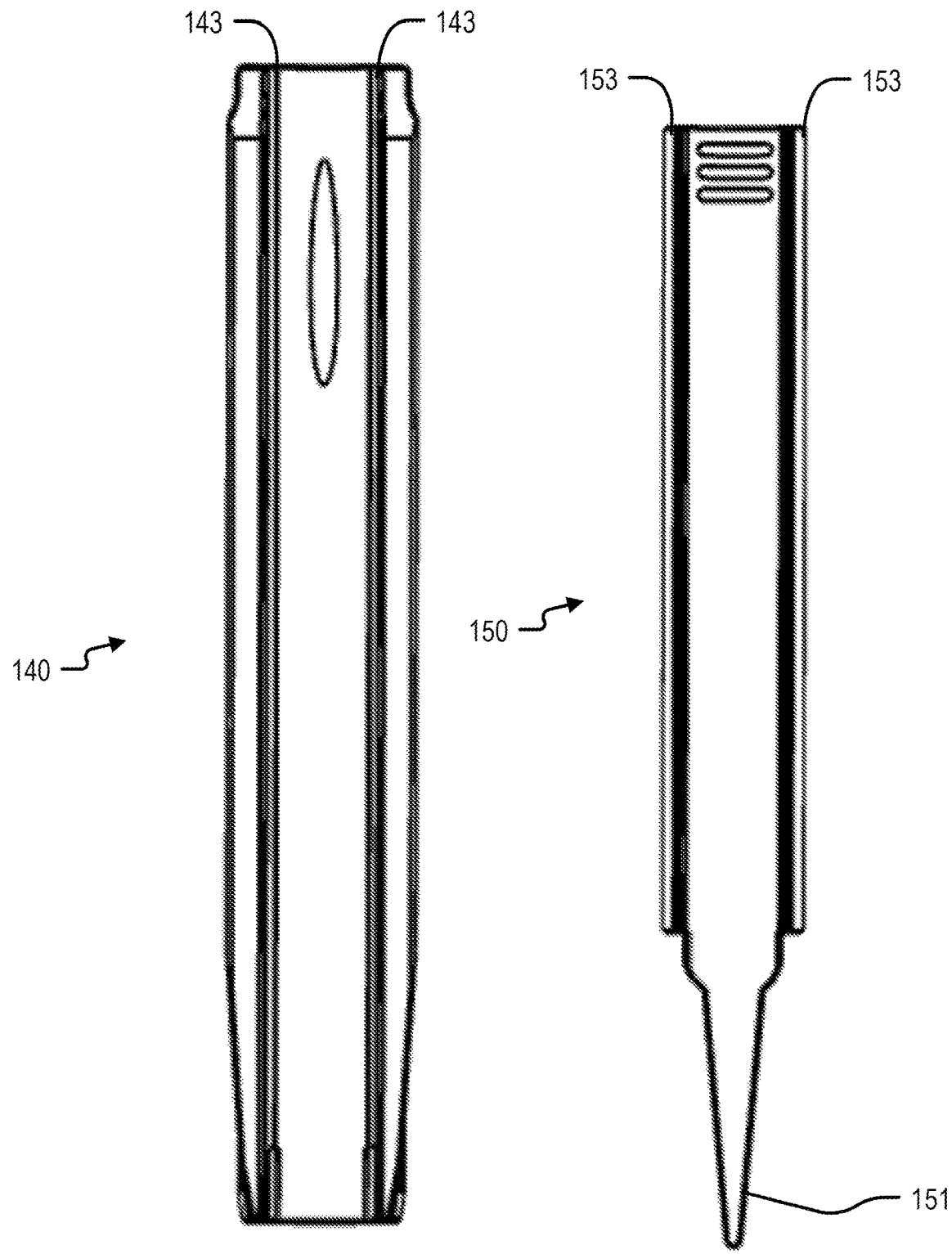
Figure 108B:
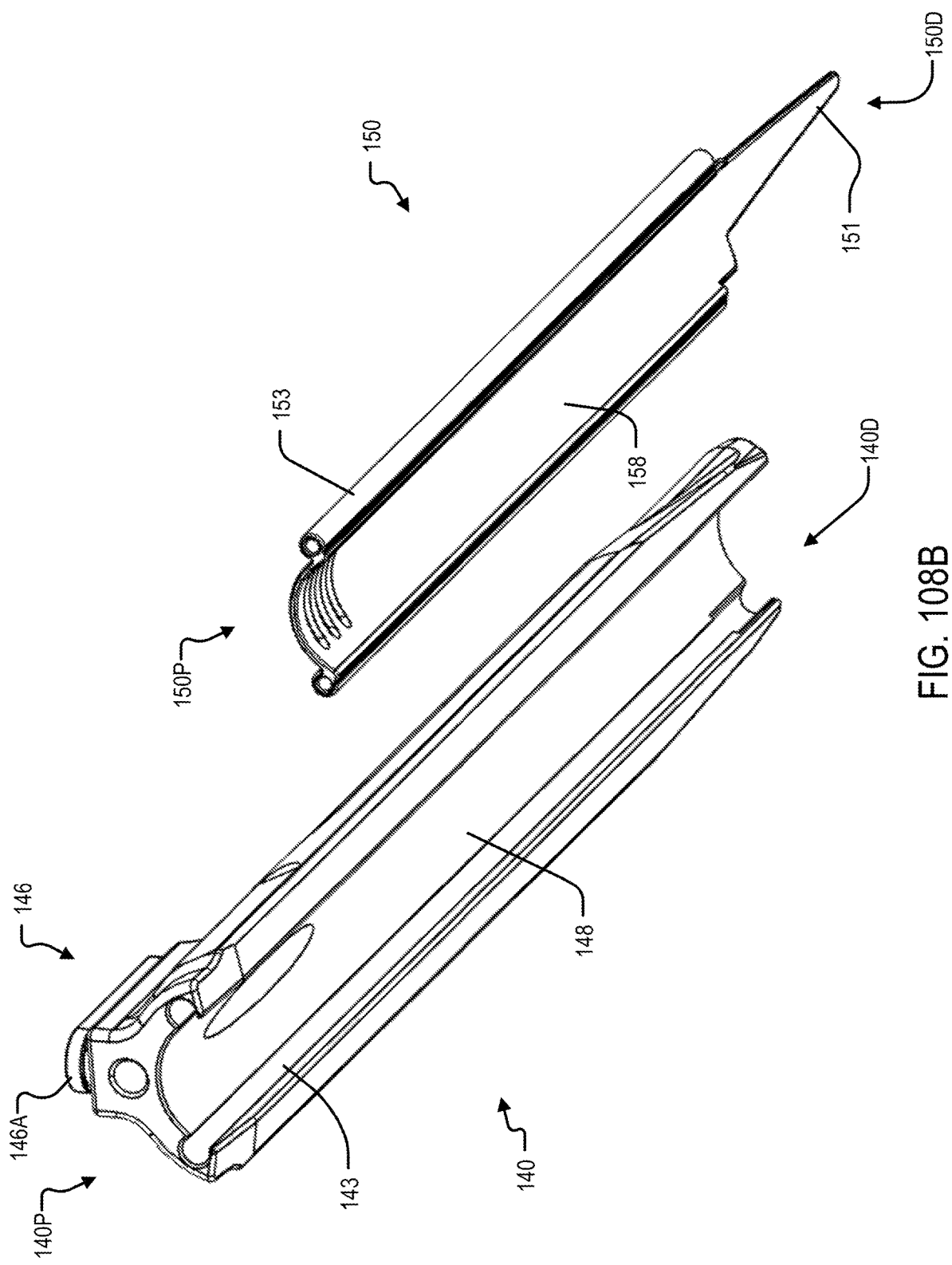
Figure 108C:
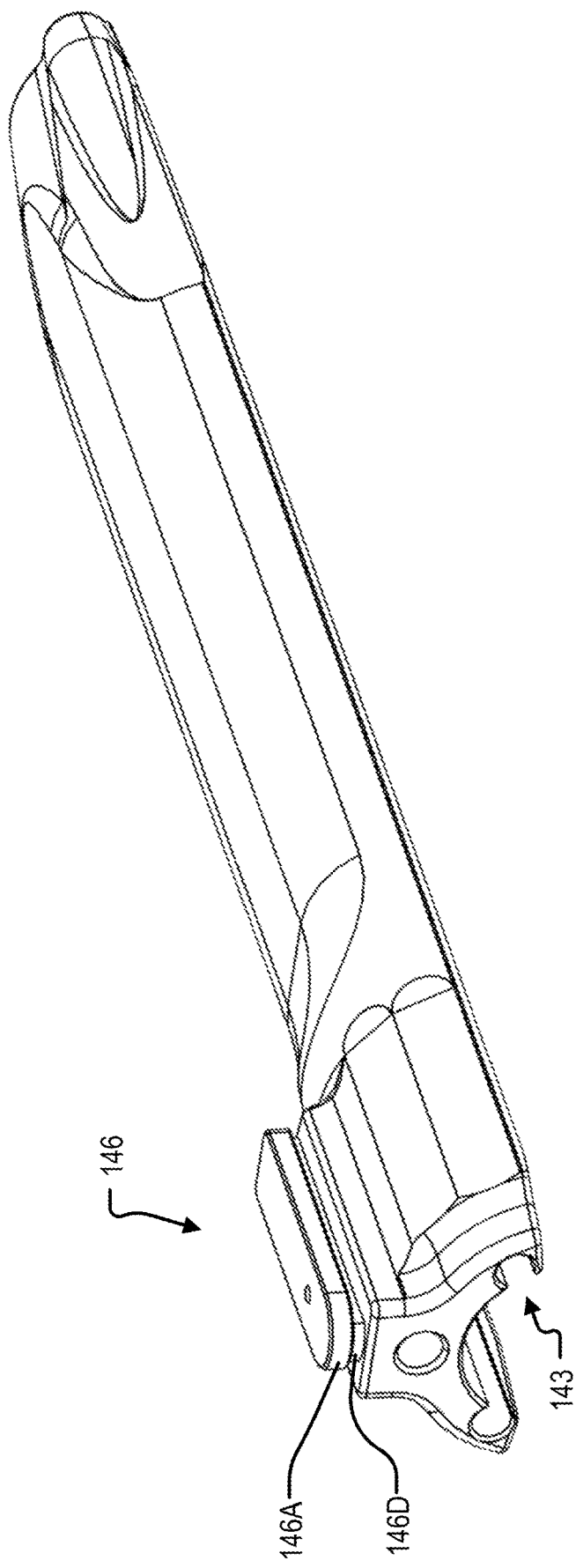
Figure 108D:
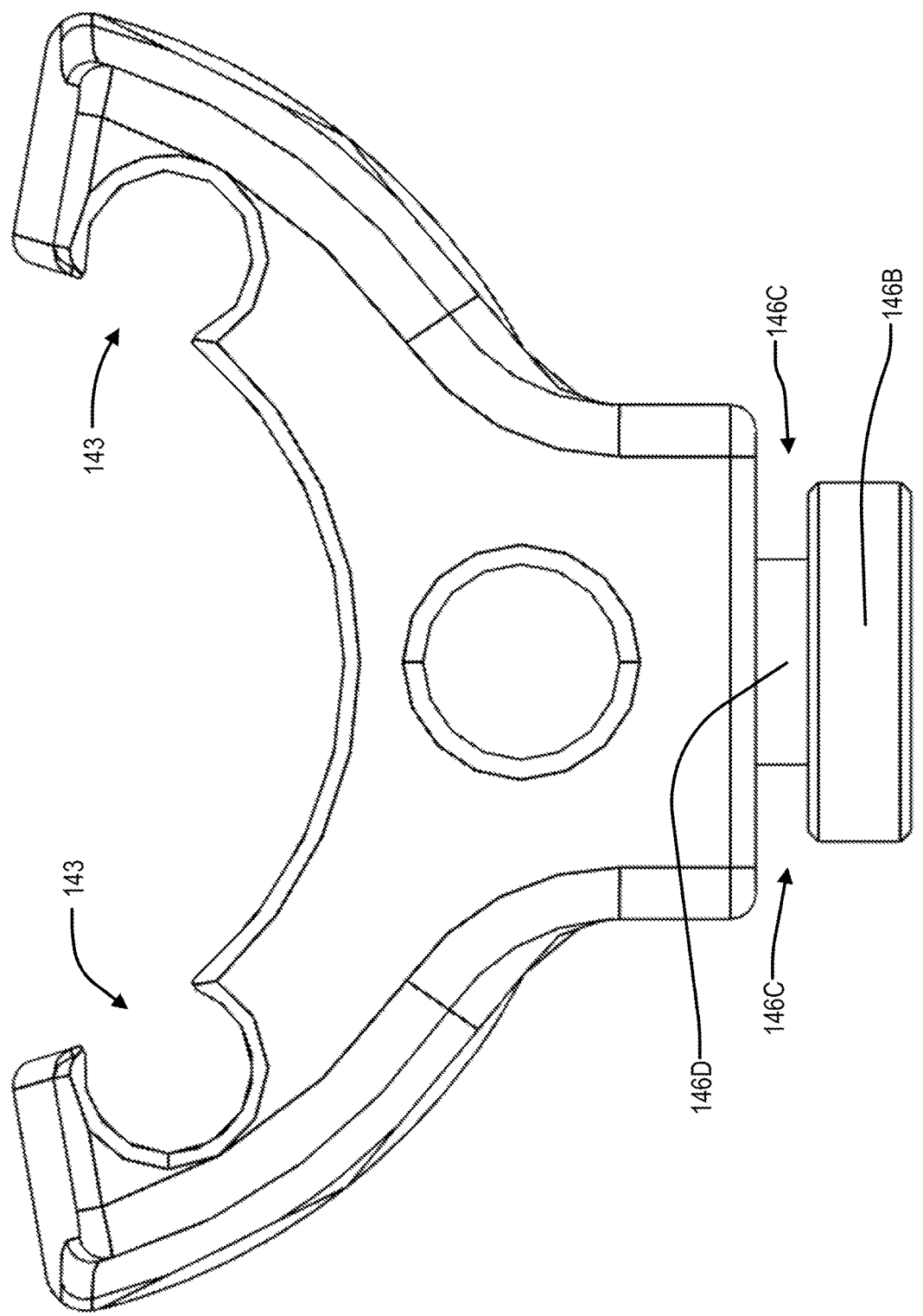
Figure 108E:
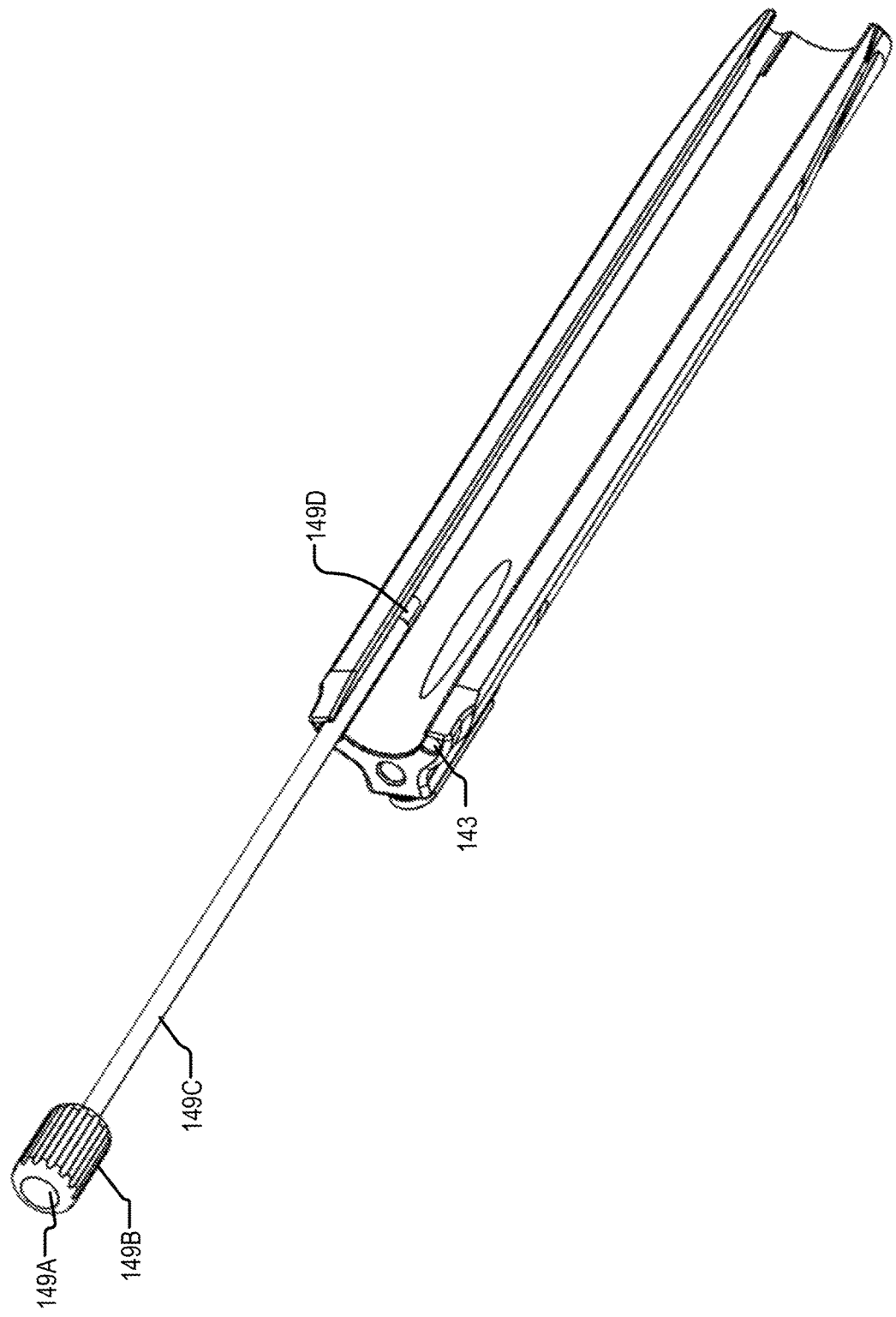

FIG. 108E is a perspective view of an impact driver for use with the modular blade and extendable blade of FIGS. 106-107.

Figure 109:
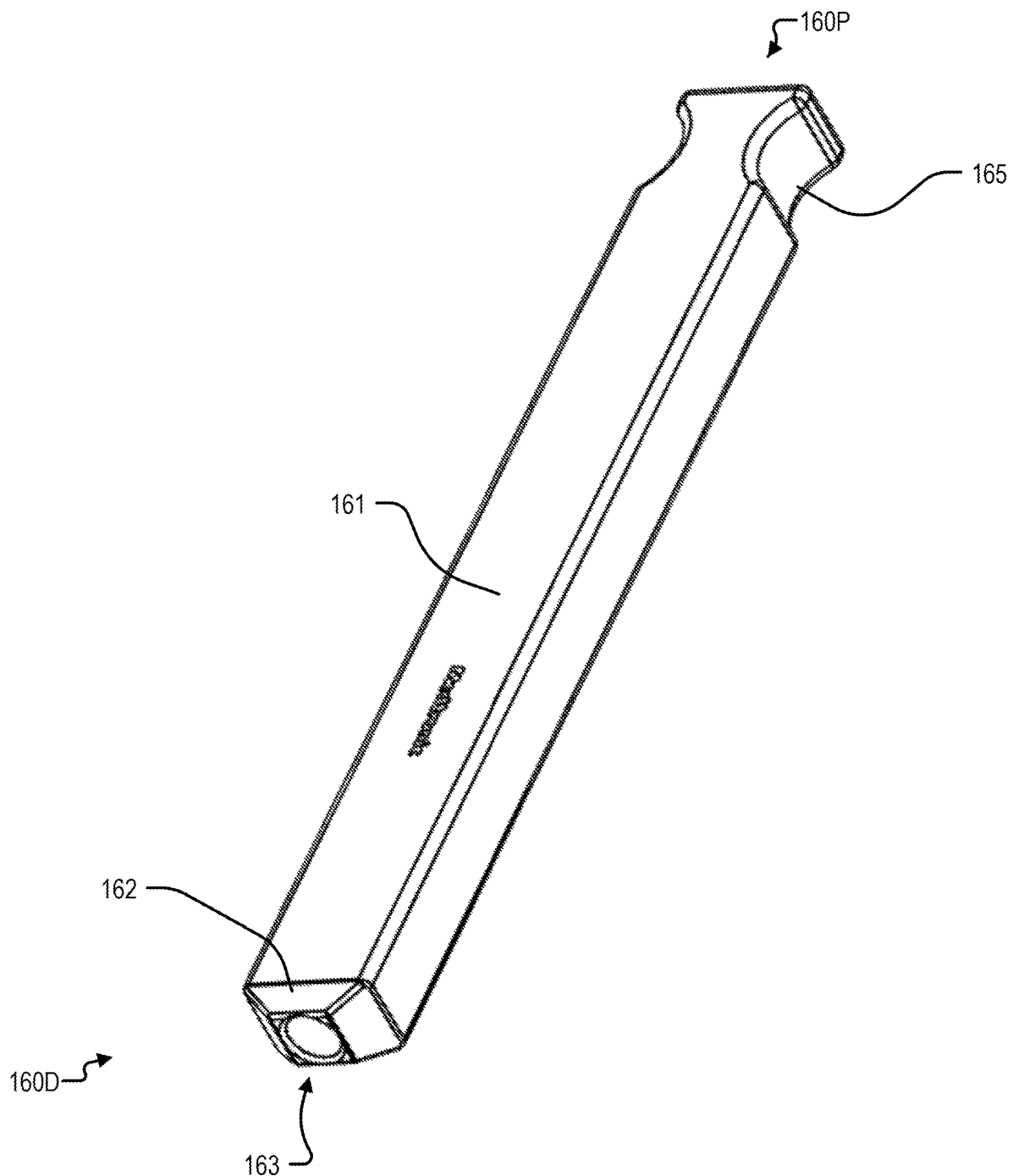

FIG. 109 is a perspective view of a square shaped dilator.

Figure 110:
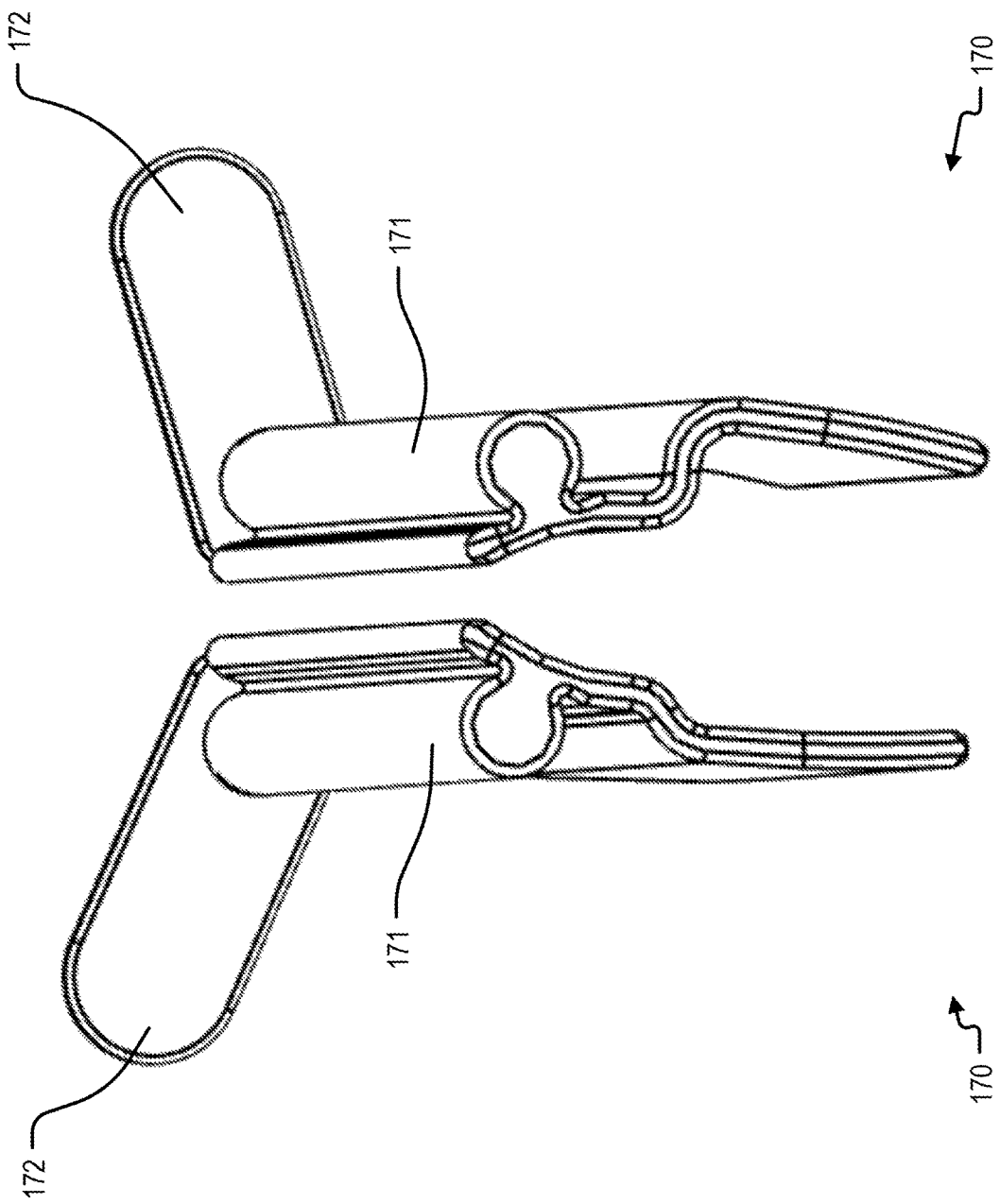

FIG. 110 is a bottom perspective view of a pair of shims for coupling to various blades disclosed herein.

Figure 111:
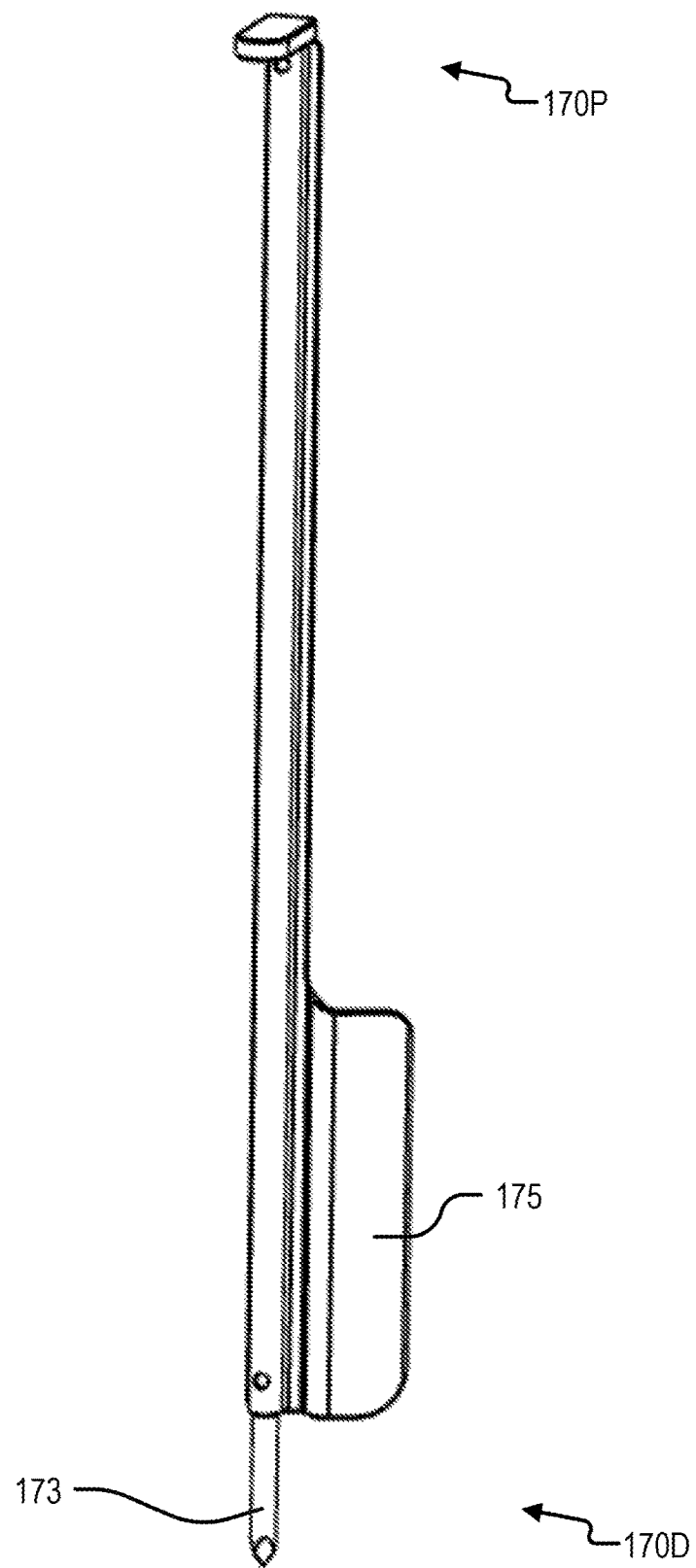

FIG. 111 is a perspective view of a relatively short shim having a pointed pin at a distal end thereof.

Figure 112:
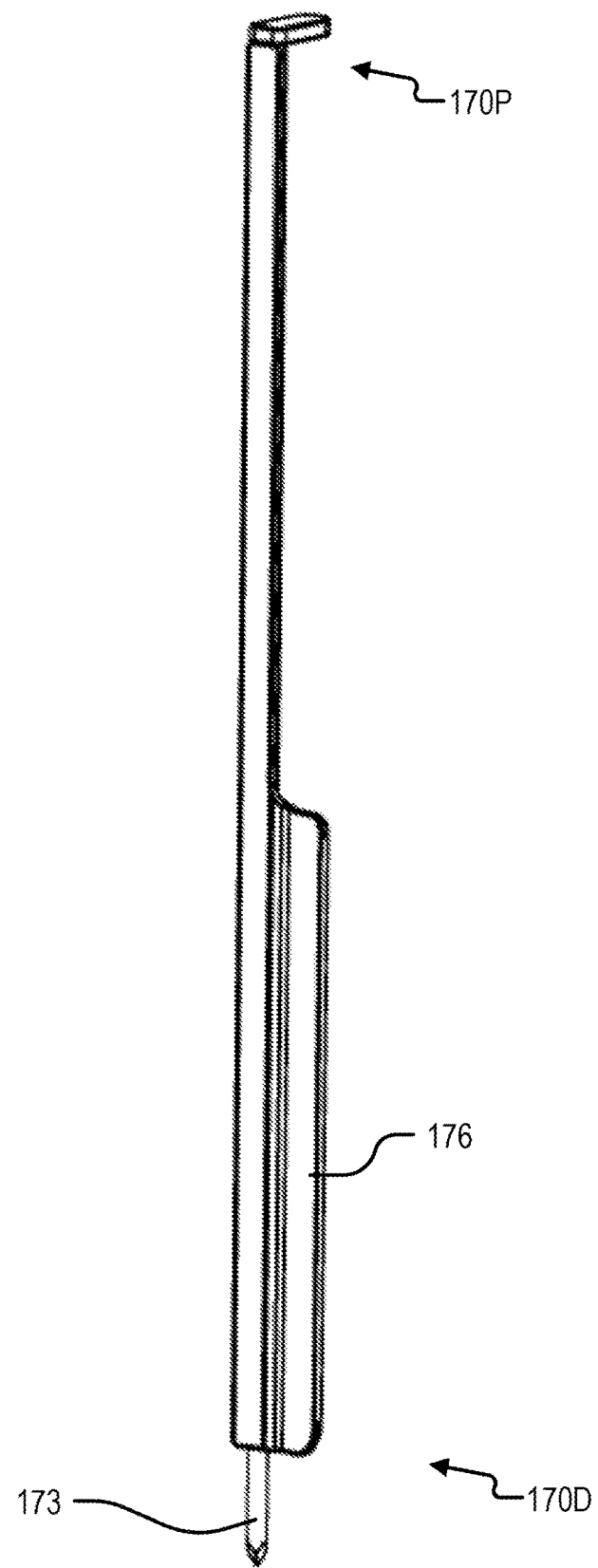

FIG. 112 is a perspective view of a relatively tall shim having a pointed pin at a distal end thereof.

Figure 113:
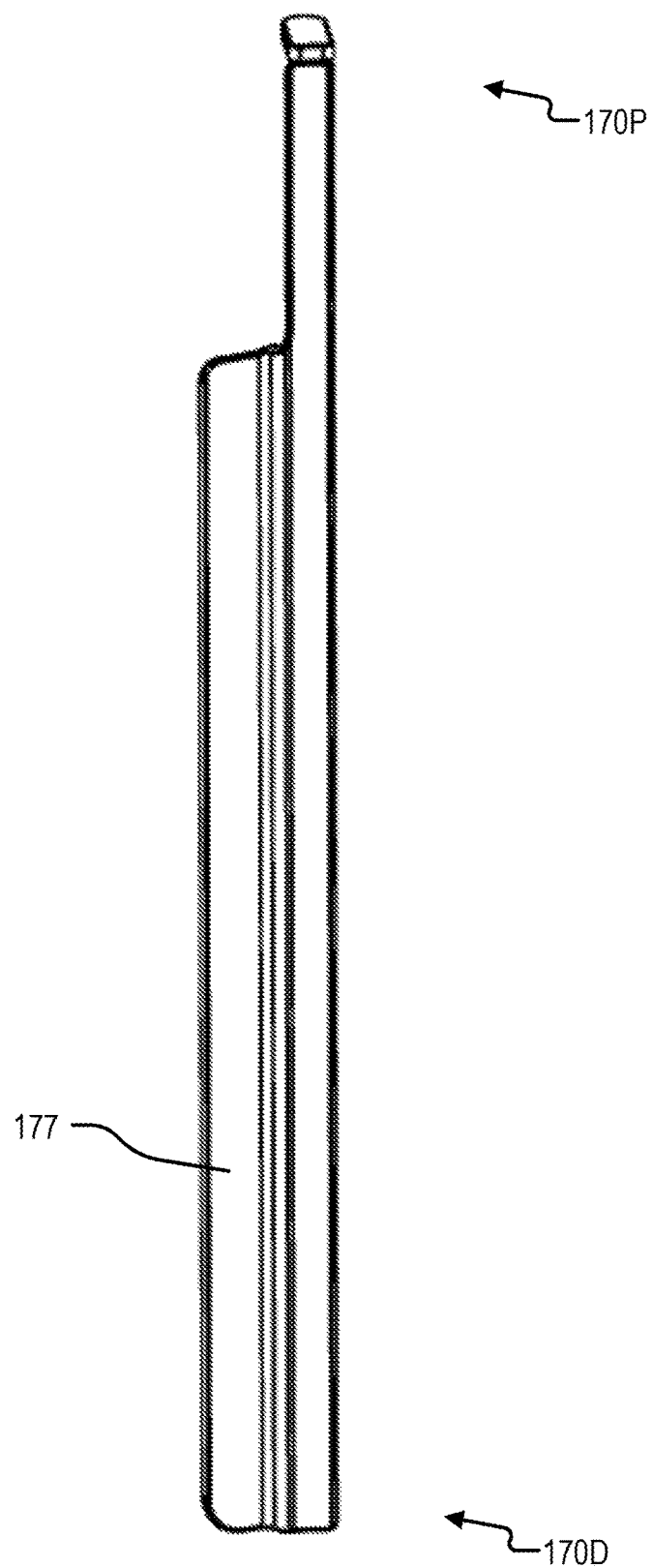

FIG. 113 is a perspective view of a relatively tall shim having a blunted distal end.

Figure 114:
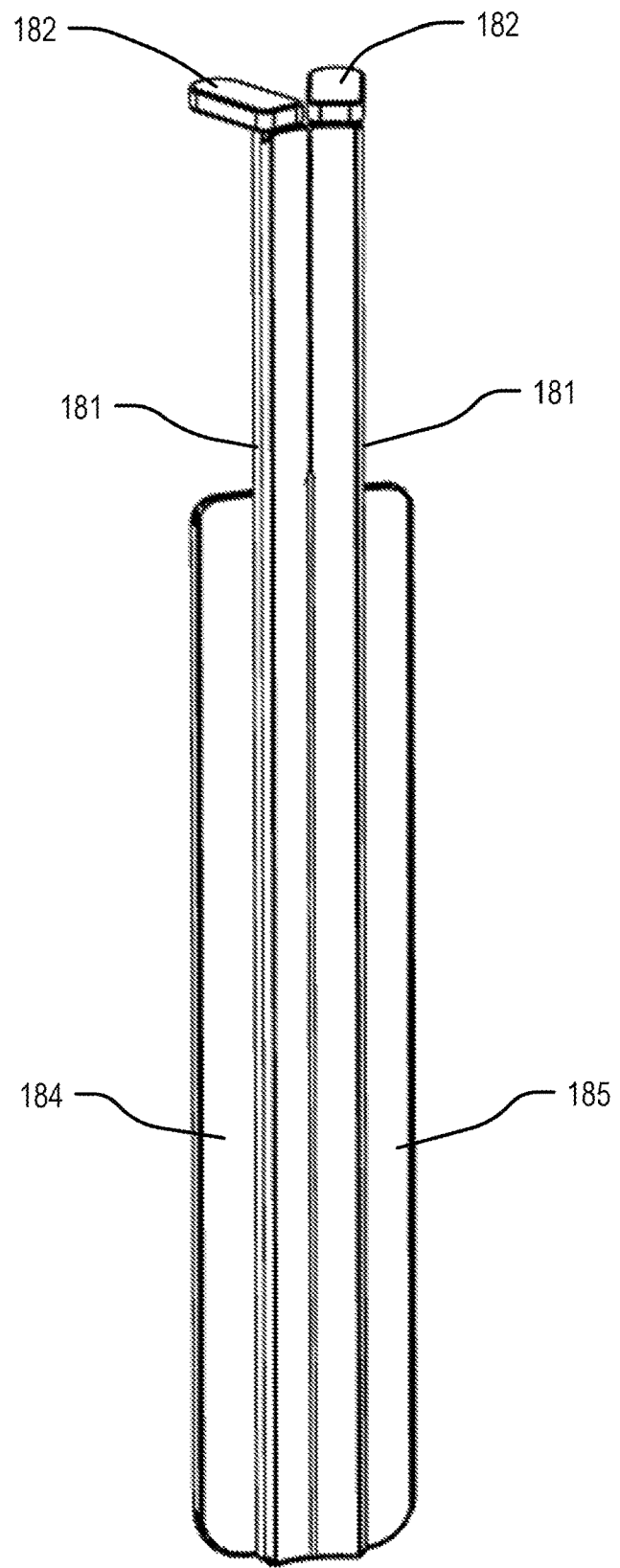

FIG. 114 is a perspective view of a double-sided shim for coupling to various blades disclosed herein.

Figure 115A:
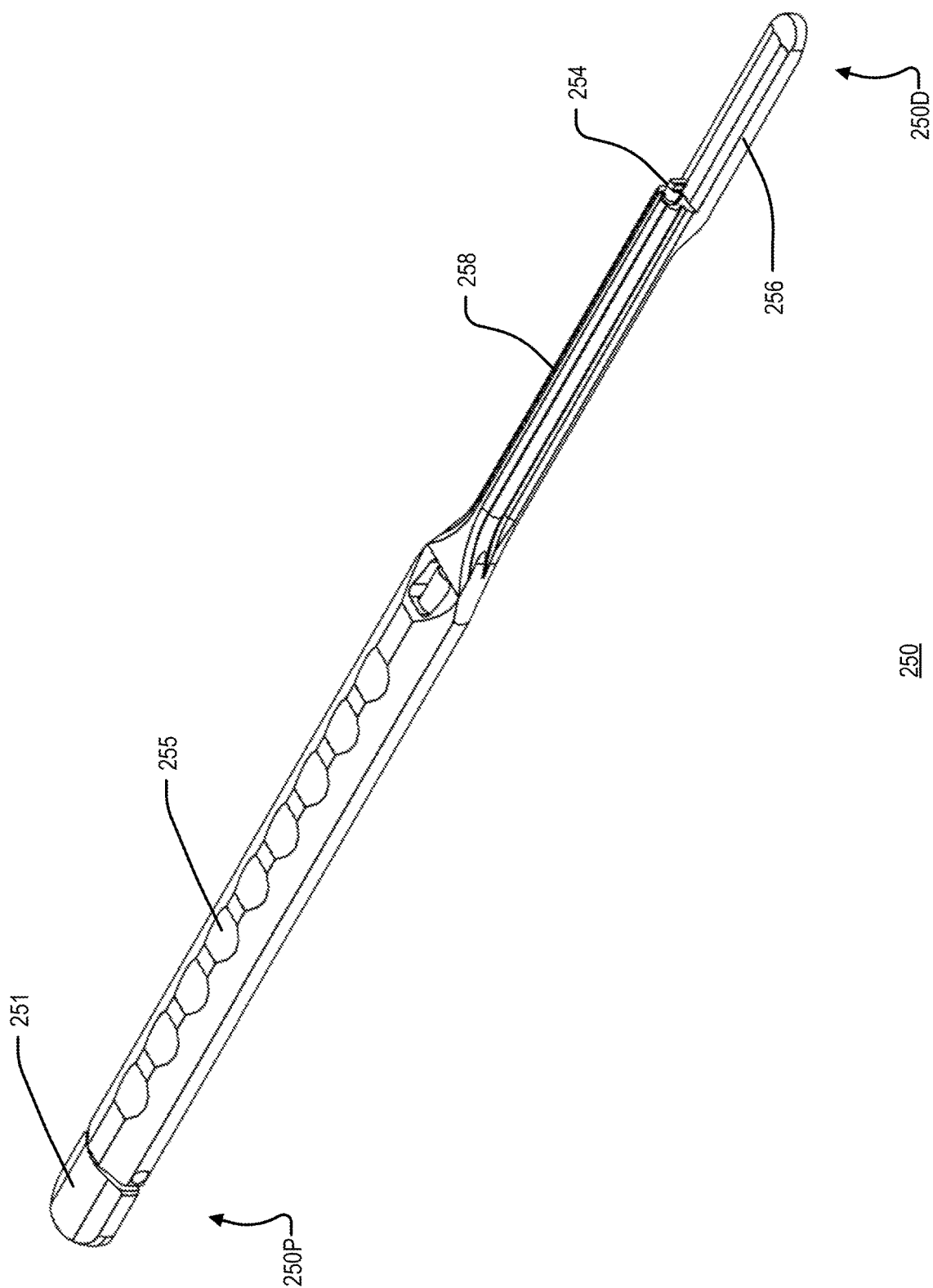

FIG. 115A is a perspective view of a blade adjustment and positioning tool.

Figure 115B:
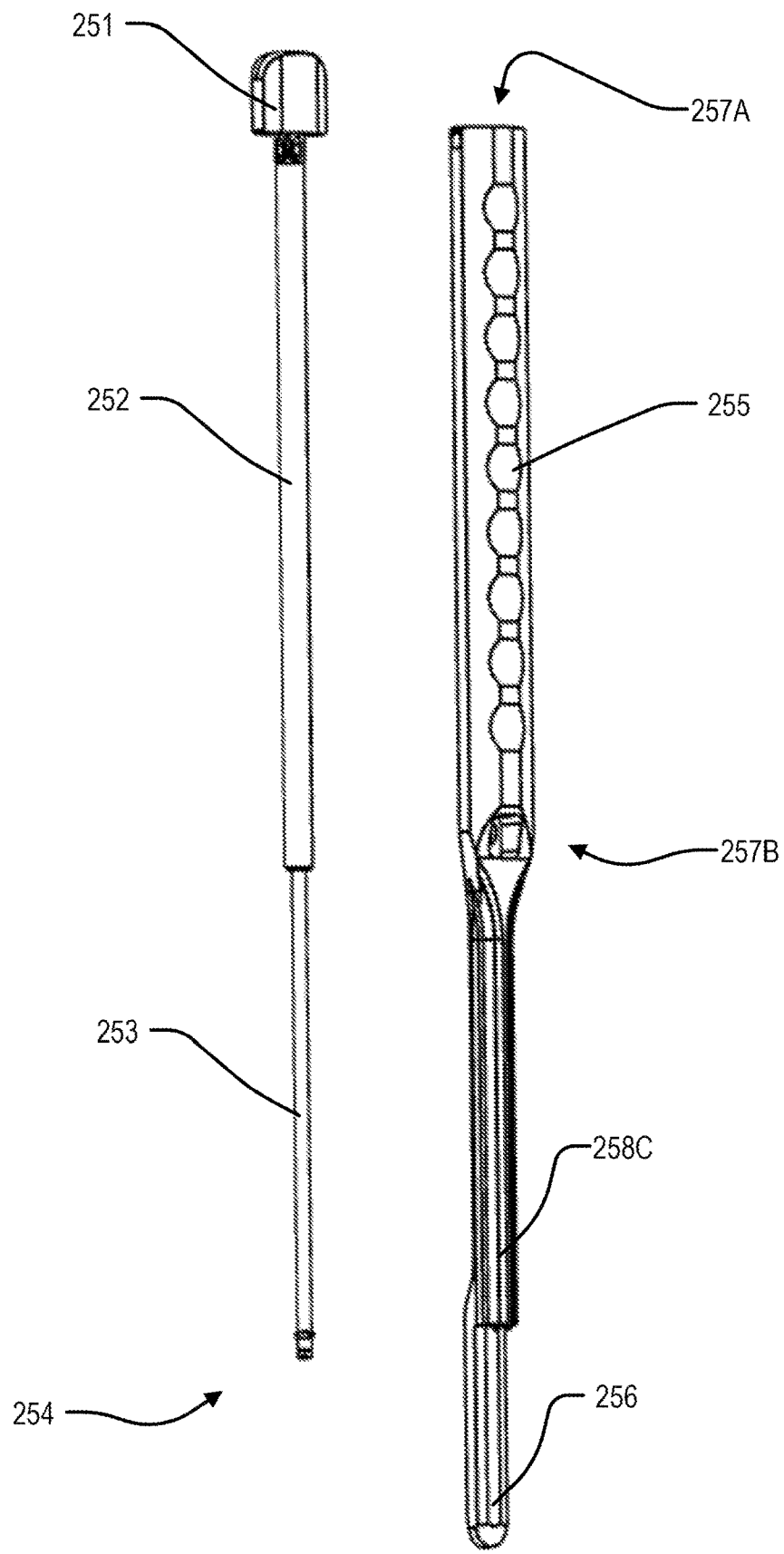

FIG. 115B is an exploded parts view of a blade adjustment and positioning tool.

Figure 116A:
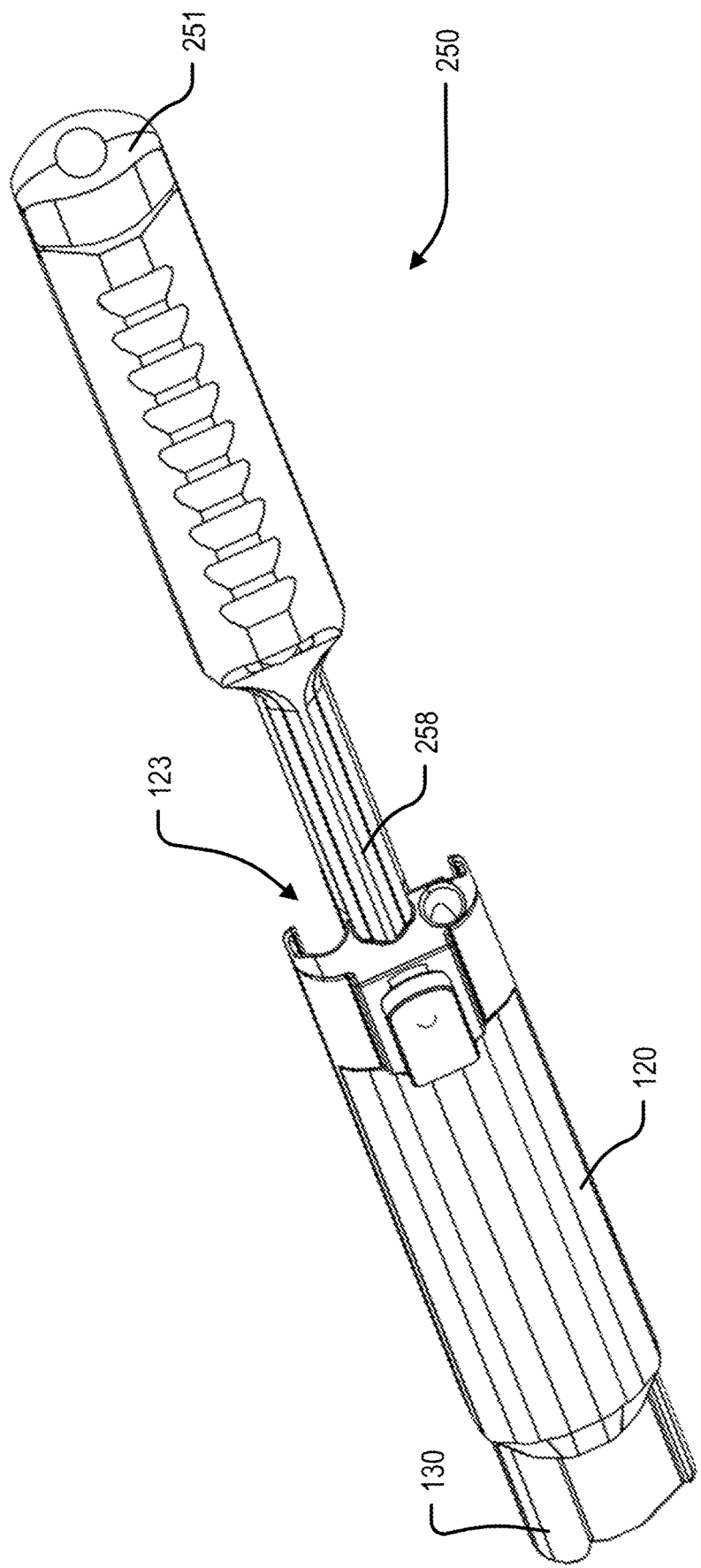

FIG. 116A is a perspective view of the blade adjustment and positioning tool engaged with a modular blade and an extendable blade.

Figure 116B:
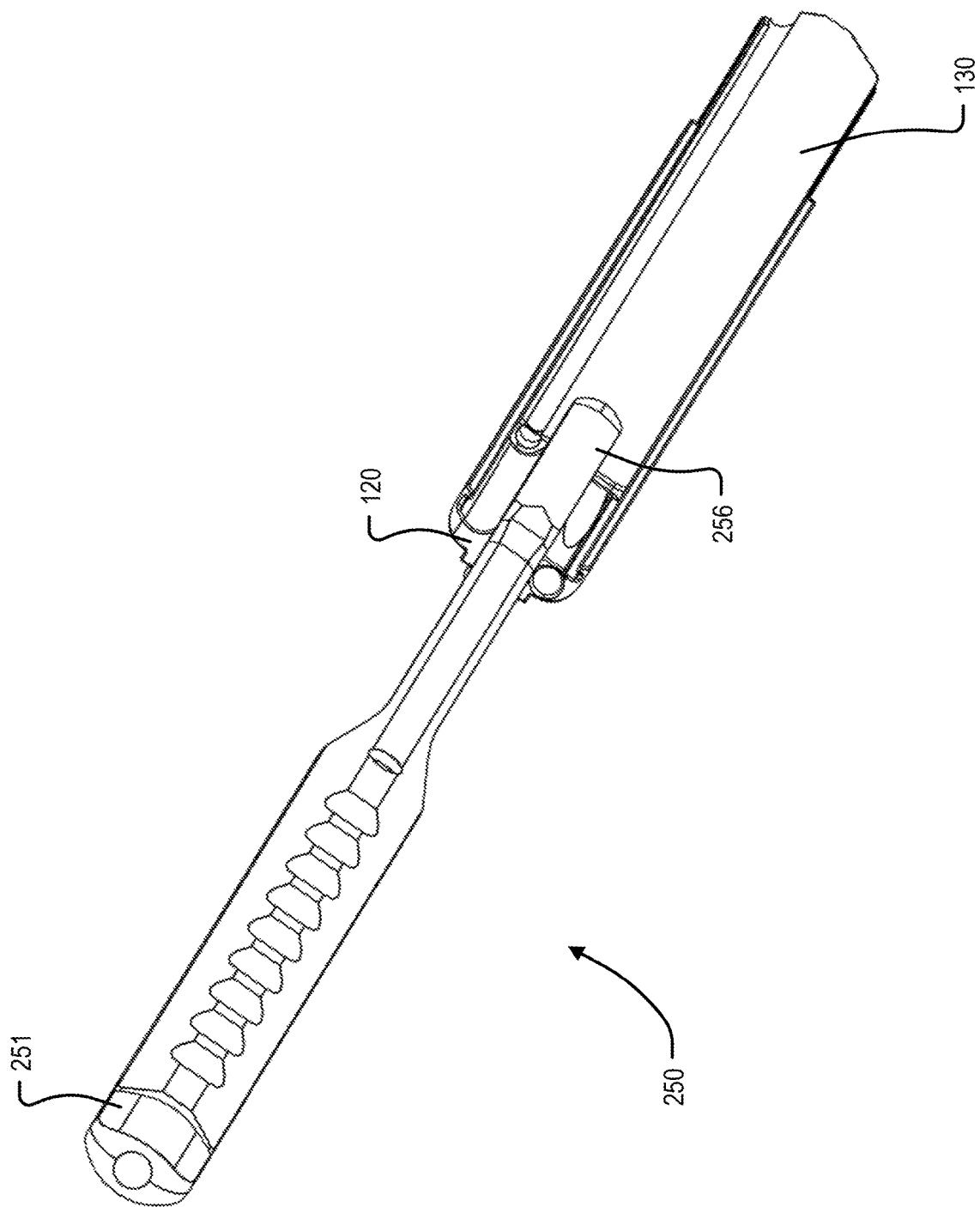

FIG. 116B is a perspective view of the blade adjustment and positioning tool engaged with a modular blade and an extendable blade.

Figure 117A:
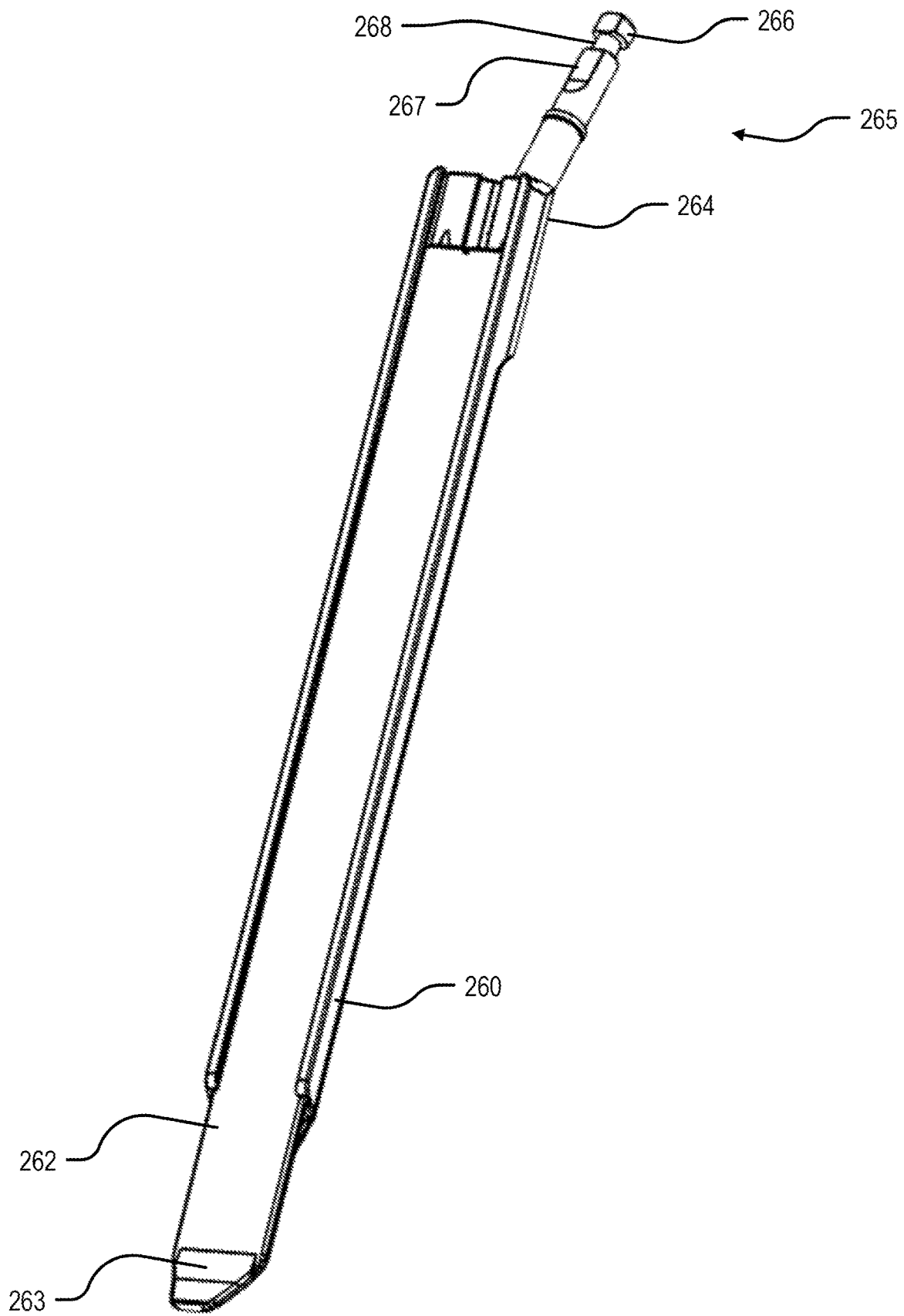

FIG. 117A is a perspective view of the inside surfaces of a modular blade and an extendable blade having a footed tip at the distal end thereof.

Figure 117B:
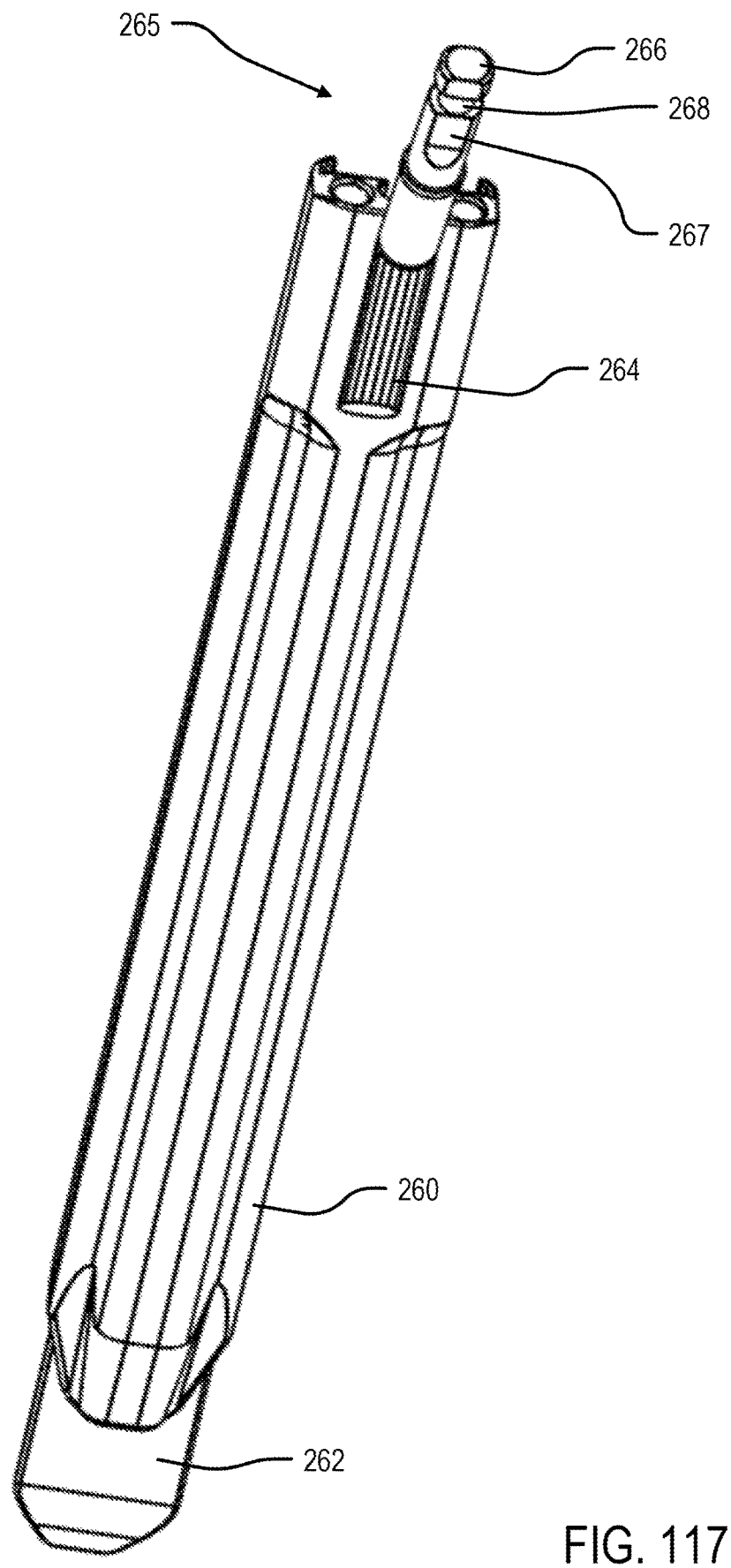

FIG. 117B is a perspective view of the modular blade and extendable blade of FIG. 117A.

Figure 118A:
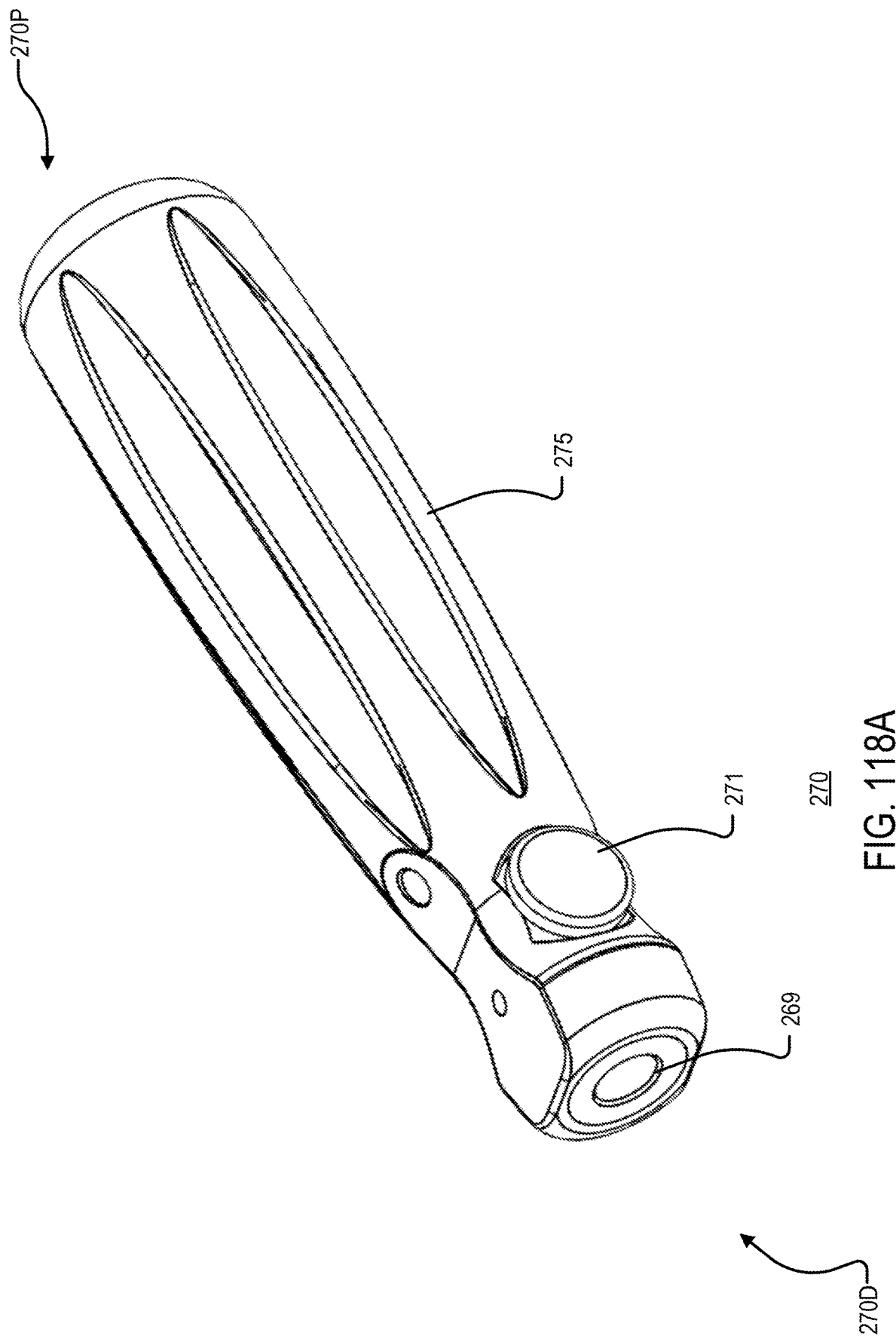

FIG. 118A is a perspective view of a quick connect handle.

Figure 118B:
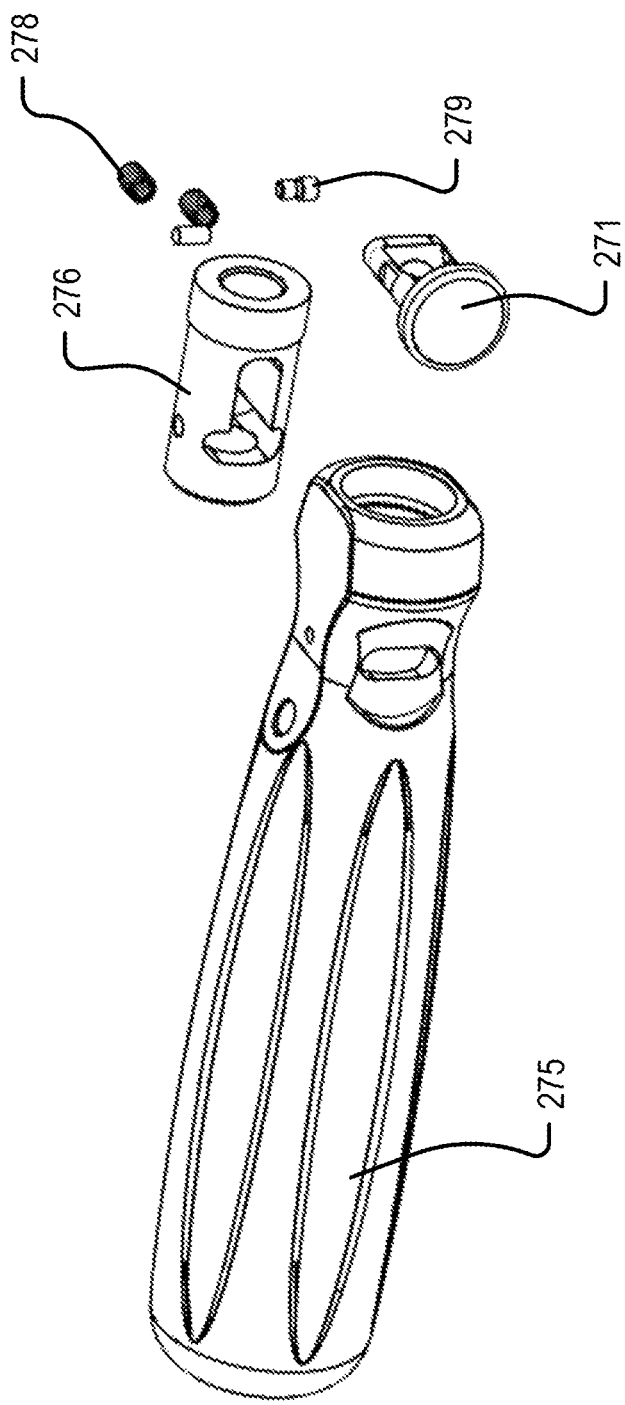

FIG. 118B is an exploded parts view of a quick connect handle.

FIG. 118C is a perspective view of a retractor mount coupler.

Figure 118D:
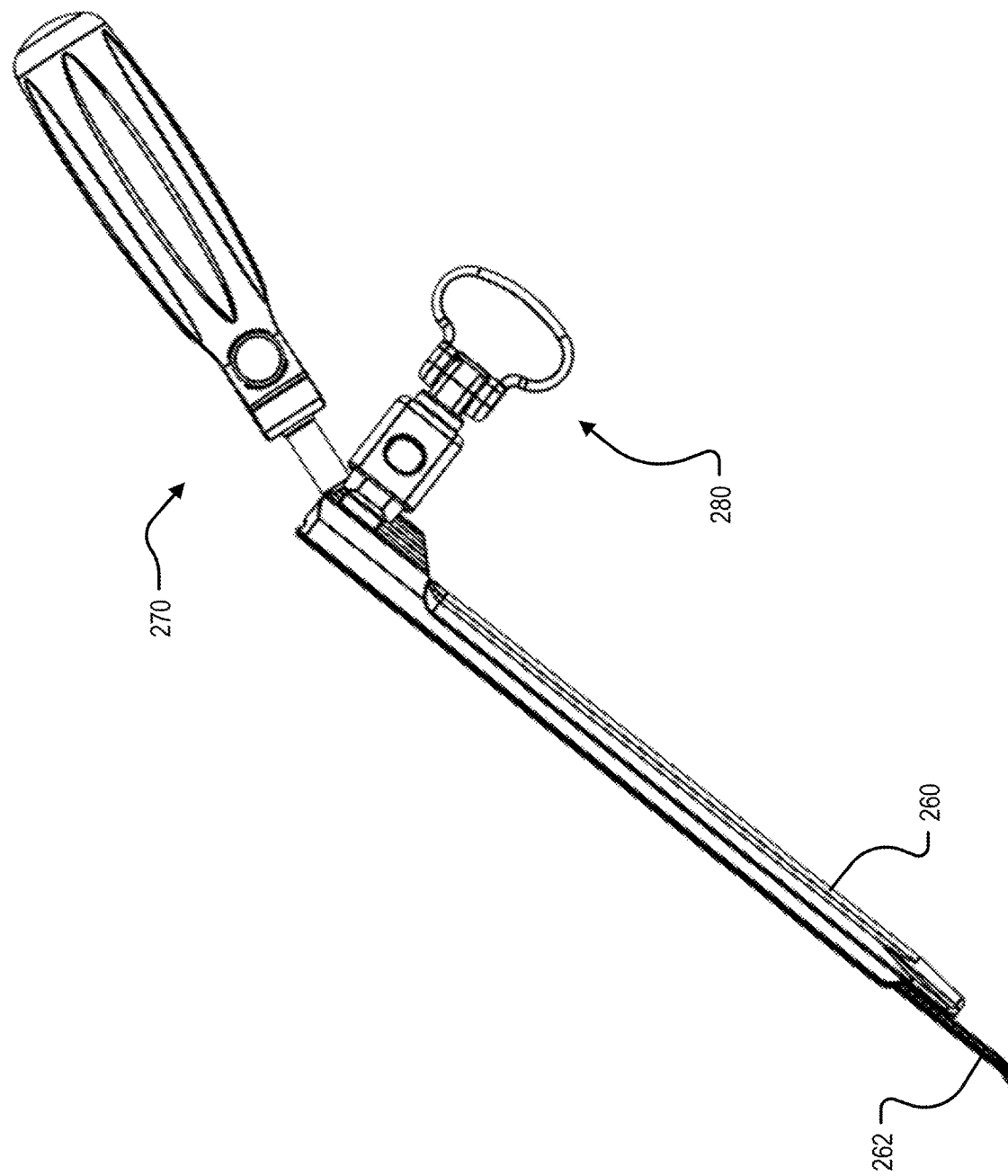

FIG. 118D is a perspective view of the modular and extendable blades of FIGS. 117A-117B coupled to the quick connect handle of FIGS. 118A-118B and the retractor mount coupler of FIG. 118C.

Figure 118E:
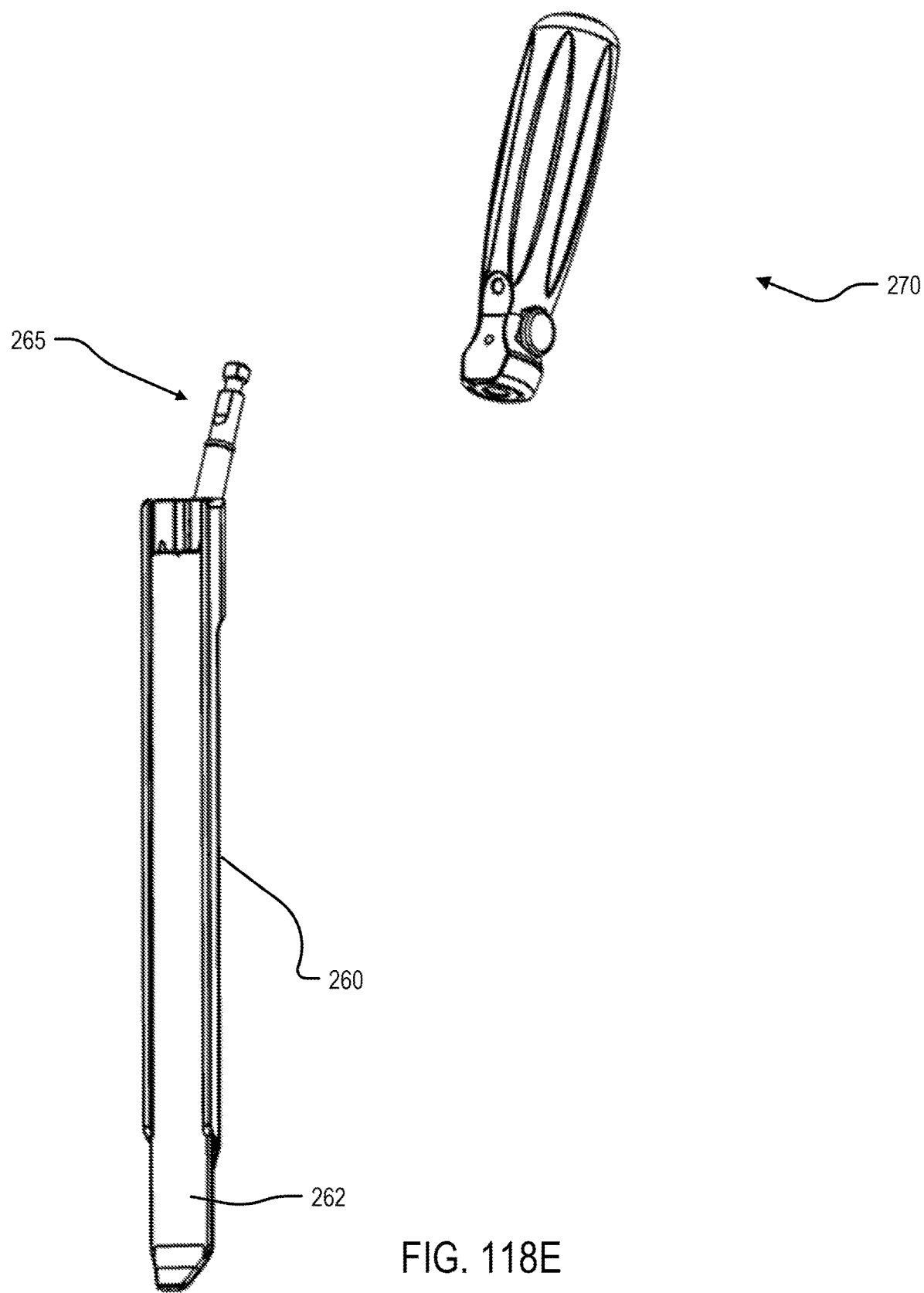

FIG. 118E is a perspective view of the modular and extendable blades of FIGS. 117A-117B before being coupled to the quick connect handle of FIGS. 118A-118B.

Figure 119:
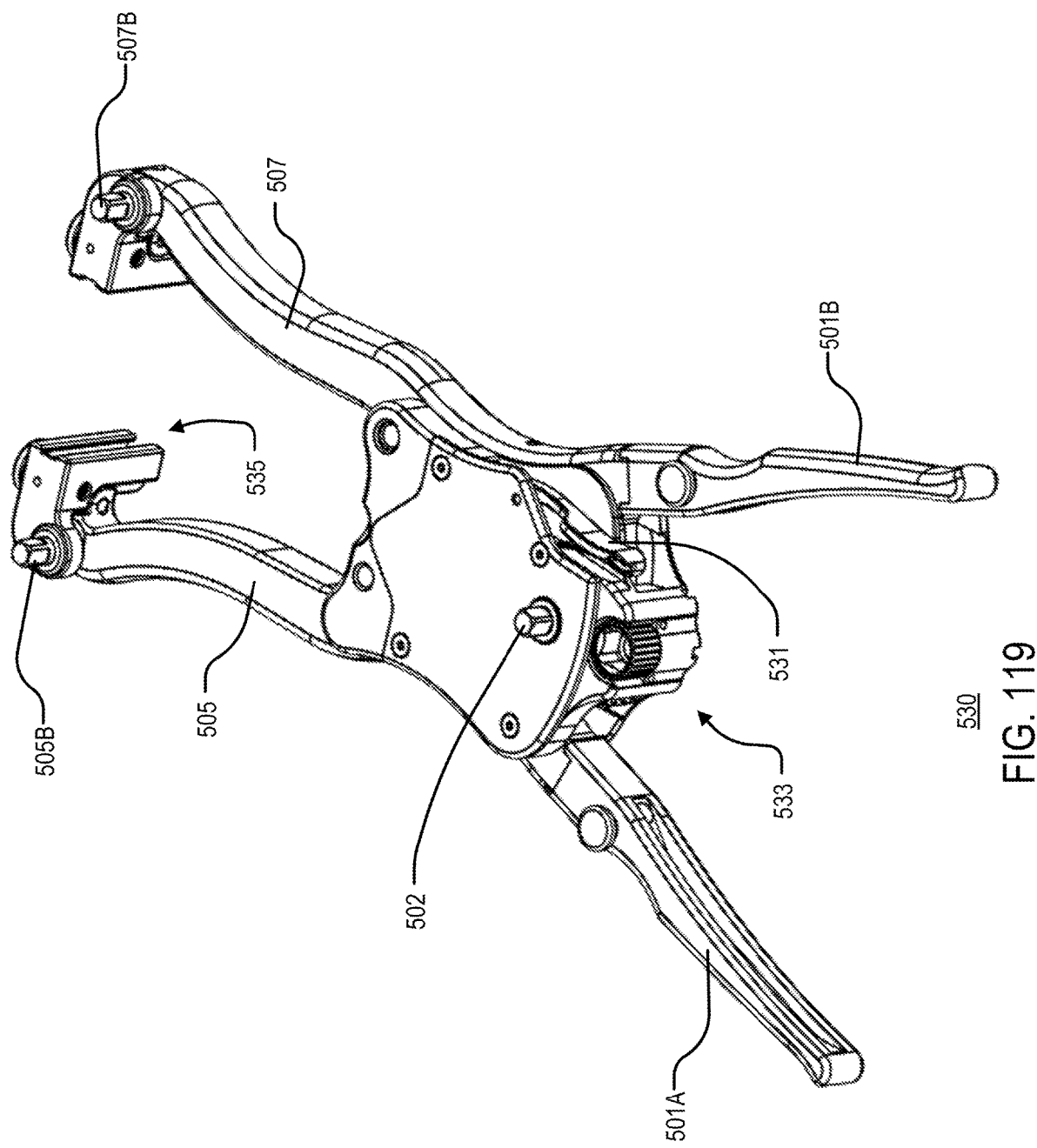

FIG. 119 is a first perspective view of an additional embodiment of a modular retractor.

Figure 120:
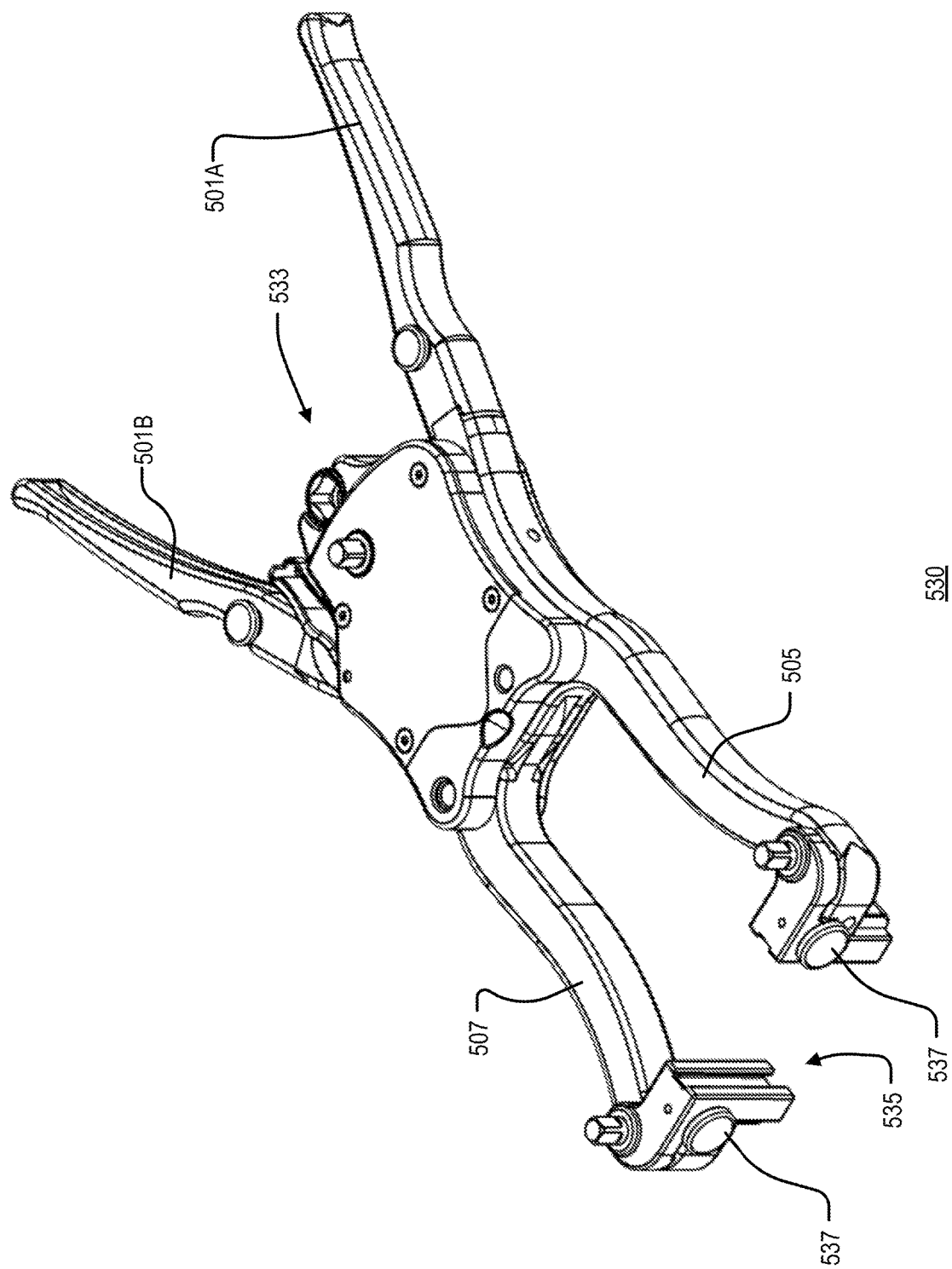

FIG. 120 is a second perspective view of the additional embodiment of the modular retractor of FIG. 119.

Figure 121A:
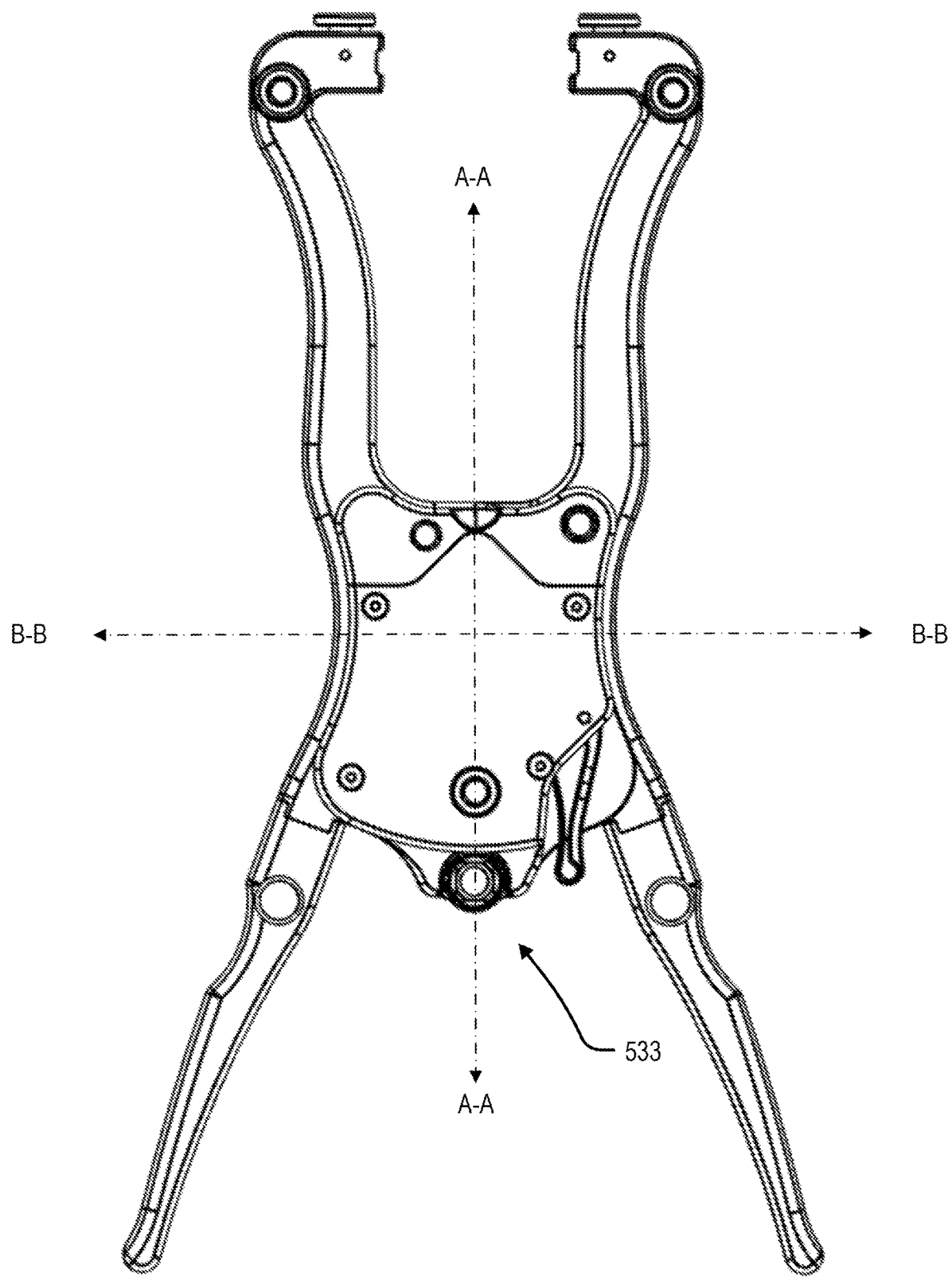

FIG. 121A is a top down view of the embodiment of FIGS. 119-120.

Figure 121B:
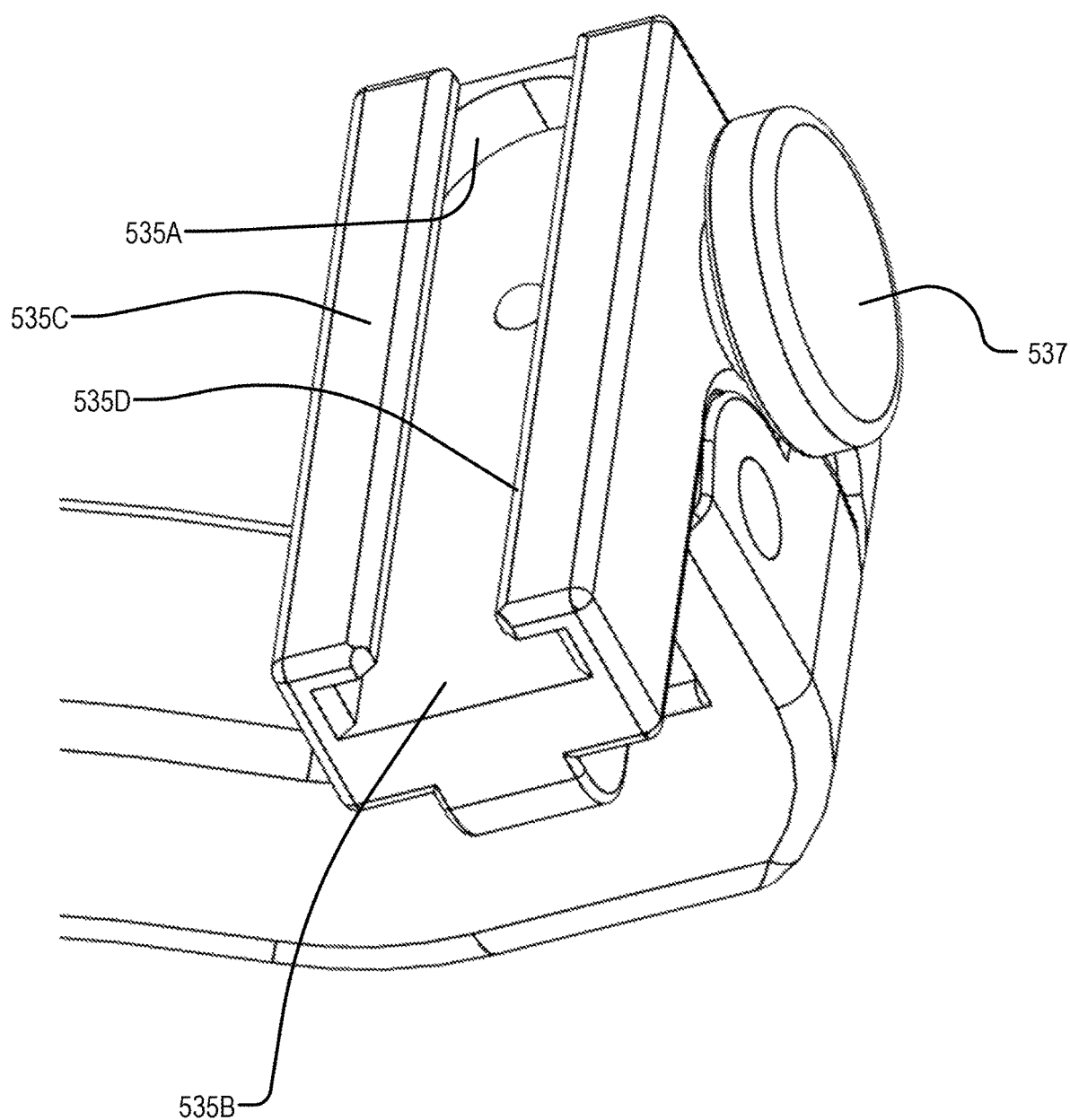

FIG. 121B is a bottom perspective view of a blade coupling portion.

Figure 122A:
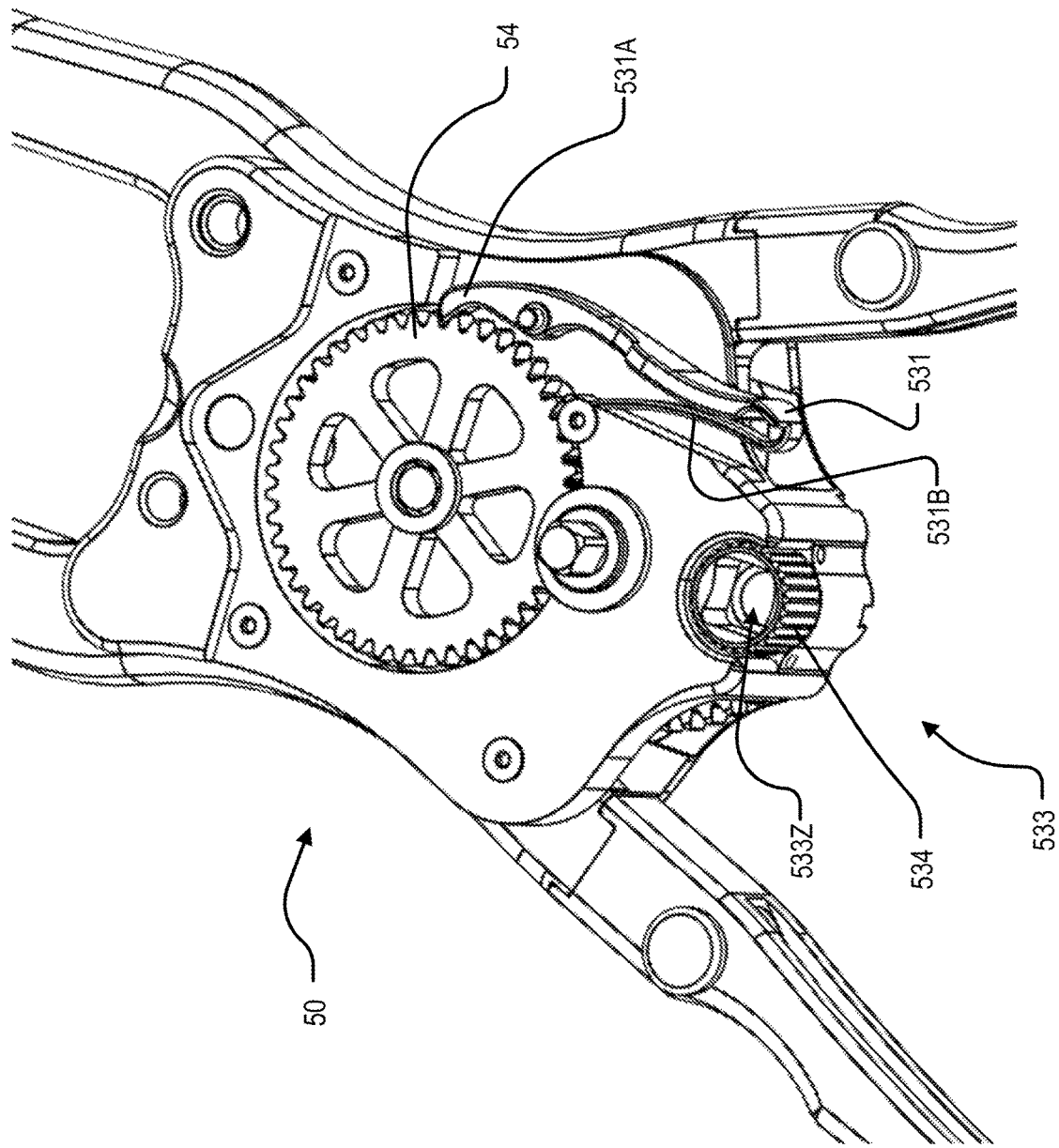

FIG. 122A is an enlarged view of the embodiment of FIGS. 119-121 from a top perspective with the top cover removed for ease of understanding of the internal gear system.

Figure 122B:
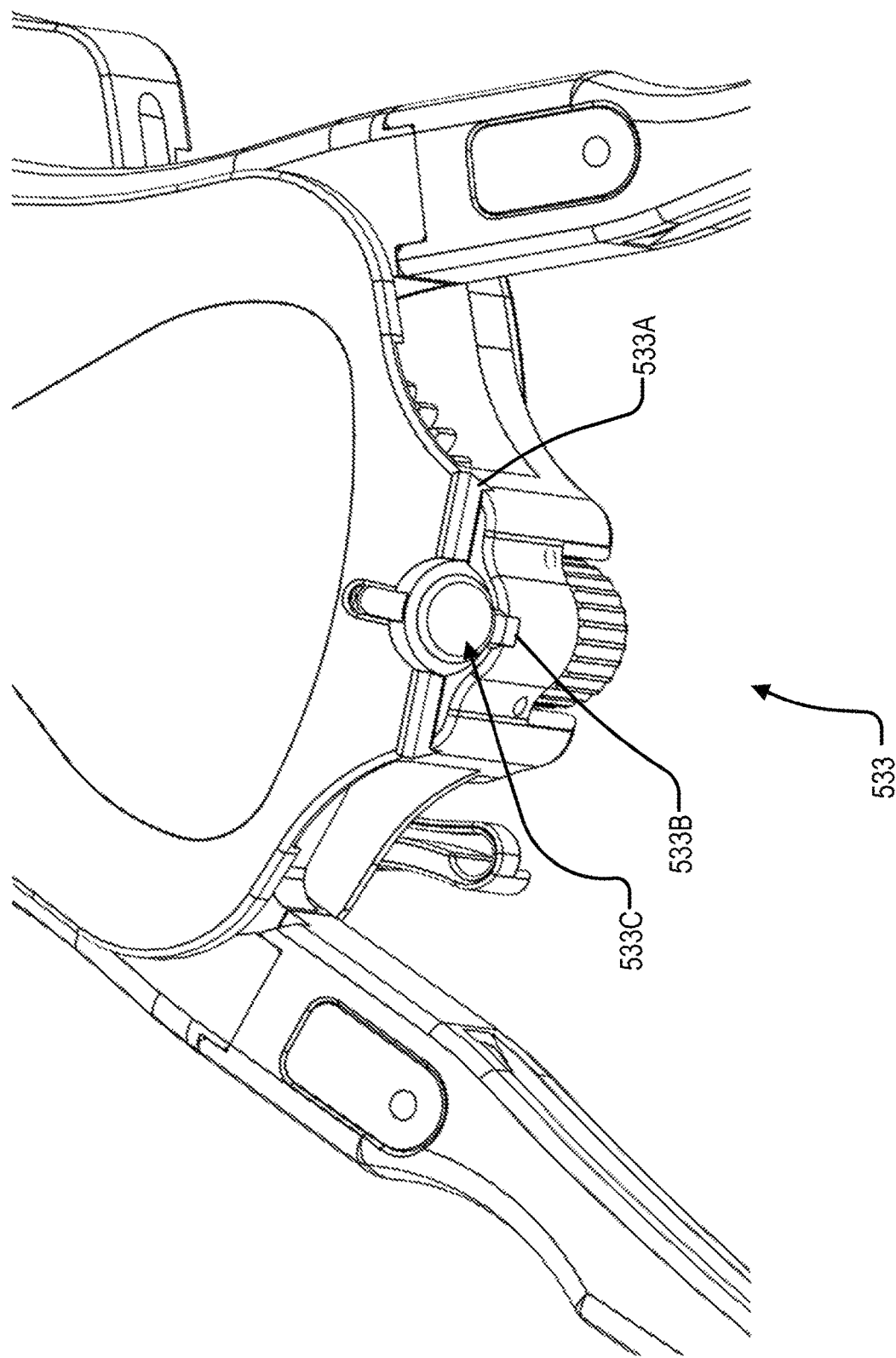

FIG. 122B is an enlarged view of the embodiment of FIGS. 119-121 from a bottom perspective showing various structural features of a table mount quick connect coupler.

Figure 123:
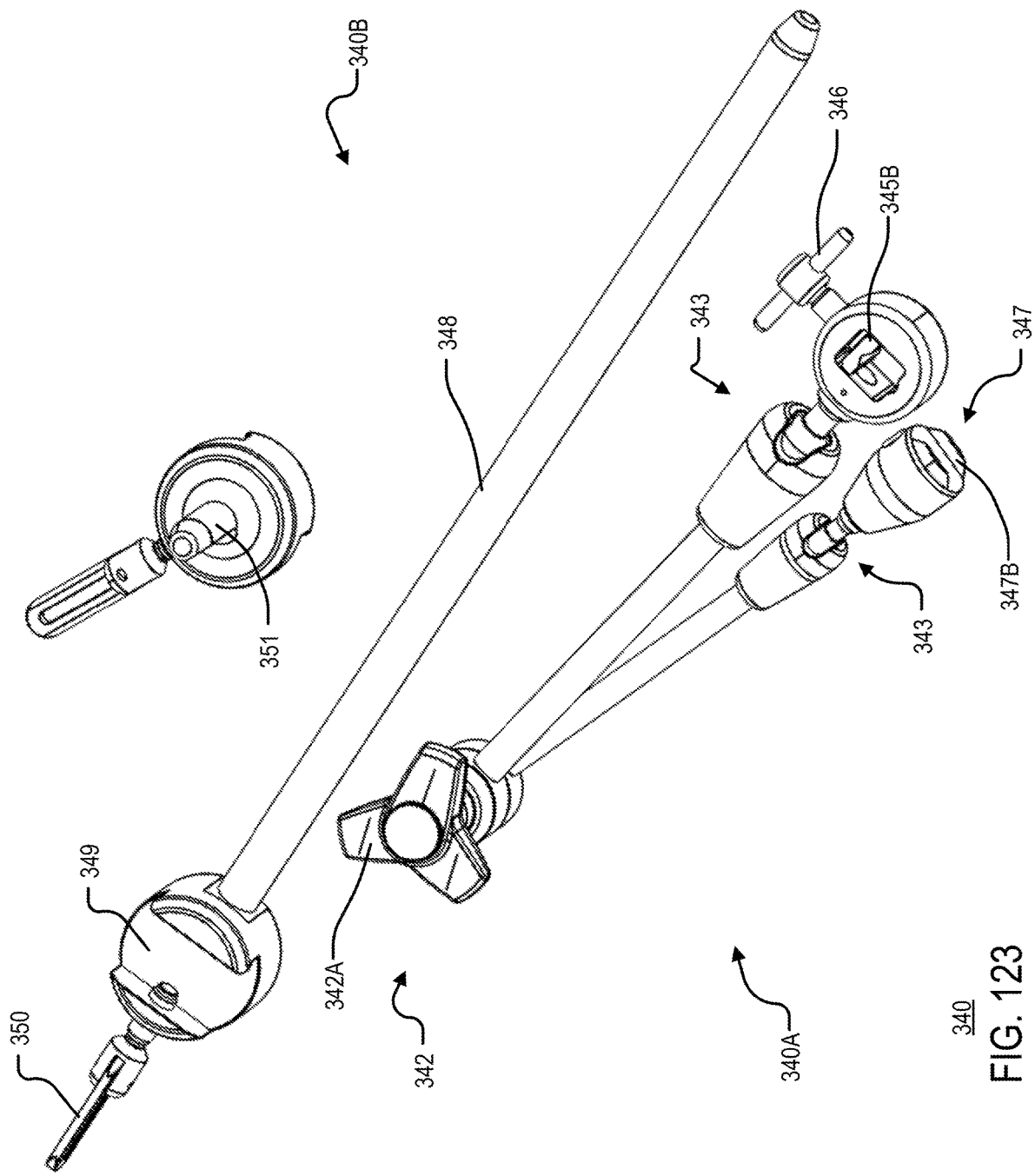

FIG. 123 is a perspective view of various armatures of a quick connect table mount system for supporting various retractor embodiments disclosed herein.

Figure 124:
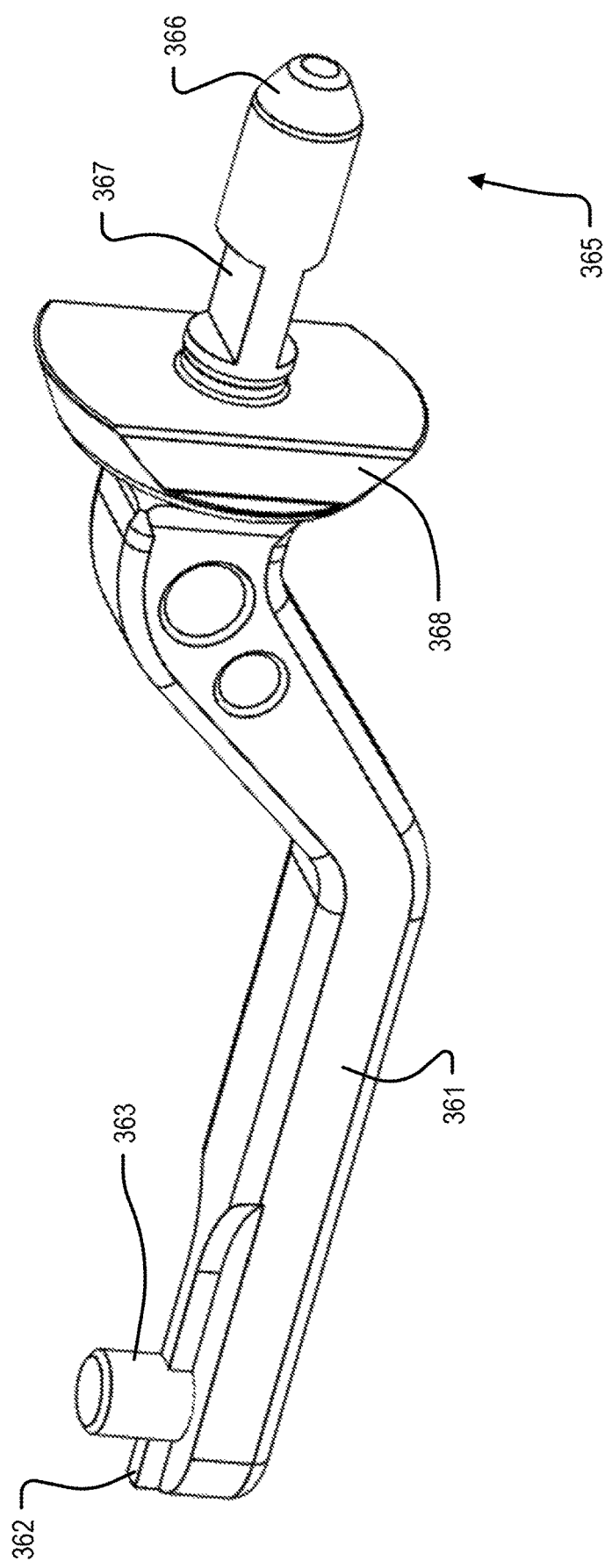

FIG. 124 is a first perspective view of a quick connect coupler for connecting various retractor embodiments to various quick connect table mount systems disclosed herein.

Figure 125:
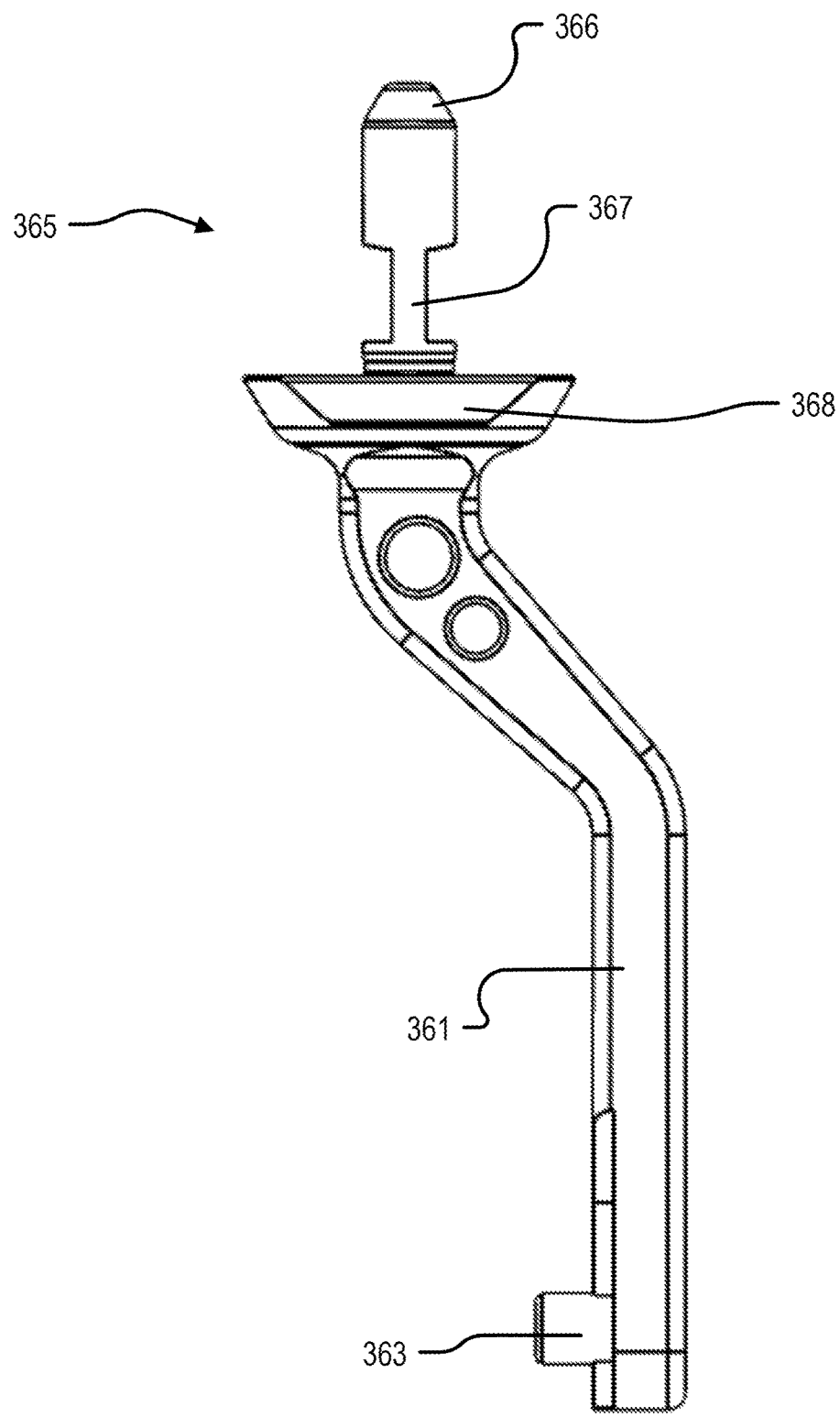

FIG. 125 is a side view of the quick connect coupler of FIG. 124.

Figure 126:
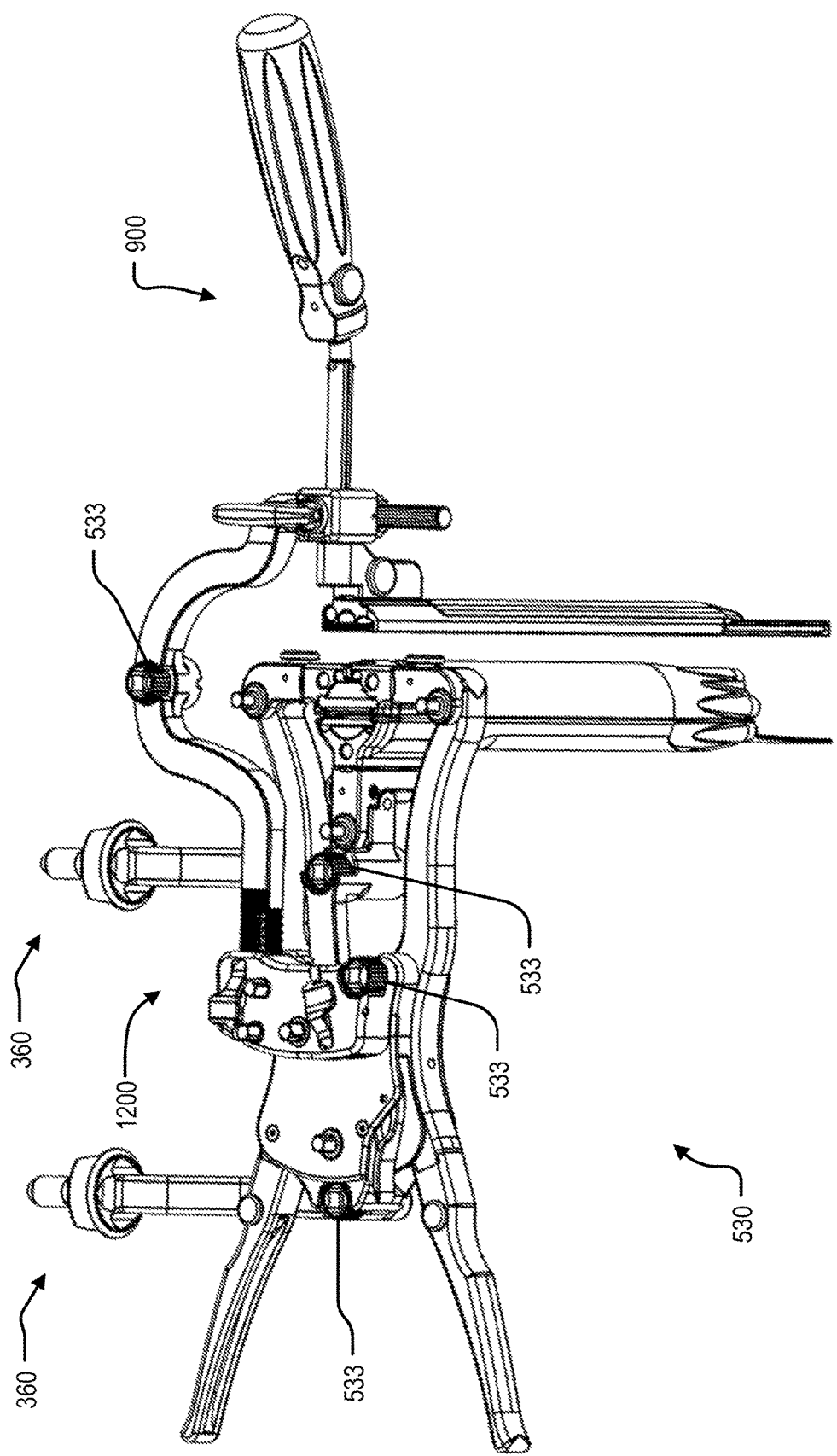

FIG. 126 is a perspective view of a modular retractor system including the quick connect couplers of FIGS. 124-125.

Figure 127:
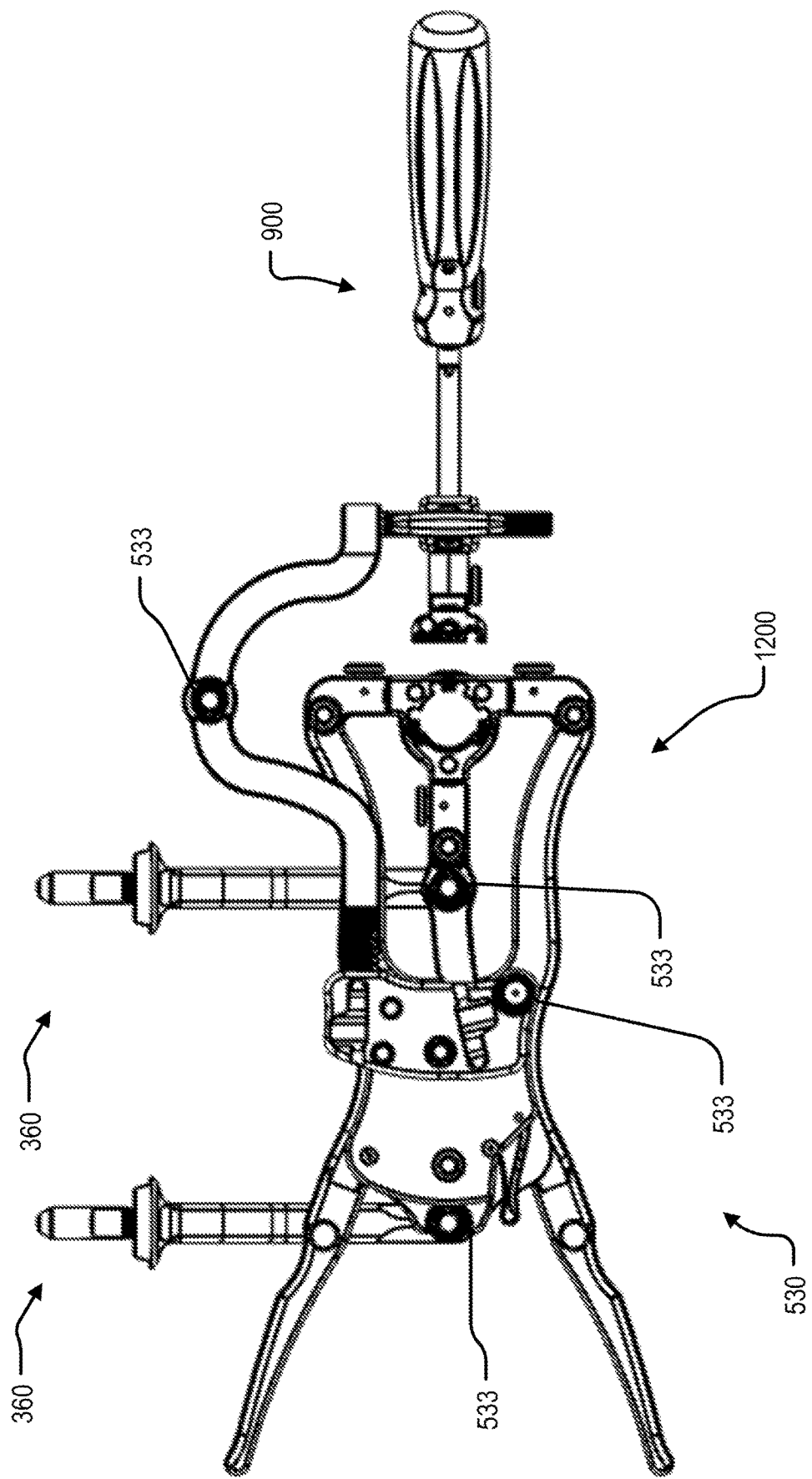

FIG. 127 is a top down view of the system of FIG. 126.

Figure 128:
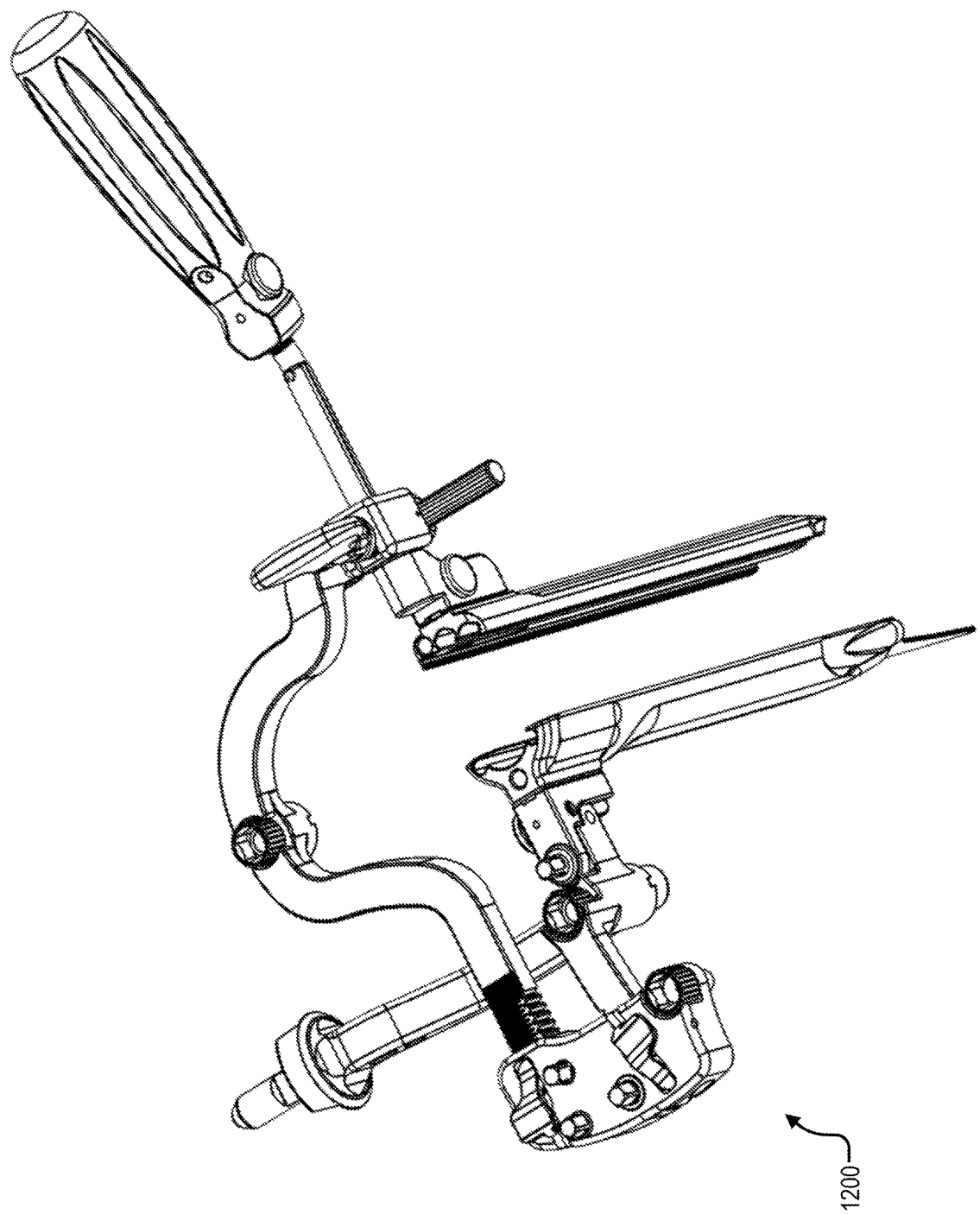

FIG. 128 is a perspective view of a secondary module that may be coupled and uncoupled with various primary retractor embodiments.

Figure 129:
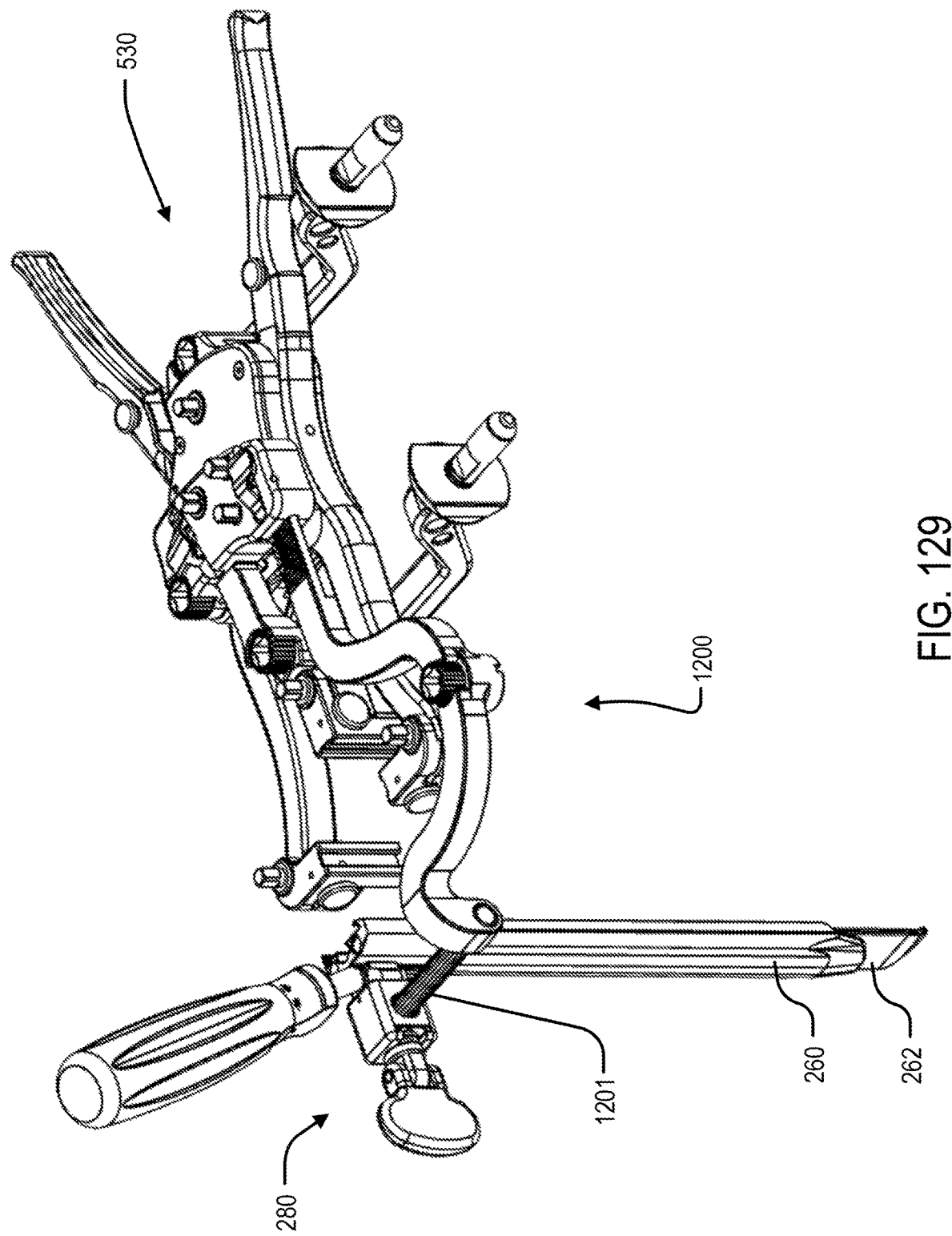

FIG. 129 is a perspective view of the secondary module of FIG. 128 coupled to a primary retractor.

Figure 130:
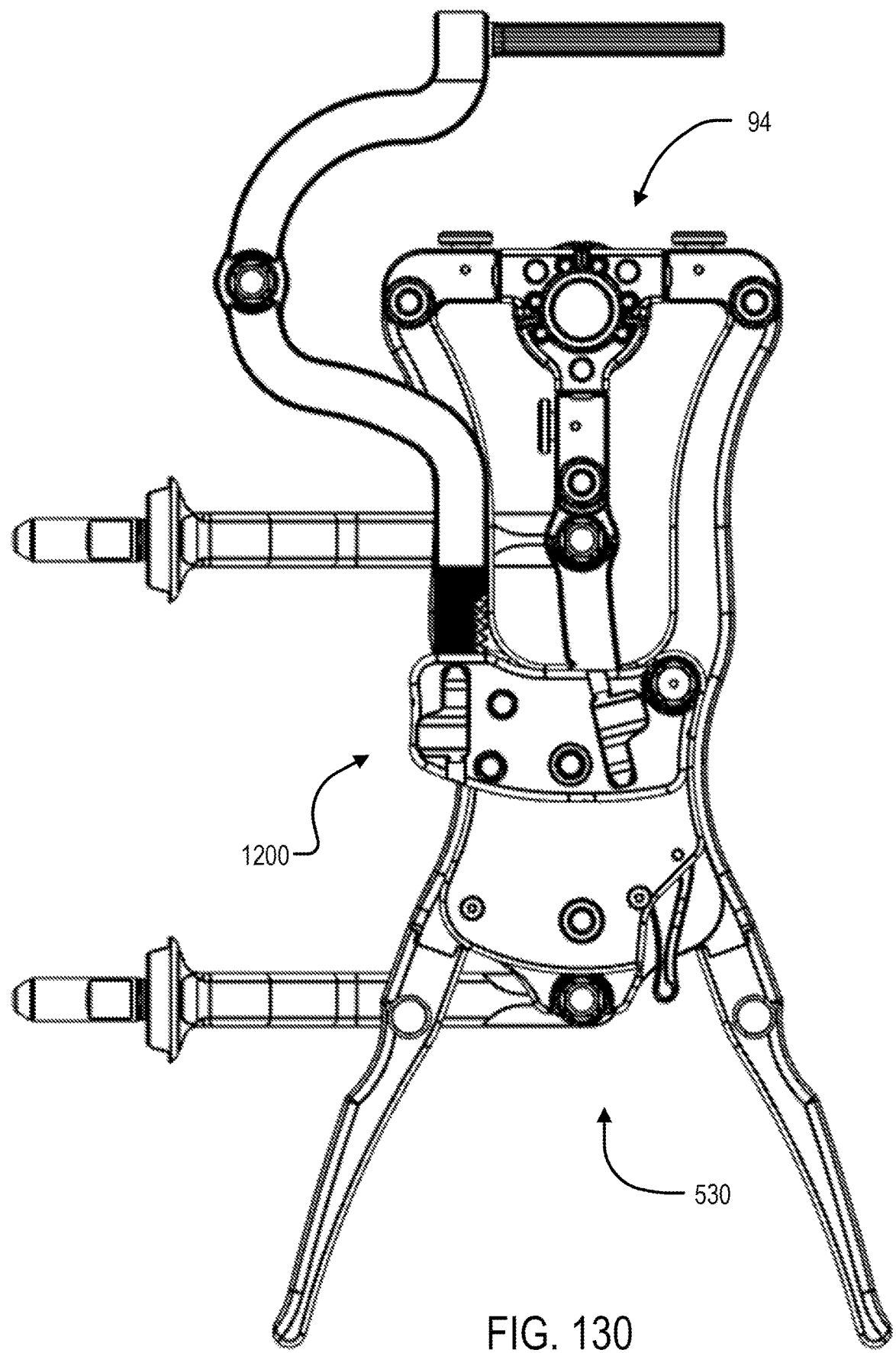

FIG. 130 is a top down view of a modular retractor supporting first and second blades to be slidably coupled to an outermost dilator.

Figure 131:
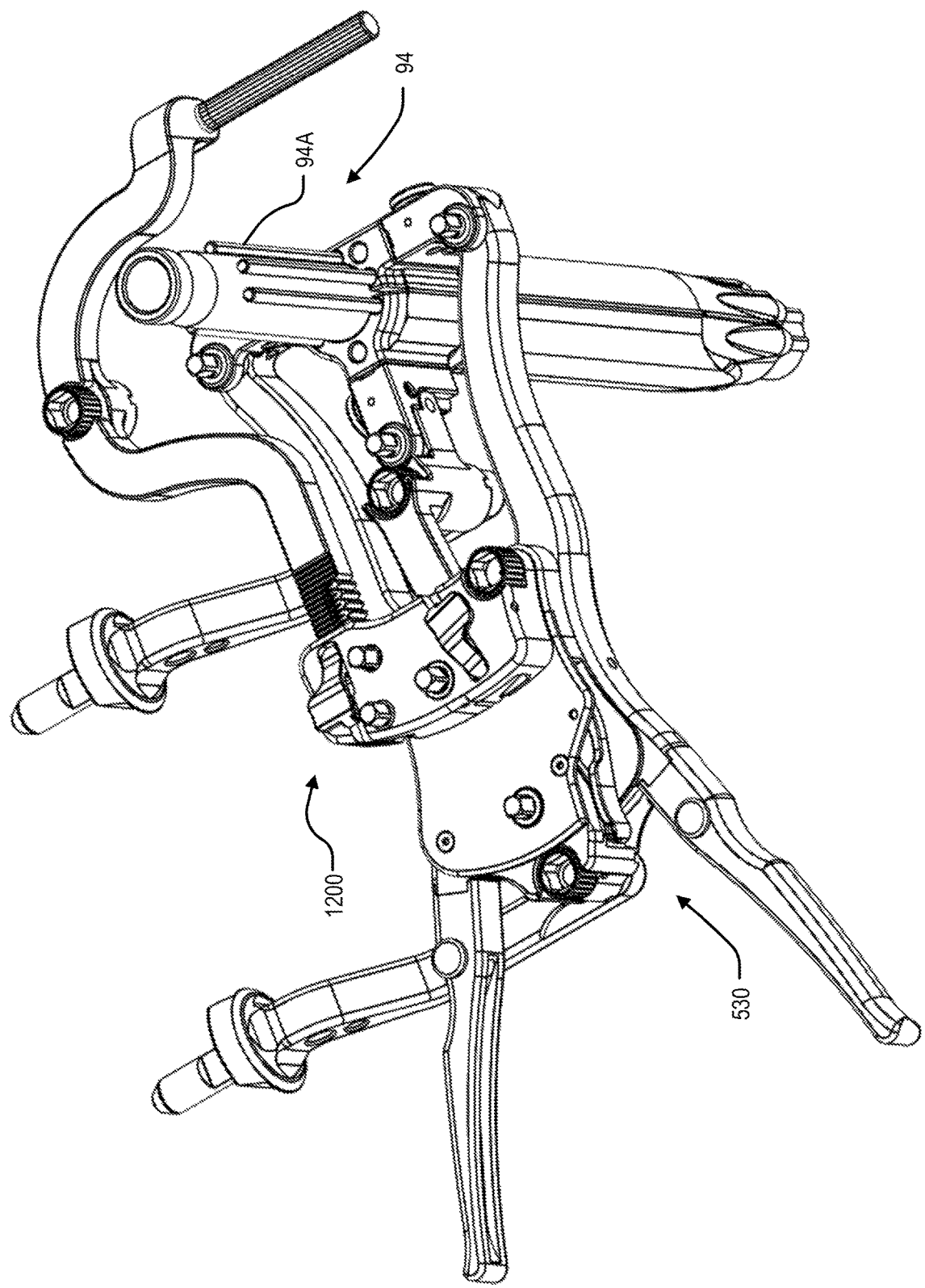

FIG. 131 is a perspective view of the three blades being slidably coupled to an outermost dilator.

DETAILED DESCRIPTION

In one aspect, exemplary embodiments describe a retractor system 100 for use with anterior, lateral, and oblique surgical techniques. At least one use of retractor system 100 is to assist in the preparation of a surgical site to enable a surgeon to access a space between vertebrae of patient's spine. The retractor system 100 may assist a surgeon in accessing a space between vertebrae by enabling highly controlled dilation of the paraspinous muscles with a set of nested dilators and retraction of the various fibers and tissues at the surgical site with the use of a plurality of independently movable and inclinable blades.

Figure 1:
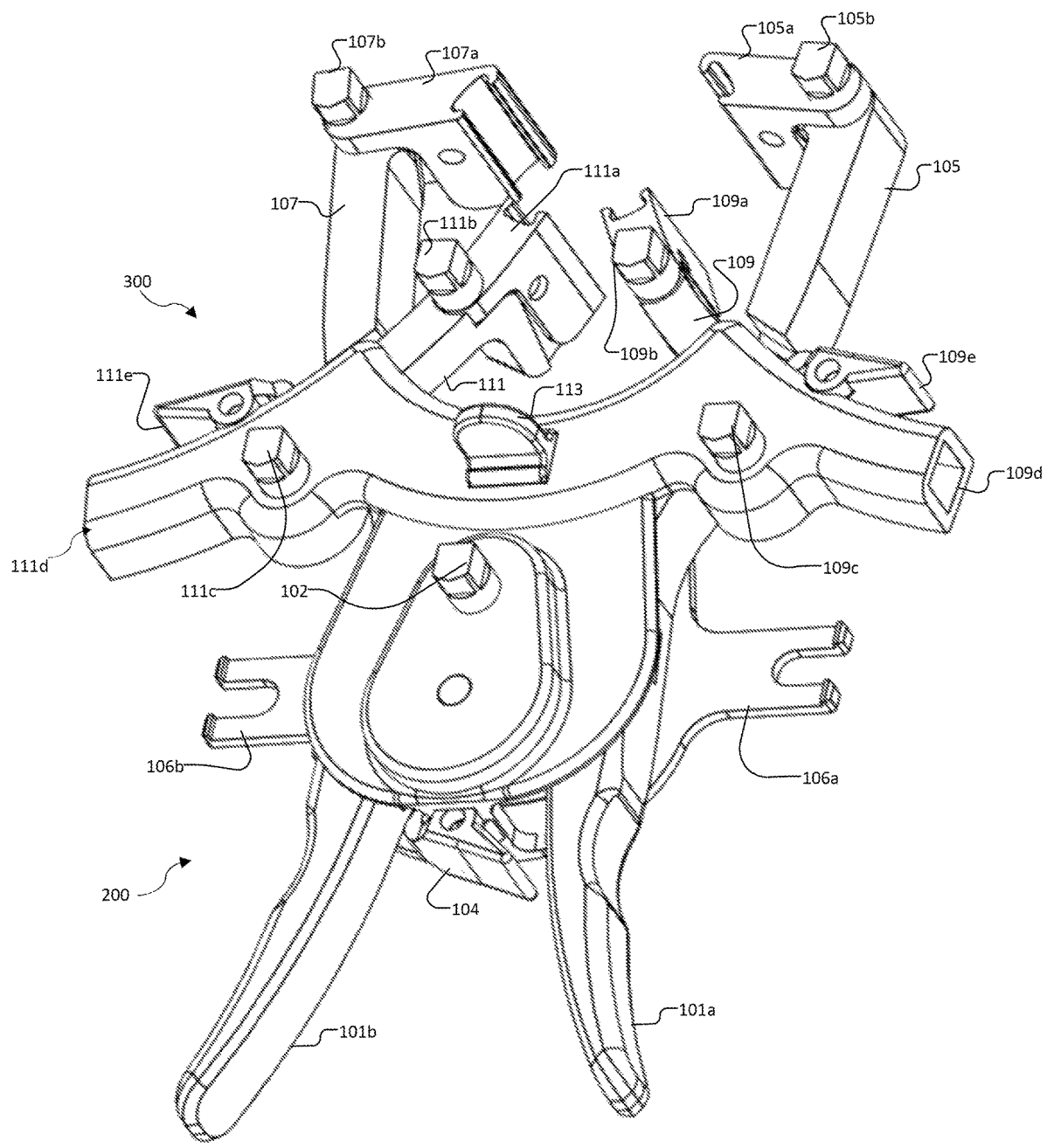
FIG. 1 is a perspective view of an exemplary embodiment of a retractor system including a primary retractor assembly and a secondary retractor assembly in accordance with the principles of the disclosure.

Referring generally to FIGS. 1-8 exemplary retractor systems for enabling access to a surgical site are disclosed. FIG. 1 is a perspective view of an exemplary embodiment of a retractor system 100 including a primary retractor assembly 200 and a secondary retractor assembly 300 in accordance with the principles of the disclosure. Retractor system 100 is highly customizable and modular. For example, the primary retractor assembly 200 may be used as a standalone retractor system without the use of secondary retractor assembly 300. Secondary retractor assembly 300 is configured to couple and uncouple on as needed basis with the primary retractor assembly 200 and secondary retractor assembly 300 can, for example, use one or two arms each having a corresponding blade.

Exemplary embodiments may include a primary retractor assembly 200 configured to open and close a first arm 105 and a second arm 107 along a first path of travel. The first path may be an arcuate path or segment defined by the length and geometry of the arms 105 and 107 and a handle pivoting mechanism 101c (see FIG. 8) configured to enable first handle 101a and second handle 101b to open and close. Other paths of travel are contemplated depending upon the geometry of the arms 105, 107 and the relative location of the handle pivoting mechanism 101c. The primary retractor assembly 200 may include a handle assembly having first and second handles 101a, 101b that are operably coupled to the first and second arms 105, 107 and configured to open and close the first and second arms 105, 107. For example, the first handle 101a may be coupled to the first arm 105 and the second handle 101b may be coupled to the second arm 107. The first and second arms 105, 107 may be operably coupled to first and second pivoting members 105a, 107a at a distal end thereof, respectively. The first and second pivoting members 105a, 107a may be configured to operably couple to first and second blades, 205, 207 (see FIG. 2), respectively, by a corresponding blade attachment mechanism as will be explained in more detail below during the discussion of FIGS. 9-13B.

In the exemplary embodiment, a first actuator 105b and a second actuator 107b are configured to adjust the angulation of first blade 205 and second blade 207, respectively. For example, the first actuator 105b may be configured to actuate the first pivoting member 105a to adjust the angulation of first blade 205 with respect to the first arm 105. Similarly, the second actuator 107b may be configured to actuate the second pivoting member 107a to adjust the angulation of second blade 207 with respect to second arm 107. In the exemplary embodiment, the first pivoting member 105a may be configured to independently adjust the angulation of first blade 205 with respect to the first arm 105 upon actuation of the first actuator 105b. Similarly, the second pivoting member 107a may be configured to independently adjust the angulation of the second blade 207 with respect to the second arm 107 upon actuation of the second actuator 107b. In disclosed embodiments, the first and second pivoting members 105a, 107a may each include a corresponding pin and socket mechanism enabling the pivoting members to pivot on a pin aperture 199 (see, e.g., FIG. 8). Additionally, the first and second pivoting members 105a, 107a may each include a corresponding blade attachment mechanism at a distal end thereof which will be explained in more detail below when discussing FIGS. 9-13.

In the exemplary embodiment, the primary retractor assembly 200 may include a primary actuator 102 that is configured to actuate a primary pinion gear mechanism 210 (see FIG. 7) to provide a precise and controlled mechanical advantage to open and close the first arm 105 and second arm 107. For example, the primary pinion gear mechanism 210 may include a primary pinion gear 210a fixedly coupled to the primary actuator 102 such that the primary actuator 102 may rotationally translate the primary pinion gear 210a. The primary pinion gear 210a may be engaged with the secondary pinion gear 210b, e.g., the primary pinion gear 210a and secondary pinion gear 210b may be toothed gears that are meshed with one another at a contact location (not illustrated). Furthermore, secondary pinion gear 210b may be fixedly coupled to tertiary pinion gear 210c which may be axially aligned with secondary pinion gear 210b and disposed directly beneath secondary pinion gear 210b (see FIG. 8). For example, secondary pinion gear 210b may share an axis of rotation with tertiary pinion gear 210c and secondary pinion gear 210b may be relatively larger in diameter than tertiary pinion gear 210c. This arrangement may resemble a two stage gear box or the like that allows for an increase in applied torque. In other embodiments, primary pinion gear mechanism 210 may be any other similar planetary gear system as would be understood by a person having ordinary skill in the relevant art. For example, those with skill in the relevant art will readily recognize that the particular diameter, tooth sizing, and tooth spacing of the primary pinion gear 210a relative to the particular diameter, tooth sizing, and tooth spacing of the secondary pinion gear 210b relative to tertiary pinion gear 210c may control the amount of force (mechanical advantage or torque) that is applied to open and close the first and second arms 105, 107.

Figure 8:
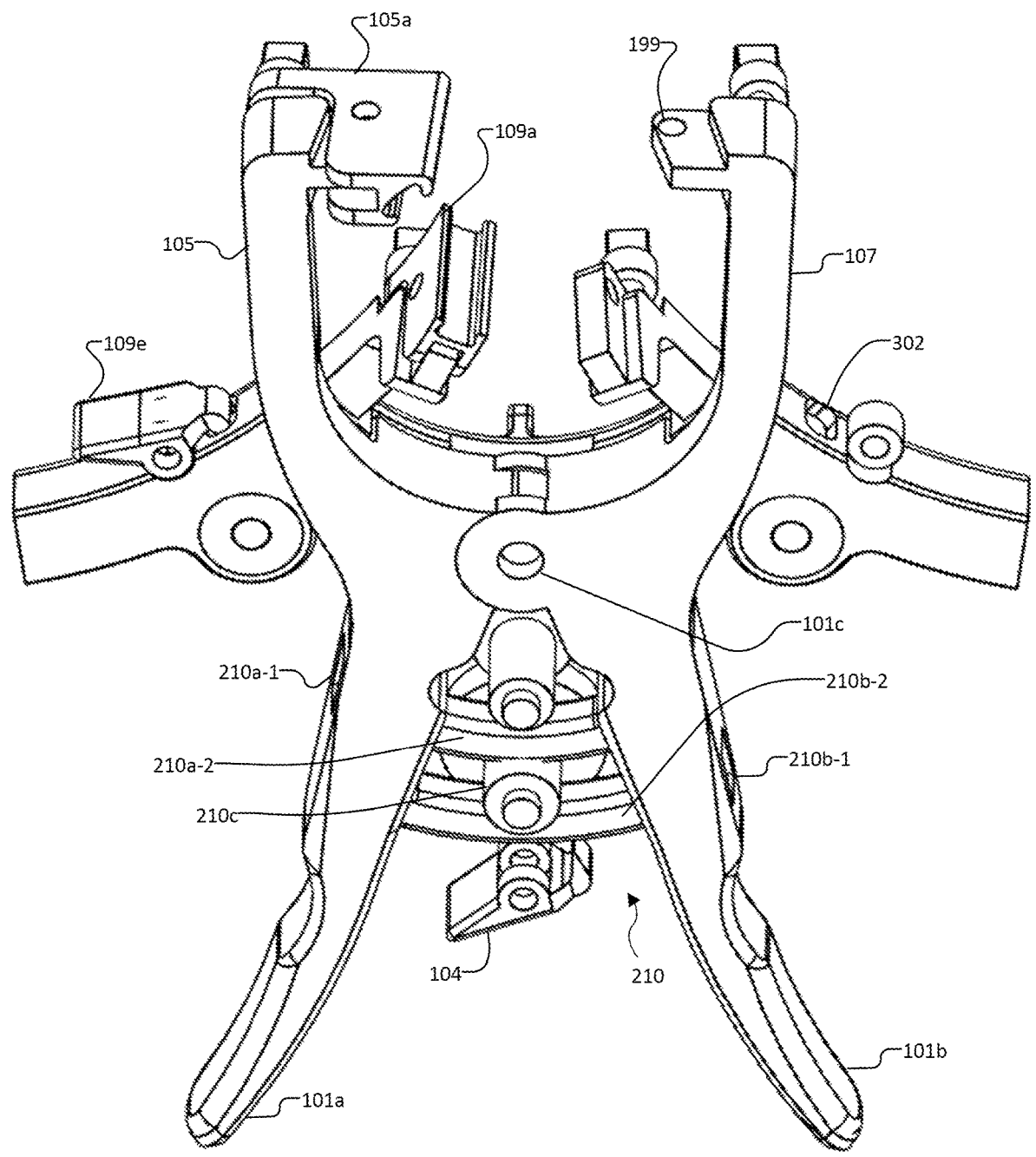
FIG. 8 is an alternate cutaway view of the retractor system of FIG. 1 in accordance with the principles of the disclosure.

In the exemplary embodiment of FIG. 8, tertiary pinion gear 210c may be meshed with a first curved rack portion 210a-2 and a second curved rack portion 210b-2 disposed opposite the first curved rack portion 210a-2. First curved rack portion 210a-2 may be fixedly coupled to second arm 101b and second curved rack portion 210b-2 may be fixedly coupled to first arm 101a. Each of curved rack portions 210a-2 and 210b-2 may feature a plurality of teeth extending along the curved body thereof and facing tertiary pinion gear 210c. The first curved rack portion 210a-2 and second curved rack portion 210b-2 may be meshed with the teeth of tertiary pinion gear 210c on opposite sides of tertiary pinion gear 210c. In this way, when primary actuator 102 is rotated, primary pinion gear 210a rotates which in turn rotates secondary pinion gear 210b and tertiary pinion gear 210c. In turn, tertiary pinion gear 210c engages teeth on each of curved rack portions 210a-2 and 210b-2 and causes handles 101a, 101b to open or close. In the disclosed embodiment, when tertiary pinion gear 210c applies force to first curved rack portion 210a-2, the first curved rack portion 210a-2 may extend through first handle 101a at a corresponding first handle aperture 210a-1. Similarly, when tertiary pinion gear 210c applies force to second curved rack portion 210b-2, the second curved rack portion 210b-2 may extend through second handle 101b at a corresponding second handle aperture 210b-1.

In disclosed embodiments, the primary pinion gear mechanism 210 may be operably coupled to the first and second handles 101a, 101b and configured to simultaneously open and close the first and second arms 105, 107 along a first path of travel. For example, the primary actuator 102 may rotationally translate the primary pinion gear mechanism 210 in a clockwise direction which in turn rotationally translates the first arm 105 and second arm 107 such that they move away from one another, i.e., they open as explained above. Likewise, the primary actuator 102 may rotationally translate the primary pinion gear mechanism 210 in a counter clockwise direction which in turn rotationally translates the first arm 105 and second arm 107 such that they move towards one another, i.e., they close as explained above. Also as explained above, the particular diameter of primary, secondary, and tertiary pinion gears 210a, 210b, and 210c may be adjusted to provide the desired amount of mechanical advantage or torque to open and close first and second arms 101a, 101b.

In disclosed embodiments, primary retractor assembly 200 may include a primary retention lever 104 disposed between the first and second handles 101a, 101b that is configured to engage the primary retractor assembly 200 to control opening and closing of the first and second arms 105, 107 and thereby retain the first and second arms 105, 107 in a specific position. In the disclosed embodiment, primary retention lever 104 may frictionally engage curved rack portion 210b-2 to control opening and closing of the first and second arms. In other embodiments, the primary retention lever 104 may engage the primary pinion gear mechanism 210 at an outside portion of the circumference of the primary pinion gear 210a (see FIG. 7) to thereby control and/or prevent rotation of the primary pinion gear 210a. For example, the primary retention lever 104 may lock the primary pinion gear mechanism 210 in place to control opening and closing of the first and second arms. In some embodiments, the primary retention lever 104 may have a biasing element (not illustrated) that causes the primary retention lever 104 to naturally urge an angled tip portion of the body of the primary retention lever 104 against a portion of the primary pinion gear mechanism 210. For example, a spring may naturally urge an angled tip portion of primary retention lever 104 to engage with a toothed portion of secondary pinion gear 210b. Additionally, the primary retention lever 104 may be moved from an engagement position where primary retention lever 104 is in direct contact with the primary pinion gear mechanism 210 to a disengaged position where primary retention lever 104 is not engaged with the primary pinion gear mechanism 210. For example, an end user such as a surgeon may depress primary retention lever 104 with their thumb to toggle primary retention lever 104 between the engaged position and the disengaged position. Furthermore, some embodiments may have a toggle feature (not illustrated) for maintaining the primary retention lever 104 in either of the engaged or disengaged positions.

In disclosed embodiments, the primary retractor assembly 200 may include a first table mount portion 106a disposed adjacent the first handle 101a and coupled to a body 200a (see FIG. 5) or housing of the primary retractor assembly 200. Similarly, the primary retractor assembly 200 may include a second table mount portion 106b disposed adjacent the second handle 101b and coupled to the body or housing of the primary retractor assembly 200. The first and second table mount portions 106a, 106b may each be attached to a surgical table (not illustrated) for fixing the primary retractor assembly 200 (and/or the retractor system 100) in a fixed location in three dimensional space. In example embodiments, the primary retractor assembly 200 may be attached to a surgical table by at least one of the first and second table mount portions 106a, 106b or by both.

At least one advantage of securing the primary retractor assembly 200 to a surgical table may be for enhanced stability and the even transfer of resultant forces from the primary actuator 102 through the first and second arms 105, 107 to the first and second blades 205, 207 and vice versa. For example, when the primary retractor assembly 200 is fixed to the surgical table and the primary actuator 102 is translated to open the first and second arms 105, 107 the primary pinion gear mechanism 210 may apply a precise controlled amount of force to open the first and second arms 105, 107 to thereby gently retract the tissue of a patient in a controlled manner. Additionally, when the primary retractor assembly 200 is fixed to the surgical table, it may be easier for an end user to independently move only one of the handles 101a, 101b with respect to the surgical table. When moving only one of the handles 101a, 101b the corresponding arm 105, 107 may move relative to the other. This scenario and functionality may assist a surgeon with precise surgical techniques where it may be desirable to independently move either of the first and second arms 105, 107 along the first path of travel independently with respect to the other.

Disclosed embodiments described above may be configured to independently open and close the first arm 105 along the first path of travel by movement of the first handle 101a relative to the second handle 101b and independently open and close the second arm 107 along the first path of travel by movement of the second handle 101b relative to the first handle 101a. Additionally, because the primary pinion gear mechanism 210 includes a primary gear 210a and a secondary gear 210b operably coupled to the first and second handles 101a, 101b disclosed embodiments may be configured to provide a controlled mechanical advantage to open and close the first and second arms 105, 107 along the first path upon actuation of the primary actuator 102.

Figure 2:

FIG. 2 is a perspective view of the primary retractor assembly of FIG. 1 in accordance with the principles of the disclosure.
Figure 3:
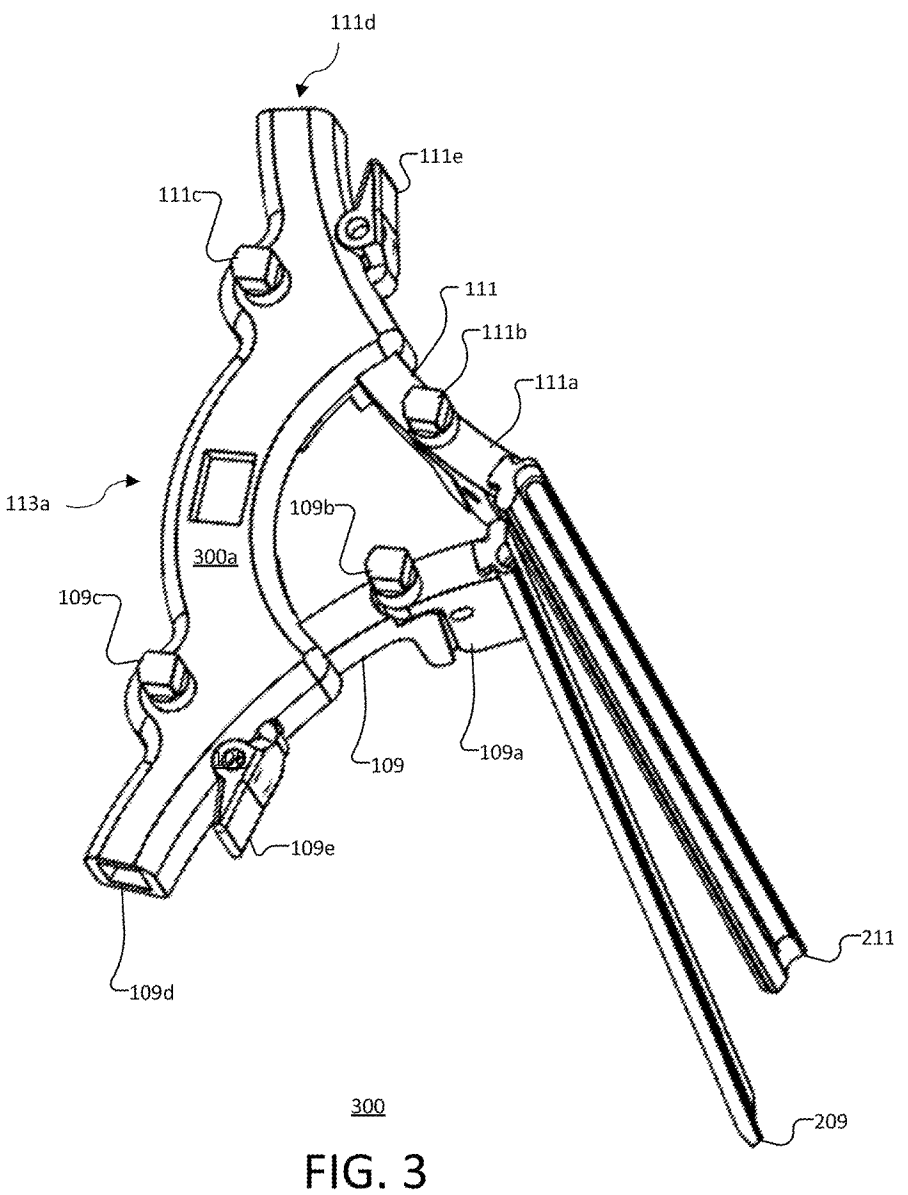
FIG. 3 is a perspective view of the secondary retractor assembly of FIG. 1 in accordance with the principles of the disclosure.
Figure 4:
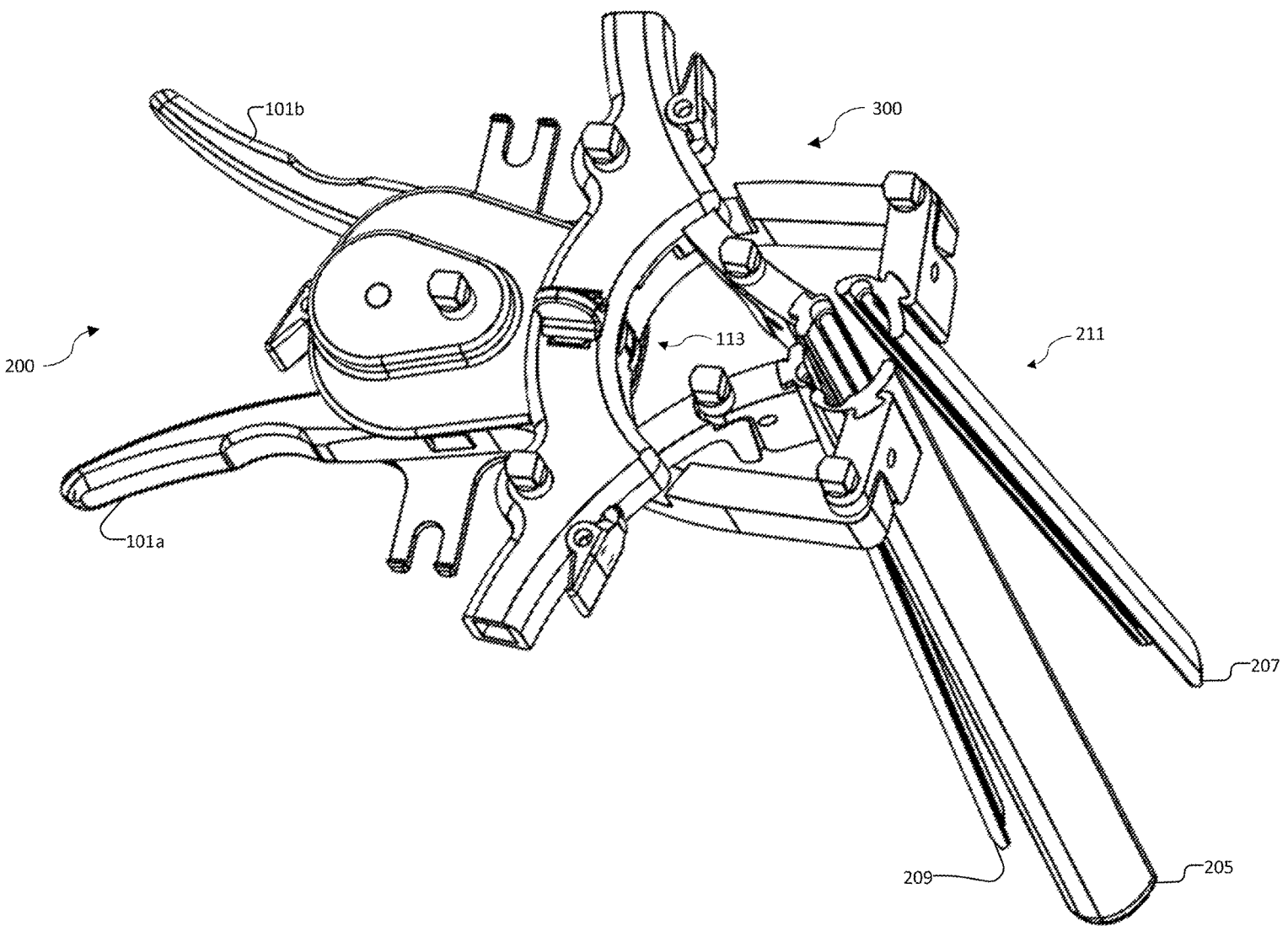
FIG. 4 is a perspective view of the retractor system of FIG. 1 including a plurality of blades in accordance with the principles of the disclosure.
Figure 5:
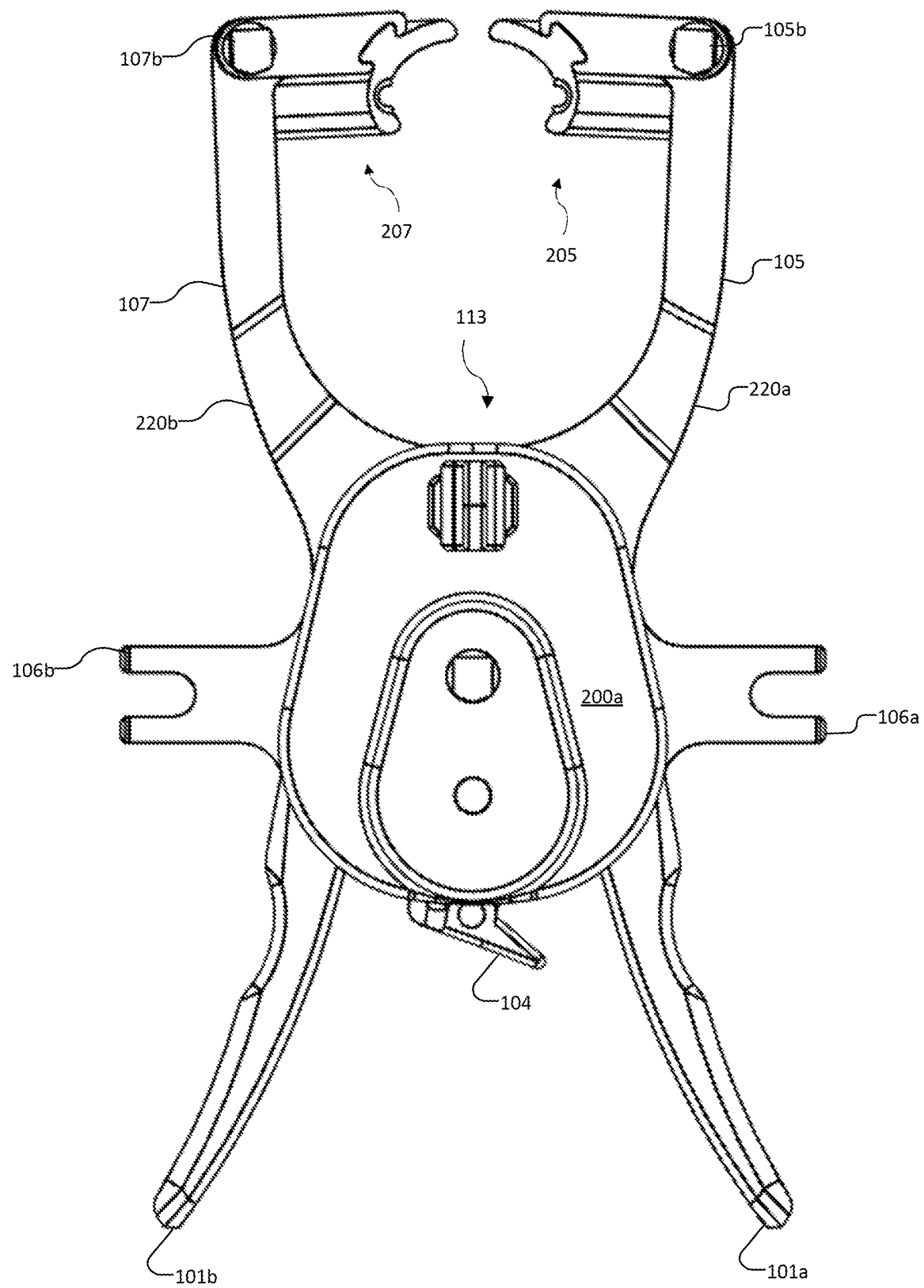
FIG. 5 is a top down view of the primary retractor assembly of FIG. 2 in accordance with the principles of the disclosure.
Figure 6:
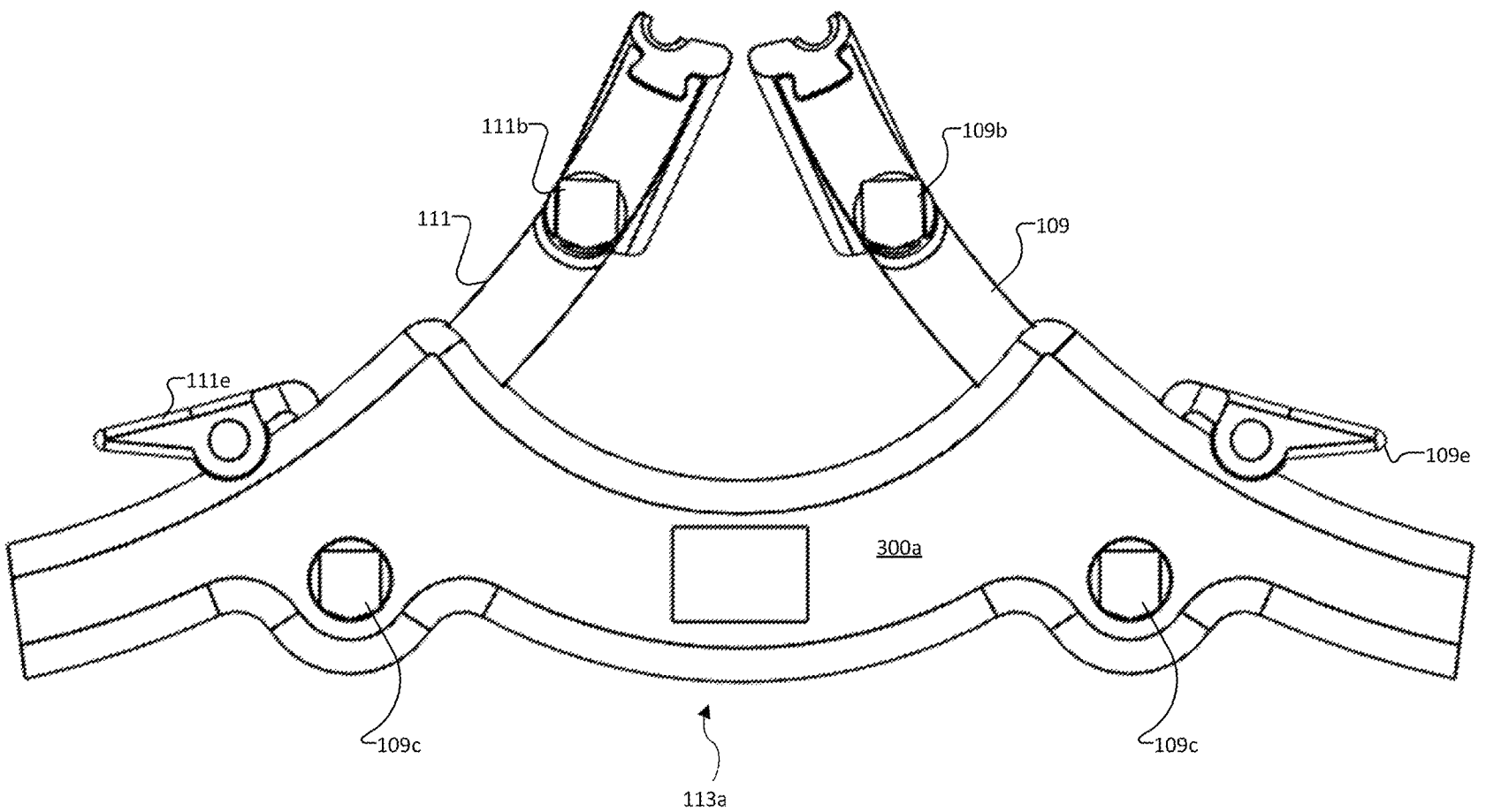
FIG. 6 is a top down view of the secondary retractor assembly of FIG. 3 in accordance with the principles of the disclosure.

In accordance with disclosed embodiments, a secondary retractor assembly 300 may be configured to couple and uncouple from the primary retractor assembly 200 via a first recessed key portion 220a disposed on the first arm 105 and a second recessed key portion 220b disposed on the second arm 107 (see FIG. 2). Each of recessed key portions 220a, 220b may include a groove having a geometry that facilitates engagement of the primary retractor assembly 200 with the secondary retractor assembly 300 while also operably allowing the opening and closing of arms 105, 107. For example, the secondary retractor assembly 300 may have a corresponding outdent (e.g., dovetail) on an underside thereof configured to mate with an indent (e.g., dovetail groove) of the primary retractor assembly 200. Additionally, secondary retractor assembly 300 may be fixed to primary retractor assembly 200 by turnkey 113. Turnkey 113 may project from a central portion of the primary retractor assembly 200 through a central aperture 113a (see FIG. 6) of the secondary retractor assembly 300. In a first position, turnkey 113 may urge the primary retractor assembly 200 and secondary retractor assembly 300 towards each other and maintain direct contact to fixedly engage them to one another. Conversely, in a second position, turnkey 113 may be rotated such that turnkey 113 is aligned with central aperture 113a and therefore has no bearing surface to urge the primary retractor assembly 200 and secondary retractor assembly 300 towards each other. Thus, in the second position the primary retractor assembly 200 and secondary retractor assembly 300 may be disengaged from one another. Other embodiments may use alternate means to securely engage the primary retractor assembly 200 with the secondary retractor assembly 300, e.g., as fasteners, hexagonal grooves, channel locks, magnets, etc. provided that the primary retractor assembly 200 and the secondary retractor assembly 300 are securely engaged with one another such that resultant forces acting on the retractor system 100 may transfer between primary retractor assembly 200 and secondary retractor assembly 300 and also by extension to a surgical table via table mount portions 106a and/or 106b.

Secondary retractor assembly 300 may have a body portion 300a generally defining a first channel 109d and a second channel 111d. Secondary retractor assembly 300 may be configured to independently extend and contract a third arm 109 and a fourth arm 111, respectively. Although two channels 109d, 111d and two arms 109, 111 are illustrated it is contemplated that secondary retractor assembly 300 may have any number of suitable channels and arms. Additionally, it is contemplated that only a single arm, e.g., third arm 109 or fourth arm 111 will be provided in some surgical settings.

In disclosed embodiments, the secondary retractor assembly 300 may include a first channel 109d having a curved or arcuate shape for operably retaining third arm 109 therein where third arm 109 has a corresponding curved or arcuate shape. The third arm 109 may be configured to extend outwards from first channel 109d and contract within first channel 109d. Similarly, secondary retractor assembly 300 may include a second channel 111d having a curved or arcuate shape for operably retaining fourth arm 111 therein where fourth arm 111 has a corresponding curved or arcuate shape. The fourth arm 111 may be configured to extend outwards from first channel 111d and contract within second channel 111d. The geometry of the first channel 109d and third arm 109 may define a second path of travel, e.g., an arcuate path of travel defined by the arcuate shapes of the first channel 109d and third arm 109. Similarly, the geometry of the second channel 111d and fourth arm 111 may define a third path of travel, e.g., an arcuate path of travel defined by the arcuate shapes of the second channel 111d and fourth arm 111.

In disclosed embodiments, the secondary retractor assembly 300 may include a third actuator 109c operably disposed adjacent the first channel 109d and operably configured to extend and contract the third arm 109 via a pinion gear mechanism (not illustrated) having the same or similar components as primary pinion gear mechanism 210 of primary retractor assembly 200. For example, a toothed pinion P1 (see FIG. 7) may be coupled to actuator 109c and may operably engage a corresponding rack portion (not illustrated) on an adjacent surface of arm 109 to linearly translate, e.g., curvo-linear, third arm 109 forward and backward, i.e., extend and withdraw or translate away from the operative corridor. Similarly, the secondary retractor assembly 300 may include a fourth actuator 111c operably disposed adjacent the second channel 111d and operably configured to extend and contract the fourth arm 111 via a pinion gear mechanism (not illustrated) having the same or similar components as primary pinion gear mechanism 210 of primary retractor assembly 200. For example, a toothed pinion P2 (see FIG. 7) may be coupled to actuator 111c and may operably engage a corresponding rack portion (not illustrated) on an adjacent surface of arm 111 to linearly translate, e.g., curvo-linear, fourth arm 111 forward and backward, i.e., extend and withdraw or translate away from the operative corridor. For example, actuator 109c may rotationally translate P1 in a clockwise direction which in turn linearly translates the third arm 109 arm such that it extends outward from channel 109d. Similarly, actuator 109c may rotationally translate P1 in a counter clockwise direction which in turn linearly translates the third arm 109 arm such that it contracts inward into channel 109d. Likewise, actuator 111c may rotationally translate P2 in a clockwise direction which in turn linearly translates the fourth arm 111 arm such that it extends outward from channel 111d. Similarly, actuator 111c may rotationally translate P2 in a counter clockwise direction which in turn linearly translates the fourth arm 111 such that it contracts inward into channel 109d. Accordingly, in disclosed embodiments, the third arm 109 is configured to independently extend and contract along a second path of travel upon actuation of the third actuator 109c, and the fourth arm 111 is configured to independently extend and contract along a third path of travel upon actuation of the fourth actuator 111c.

In disclosed embodiments, the third and fourth arms 109, 111 may be operably coupled to third and fourth pivoting members 109a, 111a at a distal end thereof, respectively. The third and fourth pivoting members 109a, 111a may be configured to operably couple to third and fourth blades 209, 211, respectively (see FIG. 3) by a corresponding blade attachment mechanism as will be explained in more detail below during the discussion of FIGS. 9-13B. In the exemplary embodiment, a fifth actuator 109$b$ and a sixth actuator 111$b$ are configured to adjust the angulation of third blade 209 and fourth blade 211, respectively. For example, the fifth actuator 109$b$ may be configured to actuate the third pivoting member 109$a$ to adjust the angulation of third blade 209 with respect to the third arm 109. Similarly, the sixth actuator 211$b$ may be configured to actuate the fourth pivoting member 211$a$ to adjust the angulation of fourth blade 211 with respect to fourth arm 111. In the exemplary embodiment, the third pivoting member 109$a$ may be configured to independently adjust the angulation of third blade 209 with respect to third arm 109 upon actuation of the fifth actuator 109$b$. Similarly, the fourth pivoting member 211$a$ may be configured to independently adjust the angulation of fourth blade 211 with respect to the fourth arm 111 upon actuation of the fourth actuator 111$b$.

In disclosed embodiments, the third and fourth pivoting members 209$a$, 211$a$ may each include a corresponding pin and socket mechanism enabling the pivoting members 209$a$, 211$a$ to pivot on a pin disposed in a corresponding pin aperture 199 (see, e.g., FIG. 8). Additionally, the third and fourth pivoting members 209$a$, 211$a$ may each include a corresponding blade attachment mechanism at a distal end thereof which will be explained in more detail below when discussing FIGS. 9-13.

In disclosed embodiments, the secondary retractor assembly 300 may include a first retention lever 109$e$ configured to engage the third arm 109 to control extension and contraction of the third arm 109 along the second path of travel and a second retention lever 111$e$ configured to engage the fourth arm 111 to control extension and contraction of the fourth arm 111 along the third path of travel. First and second retention levers 109$e$, 111$e$ may have the same or similar components as described above with respect to primary retention lever 104.

First retention lever 109$e$ and second retention lever 111$e$ may frictionally engage with the third arm 109 and fourth arm 111, respectively, to control and/or prevent the extension and contraction of the third arm 109 and fourth arm 111. For example, first retention lever 109$e$ and second retention lever 111$e$ may engage with a rack portion on an outside adjacent surface of the third arm 109 and fourth arm 111, respectively, through an aperture 302 (see FIG. 8) projecting through a portion of channels 109$d$, 111$d$, respectively. In some embodiments, first and second retention levers 109$e$, 111$e$ may include a biasing element having the same or similar components as explained above with respect to primary retention lever 104. In some embodiments, first retention lever 109$e$ may engage a corresponding pinion gear mechanism operably associated with actuator 109$c$ to thereby control and/or prevent rotation of the corresponding pinion gear mechanism. Similarly, second retention lever 111$e$ may engage a corresponding pinion gear mechanism operably associated with actuator 109$c$ to thereby control and/or prevent rotation of the corresponding pinion gear mechanism.

Referring generally to FIGS. 1, 7, and 9-11 the pivoting members 105$a$, 107$a$, 109$a$, and 111$a$ may each include the same or similar components and features. For example, pivoting members 105$a$, 107$a$, 109$a$, and 111$a$ may each include a corresponding pin and socket mechanism. The pin and socket mechanism of pivoting members 105$a$, 107$a$, 109$a$, and 111$a$ may be adjustable by way of actuators 105$b$, 107$b$, 109$b$, and 111$b$ such that an inclination of pivoting members 105$a$, 107$a$, 109$a$, and 111$a$ may be independently adjustable with respect to arms 105, 107, 109, and 111, respectively. In some embodiments, translation of actuators 105$b$, 107$b$, 109$b$, and 111$b$ may cause a corresponding element, such as an internal pin, set screw or the like, to urge pivoting members 105$a$, 107$a$, 109$a$, and 111$a$ to pivot outwards on a corresponding pin within a corresponding socket thereby enabling travel of pivoting members 105$a$, 107$a$, 109$a$, and 111$a$ inwards and outwards with respect to arms 105, 107, 109, and 111, respectively. In some embodiments, pivoting members 105$a$, 107$a$, 109$a$, and 111$a$ may pivot outwards, for example, within a range of 0-25 degrees, and more particularly within a range of 0-15 degrees with respect to arms 105, 107, 109, and 111.

Figure 7:
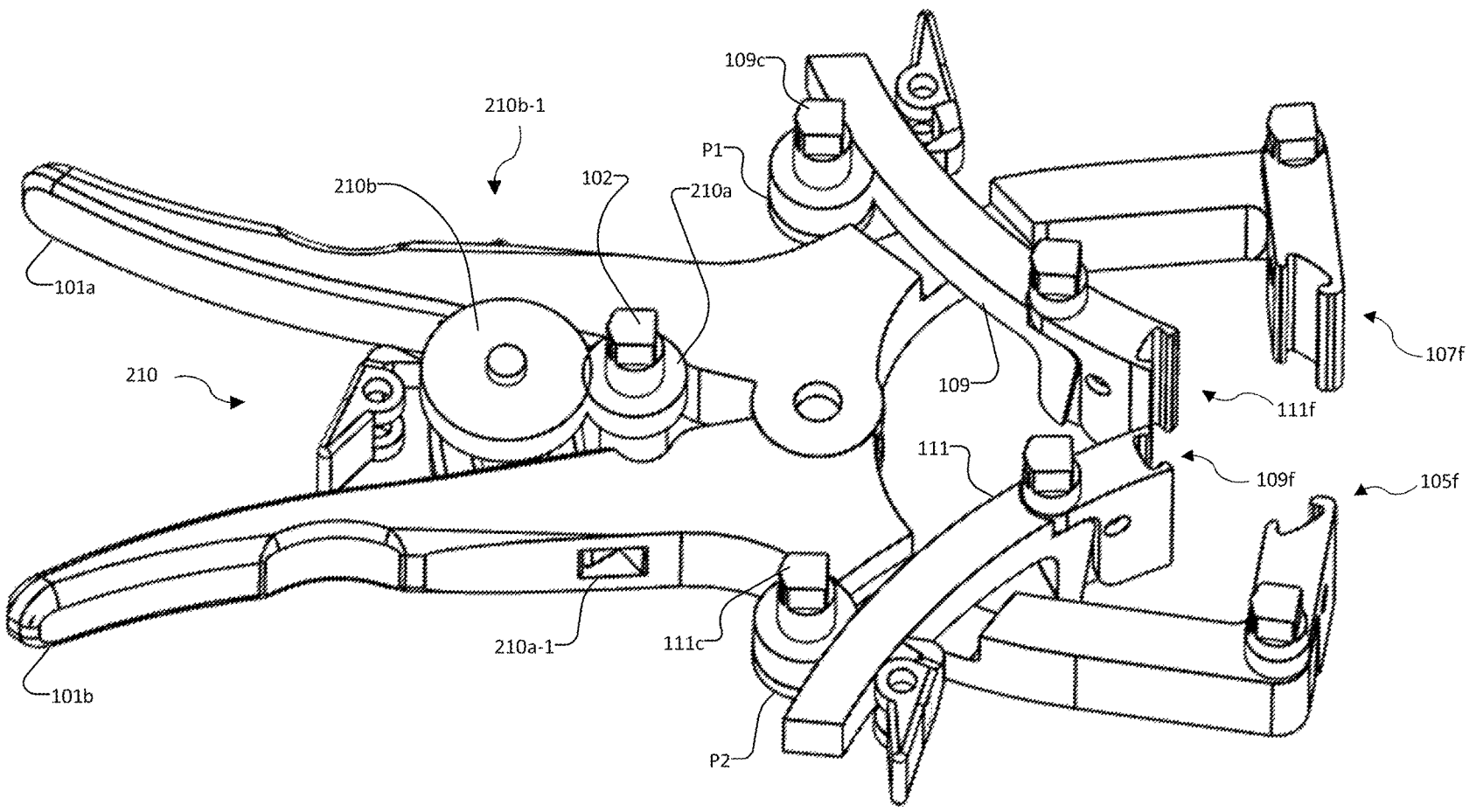
FIG. 7 is a cutaway view of the retractor system of FIG. 1 in accordance with the principles of the disclosure.

Pivoting members 105$a$, 107$a$, 109$a$, and 111$a$ may include corresponding blade attachment mechanisms 105$f$, 107$f$, 109$f$, and 111$f$, respectively (see FIG. 7). The blade attachment mechanisms 105$f$, 107$f$, 109$f$, and 111$f$, may each include a dovetail groove having a geometry that facilitates secure engagement with a corresponding one of blades 205, 207, 209, and 211. For example, blade attachment mechanisms 105$f$, 107$f$, 109$f$, and 111$f$, may have an indent portion on an inside surface thereof facilitating secure engagement with an outdent portion disposed on an outside surface of blades 205, 207, 209, and 211 respectively. In some embodiments, the dovetail grooves of the blade attachment mechanisms 105$f$, 107$f$, 109$f$, and 111$f$, are tapered, and may for example be conically tapered, from one end to the other end to further securely retain blades 205, 207, 209, and 211. In other embodiments, the blade attachment mechanisms 105$f$, 107$f$, 109$f$, and 111$f$, may take alternate shapes, and have varying configurations provided that the shape thereof can securely engage with a corresponding one of blades 205, 207, 209, and 211. For example, an indent such as a square channel, hexagonal channel, or the like dimensioned to match to a corresponding outdent. Additionally, the blade attachment mechanisms 105$f$, 107$f$, 109$f$, 111$f$ may have an outdent portion (rather than an indent portion as illustrated) and blades 205, 207, 209, and 211 may have an indent portion (rather than an outdent portion as illustrated).

Figure 9:
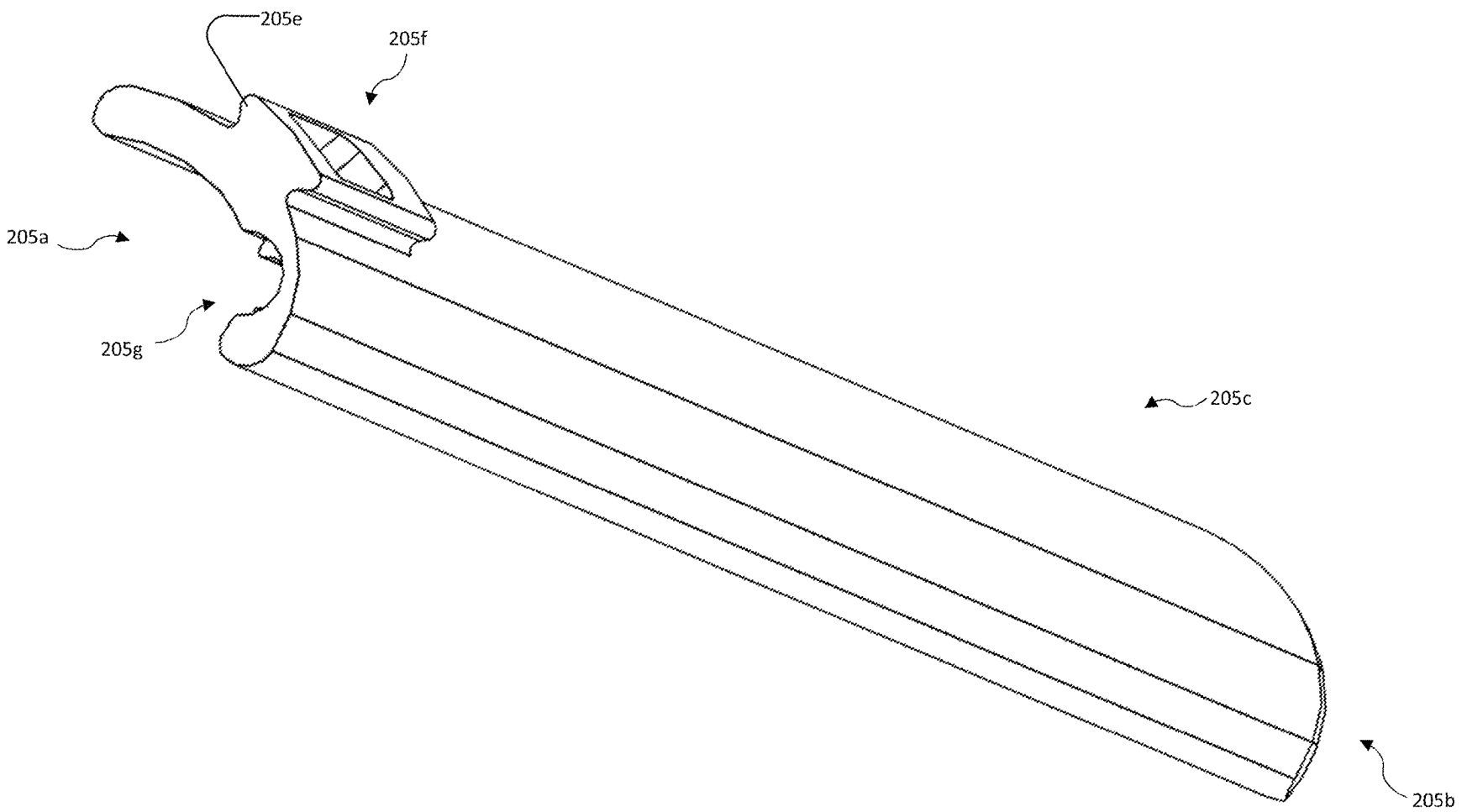
FIG. 9 is a perspective view of an exemplary blade for use with the retractor system of FIG. 1 in accordance with the principles of the disclosure.
Figure 10:
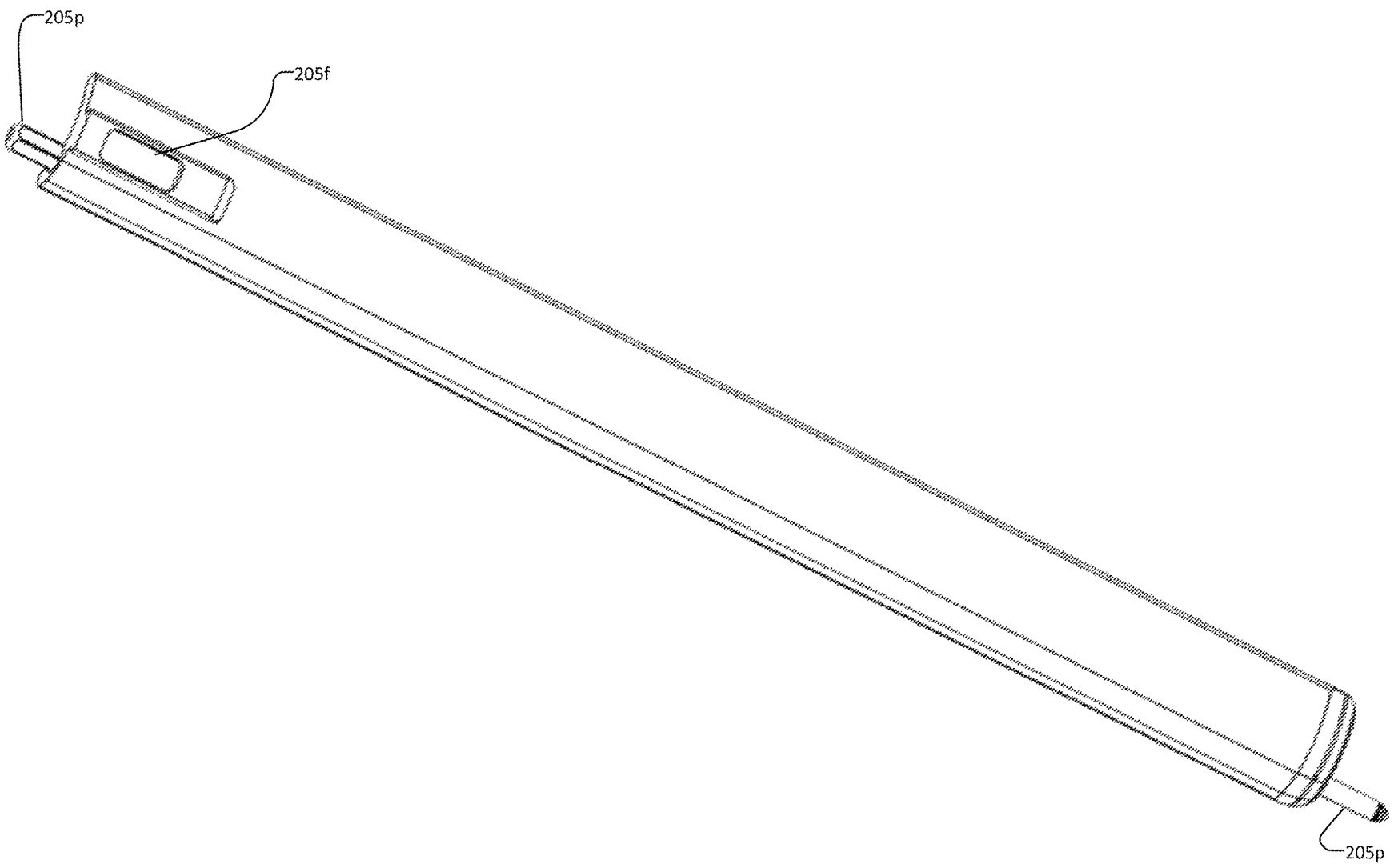
FIG. 10 is an alternate perspective view of an exemplary blade and pin for use with the retractor system of FIG. 1 in accordance with the principles of the disclosure.
Figure 11:
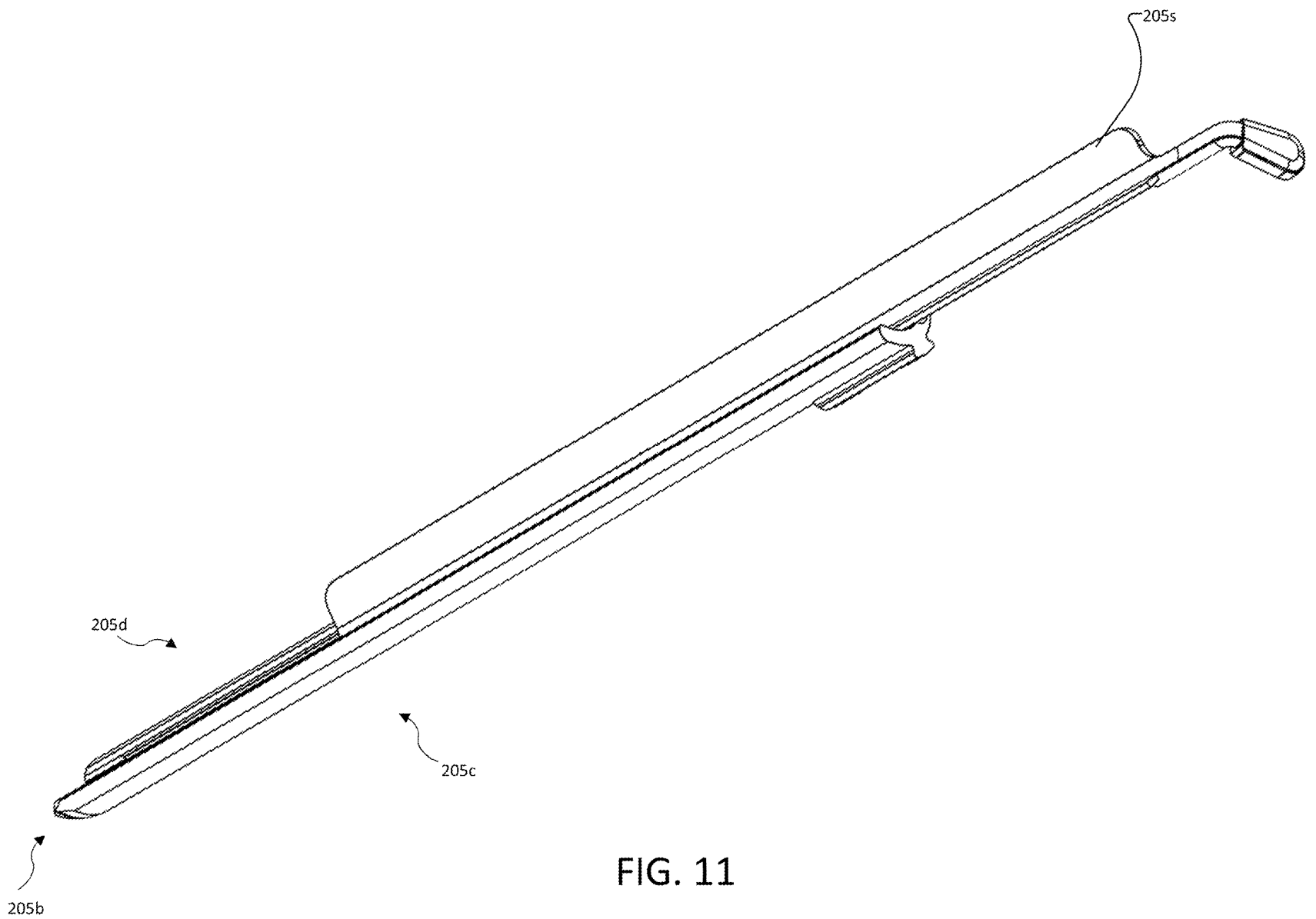
FIG. 11 is a perspective view of an exemplary blade and shim for use with the retractor system of FIG. 1 in accordance with the principles of the disclosure.

Referring generally to FIGS. 9-13B exemplary blades, shims, and dilators for use with, e.g., retractor system 100, are disclosed. Referring to FIGS. 9-11, an exemplary blade, e.g., first blade 205 is illustrated. It shall be understood that characteristics of first blade 205 may be found throughout each of blades 205, 207, 209, and 211 and the foregoing description is described with respect to first blade 205 solely for convenience of explanation. Moreover, although first blade 205 is illustrated as a relatively long and narrow curved blade 205 it can take any shape suitable for any particular type of surgery application. Indeed, it is contemplated that retractor system 100 is suitable for a multitude of different blades having different lengths, widths, and cross-sectional shapes thereof that can couple and uncouple to secondary blades, tools, and shims. For example, relatively shorter and wider blades having generally planar surfaces are contemplated. Furthermore, blade 205 may feature any number or type of secondary coupling members where shims, for example, may couple thereto. In at least one embodiment, blade 205 may have a relatively narrow portion at one end and fan out to a relatively wider portion at the opposite end, i.e., the blade 205 may have a width that increases along the length thereof from one end to the other end. Additionally, blade 205 may include channels, grooves, indents, outdents, etc. for fixation of secondary members such as shims, light fixtures other diagnostic tools such as endoscopes, electrodes, temperature sensors, suction devices, and etc.

In the exemplary embodiment, blade 205 has a proximate side 205a, a distal side 205b opposite the proximate side, an outside surface 205c and an inside surface 205d opposite the outside surface 205c. The proximate side 205a may be operably coupled to a distal end of pivoting member 105a via an engagement feature 205e disposed on the outside surface 205c of blade 205, for example. In some embodiments, blade 205 may include an elastic material allowing it to deflect at least partially. Additionally, in some embodiments a blade removal instrument may be required to install and/or remove blade 205 from a blade attachment mechanism.

In the disclosed embodiment, engagement feature 205e is the outdent portion of a dovetail groove, i.e., the dovetail. In other embodiments, engagement feature 205e may be a lap joint, tongue and groove type joint, a doweled butt joint, etc. In the exemplary embodiment, engagement feature 205e features an indent portion 205f. Indent portion 205f may be a socketed portion facilitating secured engagement and retention with blade attachment mechanism 105f. For example, indent portion 205f may house a spring clip (not illustrated) to hold blade 205 in secure engagement with blade attachment mechanism 105f. In embodiments that include a spring clip, a corresponding release tool or lever may be inserted into the indent portion 205f to release the biasing force of the spring and thereby uncouple the blade 205 from blade attachment mechanism 105f. In other embodiments, engagement feature 205e may have an aperture for running a diagnostic tool such as an electrode or endoscope there through. In some embodiments, blade 205 may be conductive such that it may communicate with an external diagnostic tool (not illustrated). For example, blades may include a conductive material such as a metal like copper and be conductive and/or have terminals for electrical conduction between conductive pads placed external to retractor system 100. In some embodiments, blade 205 may include partially conductive features, e.g., a semiconductor and/or other passive electrical devices such as resisters, diodes, and etc. In other embodiments, blade 205 may be an insulator such that it does not interfere with electrical signal processing of the aforementioned electrical devices.

In the exemplary embodiment, first blade 205 may include a longitudinal groove 205g extending longitudinally along the inside surface 205d that is sized accordingly to house and retain a corresponding pin 205p therein. In at least one embodiment, pin 205p may securely attach to a vertebra of a patient's spine by socketing in to the vertebrae or screwing into the vertebrae. In some embodiments, pin 205p may be a conductive pin having a sensor at a distal end thereof or pin 205p may be a hollow pin that houses electrical components and wiring therein. In other embodiments pin 205p is purely mechanical in nature. In at least one embodiment, pin 205p may be used to facilitate attachment of a shim 205s to an inside surface 205d of blade 205. Shim 205s may laterally extend from a side surface of the blade 205 and include a gripping portion at a proximate side thereof. Shim 205s may also extend from the blade 205 to increase the operative length thereof and/or extend laterally to increase the operative width thereof. In some embodiments, the first, second, third, and fourth blades 105, 107, 109, 111 are each configured to operably couple to a corresponding first, second, third, and fourth shim laterally projecting from a side portion thereof. In other embodiments, diagnostic tools such as an electrode, endoscope, fiber optic, light emitting diode or the like may extend along groove 205g. In other embodiments still, a second groove (not illustrated) similar to groove 205g may be provided so that a combination of the above described features may be used. For example, groove 205g may house a corresponding pin 205p and the second groove (not illustrated) may enable a diagnostic tool or the like to extend along the second groove (not illustrated).

Figure 12:
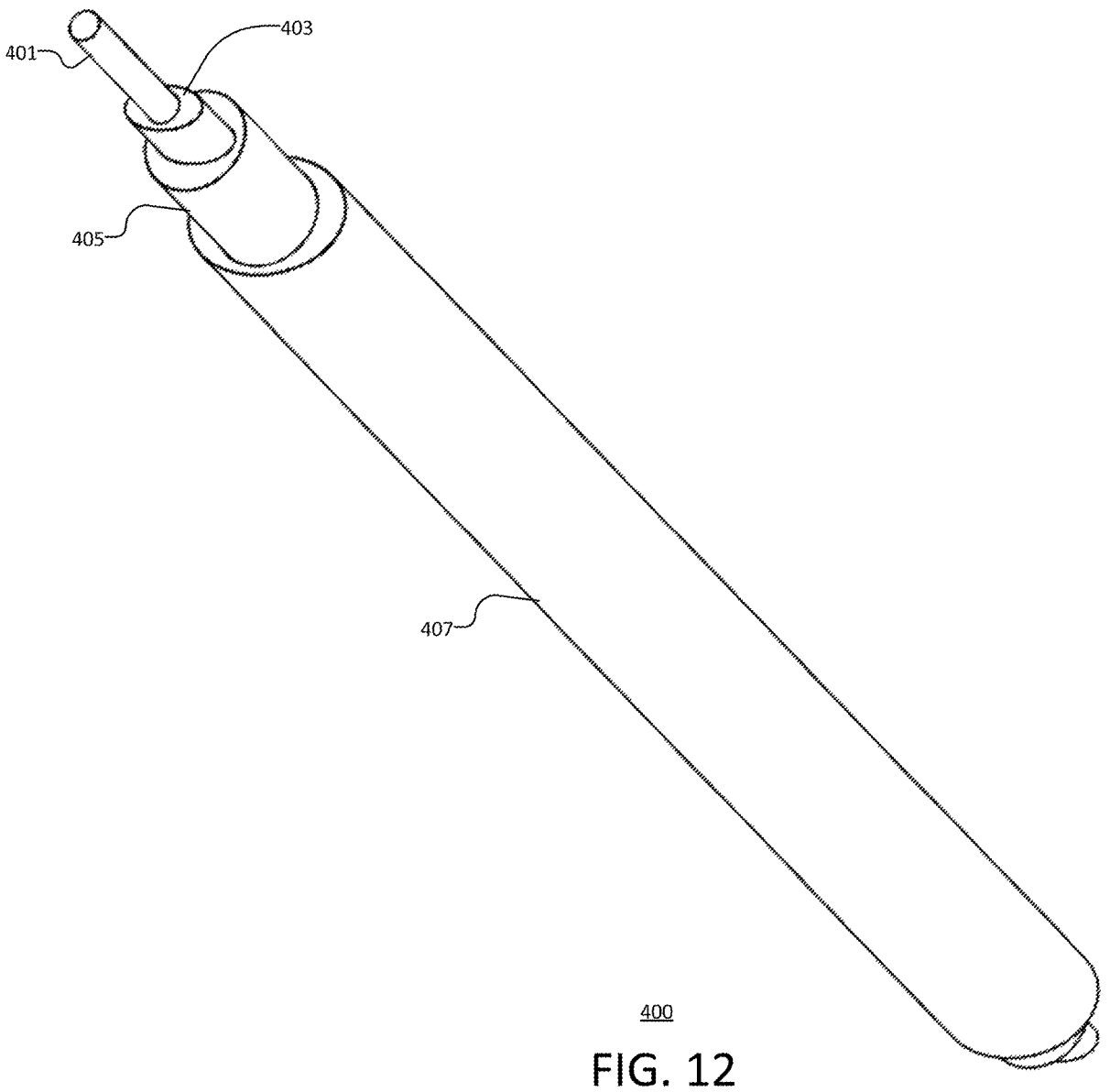
FIG. 12 is a perspective view of an exemplary set of nested dilators for coordinated use with the retractor system of FIG. 1 in accordance with the principles of the disclosure.

Referring to FIG. 12 an exemplary set of nested dilators 400 is illustrated. Exemplary dilators 400 may include a neuro monitoring sensor or the like to help guide insertion of the dilators through muscle fibers. The set of nested dilators 400 may include a series of dilators having alternating circular and ellipsis (oval) cross sectional shapes or oblong cross-sectional shapes. For example, a first dilator 401 having a relatively small circular cross section is surrounded by a second dilator 403 having an ellipsis, or oval shaped cross section. The size and shape of the circular cross section of the first dilator 401 may be defined by a radius extending from a center point thereof and the shape of the ellipsis cross section may be defined by a major axis and a minor axis extending perpendicularly with respect to one another from a center point thereof.

In the exemplary embodiment, the second dilator 403 may, for example, have an ellipsis or elliptical cross section, or other cross sections, for example bi-convex or elongated and substantially flat sides with convex ends, and may have a curvature but may not be circular or elliptical, some such embodiments having a minor axis roughly corresponding to the radius of the circular cross section of first dilator 401. For example, the minor axis of the ellipsis cross section of the second dilator 403 may only be slightly larger than the radius of the circular cross section of the first dilator 401, and the major axis of the ellipsis cross section of the second dilator 403 may be relatively larger than the radius of the circular cross section of the first dilator 401 and the minor axis of the ellipsis cross section of the second dilator 403. In some embodiments, the major axis of the ellipsis cross section of second dilator 403 may be roughly twice as large as the radius of the circular cross section of first dilator 401. In some embodiments, the major axis of the ellipsis cross section of the second dilator 403 may be twice as large as the minor axis of the ellipsis cross section of the second dilator 403. At least one advantage to this arrangement of alternating cross sections is that the second dilator 403 may be insert around the first dilator 401 between fibers of a muscle, e.g., the paraspinous muscle, such that the major axis of the second dilator 403 is initially arranged parallel with the fibers of the paraspinous muscle and can therefore be insert around the first dilator 401. Once inserted around the first dilator 401, second dilator 403 can be rotated such that the major axis of second dilator 403 is perpendicular to the orientation of the fibers of the paraspinous muscle thereby gently separating the fibers by orienting the second dilator 403 such that the major axis area of the second dilator 403 gently and controllably applies pressure to separate the fibers.

A third dilator 405 having a circular cross section may be insert around the second dilator 403. The size and shape of the circular cross section of the third dilator 405 may be defined by a radius extending from a center point thereof. For example, the third dilator 405 may have a circular cross-sectional shape having a radius roughly corresponding to the major axis of the second dilator 403. The third dilator 405 can freely rotate around the second dilator 403 and features a circular cross section having a radius that is only slightly larger than the cross-sectional major axis of the second dilator 403. A fourth dilator 407 having an ellipsis cross section (oval) may be insert around the third dilator 405. The fourth dilator 407 may be defined by an ellipsis cross section having a minor axis that is only marginally larger than the cross sectional radius of the third dilator 405, i.e., the cross sectional minor axis of the fourth dilator roughly corresponds to the cross sectional radius of the third dilator 405. Additionally, the cross-sectional major axis of the fourth dilator 407 is relatively larger than the cross sectional radius of the third dilator 405 and the cross sectional minor axis of the fourth dilator. In some embodiments, the major axis of the ellipsis cross section of fourth dilator 407 may be roughly twice as large as the radius of the circular cross section of third dilator 405. In some embodiments, the major axis of the ellipsis cross section of the fourth dilator 407 may be twice as large as the minor axis of the ellipsis cross section of the fourth dilator 407. At least one advantage to this arrangement of alternating cross sections is that the fourth dilator 407 may be insert around the third dilator 405 between fibers of a muscle, e.g., the paraspinous muscle, such that the major axis of the fourth dilator 407 is initially arranged parallel with the fibers of the paraspinous muscle and can therefore be insert around the third dilator 405. Once inserted around the third dilator 405, fourth dilator 407 can be rotated such that the major axis of fourth dilator 407 is perpendicular to the orientation of the fibers of the paraspinous muscle thereby gently separating the fibers by orienting the fourth dilator 407 such that the major axis area of the fourth dilator 407 gently and controllably applies pressure to separate the fibers.

Figure 13A:
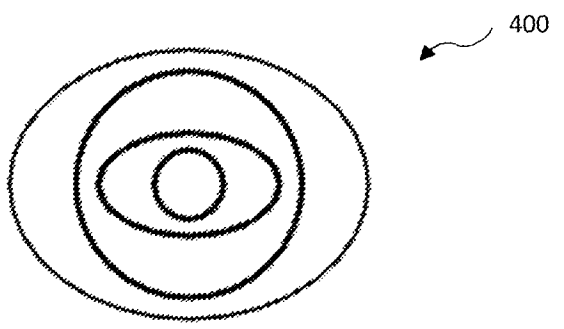
FIG. 13A is a top down view of the set of nested dilators of FIG. 12.
Figure 13B:
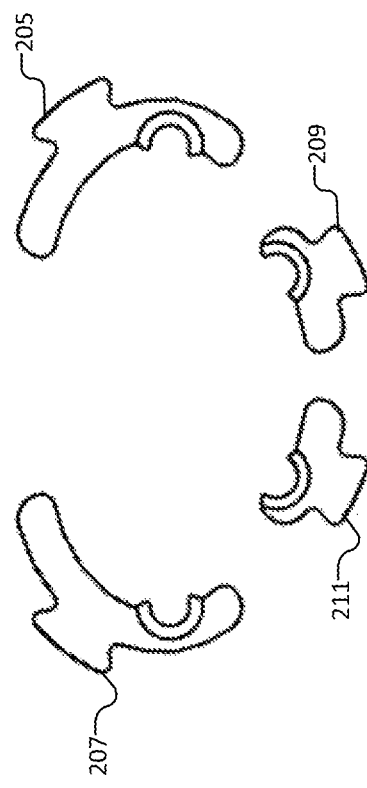
FIG. 13B is a top down view of a plurality of blades for use with the retractor system of FIG. 1 in accordance with the principles of the disclosure.

FIG. 13A is a top down view of the set of nested dilators 400 as explained above. As illustrated a set of nested dilators 400 that may sequentially gently separate fibers of a muscle are illustrated. The set of nested dilators 400 may be insert sequentially and rotated on an as needed basis to gently dilate an anatomical feature. FIG. 13B is a top down view of blades 205, 207, 209, and 211. As illustrated blades 205, 207 are relatively larger in width than blades 209, and 211.

Figure 14:
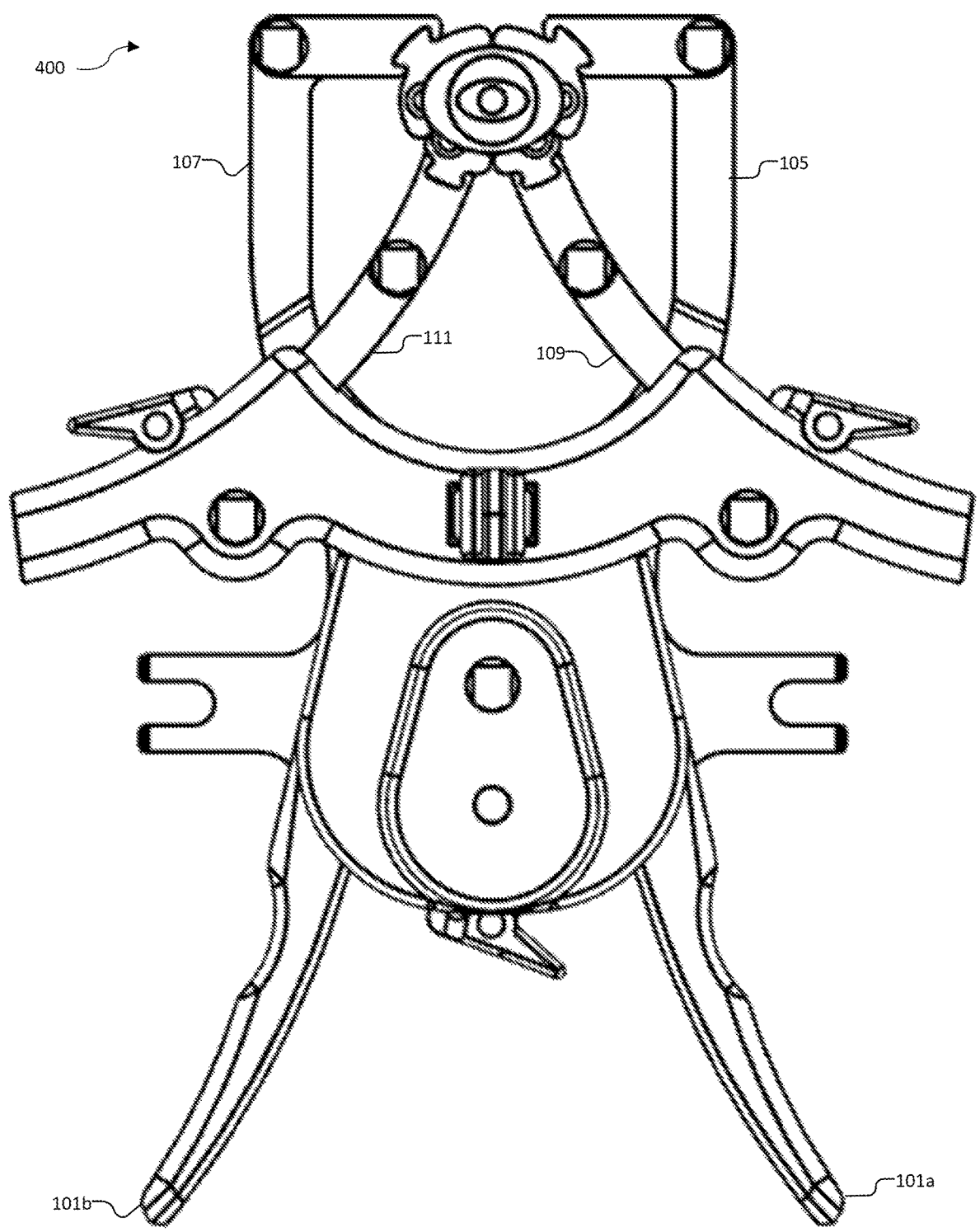
FIG. 14 is a top down view of an exemplary retractor system having a plurality of blades surrounding a set of nested dilators in accordance with the principles of the disclosure.
Figure 15:
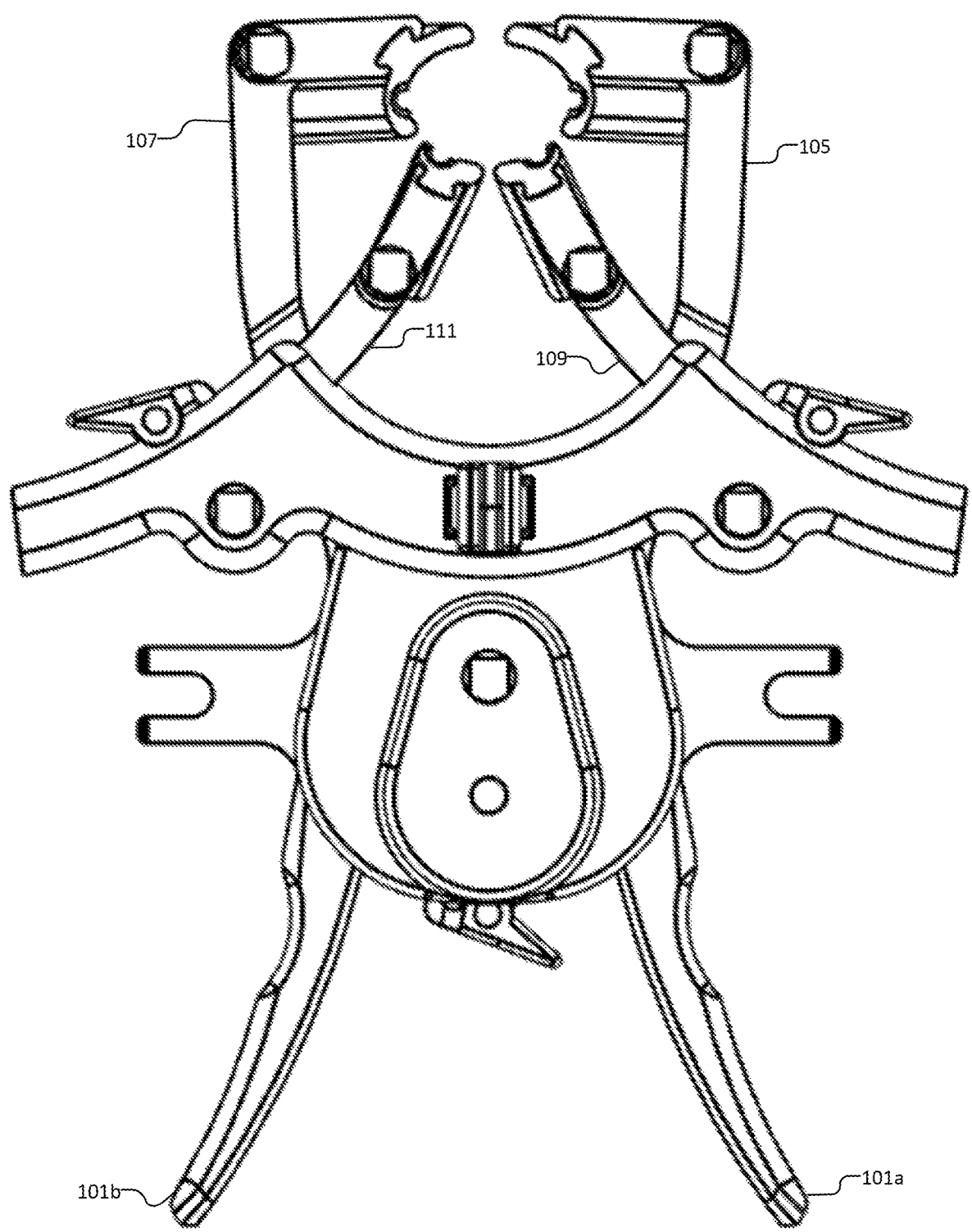
FIG. 15 is a top down view of an exemplary retractor system of FIG. 14 in a first partially expanded position after removal of the set of nested dilators in accordance with the principles of the disclosure.
Figure 16:
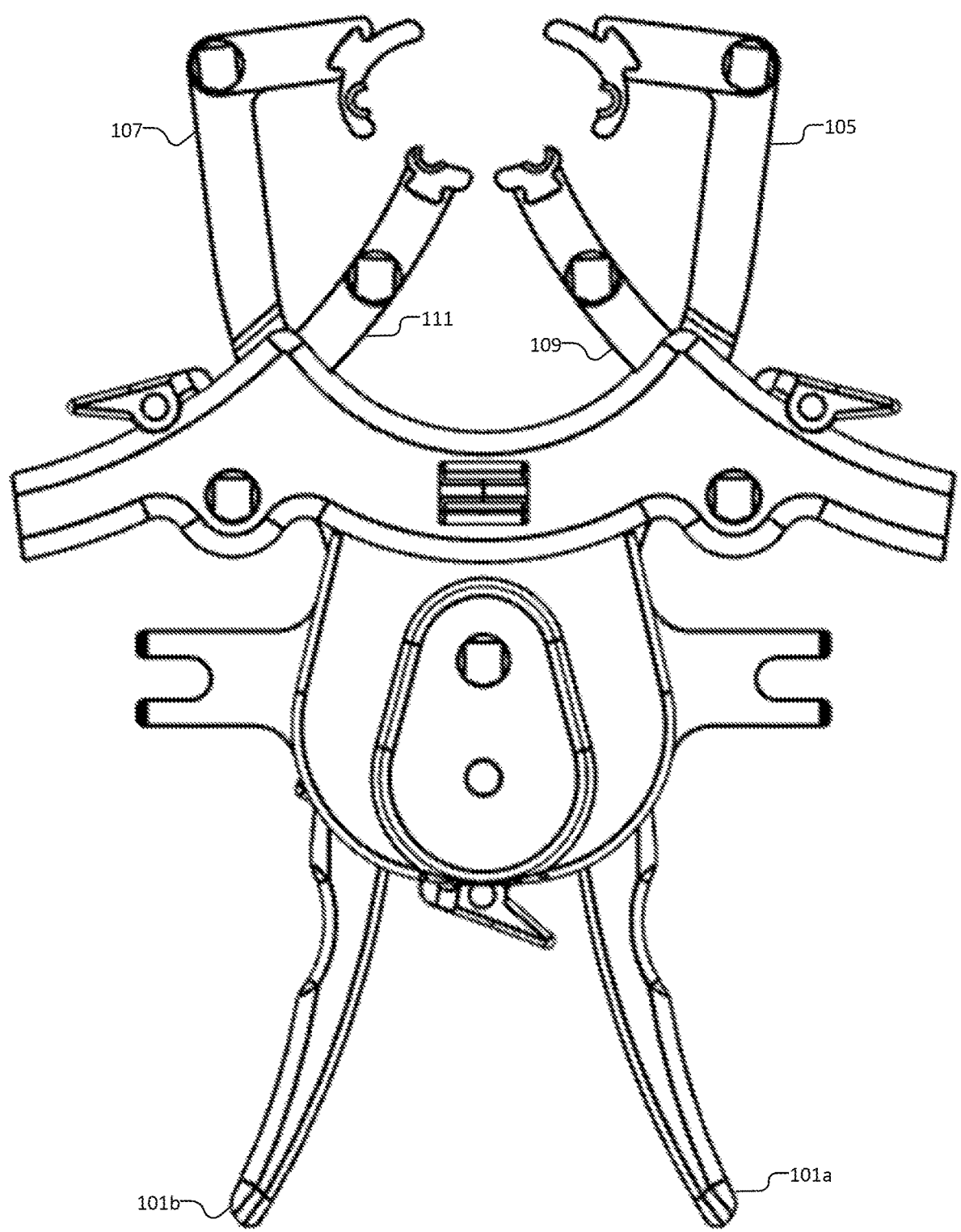
FIG. 16 is a top down view of an exemplary retractor system of FIG. 14 in the first partially expanded position in accordance with the principles of the disclosure.
Figure 17:
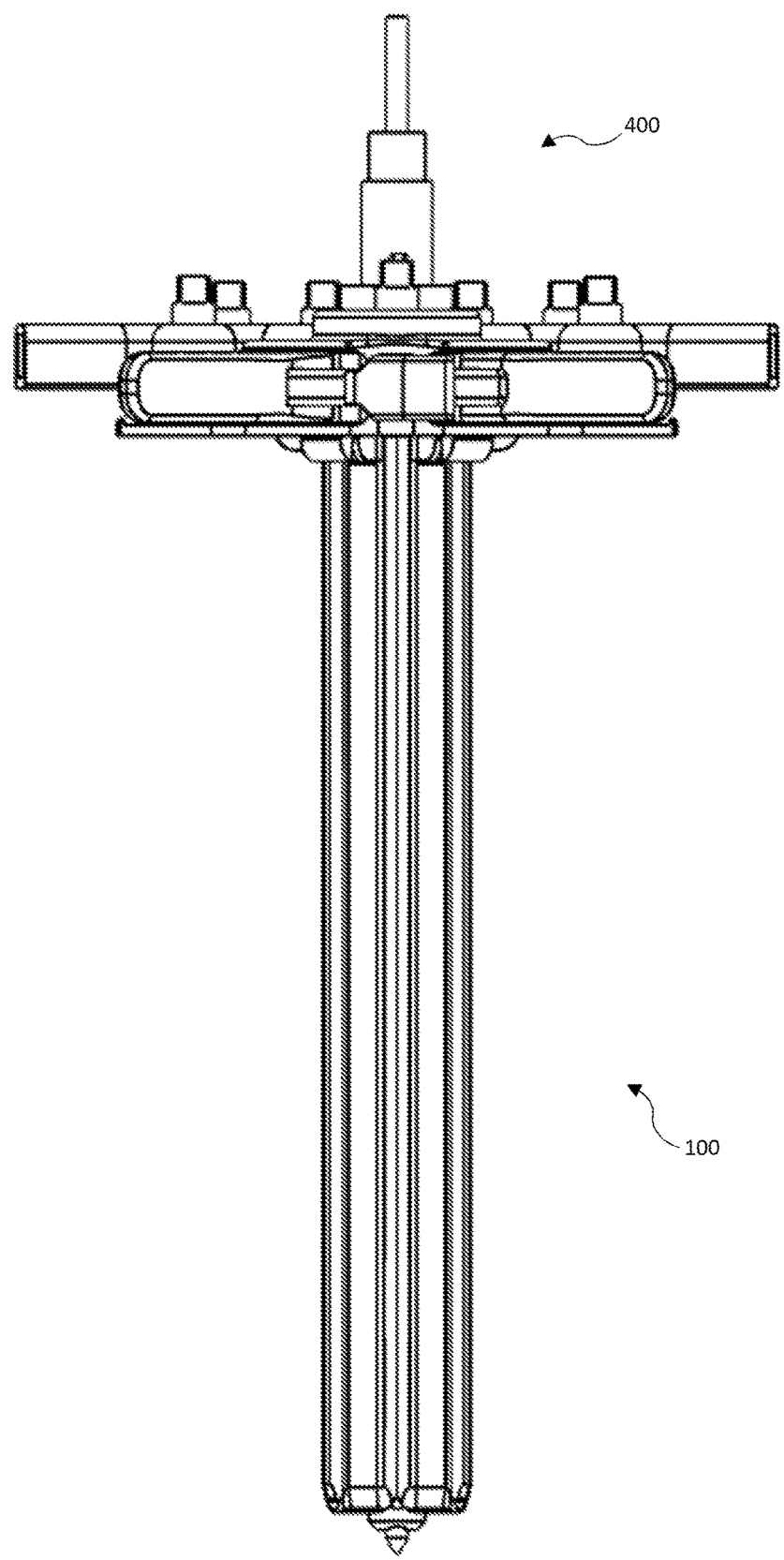
FIG. 17 is a side view of the exemplary retractor system of FIG. 14 having a plurality of blades surrounding a set of nested dilators in accordance with the principles of the disclosure.

FIGS. 14-19 illustrate various positions and modes of operation of retractor system 100 in use with the set of nested dilators 400. For example, in FIG. 14, retractor system 100 is shown in a closed position where arms 105, 107 are closed and surround, at least partially, the set of nested dilators 400. Additionally, arms 109, 111 are fully extended and surround, at least partially, the set of nested dilators 400. In FIG. 14, the inside surfaces of blades 205, 207, 209, and 211 (not labelled in FIG. 14) together surround and contact an outside surface of a fourth dilator 407 (not labelled in FIG. 14). For example, the blades 205, 207, 209, and 211 surround and contact a set of nested dilators 400. For example still, a side surface of each of blades 205, 207, 209, and 211 contacts an adjoining side surface of a different adjacent blade of the blades 205, 207, 209, and 211 thereby forming a closed shape. FIG. 17 is a side view of the arrangement of FIG. 14.

Figure 18:
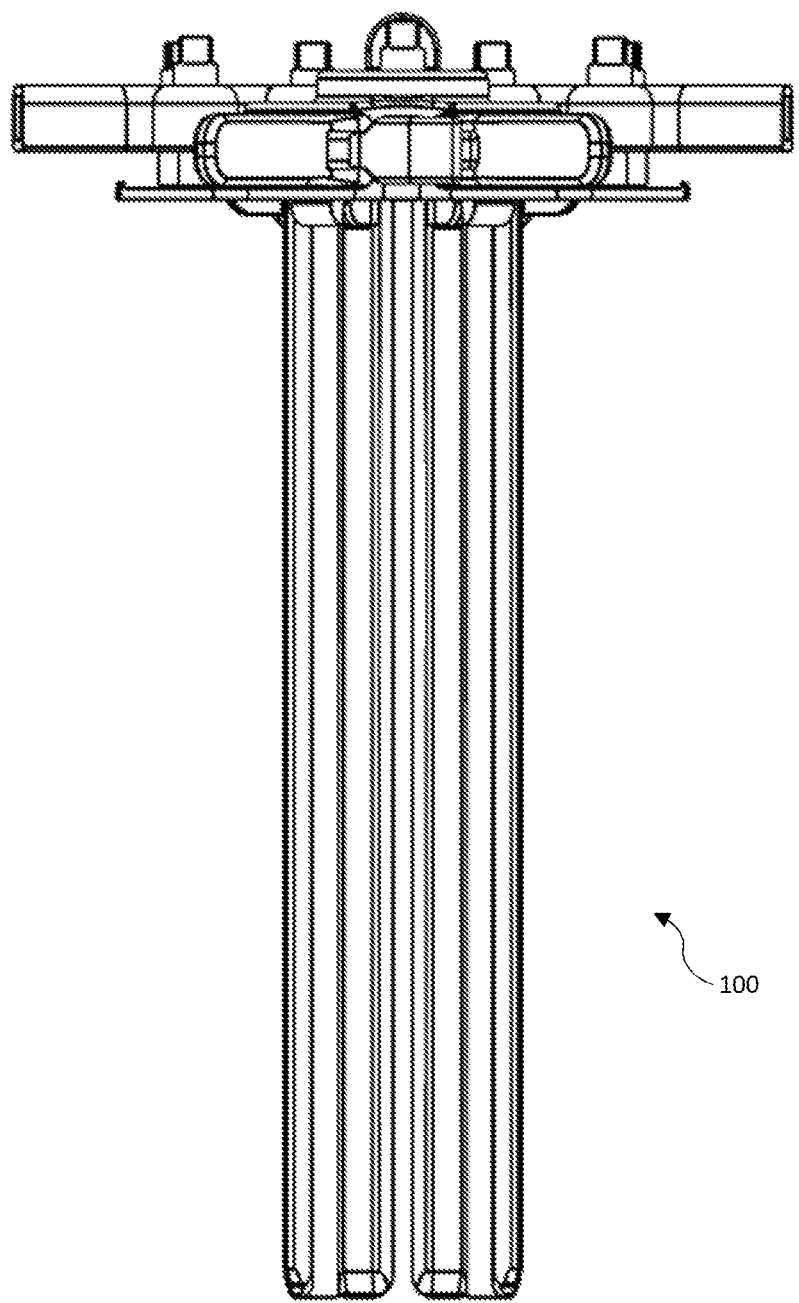
FIG. 18 is a side view of the exemplary retractor system of FIG. 14 in a second expanded position in accordance with the principles of the disclosure.
Figure 19:
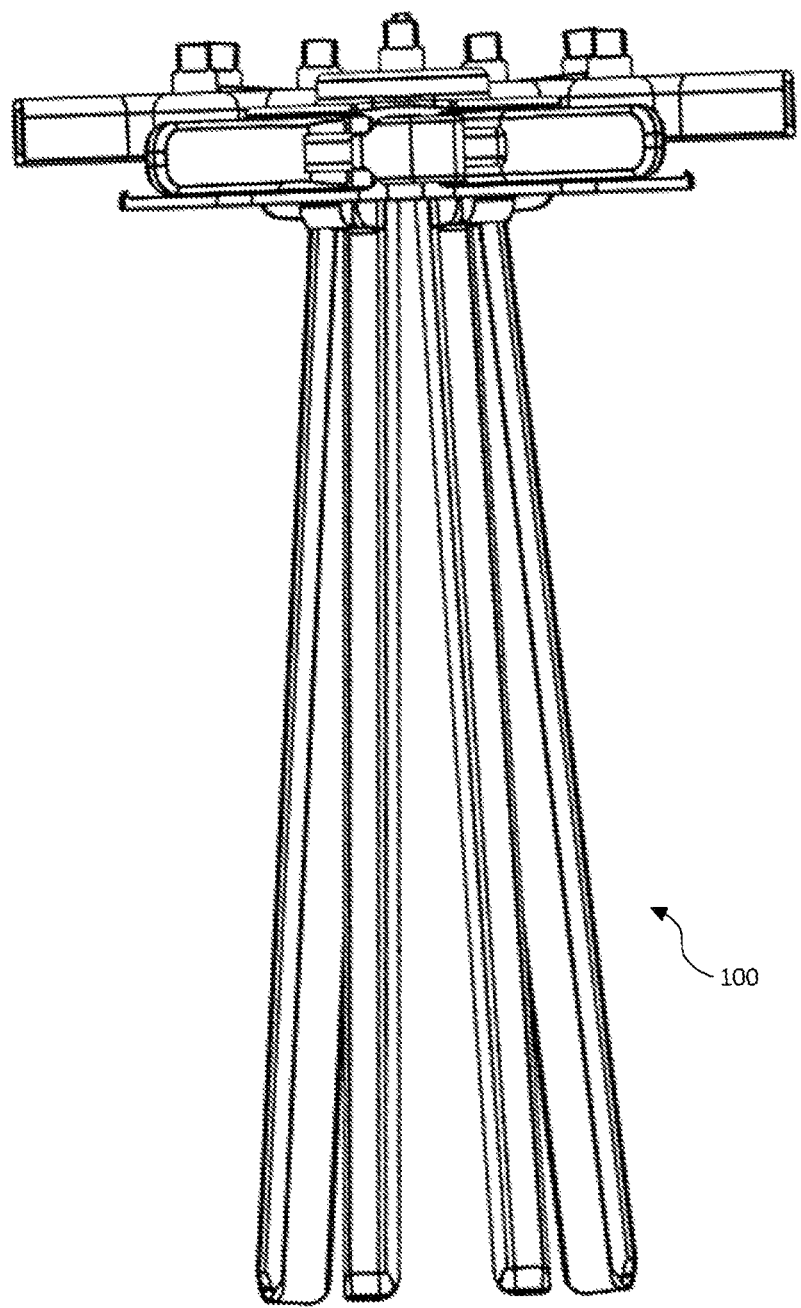
FIG. 19 is a side view of the exemplary retractor system of FIG. 14 in the second expanded position in accordance with the principles of the disclosure.

In FIG. 15, the set of nested dilators 400 is removed and the retractor system 100 is adjusted to a first partially opened position where arms 105, 107 are partially opened and arms 109, 111 are partially contracted. FIG. 18 is a side view of the first partially opened arrangement of FIG. 15. In FIG. 16, the retractor system is adjusted to a second partially opened position where arms 105, 107 are further opened and arms 109, 111 are further contracted. FIG. 18 is a side view of the second partially opened arrangement of FIG. 16. FIG. 19 shows the angulation of each blade being adjusted outward approximately 15 degrees from the side view of FIG. 18.

Additional Retractor Embodiments

Figure 20:
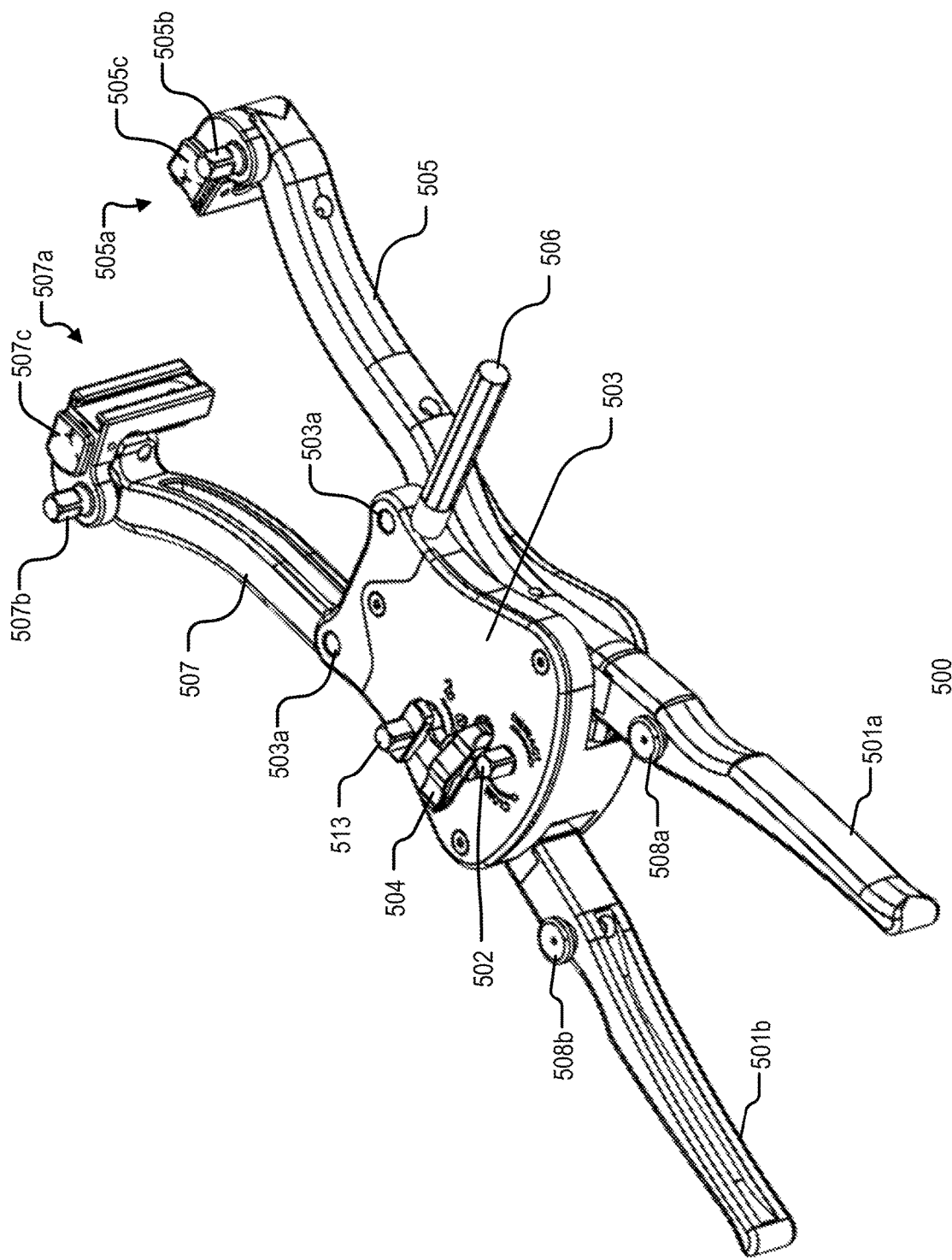
FIG. 20 is a perspective view of a modular retractor.
Figure 81:
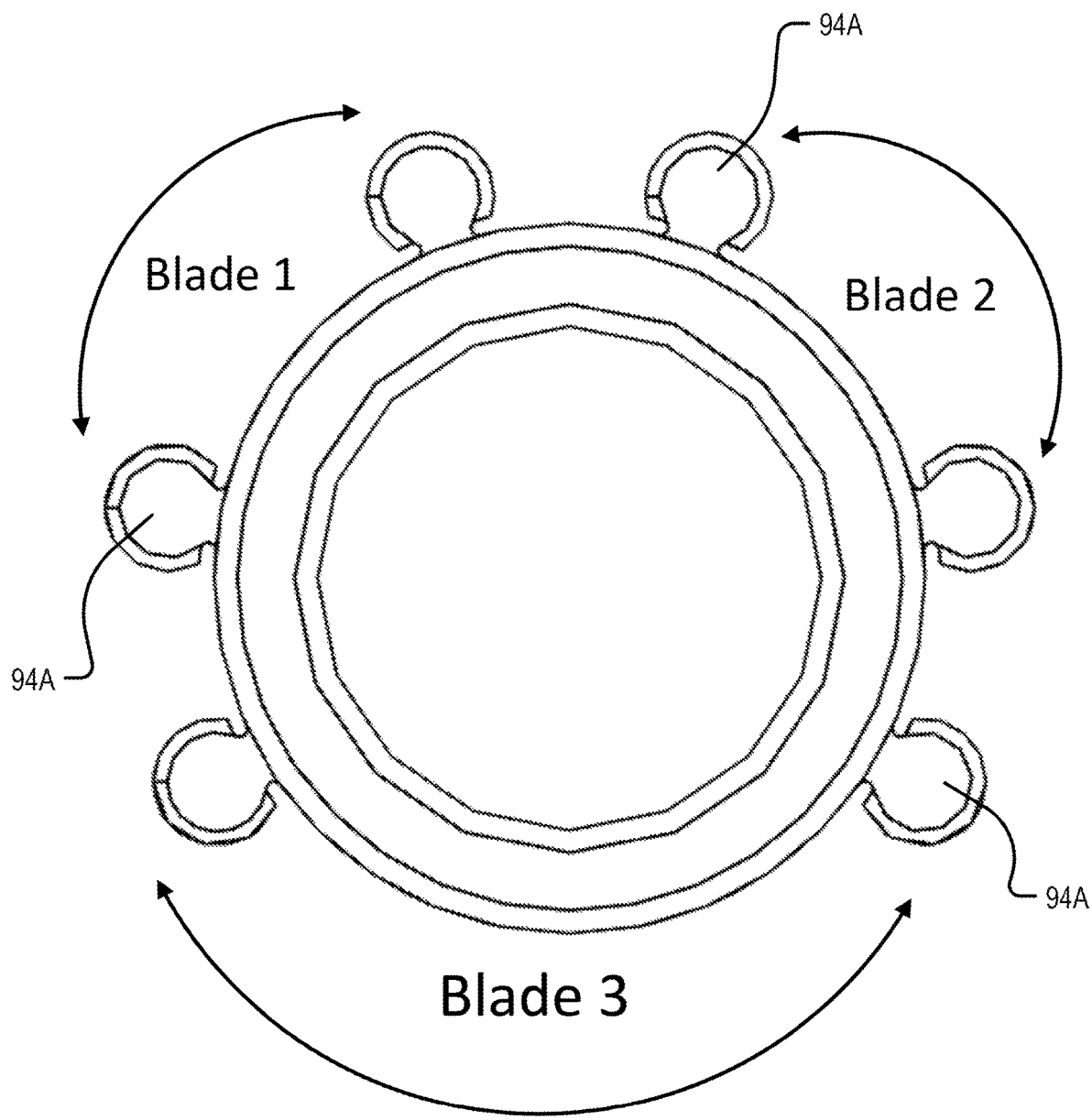
FIG. 81 is a top down view of the various dilators of embodiment of FIG. 80C.

Referring generally to FIGS. 20-81 an example modular retractor system including a modular retractor 500 and various add on retractor modules 600, 700, 800, 900, 1000, and 1100 for use with modular retractor 500 are disclosed. In some embodiments, modular retractor 500 may include the same, substantially the same, and/or similar components and functionality as primary retractor 100 and the associated blades, dilators, and secondary retractor assembly 300. Accordingly, those with skill in the art will understand the general principles, modes of operation, and associated methods of each example embodiment may be combined and/or modified in view of the skill of a person of ordinary skill in the art.

Figure 21:
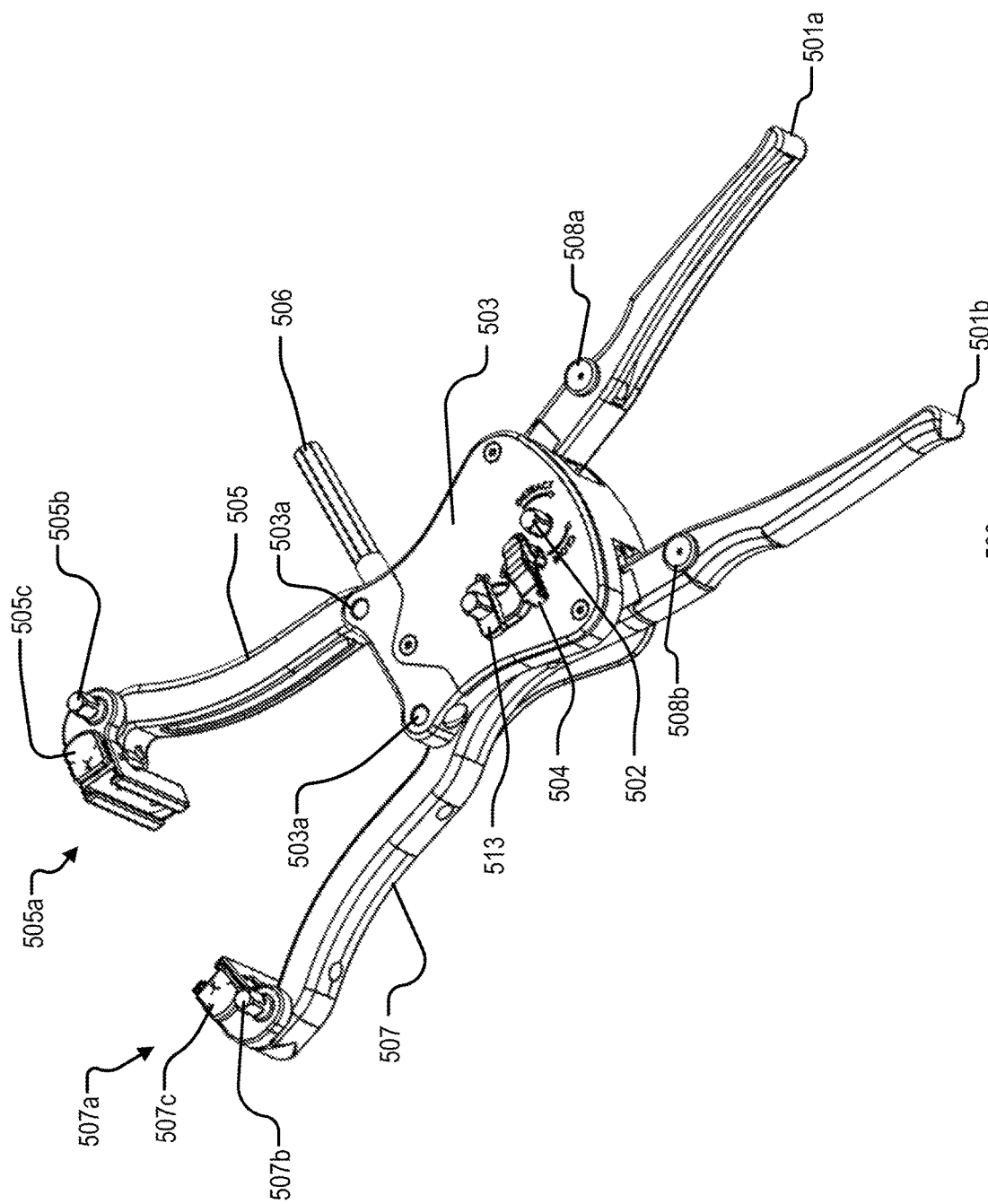
FIG. 21 is a perspective view of a modular retractor.
Figure 22:
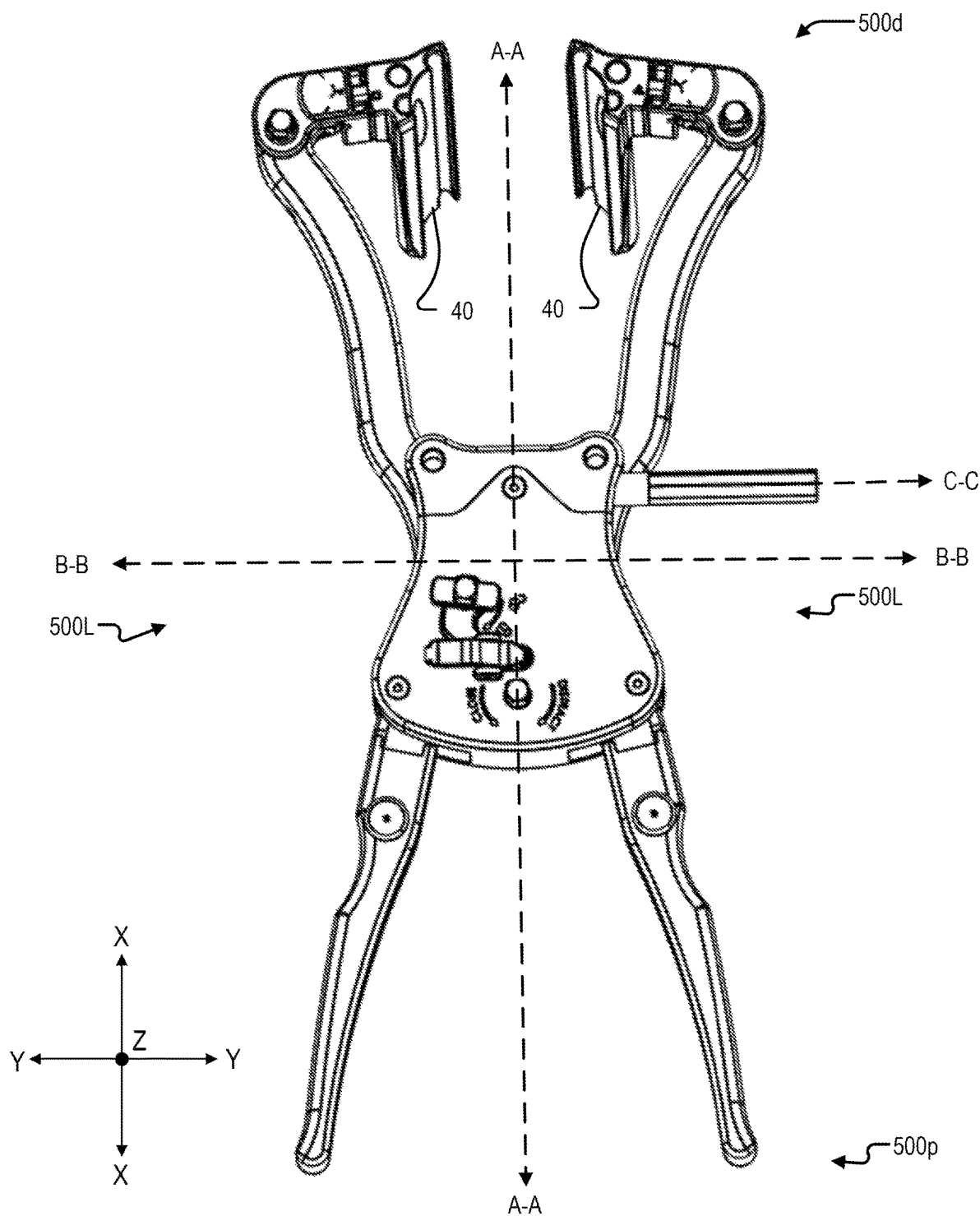
FIG. 22 is a top down view of a modular retractor.
Figure 23:
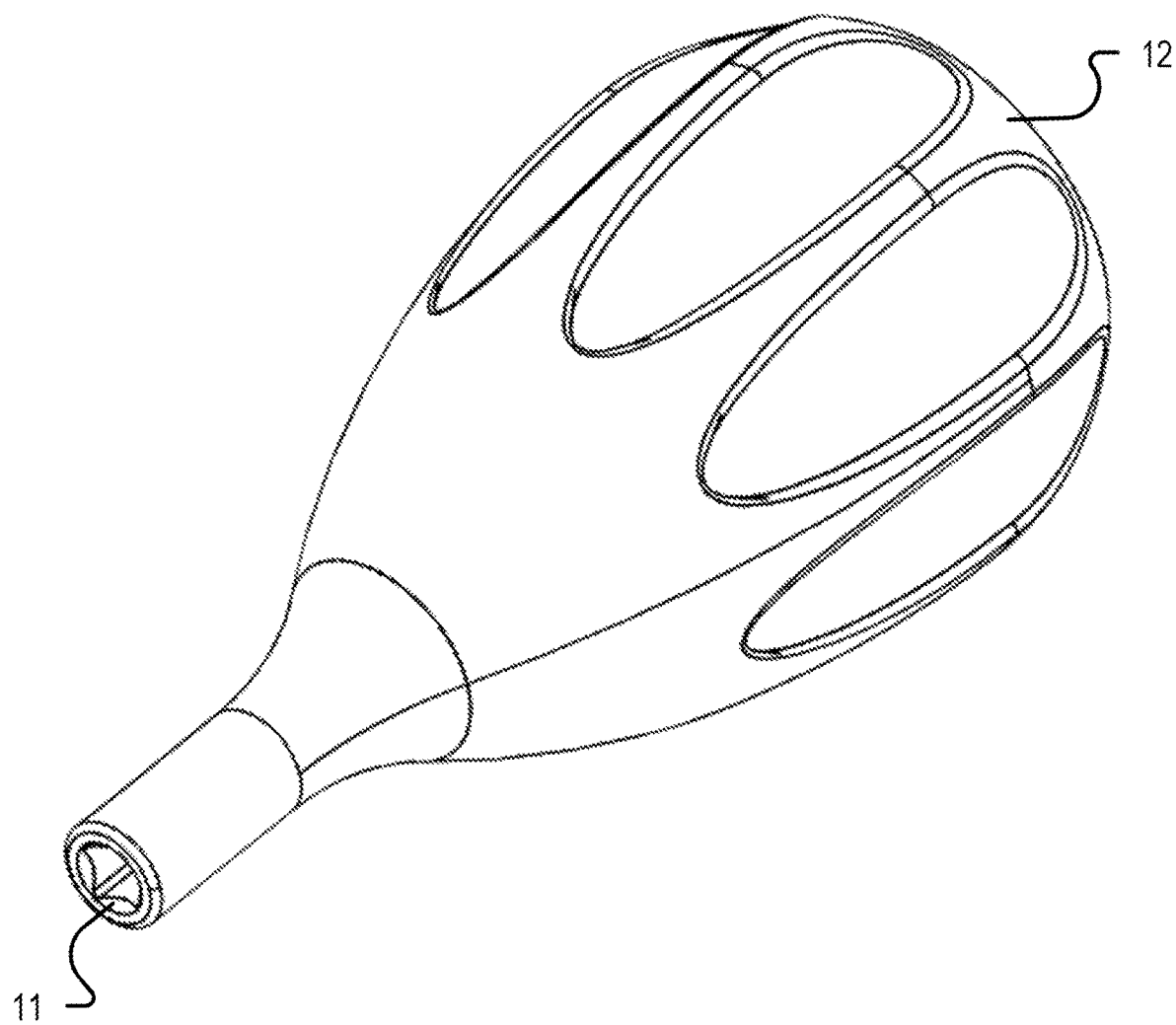
FIG. 23 is a perspective view of an adjustment tool for use with disclosed modular retractor embodiments.
Figure 24:
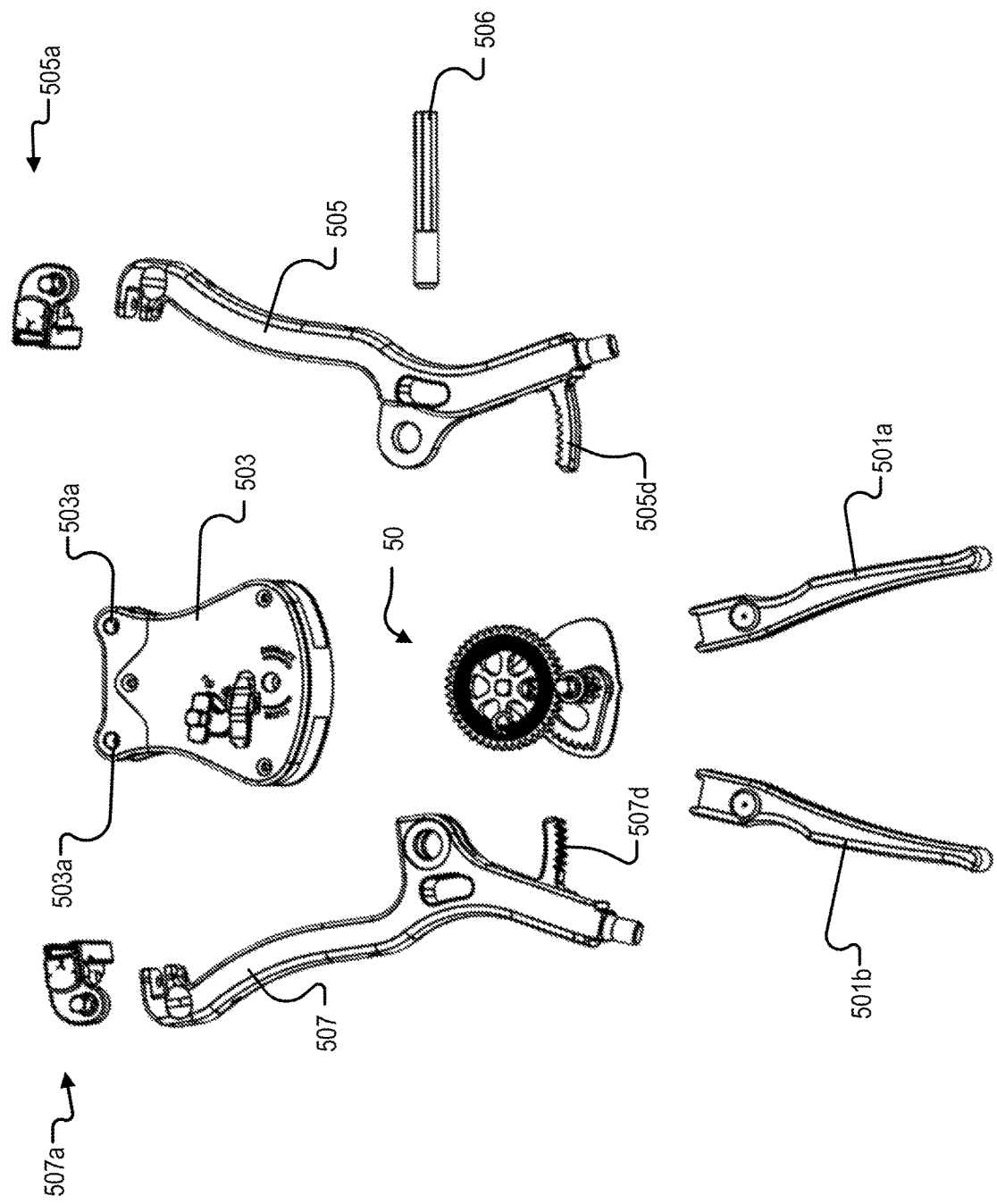
FIG. 24 is a top down exploded parts view of a modular retractor.
Figure 25:
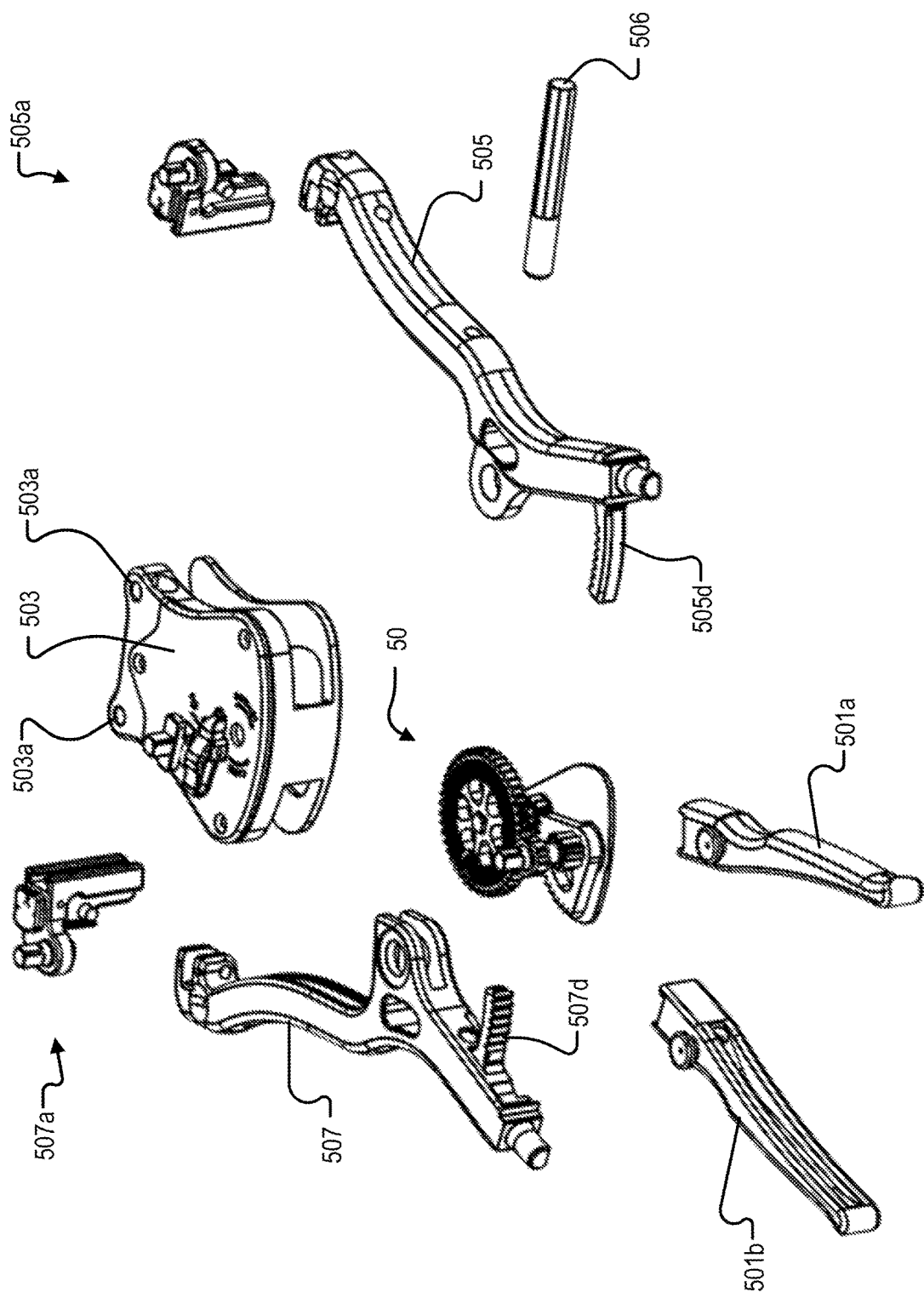
FIG. 25 is a perspective exploded parts view of a modular retractor.
Figure 26A:
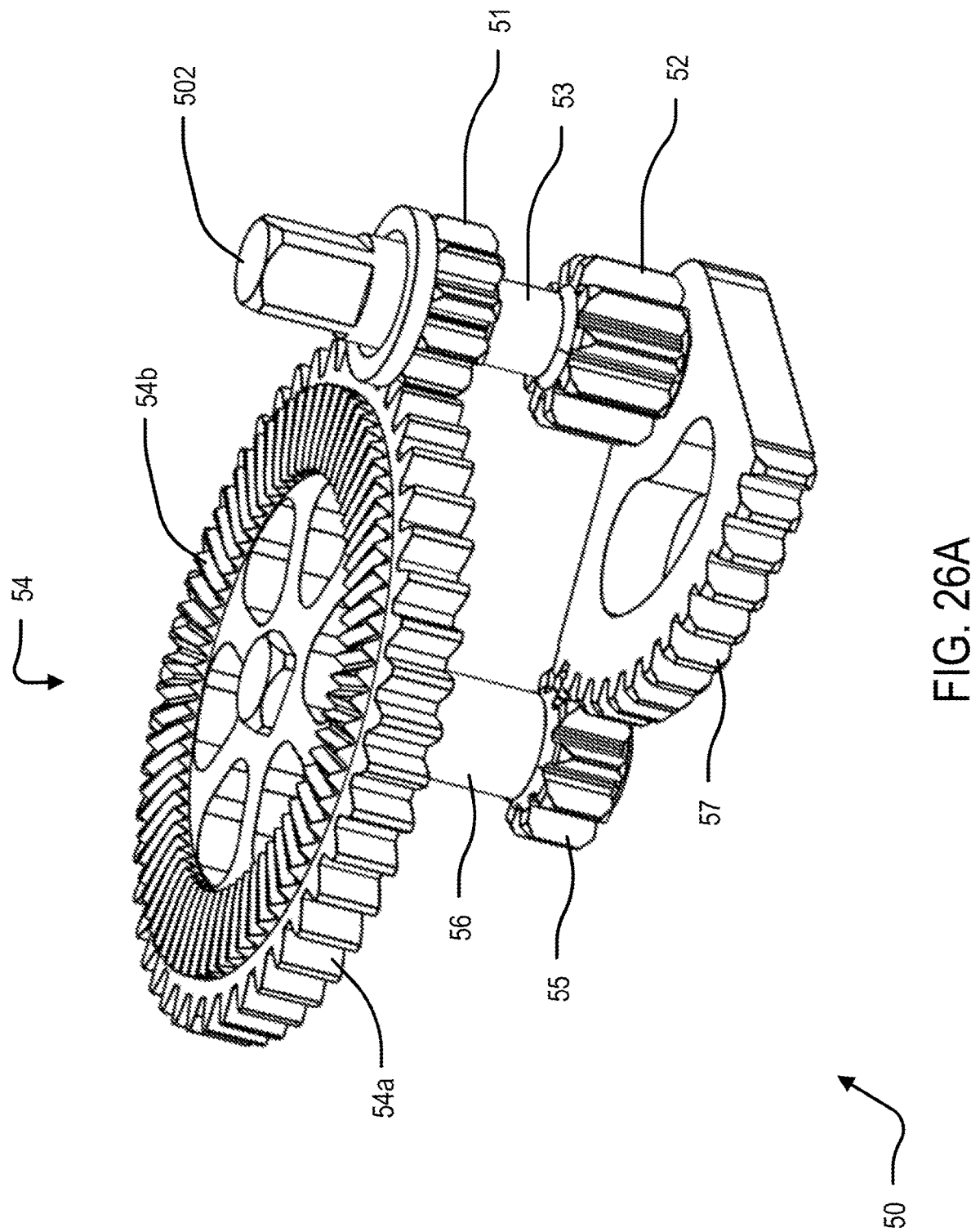
FIG. 26A is a perspective view of a distraction mechanism for use with disclosed modular retractor embodiments.
Figure 26B:
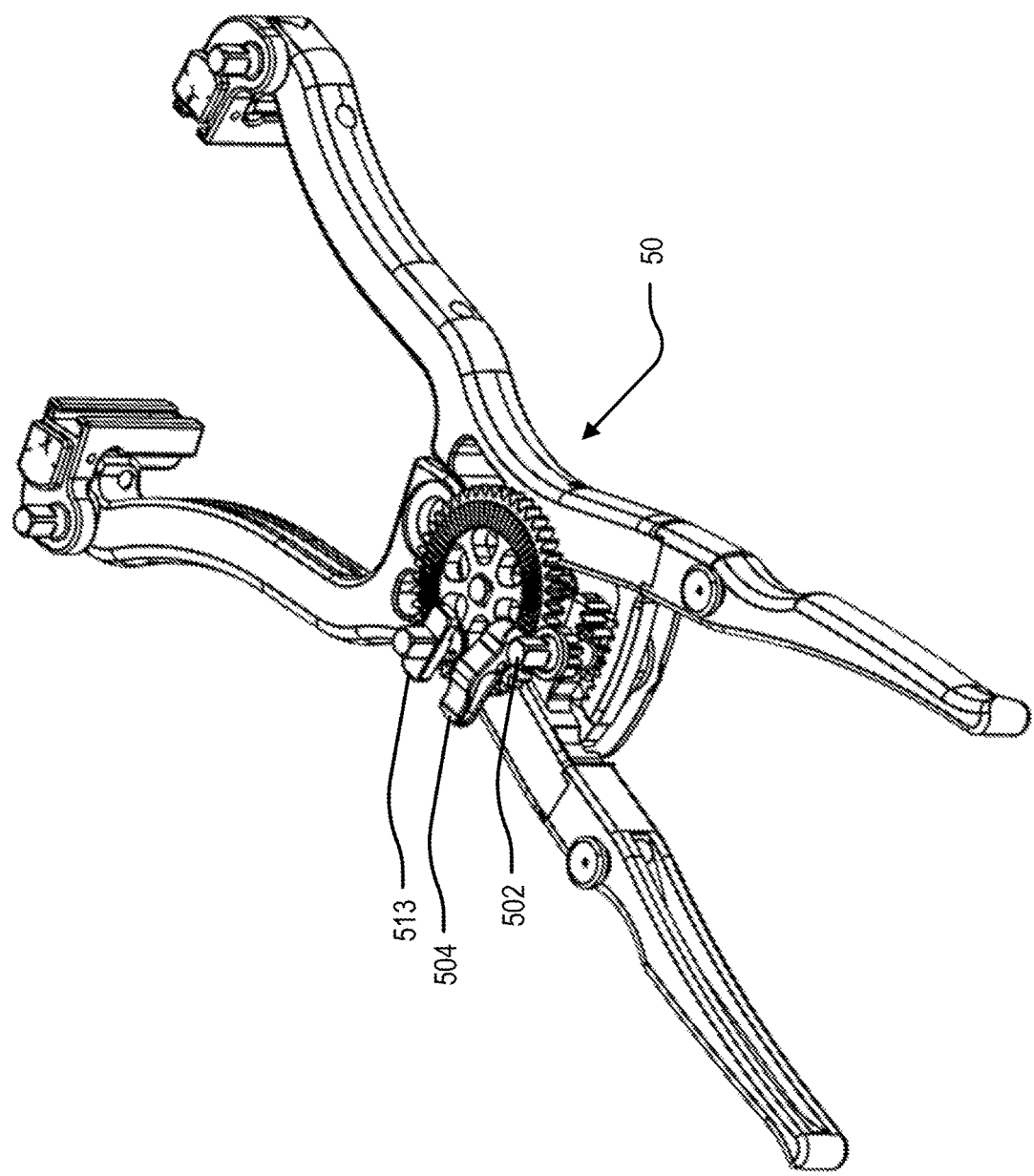
FIG. 26B is a top perspective view of a distraction mechanism.
Figure 26C:
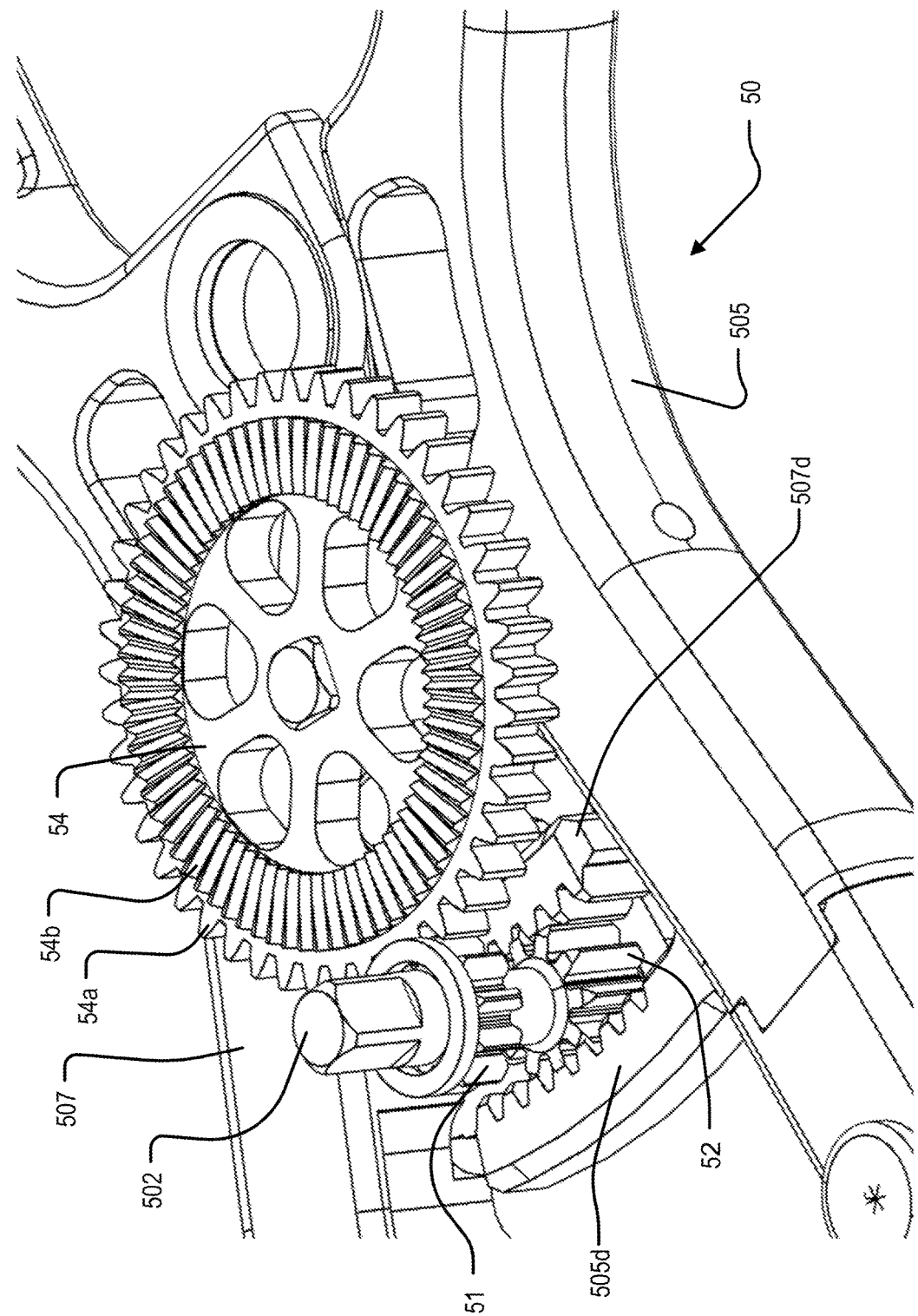
FIG. 26C is an enlarged top perspective view of a distraction mechanism.
Figure 26D:
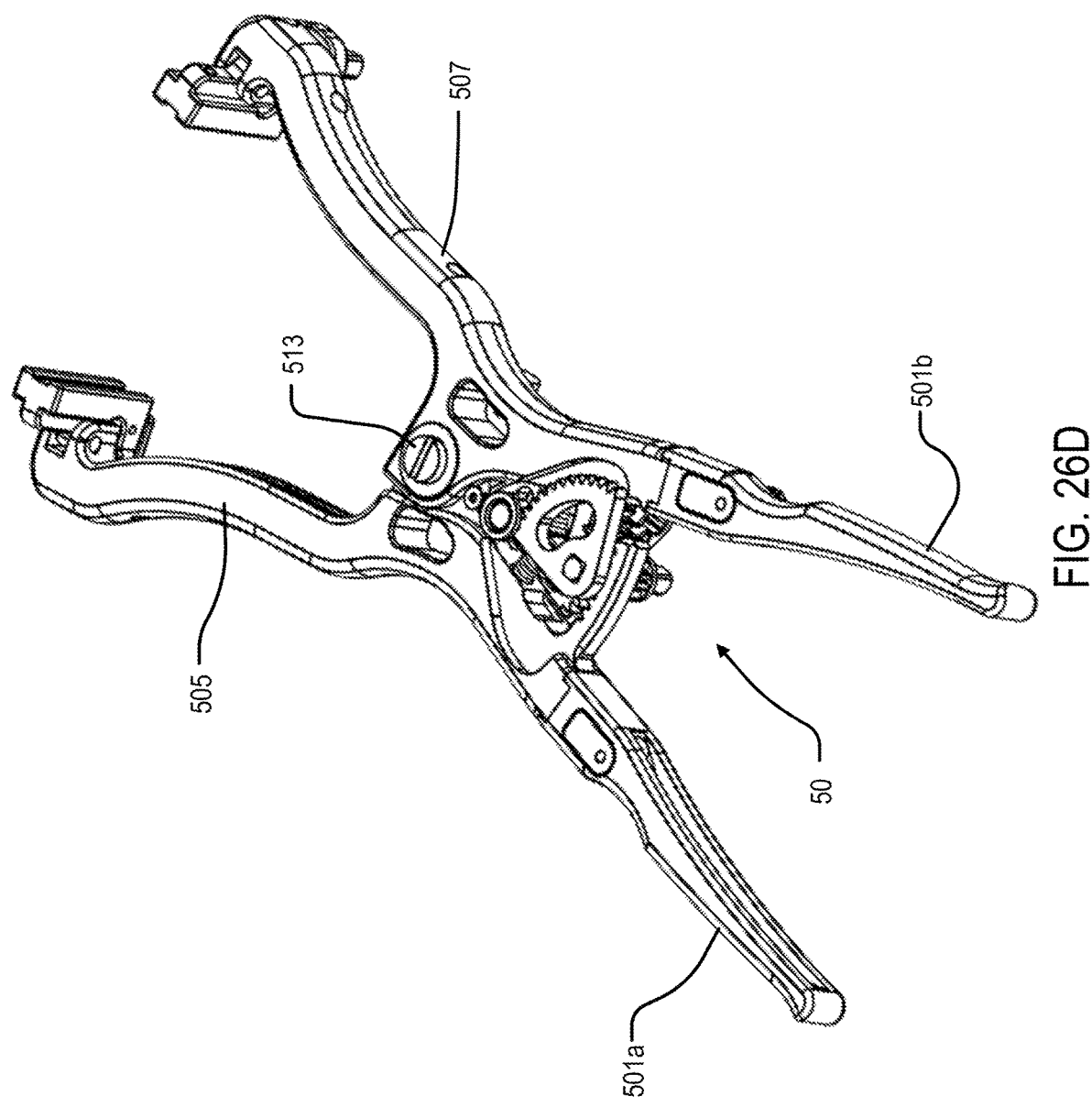
FIG. 26D is a bottom perspective view of a distraction mechanism.
Figure 26E:
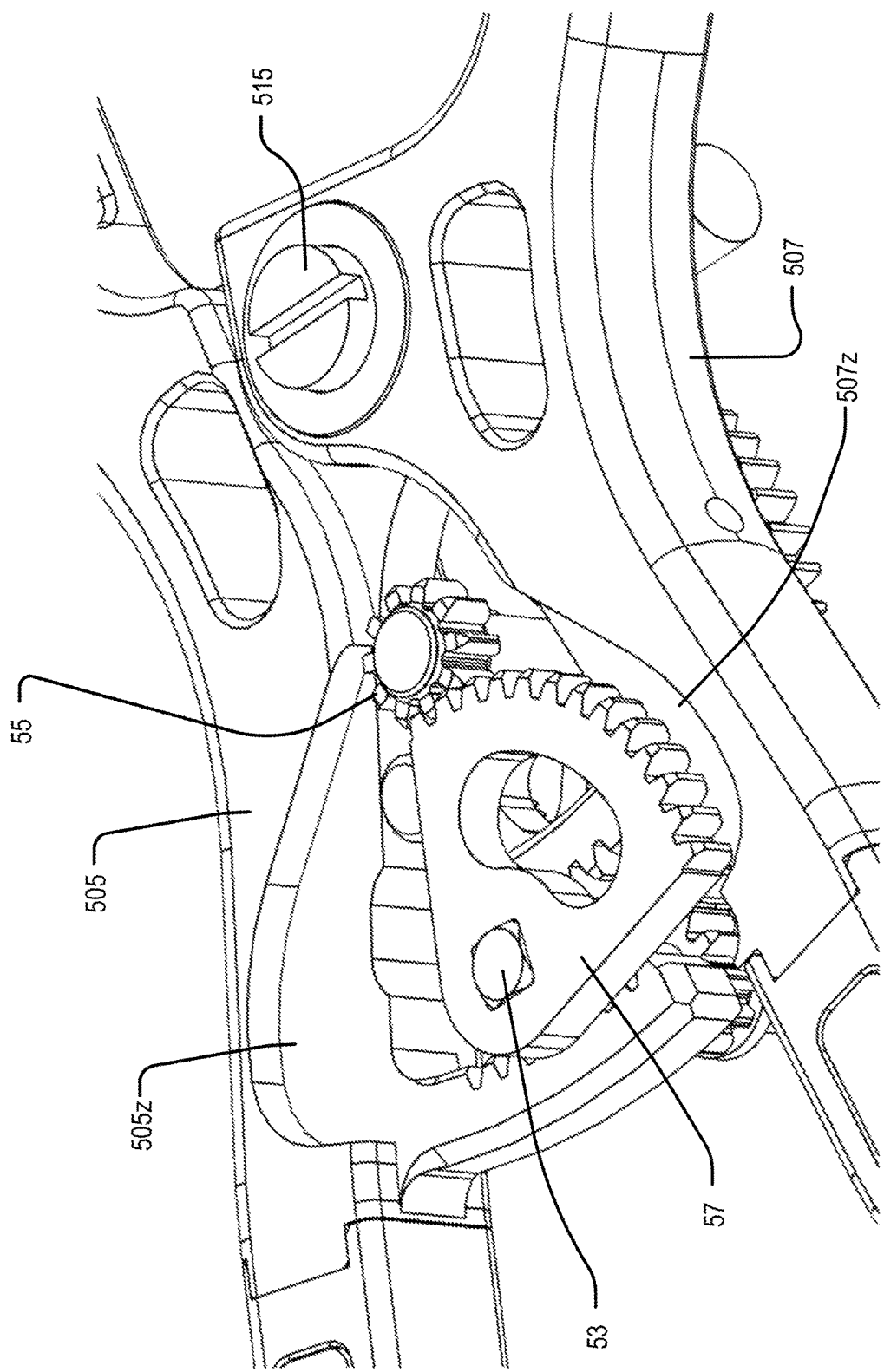
FIG. 26E is an enlarged bottom perspective view of a distraction mechanism.
Figure 27A:
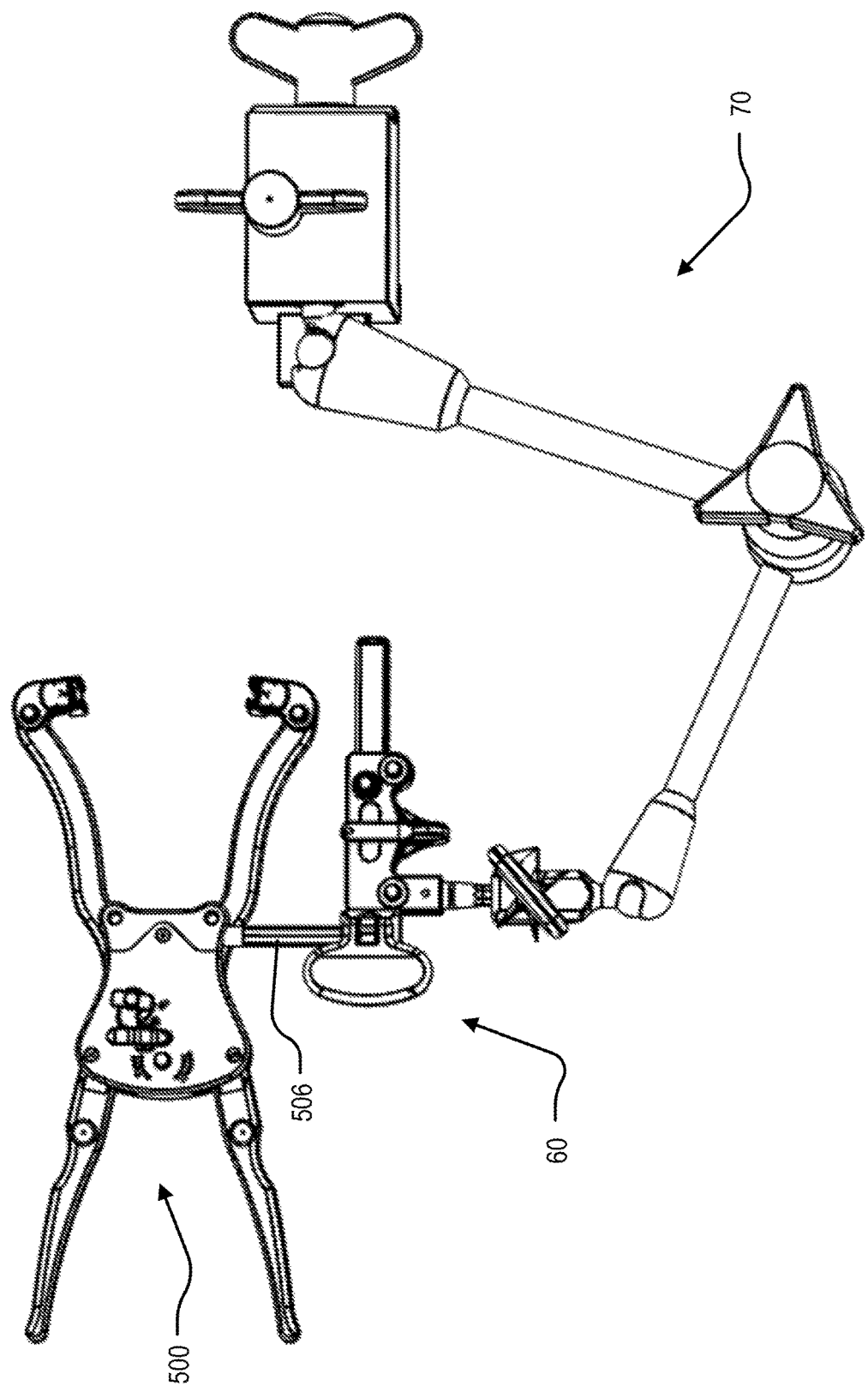
FIG. 27A is a top down view of a modular retractor coupled to a table mount.
Figure 27B:
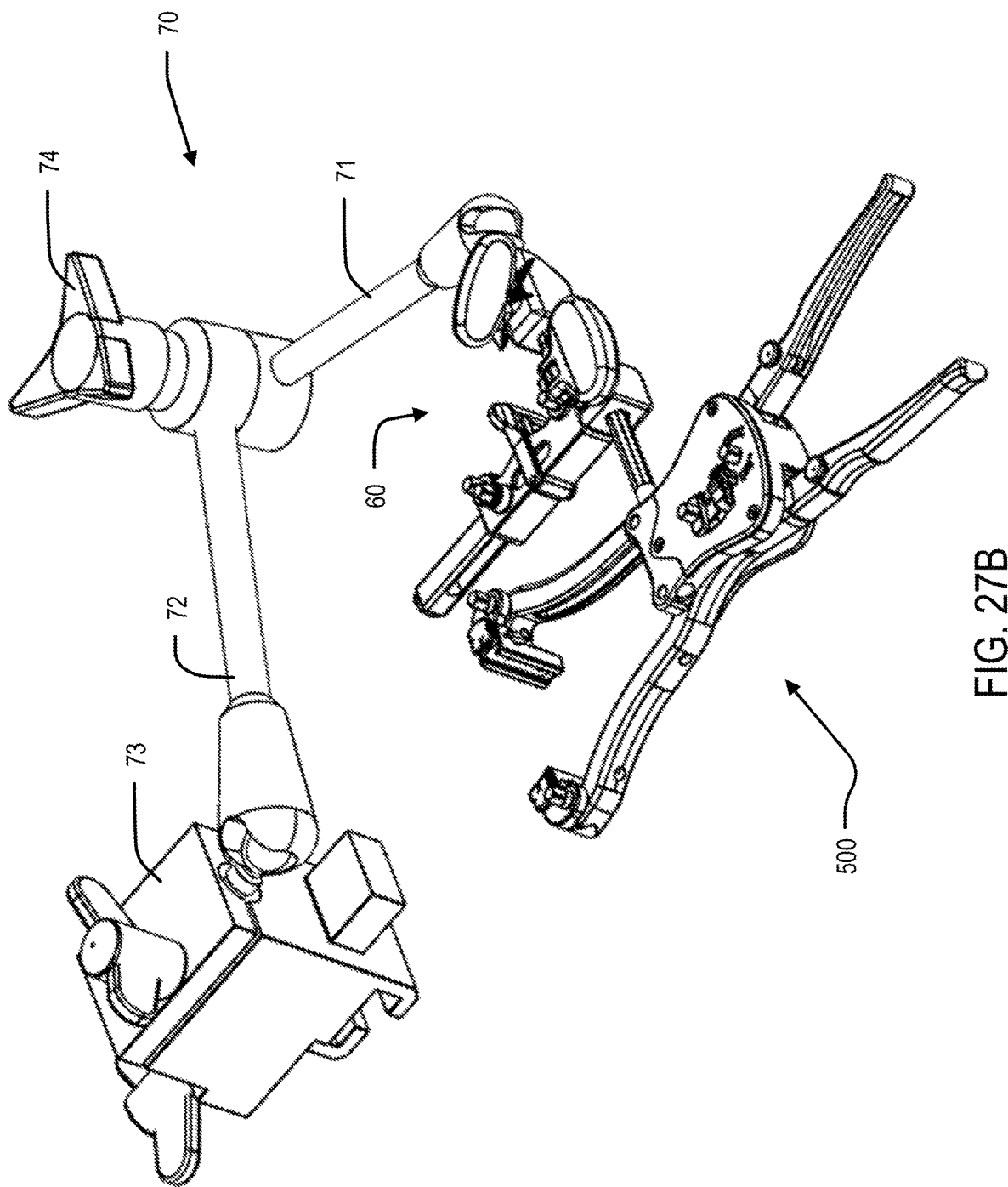
FIG. 27B is a perspective view of a modular retractor coupled to a table mount.
Figure 28A:
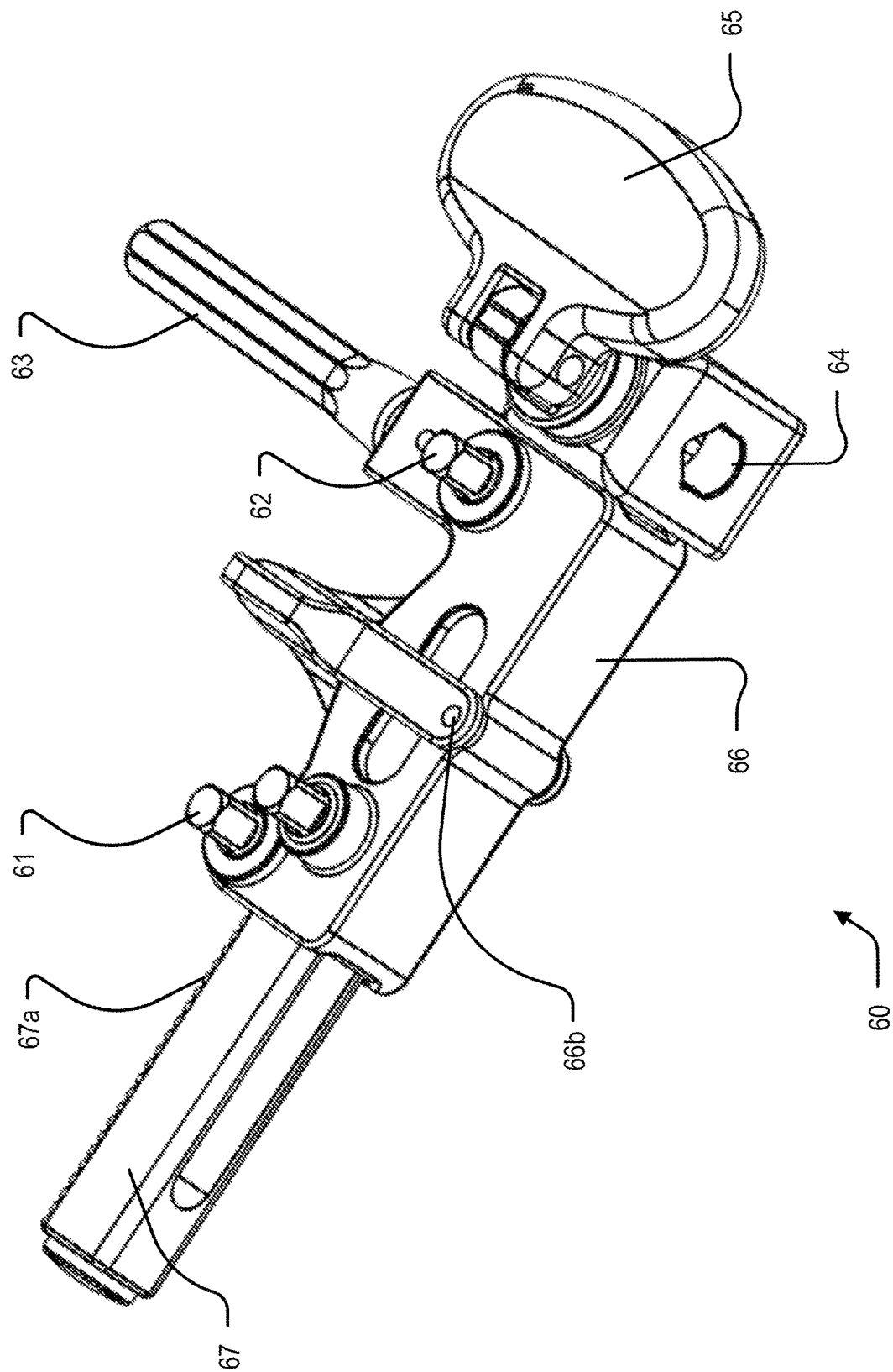
FIG. 28A is a perspective view of a table mount rack.
Figure 28B:
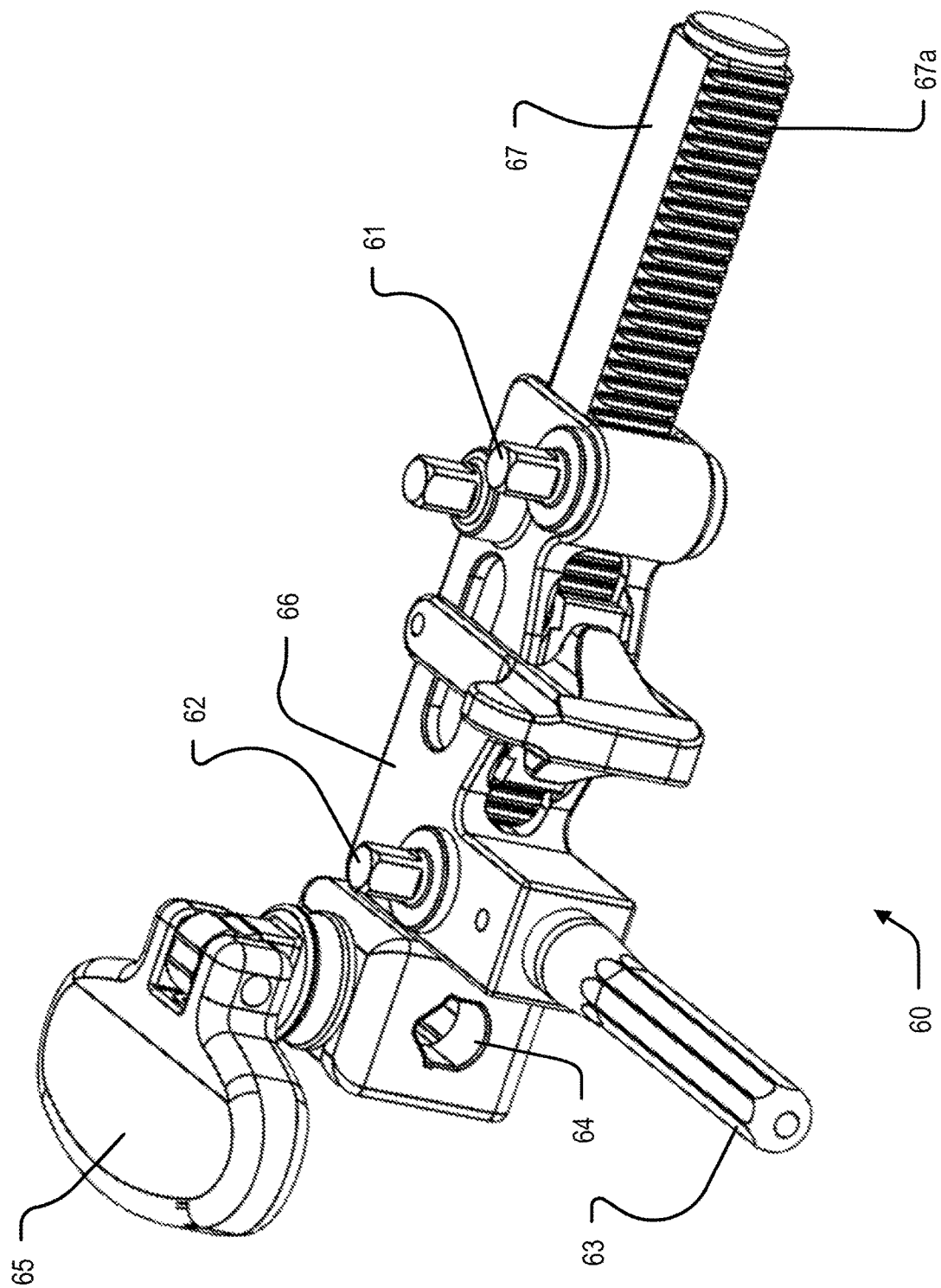
FIG. 28B is a perspective view of a table mount rack.
Figure 28C:
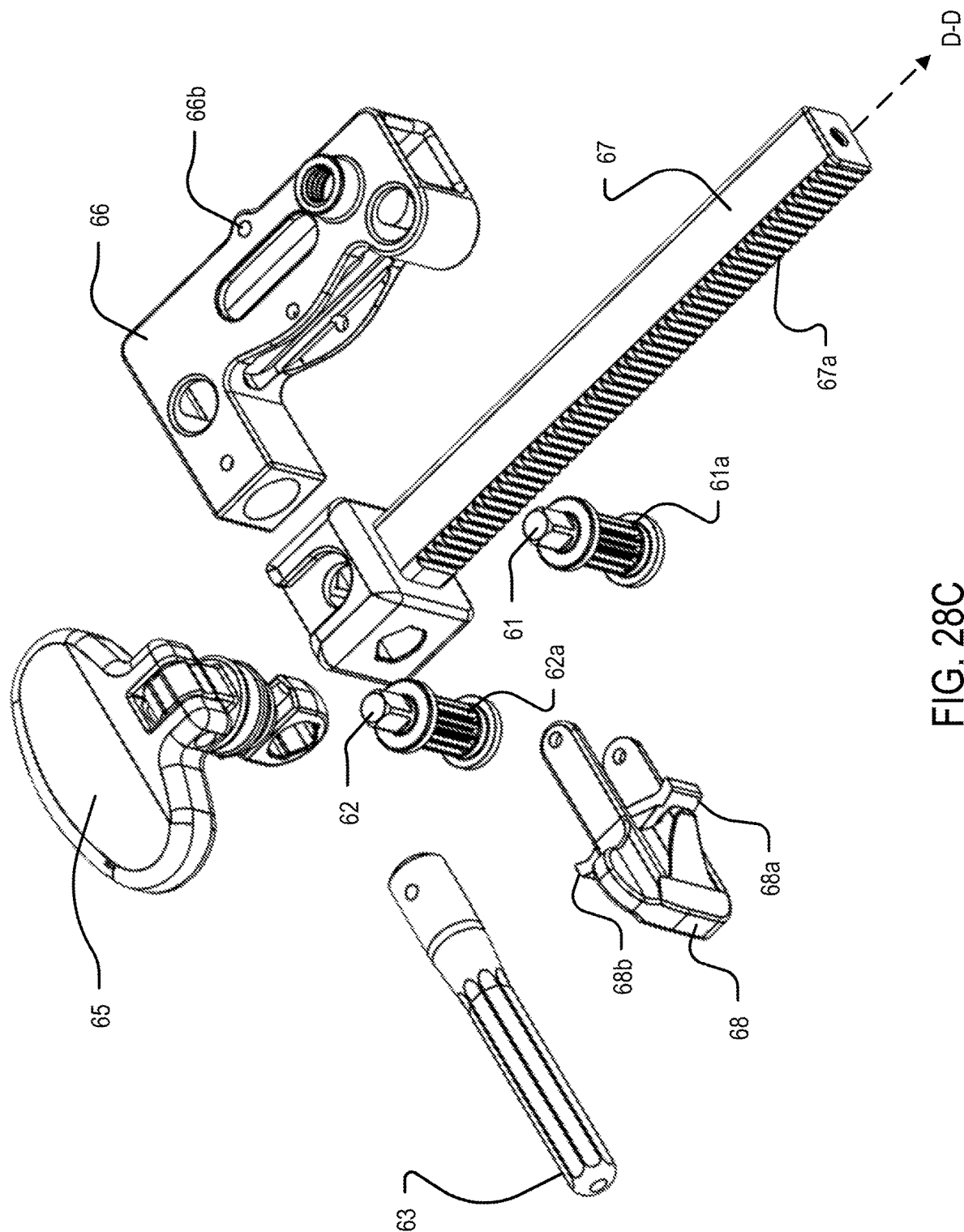
FIG. 28C is an exploded parts view of a table mount rack.

With reference to FIGS. 20-28C a modular retractor 500 for enabling access to a surgical site, an adjustment tool 10, a table mount 70, and a table mount rack module 60 are disclosed. FIGS. 20-21 are perspective views of a modular retractor 500 and FIG. 22 is a top down view of the modular retractor 500 showing various axes and directions of operation. FIG. 23 is a perspective view of an adjustment tool 10 for use with disclosed modular retractor 500 embodiments. FIGS. 24-25 are exploded parts views of a modular retractor 500. FIGS. 26A-26E are various views of a distraction mechanism 50 for use with disclosed modular retractor 500 embodiments. FIGS. 27A and 27B are various views of a modular retractor 500 coupled to a table mount 70. FIGS. 28A-28C are various views of a table mount rack module 60.

Modular retractor 500 is highly customizable and may be considered modular for reasons that will be readily apparent and explained in further detail below. For example, the modular retractor 500 may be used as a standalone retractor system without the use of additional add on modules or modular retractor 500 may be used with any of the disclosed modules discussed herein unless the context clearly suggests otherwise.

Modular retractor 500 may be configured to distract and retract a first arm 505 along a path of travel and a second arm 507 along a different path of travel. The various paths of travel may be an arcuate path or segment defined by the length and geometry of the arms 505 and 507, respectively, and a handle pivoting mechanism 515 (see FIG. 26D). Handle pivoting mechanism 515 may be configured to enable first handle 501a and second handle 501b to open and close, for example. Handle pivoting mechanism 515 may be a pin, screw, or the like, for example. Other paths of travel than those specifically shown are contemplated and those paths of travel may depend upon the geometry of the arms 505, 507 and the relative location of the handle pivoting mechanism 515. The modular retractor 500 may include a handle assembly having first and second handles 501a, 501b that are removably coupled to the first and second arms 505, 507 and configured to open and close the first and second arms 505, 507. For example, the first handle 501a may be coupled to the first arm 505 and the second handle 501b may be coupled to the second arm 507. Additionally, the arms 505, 507 may extend through side channels of the body 503, respectively, and/or be pivotable relative to body 503 and/or be operably coupled to body 503. In various embodiments, the first handle 501a and second handle 501b may be removed and are held in place by first handle connection pin 508a and second handle connection pin 508b, for example. In various embodiments, the connection pins 508a, 508b may be a pin, screw, knob, turnkey, and/or retaining fastener that a surgeon may quickly remove to uncouple the handle 501*a*, 501*b*, for example. Furthermore retractor 500 may include a table mount 506 extending in the lateral direction from body 503. At least one advantage of having the first and second handles 501*a*, 501*b* be removable is greater freedom in performing a surgery due to the reduced structure adjacent a target surgical location, for example. For example still, after a surgeon has retracted a patient tissue, the surgeon may remove the handles 501*a*, 501*b* to prevent bumping into them.

In various embodiments, the first and second arms 505, 507 may be coupled to first and second pivoting members 505*a*, 507*a* at a distal end thereof, respectively. The first and second pivoting members 505*a*, 507*a* may be configured to operably couple to first and second blades, 40 (see FIG. 22), respectively, by a corresponding blade attachment mechanism 505*c*, 507*c* as will be explained in more detail below. In the example embodiment, a first actuator 505*b* and a second actuator 507*b* are configured to adjust the angulation of first blade 40 and second blade 40, respectively. For example, the first actuator 505*b* may be configured to actuate the first pivoting member 505*a* to adjust the angulation of first blade 40 with respect to the first arm 505. Similarly, the second actuator 507*b* may be configured to actuate the second pivoting member 507*a* to adjust the angulation of second blade 40 with respect to second arm 507. In the example embodiment, the first pivoting member 505*a* may be configured to independently adjust the angulation of first blade 40 with respect to the first arm 505 upon actuation of the first actuator 505*b*. Similarly, the second pivoting member 507*a* may be configured to independently adjust the angulation of the second blade 40 with respect to the second arm 507 upon actuation of the second actuator 507*b*. In disclosed embodiments, the first and second pivoting members 505*a*, 507*b* may each include a corresponding pin and socket mechanism enabling the pivoting members to pivot on a pin aperture 199 (see, e.g., FIG. 8).

As shown in FIG. 22, modular retractor 500 may extend in a longitudinal direction from a proximal end 500*p* to a distal end 500*d* in a longitudinal direction (or proximal-to-distal direction) parallel to longitudinal axis A-A. Additionally, modular retractor 500 may extend in a lateral direction (or widthwise direction) parallel to lateral axis B-B. The longitudinal axis A-A may be perpendicular to the lateral axis B-B and intersect at body 503 at a medial location of retractor 500, for example. In various embodiments, and as shown by the Cartesian coordinate system in FIG. 22A, the longitudinal direction may be understood as the X direction and the lateral direction may be understood as the Y direction. Furthermore, a depth and/or thickness of modular retractor may be understood as the Z direction or vertical direction when viewed in a plan view.

FIG. 23 is a perspective view of an adjustment tool 10 for use with disclosed modular retractor 500 embodiments. In the example illustration, adjustment tool 10 may include a drive end 11 and a handle end 12, for example. Drive end 11 may have a size and shape configured to rotate various actuators of modular retractor 500, for example. In various embodiments, drive end 11 may take the shape of a hexolobular drive end, a hex drive end, a torx drive end, a polygonal drive end, a square drive end, or the like. Similarly, actuators 502, 507*b*, 505*b* may take any corresponding shape, for example.

FIG. 24 is a top down exploded parts view of a modular retractor 500 and FIG. 25 is a perspective exploded parts view of a modular retractor 500. In the example embodiment, arm 505 may include a rack portion 505*d* at a distal end thereof and arm 507 may include a rack portion 507*d* at a distal end thereof, for example. In various embodiments, rack portions 505*d*, 507*d* may be curved and be disposed at different relative distances from the distal end of the respective handle 505, 507, for example. Additionally rack portions 505*d*, 507*d* may be meshed with and movable by distraction mechanism 50, for example. Distraction mechanism 50 may be operably drivable by actuator 502, for example. Distraction mechanism 50 may include a plurality of gears to provide a mechanical advantage to open and close the arms 505, 507 as will be explained in further detail below.

FIGS. 26A-26E are various views of a distraction mechanism 50 for providing a mechanical advantage to distract and retract arms 505, 507. Distraction mechanism 50 may principally be formed of a plurality of spur gears 51, 52, 54, 55, and a partial spur gear 57 that are meshed together and sized appropriately for providing a mechanical advantage to distract and/or retract arms 505, 507. For example, primary actuator 502 may be connected to first spur gear 51 and second spur gear 52 by shaft 53, for example. In the example embodiment, primary actuator 502, spur gears 51, 52, and shaft 53 are coaxially aligned in the vertical direction. Additionally, a partial spur gear 57 may attached to shaft 53. Partial spur gear 57 may be understood as a portion and/or slice of a relatively large spur gear having a central axis of rotation coincident with shaft 53, for example. In the example embodiment, partial spur gear 57 may have an axis of rotation coincident with shaft 53, for example. Additionally, first spur gear 51 may be meshed with third spur gear 54. In turn, third spur gear 54 may be connected to fourth spur gear 55 by shaft 56. Third spur gear 54, shaft 56, and fourth spur gear 55 may be coaxially aligned. In the example embodiment, third spur gear 54 is a relatively large spur gear and fourth spur gear 55 is a relatively small spur gear. Those with skill in the art will understand this arrangement may be advantageous for providing a relatively great mechanical advantage to perform distraction and/or retraction of arms 505, 507, for example. In the example embodiment, fourth spur gear 55 may be meshed with partial spur gear 57. In this way, distraction mechanism 50 may comprise a plurality of spur gears having various teeth and recesses that are meshed and/or interconnected to one another.

FIG. 26B is a top perspective view of a distraction mechanism 50 and FIG. 26C is an enlarged top perspective view of distraction mechanism 50 with some parts removed for ease of understanding. In the example embodiment, third spur gear 54 may include teeth 54*a* symmetrically radially disposed on a side surface around the circumference of third spur gear 54 and a rack 54*b* may be radially disposed on a top surface of third spur gear 54 proximate the edge of spur gear 54, for example. Primary pawl 504 may be configured to engage circular rack 54*b* to allow spur gear 54 to rotate in a first direction (counter clockwise direction) and prevent third spur gear 54 from rotating in a second direction (clockwise direction). For example, primary pawl 504 may be disposed on a pivoting hinge and be biased such that a hook portion may be pushed downward against rack 54*b* such that the hook portion is meshed within a valley between any pair of the teeth of rack portion 54*b*, for example. In operation, an end user may rotate primary actuator 502 (via tool 10, e.g.) counter clockwise such that primary pawl 504 moves in and out of the various valleys between teeth of rack portion 54*b*. Notably, due to pawl 504 being biased against rack 54*b*, pawl 504 may prevent third spur gear 54 from rotating in the clockwise direction. For example, as arms 505, 507 are opened patient tissue may apply a closing force attempting to push arms 505, 507 back towards a closed position and pawl 504 may prevent and/or suppress arms 505, 507 from moving into a closed position. Additionally, in various embodiments pawl 504 may be depressible at a lateral end thereof opposite the hook portion that is engaged with rack 54b such that the hook portion of pawl 504 is moved upward in the vertical direction and prevented from engaging with rack 54b such that arms 505, 507 may be closed if and when desired. Furthermore, in FIG. 26C it is shown that spur gear 52 is meshed with rack portion 505d of arm 505 and rack portion 507d of arm 507. For example, rack portion 507d is meshed with a distal side of spur gear 52 and rack portion 505d is meshed with a proximate side of spur gear 52. Accordingly, rotation of spur gear 52 in a first direction will cause arms 505, 507 to distract outward by an equal amount and rotation of spur gear 52 in a second direction opposite the first direction will cause arms 505, 507 to retract inward by an equal amount. Alternatively, an end user may squeeze handles 501a, 501b to cause distraction and/or retraction by an equal amount which will also cause rotation of the various gears of distraction mechanism 50.

FIG. 26D is a bottom perspective view of distraction mechanism 50 and FIG. 26E is an enlarged bottom perspective view of distraction mechanism 50. In the example embodiment, the underside of partial spur gear 57 is shown as being meshed with spur gear 55 and being rotatably engaged with drive shaft 53. Additionally, suitable cutout portions 505z, 507z may be provided in the first handle 505 and second handle 507 that allow partial spur gear 57 to rotate a suitable distance when expanding arms 505, 507 such that partial spur gear 57 is fully contained within body 503 and does not clash with handles 505, 507, for example.

FIG. 27A is a top down view of a modular retractor 500 coupled to a table mount rack module 60 which is in turn coupled to a table mount 70. FIG. 27B is a perspective view of a modular retractor 500 coupled to a table mount rack module 60 which is in turn coupled to a table mount 70. In the example embodiment, the table mount 70 may be connected to and rigidly supported by a surgeons table via table mount portion 73, for example. Arms 72 and 71 may be adjustable by way of adjustment knob 74 to position table rack module 60 at a suitable location, for example.

FIGS. 28A and 28B are perspective views of a table mount rack module 60. FIG. 28C is an exploded parts view of table mount rack module 60. In the example embodiment, table mount rack module 60 may include an aperture 64 having a size and shape that corresponds to a size and shape of table mount arm 506 of modular retractor 500, for example. Depressible lever 65 may be used to lock table mount arm 506 when table mount arm 506 is insert inside of aperture 64, for example as shown in FIGS. 27A and 27B. Additionally, table mount arm 506 may slide in and out of aperture 64 to facilitate positioning modular retractor 500, for example. Table mount module 60 may include a connection arm 63, which may be insert into a corresponding aperture of table mount 70, for example as shown in FIGS. 27A and 27B to secure table mount rack module 60 to table mount 70. Connection arm 63 may be rigidly secured to body portion 66, for example. Additionally, extendable arm 67 may slide forward and backward through body 66 by a rack and pinion mechanism. For example, actuators 61, 62 may be securely coupled to body 66 and may each have pinion portions 61a, 62a having teeth that engage with rack portion 67a of extendable arm 67. Accordingly, rotation of actuator 61 and/or actuator 62 may rotate pinion portions 61a and/or 62a such that teeth of pinion portions 61a, 62a cause extendable arm 67 to move forward and/or backward depending on the direction actuators 61 and/or 62 are rotated. Additionally, table mount rack module 60 may include a pawl 68 having a first hook portion 68a and/or a second hook portion 68b, for example. Pawl 68 may be pivotally coupled to body portion 66 at a pivot location 66b by a pin, for example. Pivot location 66b may enable pawl 68 to be toggled between a first position where pawl 68 allows extendable arm 67 to move forward but prevents extendable arm 67 from moving backward in the opposite direction. Similarly, in various embodiments, pawl 68 may be toggled to a second position where pawl 68 allows extendable arm 67 to move backward but prevents extendable arm 67 from moving forward. In some embodiments, pawl 68 may be moved to a third position, in the middle of the first position and second position, where pawl 68 prevents extendable arm 67 from moving forward and backwards. For example, in some embodiments, and in a third position pawl 68 may lock extendable arm 67 from relative motion in the forward and backwards direction. Other embodiments may utilize a locking element (not illustrated) to secure extendable arm 67 in an appropriate position. In this way, table rack module 60 may facilitate the relative motion of modular retractor 500 forward and backward in a direction defined by axis D-D of extendable arm 67. Additionally, table rack module 60 may facilitate the relative motion of modular retractor 500 from side to side in a direction defined by an extension direction C-C of table mount 506 (see FIG. 22), for example.

Figure 29:
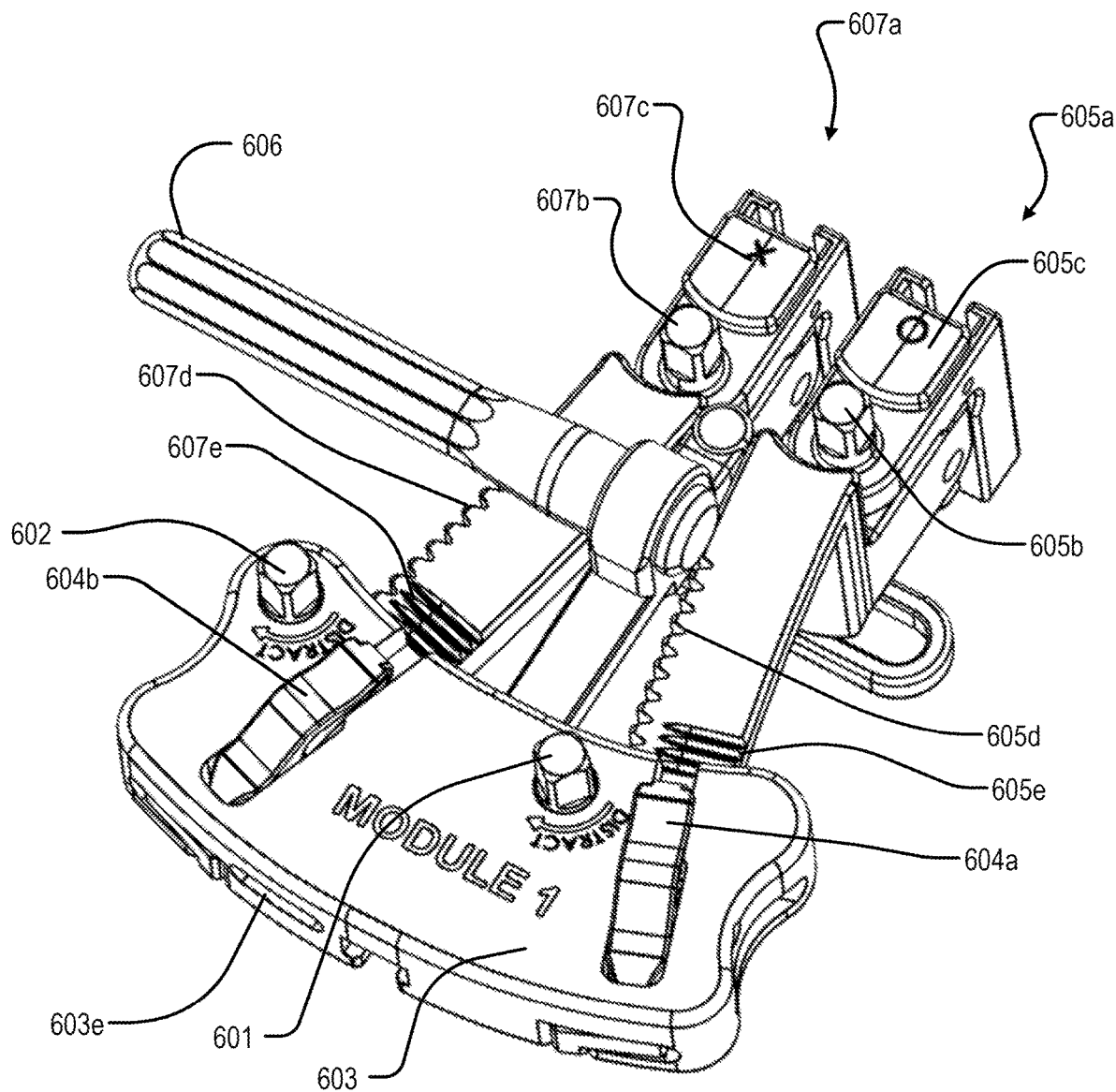
FIG. 29 is a top perspective view of a first module for use with disclosed modular retractor embodiments.
Figure 30:
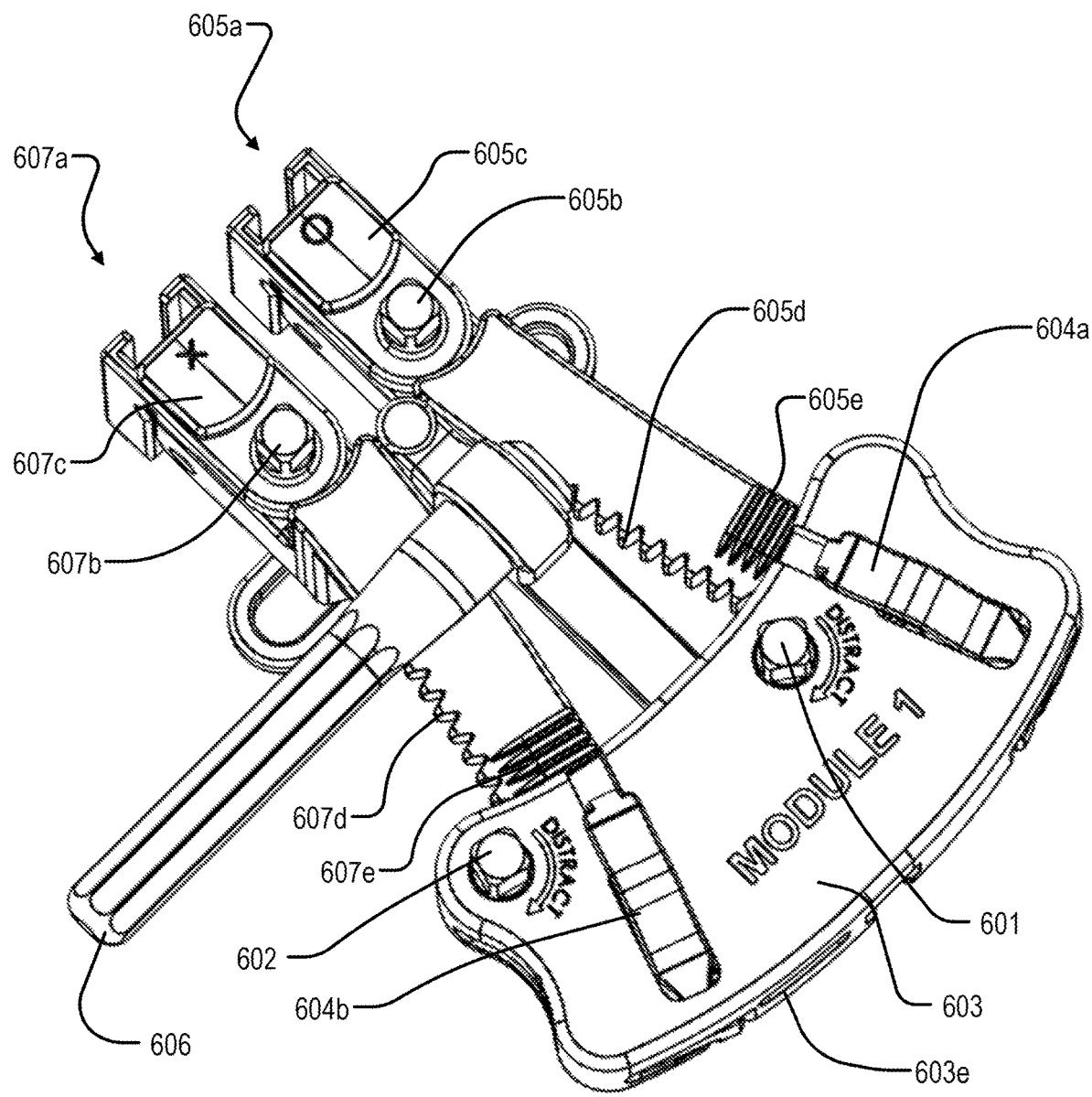
FIG. 30 is a top perspective view of a first module for use with disclosed modular retractor embodiments.
Figure 31A:
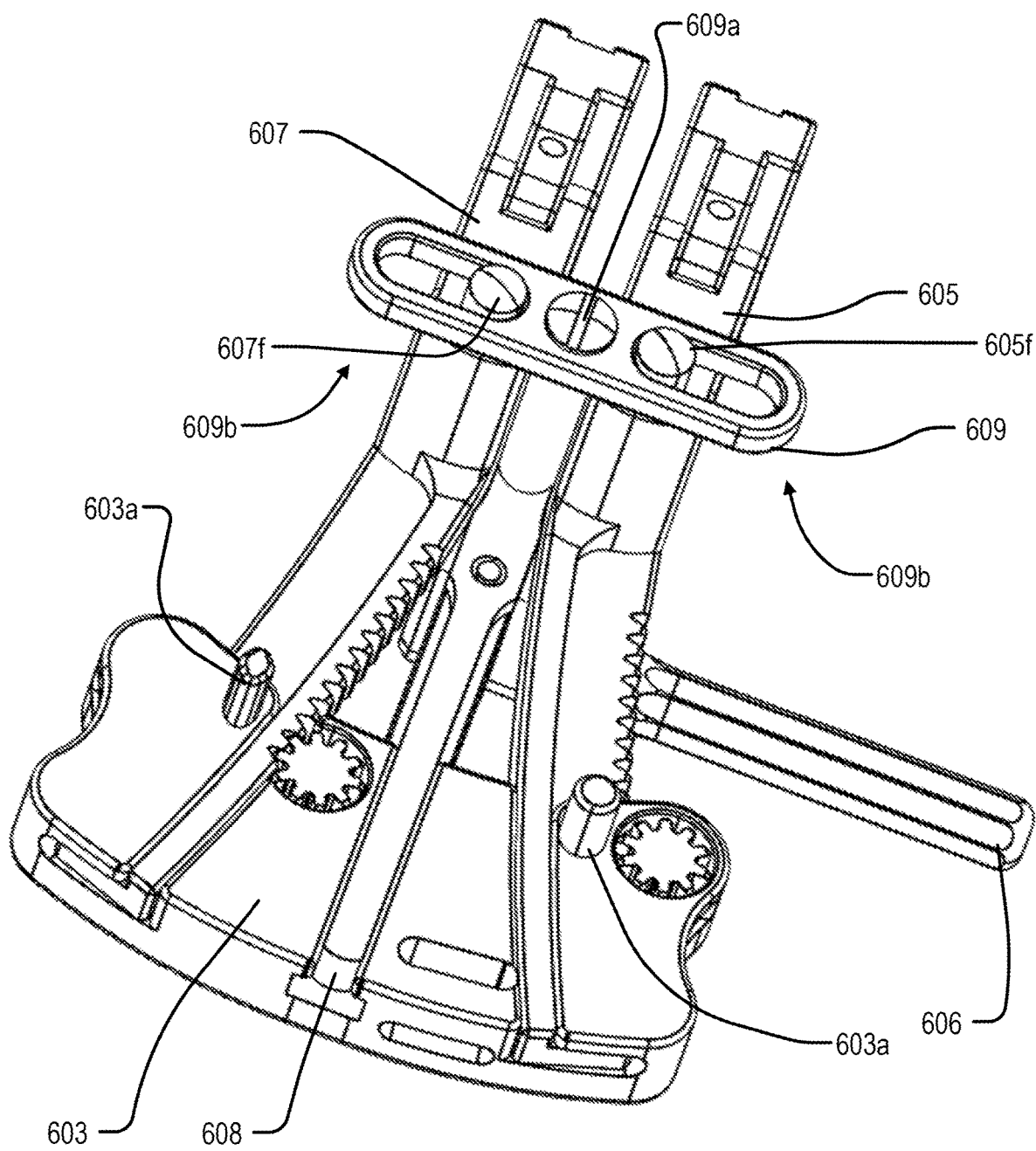
FIG. 31A is a bottom perspective view of a first module for use with disclosed modular retractor embodiments.
Figure 31B:
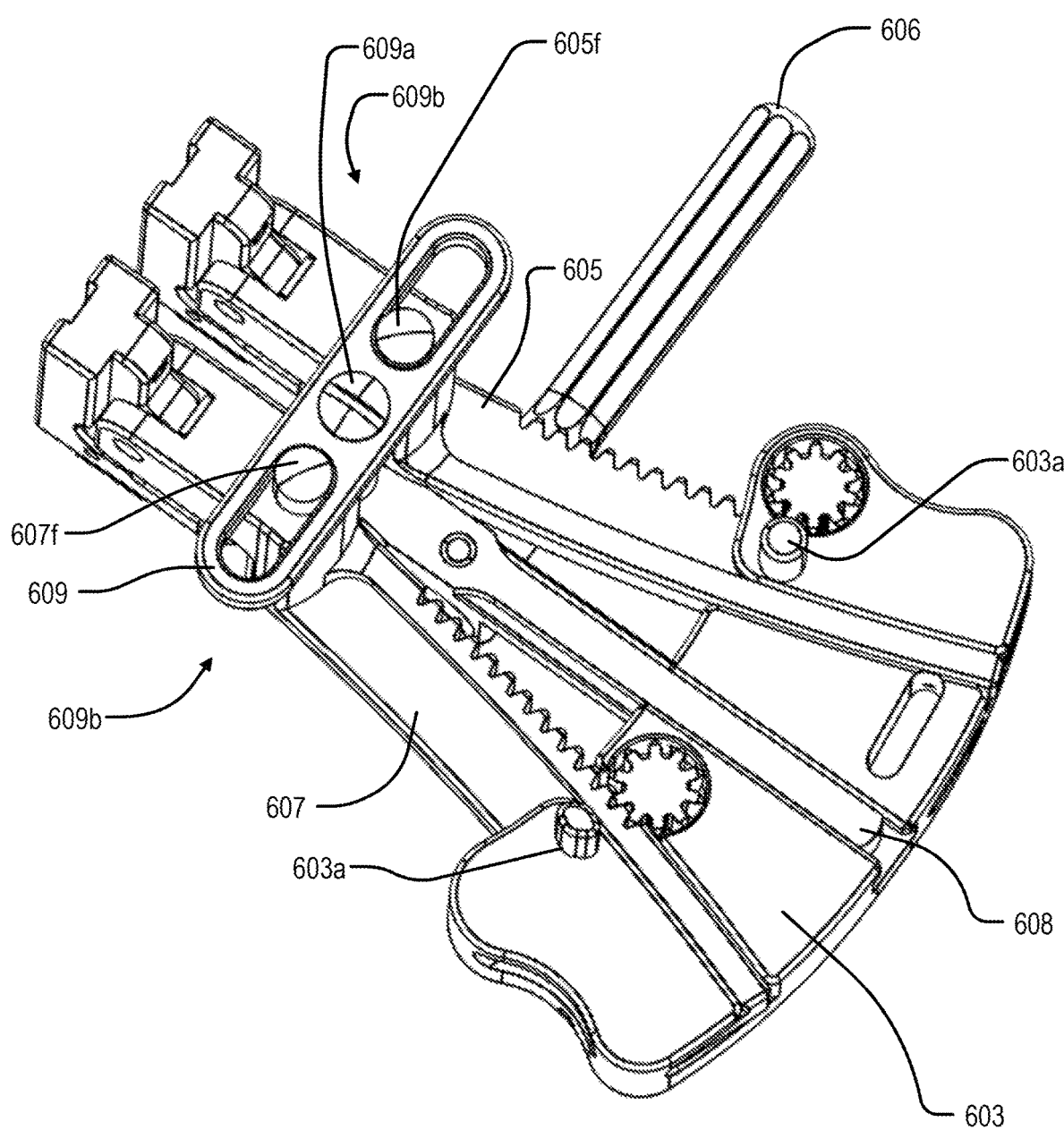
FIG. 31B is a bottom perspective view of a first module for use with disclosed modular retractor embodiments.
Figure 32:
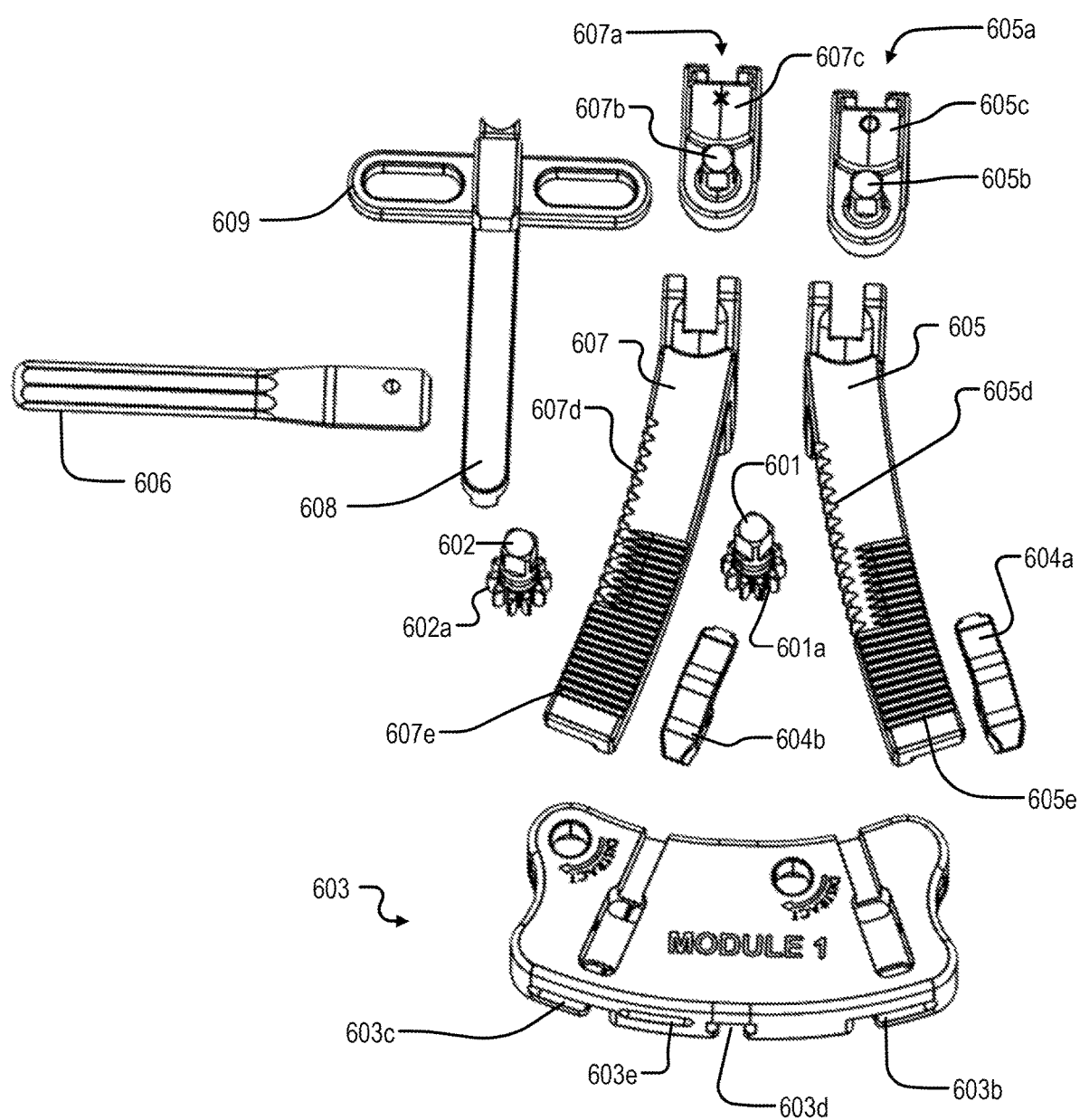
FIG. 32 is an exploded parts view of a first module for use with disclosed modular retractor embodiments.
Figure 33A:
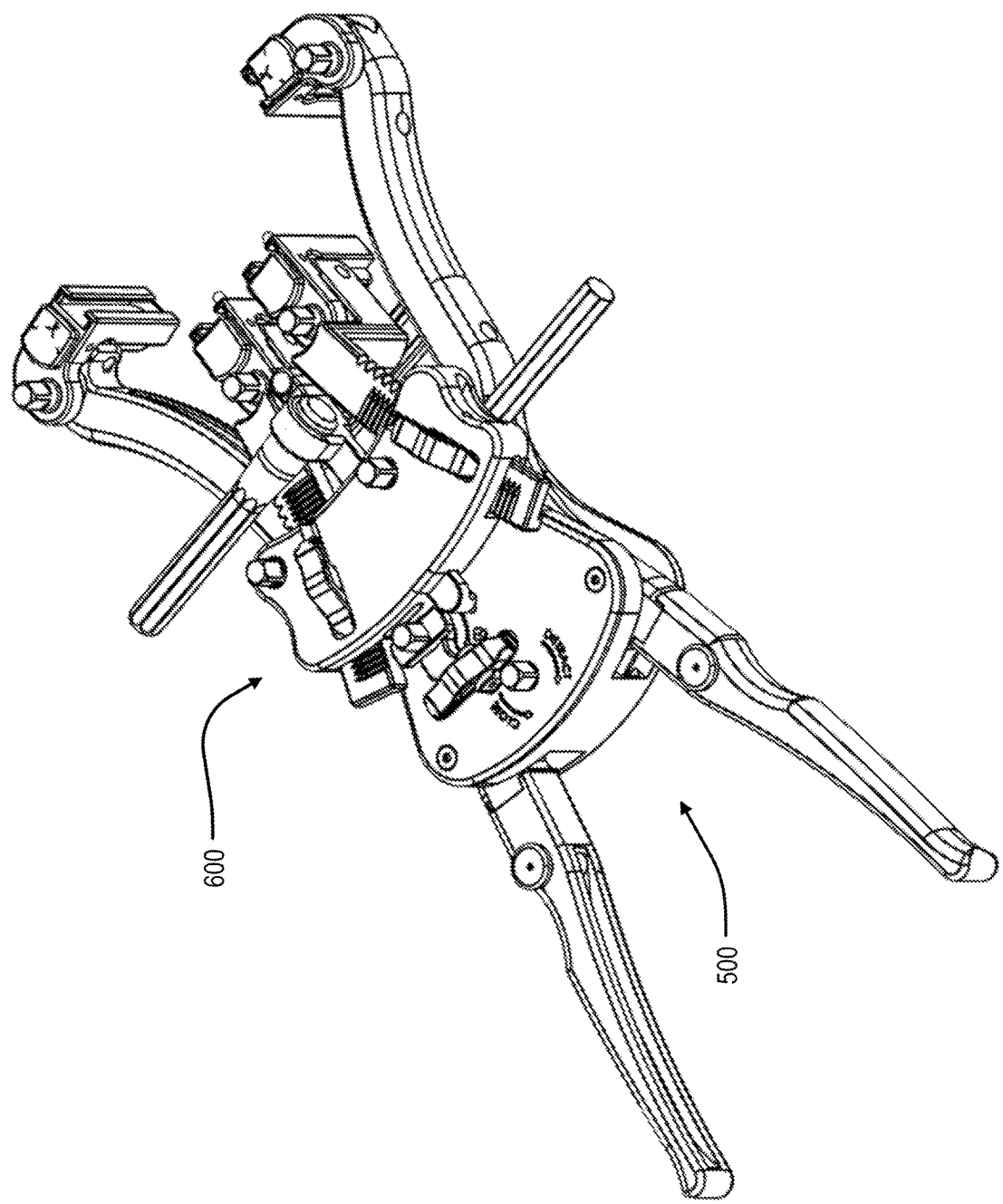
FIG. 33A is a perspective view of a first module coupled to a modular retractor.
Figure 33B:
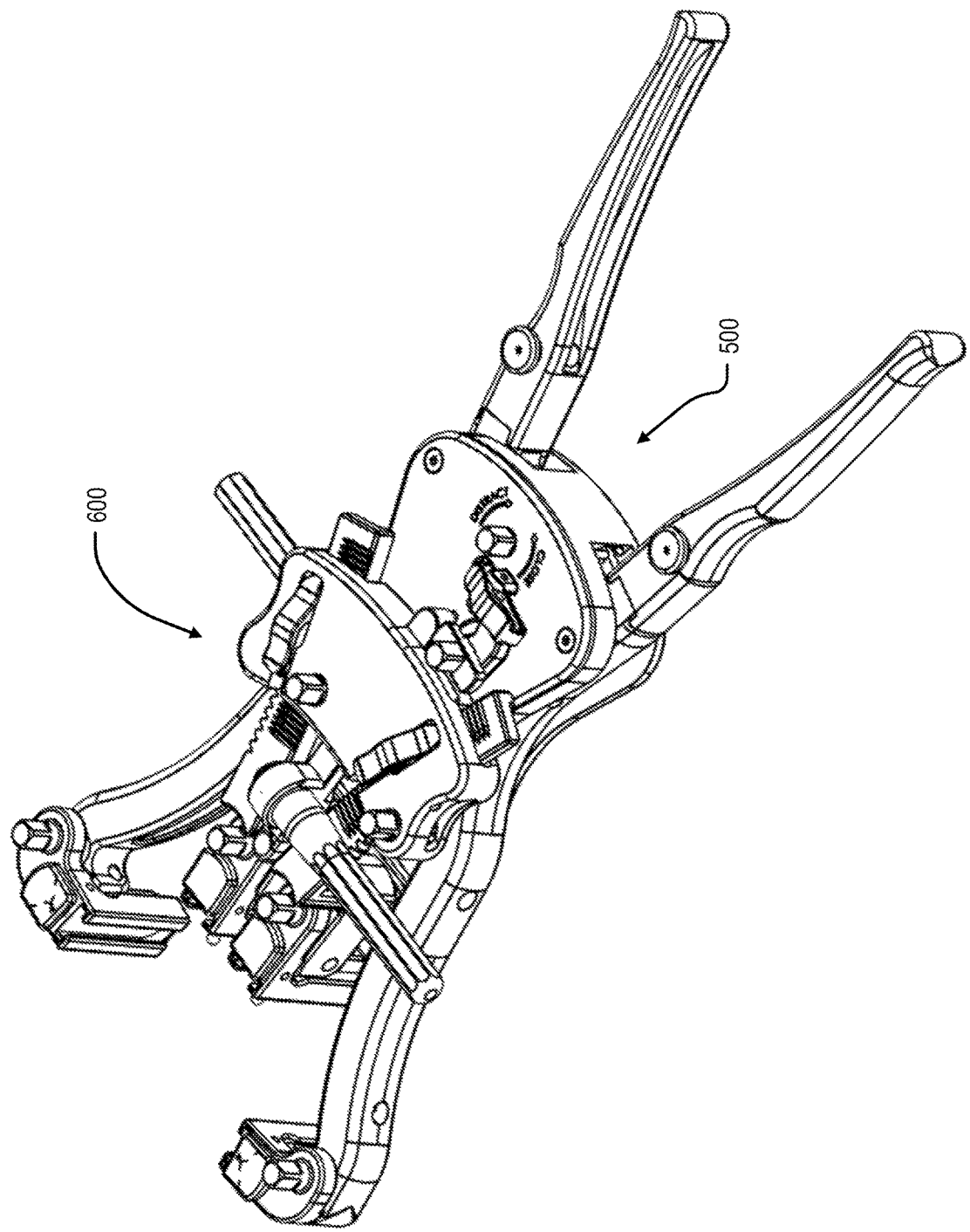
FIG. 33B is a perspective view of a first module coupled to a modular retractor.
Figure 34:
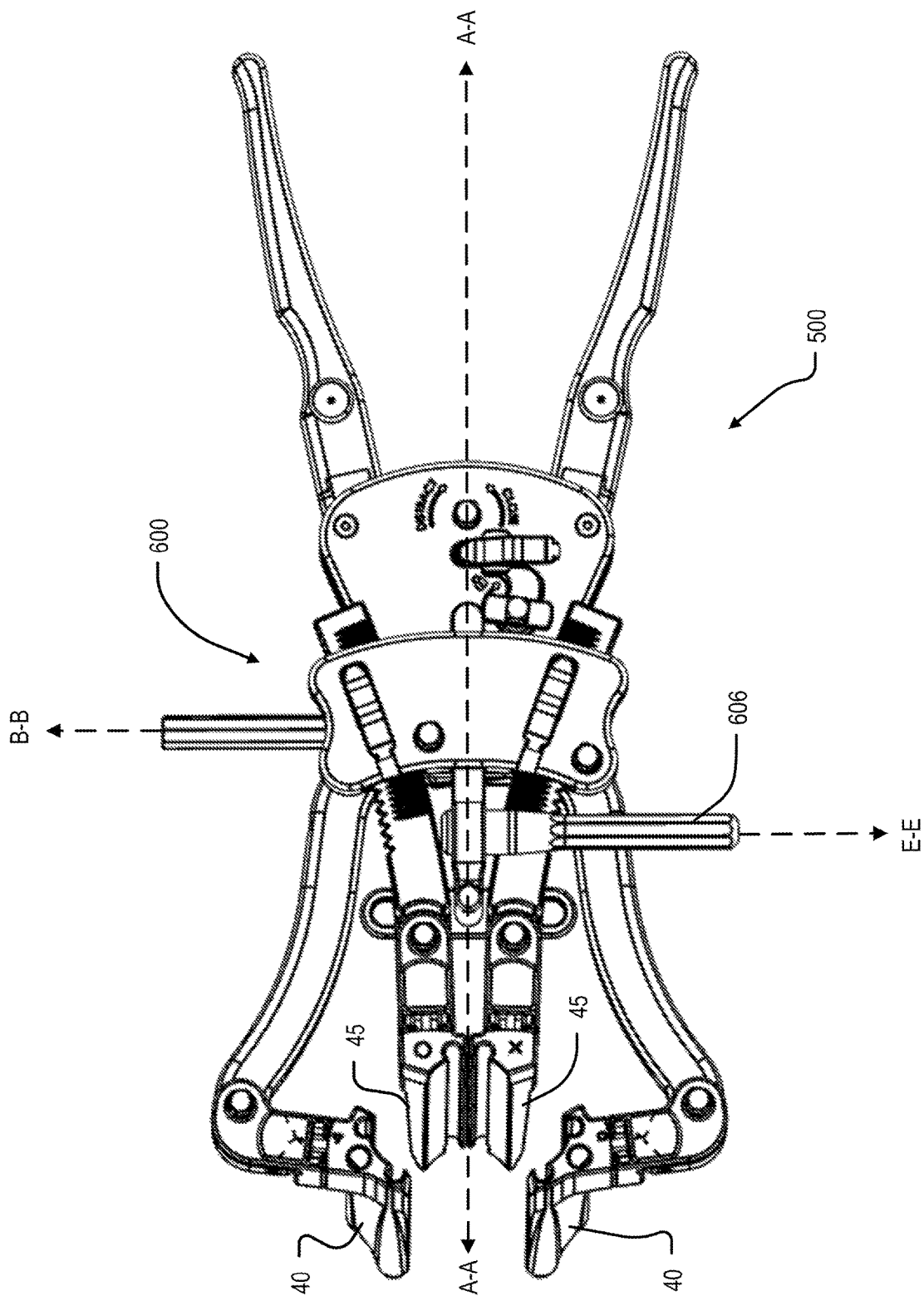
FIG. 34 is a top down view of a first module coupled to a modular retractor and a plurality of blades.

Referring generally to FIGS. 29-34 a first module 600 is disclosed. FIGS. 29 and 30 are top perspective views of a first module 600 and FIGS. 31A and 31B are bottom perspective views of a first module 600. FIG. 32 is an exploded parts view of a first module 600 and FIGS. 33A-34 are various perspective views of first module 600 coupled to modular retractor 500.

In accordance with disclosed embodiments, first module 600 may be configured to couple and uncouple from modular retractor 500 at connection points 503a, for example (see FIG. 20). In various embodiments, the first module 600 may have at least one corresponding connection point 603a on an underside thereof (see FIG. 31A) configured to couple, connect, and/or mate with a connection point 503a of the modular retractor 500. In the example embodiment, connection points 503a are indented apertures and connection points 603a are outdented posts having a corresponding size and shape to one another, respectively. In some embodiments, connection points 503a, 603a, may have slotted rails and/or grooves to facilitate a connection and/or prevent rotation of first module 600 relative to modular retractor 500, for example. Similarly, and in the example embodiment, one connection point of connection points 603a may be shaped like a circular post and the other connection point 603a may be shaped like an oval post to facilitate mating the first module 600 with modular retractor 500 in an appropriate orientation. Additionally, first module 600 may be locked to modular retractor 500 by lock 513 (see FIG. 20). Lock 513 may be pivotable such that in a locked position a flange portion of lock 513 may pivot into a locking aperture 603e of first module 600, for example. Similarly, in an unlocked position the flange portion of lock 513 may be unseated from aperture 603e. Other embodiments may use alternate means to securely engage the modular retractor 500 with the first module 600, e.g., as fasteners, hexagonal grooves, channel locks, magnets, etc. provided that the modular retractor 500 and the first module 600 are securely engaged with one another such that resultant forces acting on the modular retractor 500 may transfer between modular retractor 500 and first module 600.

First module 600 may include a first arm 605 and a second arm 607 that extend through body 603. First arm 605 may extend through body 603 through a first contoured channel 603b and second arm 607 may extend through body 603 through a second contoured channel 603c, for example (see FIG. 32). In various embodiments, contoured channels 603b, 603c may be L shaped channels. First module 600 may be configured to independently extend first arm 605 along a first path of travel and independently extend second arm 607 along a second path of travel by independent rack and pinion mechanisms, for example. The first path and second path may be an arcuate path or segment defined by the length and geometry of the arms 605 and 607, for example. In various embodiments, the first path and second path may symmetrically fan out with respect to one another. Other paths of travel than those specifically shown are contemplated, e.g., a linear path.

First module 600 may include a table mount 606 extending laterally from a side surface thereof. Table mount 606 may facilitate the relative motion of first module 600 (and/or modular retractor 500 when coupled thereto) from side to side in a direction defined by an extension direction E-E of table mount 606 (see FIG. 34), for example. Table mount 606 may be securely coupled to sliding frame 608. Sliding frame 608 may be configured to slide forward and backward through sliding frame aperture 603d of body 603, for example (see FIG. 32). Additionally, in various embodiments, sliding frame 608 may be configured to support first and second arms 605, 607 at a bottom surface of first and second arms 605, 607 proximate first pivoting member 605a and second pivoting member 607a, respectively (see FIGS. 31A and 31B). In various embodiments, support portion 609 may be pivotable relative to sliding frame 608 by pivot point 609a, for example. In various embodiments, the first arm 605 may include first post 605f and second arm 607 may include second post 607f that extend through corresponding slotted apertures 609b, respectively, of support portion 609. In this way, and due in part to the size and geometry of the slotted apertures 609b, support portion 609 may support both first arm 605 and second arm 607 while also enabling first and second arms 605, 607 to be independently movable relative to one another, for example. In some embodiments, pivot point 609a may be replaced by a non pivoting fastener such that first arm 605 and second arm 607 are not independently movable relative to one another (not illustrated) and distract and retract by equal amounts.

First module 600 may be configured to extend first arm 605 by activation of actuator 601, e.g., by rotation of actuator 601. Actuator 601 may be securely attached to body portion 603 and include a pinion portion 601a (pinion gear and/or spur gear) having teeth that engage with and are meshed with curved rack portion 605d disposed on a side surface of first arm 605, for example. Accordingly, rotation of actuator 601 may rotate pinion portion 601a such that teeth of pinion portion 601a causes first arm 605 to move forward and/or backward depending on the direction actuator 601 is rotated. Additionally, first module 600 may include a first pawl 604a that may be configured to engage the curved rack portion 605e disposed on a top surface of first arm 605, for example. First pawl 604a may be configured to allow pinion portion 601a to rotate in a first direction (counter clockwise direction) and prevent pinion portion 601a from rotating in a second direction (clockwise direction). For example, first pawl 604a may be disposed on a pivoting hinge and be biased by a spring or the like such that a hook portion may be pushed downward against rack 605e such that the hook portion is meshed within a valley between any pair of the teeth of rack portion 605e, for example. In operation, an end user may rotate actuator 601 (via tool 10, e.g.) counter clockwise such that pawl 604a moves in and out of the various valleys between teeth of rack portion 605e while first arm 605 extends outward away from body 603. Notably, due to pawl 604e being biased against rack portion 605e, pawl 604a may prevent first arm 605 from being pushed in an opposite direction. For example, as arm 605 is distracted outward patient tissue may apply a closing force attempting to push arm 605 back towards body 603 and pawl 604a may prevent and or suppress this closing force. Additionally, in various embodiments pawl 604a may be depressible at a lateral end thereof opposite the hook portion that is engaged with rack 605e such that the hook portion of pawl 604a is moved upward in the vertical direction and prevented from engaging with rack 605e such that arm 605 may be closed if and when desired.

First module 600 may be configured to extend second arm 607 by activation of actuator 602, e.g., by rotation of actuator 602. Actuator 602 may be securely attached to body portion 603 and include a pinion portion 602a (pinion gear and/or spur gear) having teeth that engage with and are meshed with curved rack portion 607d disposed on a side surface of second arm 607, for example. Accordingly, rotation of actuator 602 may rotate pinion portion 602a such that teeth of pinion portion 602a causes second arm 607 to move forward and/or backward depending on the direction actuator 602 is rotated. Additionally, first module 600 may include a second pawl 604b that may be configured to engage the curved rack portion 607e disposed on a top surface of second arm 607, for example. Second pawl 604b may operate in the same, substantially the same, and/or similar manner as explained above with respect to first pawl 604a. Accordingly, duplicative description will be omitted.

In various embodiments, the first and second arms 605, 607 may be coupled to first and second pivoting members 605a, 607a at a distal end thereof, respectively. The first and second pivoting members 605a, 607a may be configured to operably couple to third blade 45 and fourth blade 45, respectively, by a corresponding blade attachment mechanism 605c, 607c. In the example embodiment, a first blade actuator 605b and a second blade actuator 607b are configured to adjust the angulation of blades 45 respectively (see FIG. 34). For example, the first blade actuator 605b may be configured to actuate the first pivoting member 605a to adjust the angulation of blade 233 with respect to the first arm 605. Similarly, the second actuator 607b may be configured to actuate the second pivoting member 607a to adjust the angulation of blade 234 disposed therein with respect to second arm 607. In the example embodiment, the first pivoting member 605a may be configured to independently adjust the angulation of a blade with respect to the first arm 605 upon actuation of the first actuator 605b. Similarly, the second pivoting member 607a may be configured to independently adjust the angulation of a second blade with respect to the second arm 607 upon actuation of the second actuator 607b. In disclosed embodiments, the first and second pivoting members 605a, 607a may each include a corresponding pin and socket mechanism enabling the pivoting members to pivot, for example.

Figure 35:
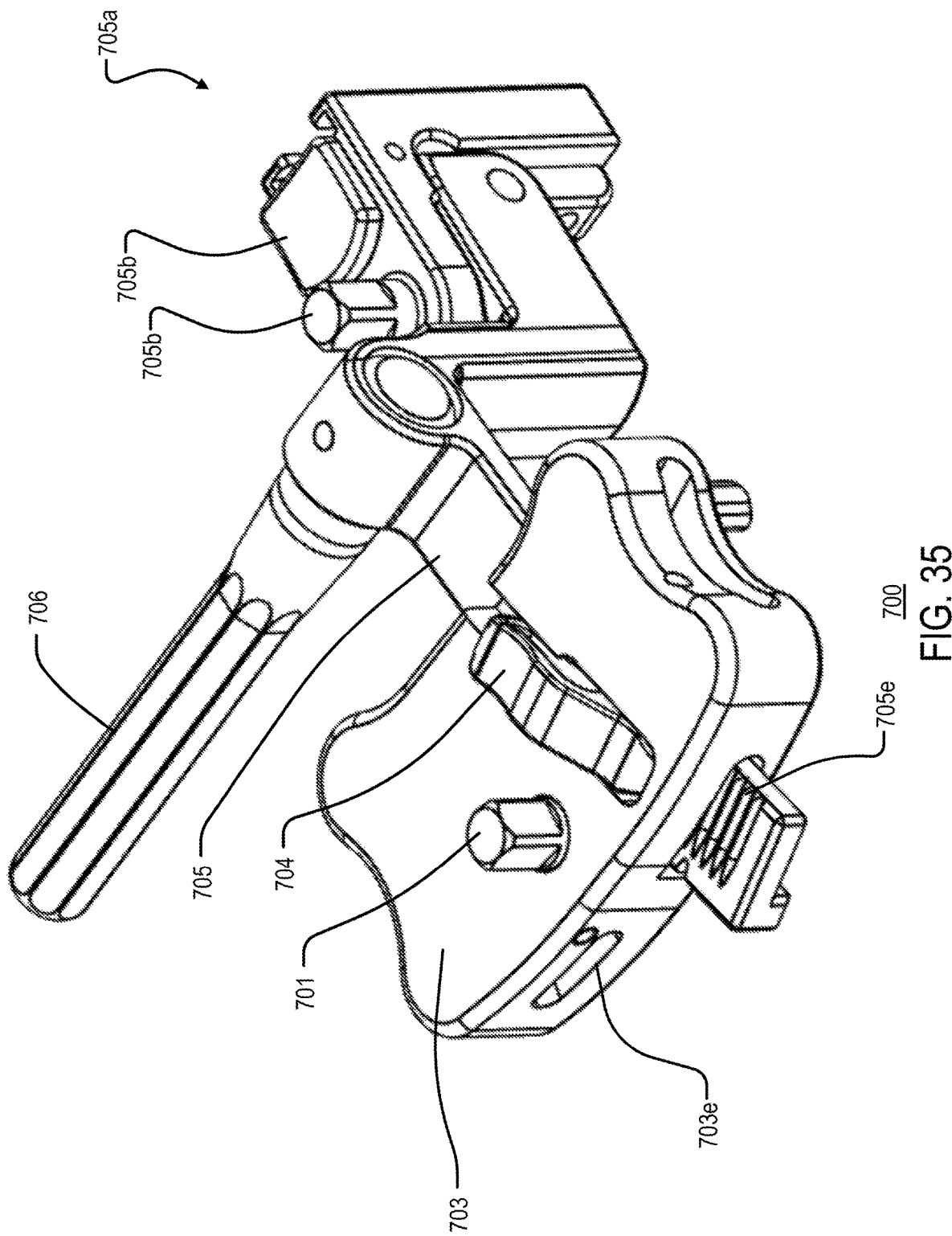
FIG. 35 is a top perspective view of a second module for use with disclosed modular retractor embodiments.
Figure 36:
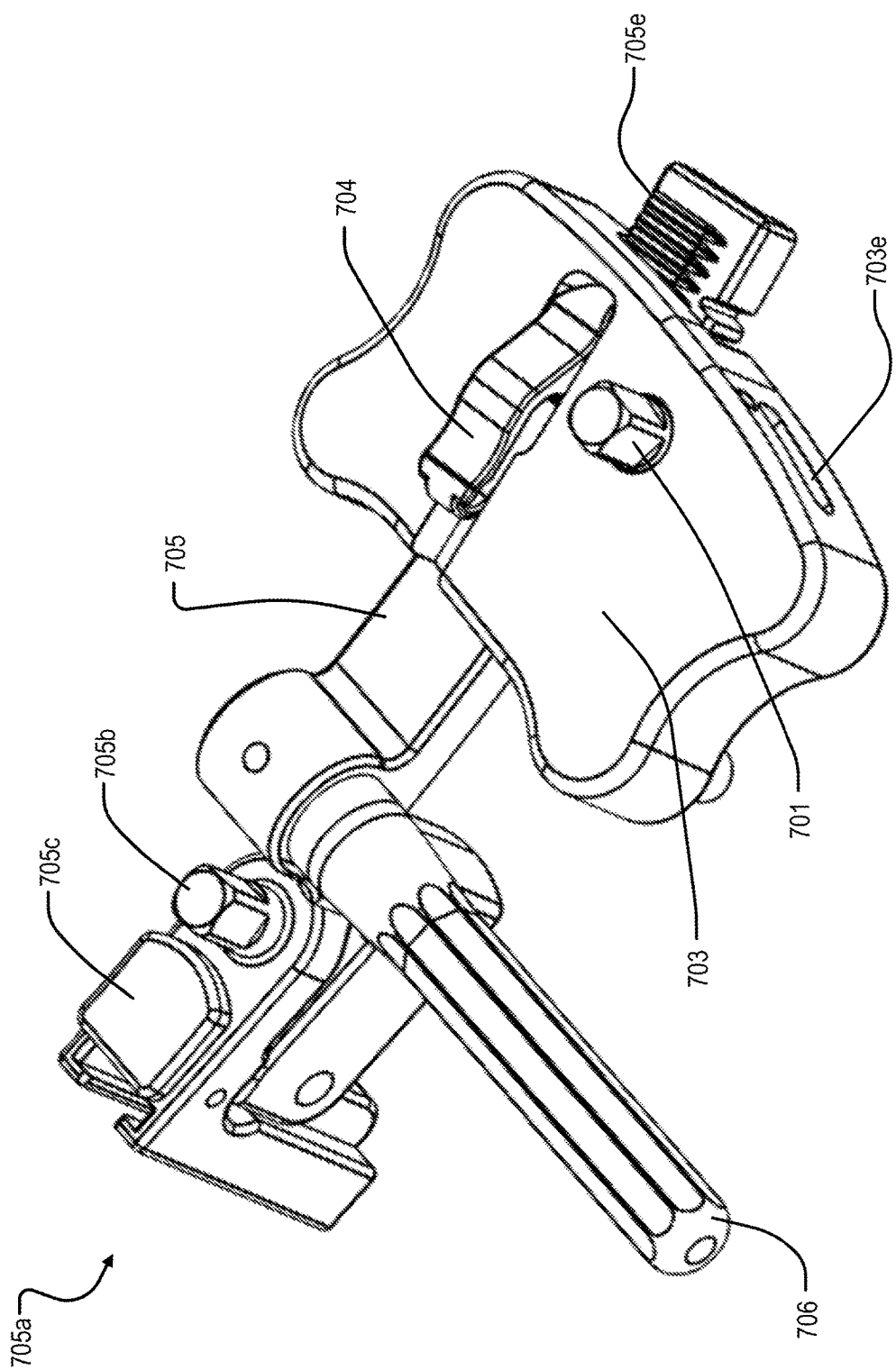
FIG. 36 is a top perspective view of a second module for use with disclosed modular retractor embodiments.
Figure 37:
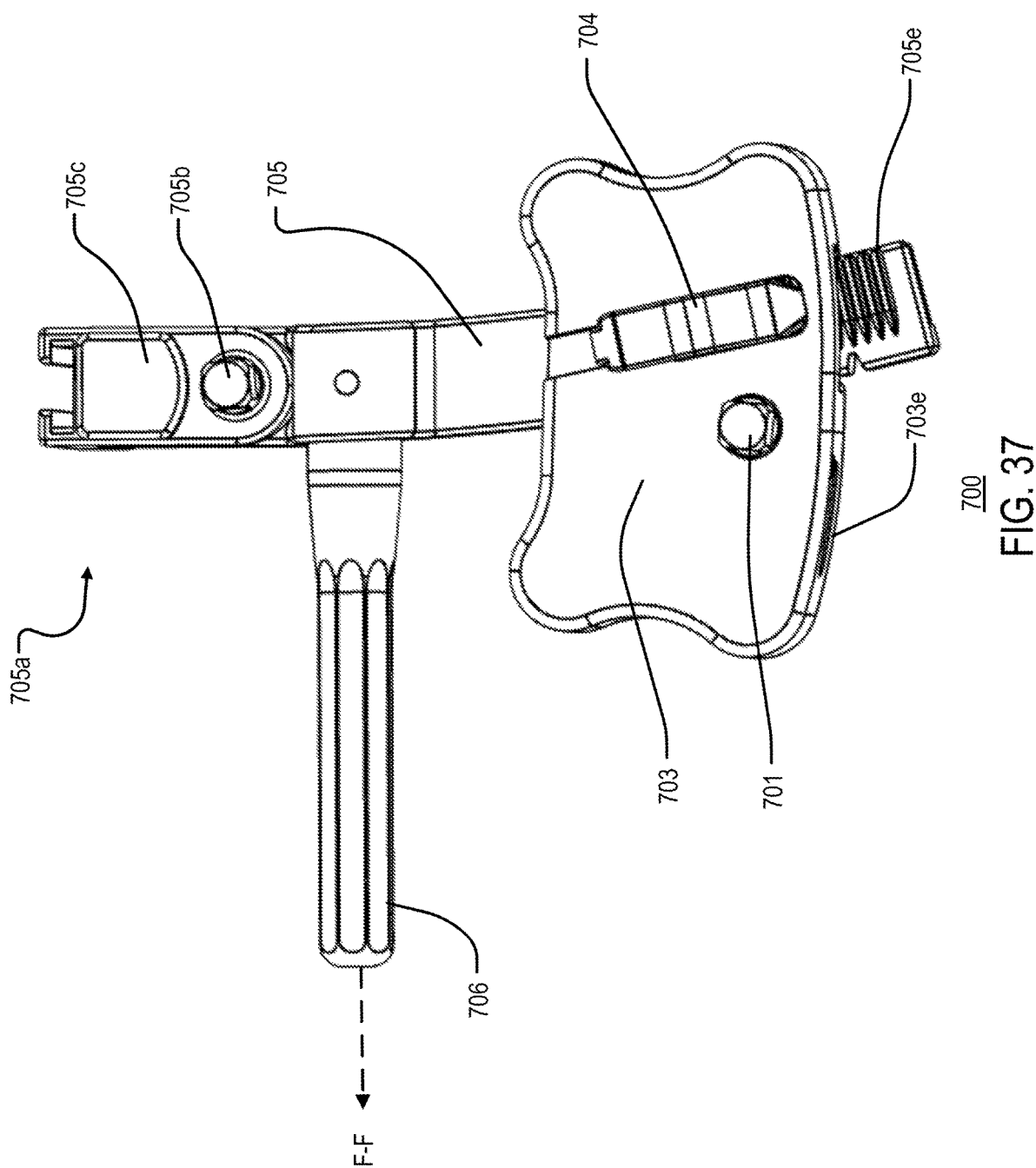
FIG. 37 is a bottom perspective view of a second module for use with disclosed modular retractor embodiments.
Figure 38:
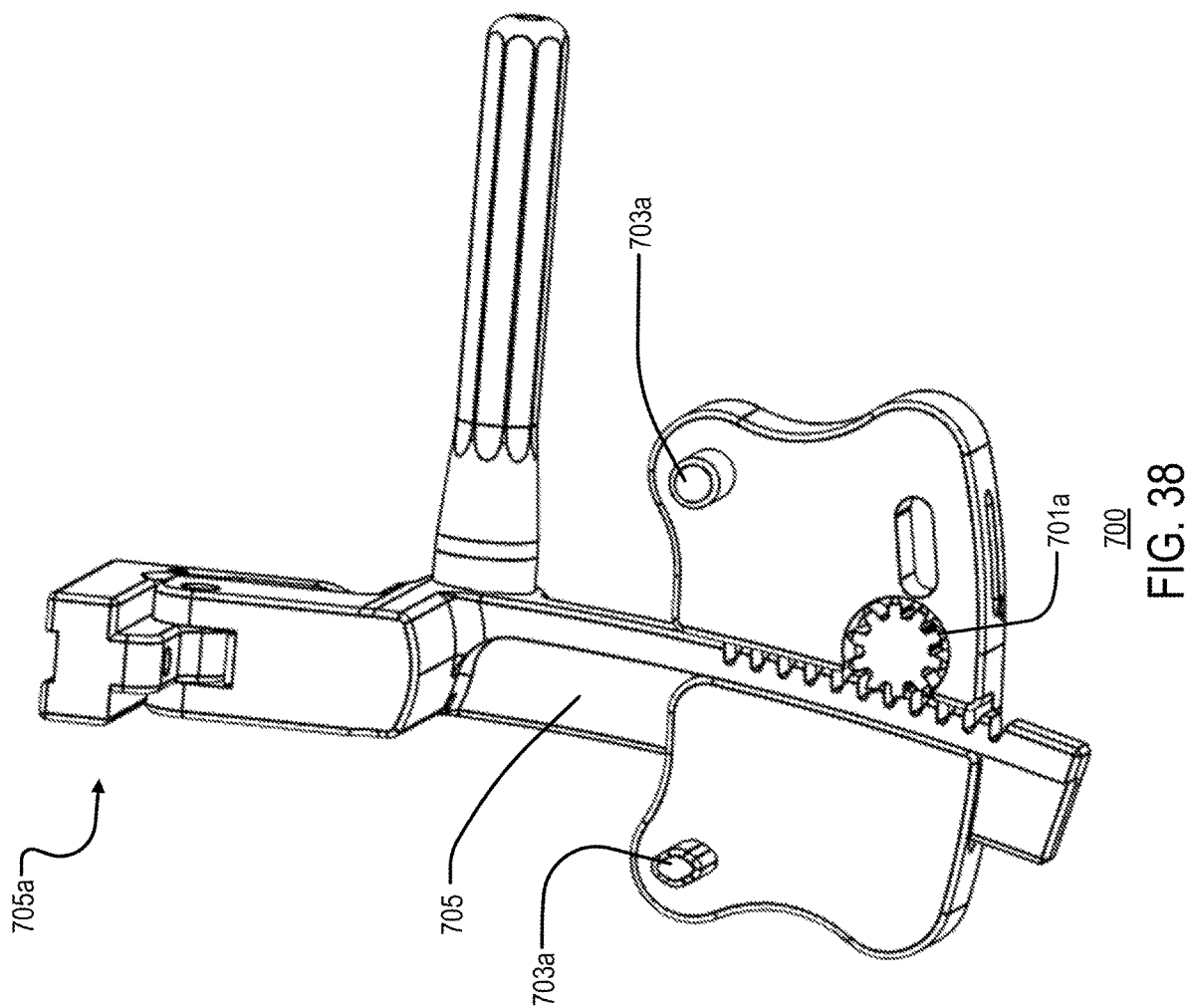
FIG. 38 is a bottom perspective view of a second module for use with disclosed modular retractor embodiments.
Figure 39:
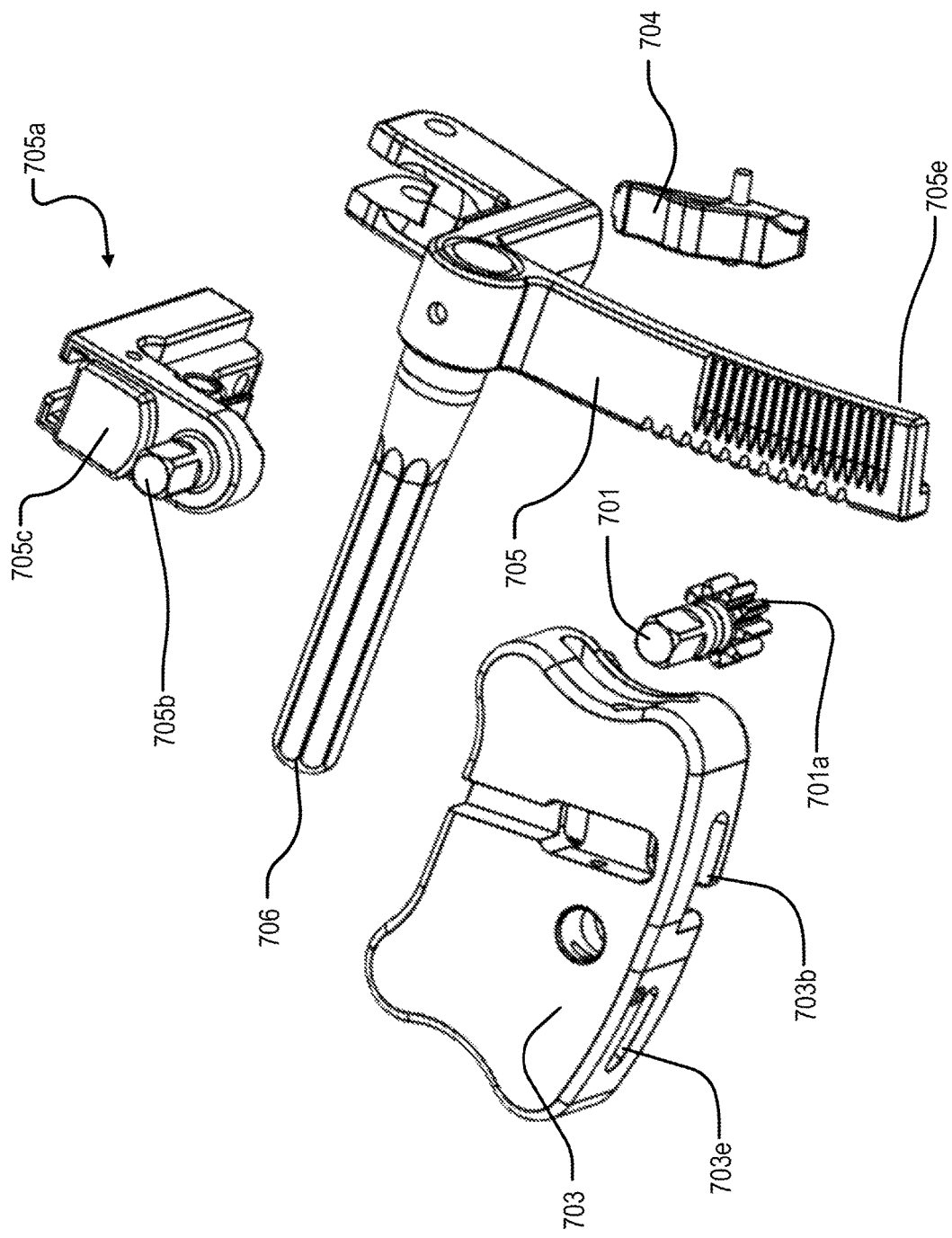
FIG. 39 is an exploded parts view of a second module for use with disclosed modular retractor embodiments.
Figure 40:
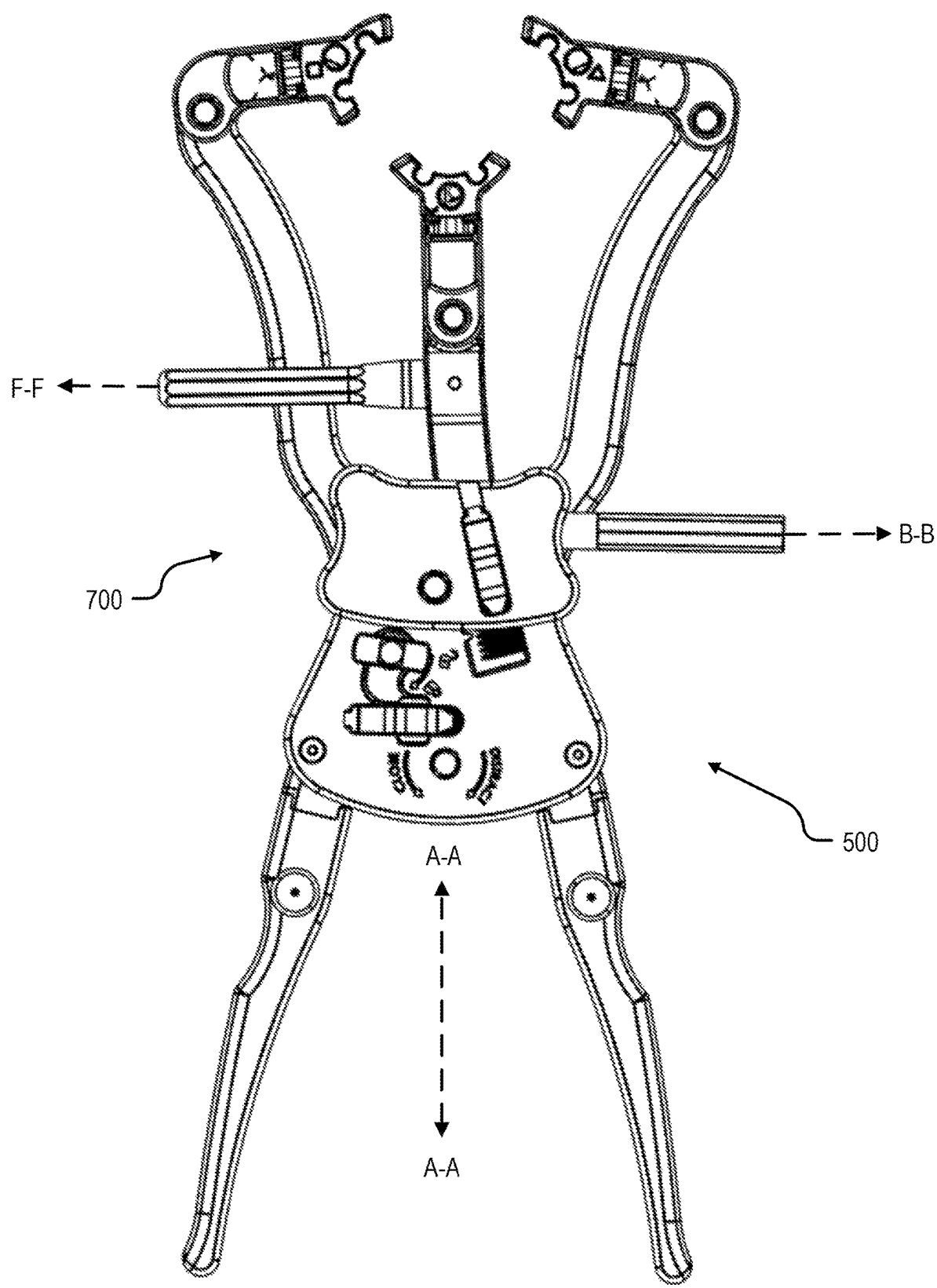
FIG. 40 is a top down view of a second module coupled to a modular retractor and a plurality of blades.

Referring generally to FIGS. 35-40 a second module 700 for use with modular retractor 500 is disclosed. FIGS. 35-36 are various top perspective views of a second module 700 and FIGS. 36-37 are various bottom perspective views of a second module 700 for use with disclosed modular retractor 500 embodiments. FIG. 39 is an exploded parts view of a second module 700 and FIG. 40 is a top down view of a second module coupled to modular retractor 500 and a plurality of blades.

In accordance with disclosed embodiments, second module 700 may be configured to couple and uncouple from modular retractor 500 at connection points 503*a*, for example (see FIG. 20). For example, the second module 700 may have at least one corresponding connection point 703*a* on an underside thereof (see FIG. 38) configured to couple, connect, and/or mate with a connection point 503*a* of the modular retractor 500 in the same, similar, and/or substantially the same manner as explained above. Accordingly, duplicative description will be omitted. Additionally, second module 700 may be locked to modular retractor 500 by lock 513 (see FIG. 20). Lock 513 may be pivotable such that in a locked position a flange portion of lock 513 may pivot into a locking aperture 703*e* of second module 700, in the same, similar, and/or substantially the same manner as explained above. Accordingly, duplicative description will be omitted.

Second module 700 may include an arm 705 that extends through body 703. Arm 705 may extend through body 703 through a first contoured channel 703*b*. Second module 700 may be configured to extend arm 705 along a path of travel by a rack and pinion mechanism, for example. The path of travel may be an arcuate path or segment defined by the length and geometry of arms 705, for example. Other paths of travel than those specifically shown are contemplated, e.g., a linear path.

Second module 700 may include a table mount 706 extending laterally from a side surface thereof. Table mount 706 may facilitate the relative motion of second module 700 (and/or modular retractor 500 when coupled thereto) from side to side in a direction defined by an extension direction F-F of table mount 706 (see FIG. 40), for example. Table mount 706 may be securely coupled directly to arm 705 (see FIG. 39), for example. Second module 700 may be configured to extend arm 705 by activation of actuator 701, e.g., by rotation of actuator 701. Actuator 701 may be securely attached to body portion 703 and include a pinion portion 701*a* (pinion gear and/or spur gear) having teeth that engage with and are meshed with curved rack portion 705*d* disposed on a side surface of arm 705, for example. Accordingly, rotation of actuator 701 may rotate pinion portion 701*a* such that teeth of pinion portion 701*a* cause arm 705 to move forward and/or backward depending on the direction actuator 701 is rotated. Additionally, second module 700 may include a first pawl 704 that may be configured to engage the curved rack portion 705*e* disposed on a top surface of arm 705, for example. First pawl 704 may be configured to allow pinion portion 701*a* to rotate in a first direction (counter clockwise direction) and prevent pinion portion 701*a* from rotating in a second direction (clockwise direction) in the same, similar, and/or substantially the same manner as previously explained. Accordingly, duplicative description will be omitted.

In various embodiments, arm 705 may be coupled to pivoting member 705*a* at a distal end thereof. Pivoting member 705*a* may be configured to operably couple to a blade 35 by blade attachment mechanism 705*c*. In the example embodiment, blade actuator 705*b* may be configured to adjust the angulation of blade 35 (see FIG. 40). For example, the blade actuator 705*b* may be configured to actuate the first pivoting member 705*a* to adjust the angulation of blade 35 with respect to arm 705. In disclosed embodiments, the first pivoting member 705*a* may include a corresponding pin and socket mechanism enabling pivot member 705*a* to pivot, for example.

Figure 41A:
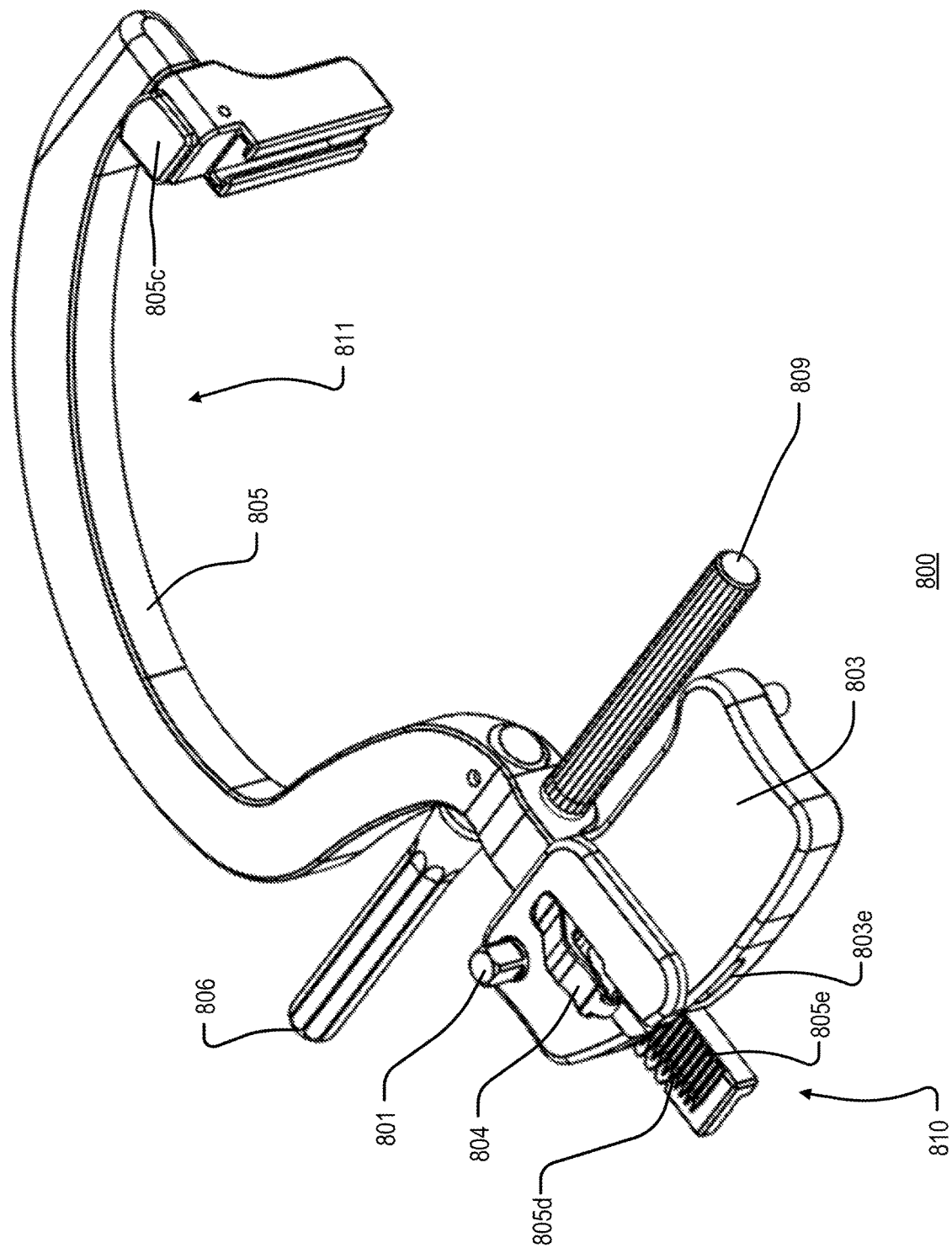
FIG. 41A is a top perspective view of a third module for use with disclosed modular retractor embodiments.
Figure 41B:
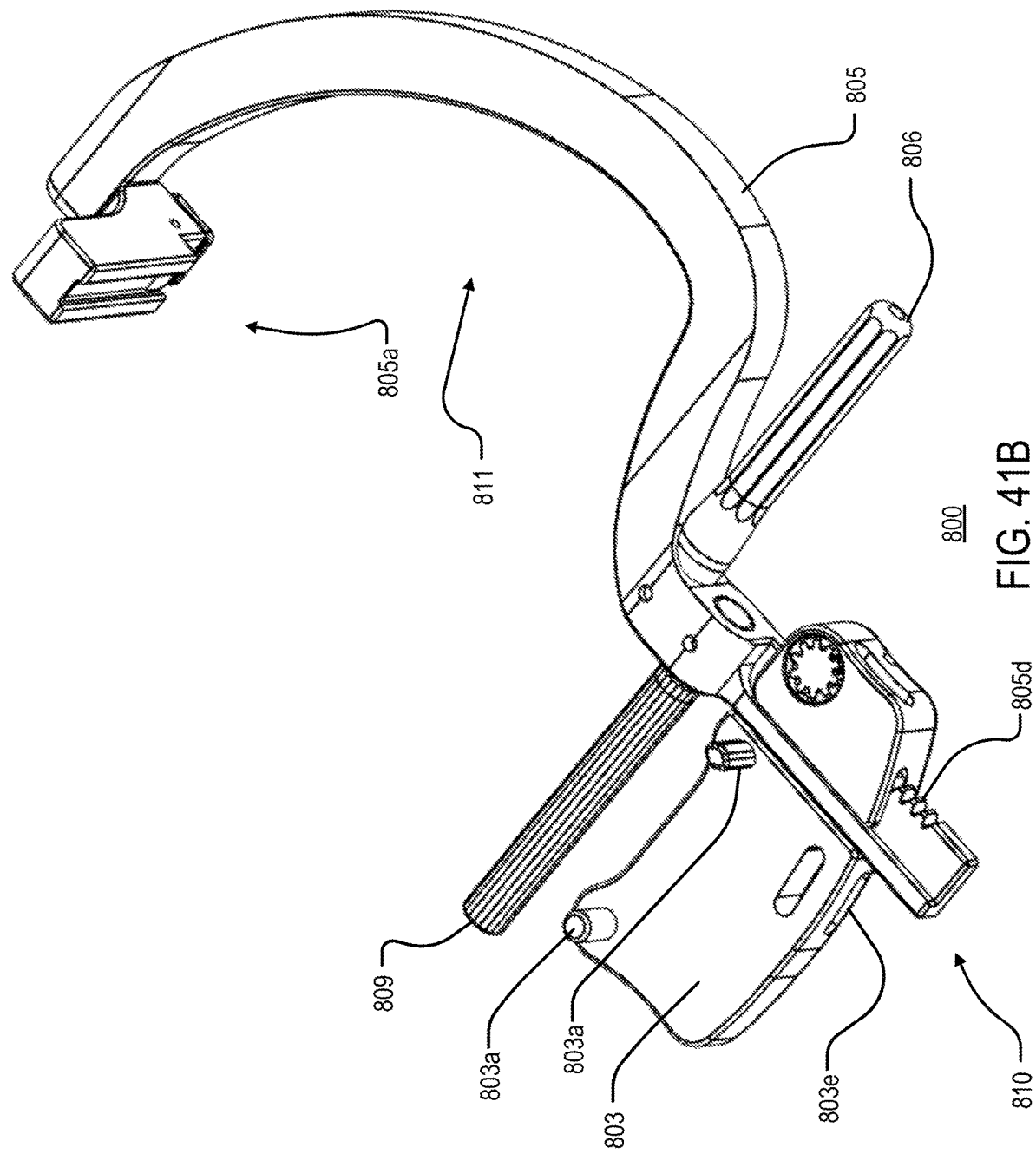
FIG. 41B is a bottom perspective view of a third module for use with disclosed modular retractor embodiments.
Figure 42:
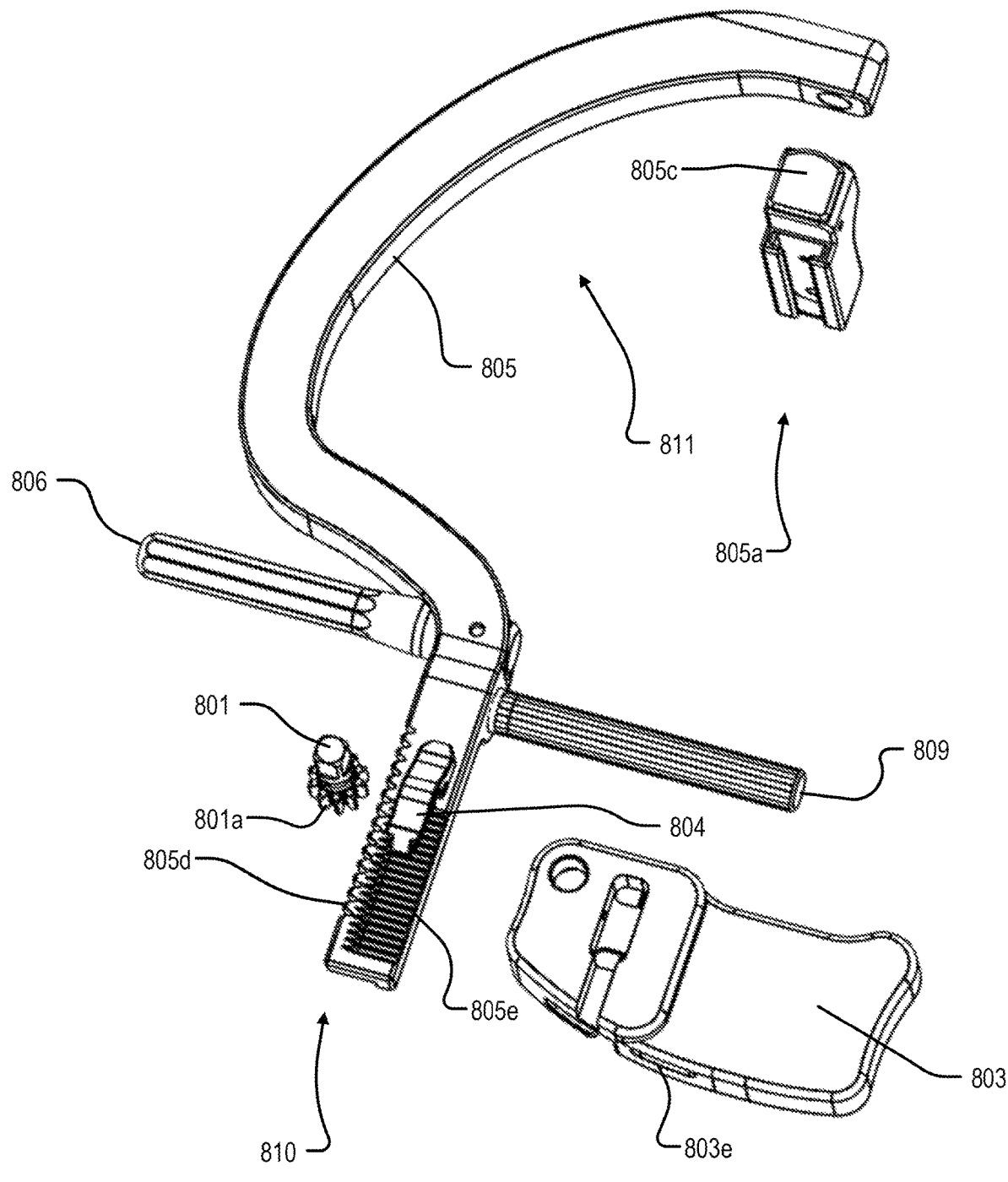
FIG. 42 is an exploded parts view of a third module for use with disclosed modular retractor embodiments.
Figure 43:
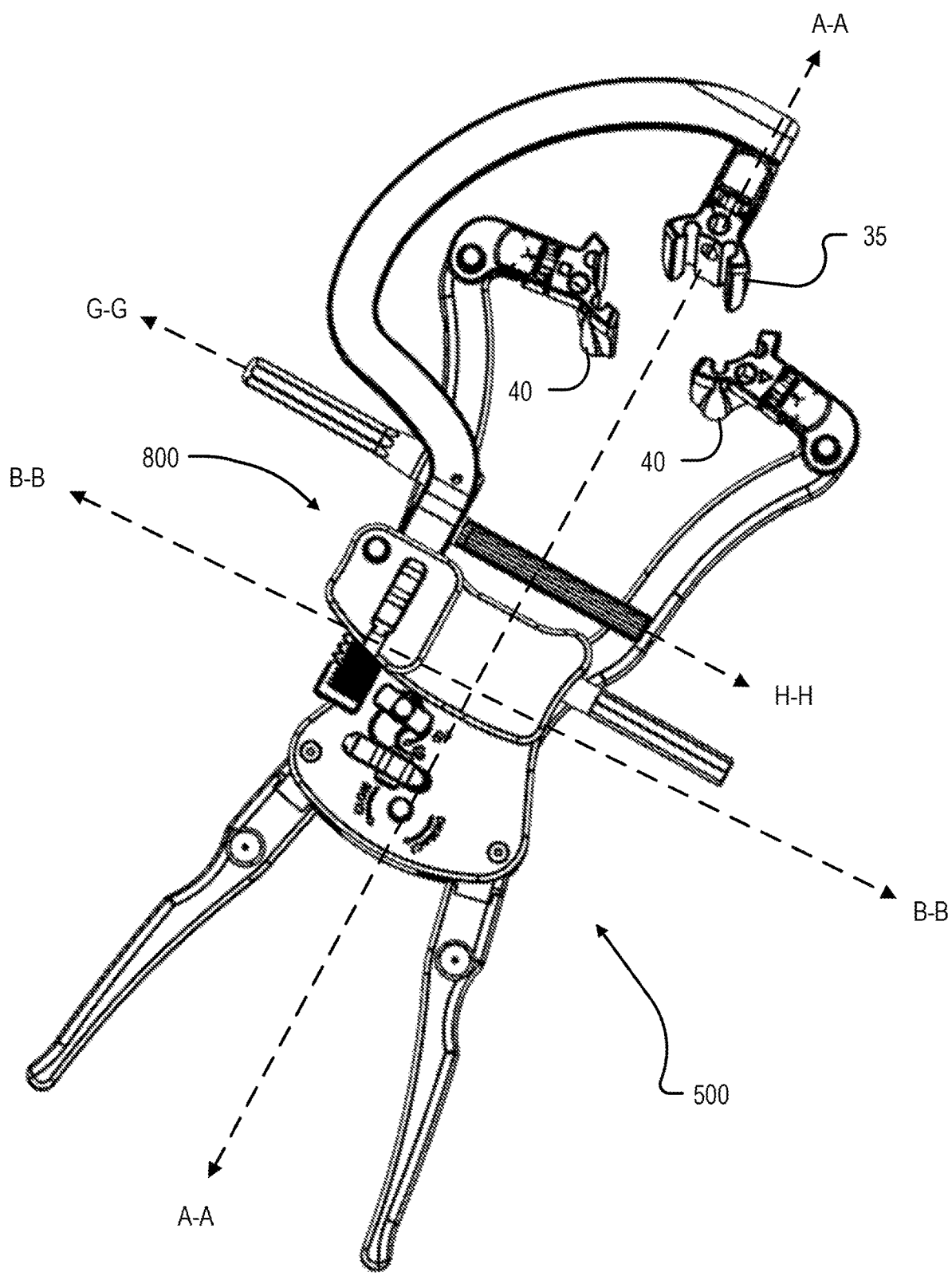
FIG. 43 is a perspective view of a third module coupled to a modular retractor.
Figure 44:
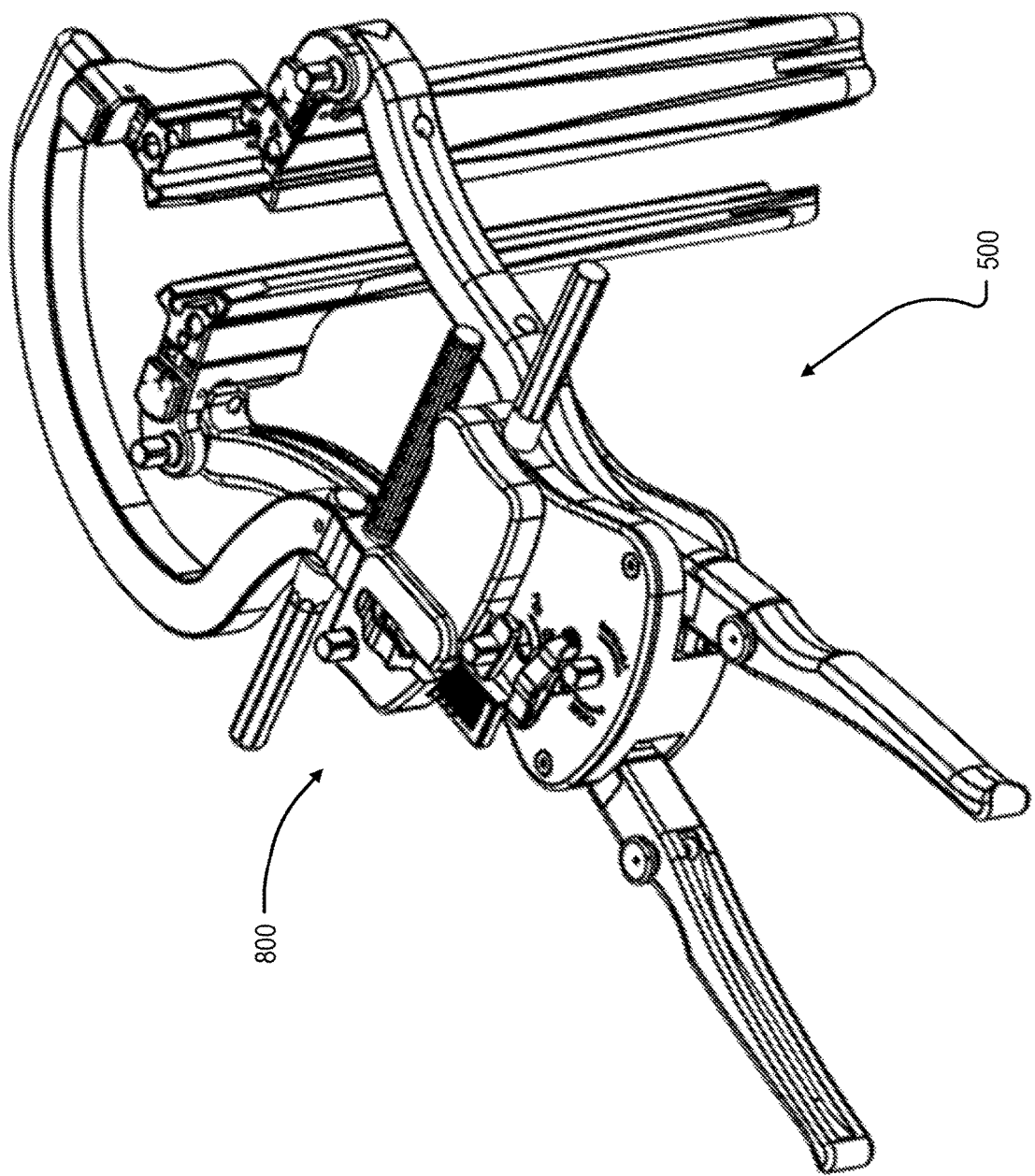
FIG. 44 is a perspective view of a third module coupled to a modular retractor and a plurality of blades.

Referring generally to FIGS. 41A-44 a third module 800 for use with the modular retractor 500 is disclosed. FIG. 41A is a top perspective view of a third module 800 and FIG. 41B is a bottom perspective view of a third module 800. FIG. 42 is an exploded parts view of a third module 800. FIG. 43 is a perspective view of a third module 800 coupled to a modular retractor 500 and FIG. 44 is a perspective view of a third module 800 coupled to a modular retractor 500 and a plurality of blades.

In accordance with disclosed embodiments, third module 800 may be configured to couple and uncouple from modular retractor 500 at connection points 503*a*, for example (see FIG. 20). For example, the third module 800 may have at least one corresponding connection point 803*a* on an underside thereof (see FIG. 41B) configured to couple, connect, and/or mate with a connection point 503*a* of the modular retractor 500 in the same, similar, and/or substantially the same manner as previously explained. Accordingly, duplicative description will be omitted. Additionally, third module 800 may be locked to modular retractor 500 by lock 513 (see FIG. 20). Lock 513 may be pivotable such that in a locked position a flange portion of lock 513 may pivot into a locking aperture 803*e* of third module 800, in the same, similar, and/or substantially the same manner as previously explained. Accordingly, duplicative description will be omitted.

Third module 800 may include an arm 805 that includes a straight portion 810 and a C shaped curved portion 811. Straight portion 810 of arm 805 may extend through body 803 and move forward and backward in a longitudinal direction, for example. As seen best in FIG. 43, when third module 800 is coupled to modular retractor 500 the C shaped curved portion 811 extends laterally outward in a lateral direction B-B farther than the farthest lateral edge of arm 807. For example, the C shaped curved portion 811 does not obscure a surgeons viewing area and/or access to a surgical site. Furthermore, third module 800 may orient and/or support a blade 35 such that the blade faces the body portion 803 of third module 800, the body portion of modular retractor 500, and is also symmetrically disposed relative to the first arm 505 and second arm 507 of modular retractor 500. For example, the C shaped curved portion 811 may support a blade 35 at a distal most position that is aligned in the longitudinal axis A-A of modular retractor 500 (see FIG. 43). The straight portion 810 of arm 805 may extend through body 803 through a first contoured channel. In various embodiments, the contoured channel 803*b* may be an L shaped channel, for example. Third module 800 may be configured to extend arm 805 along a path of travel by a rack and pinion mechanism, for example. The path of travel may be linear path, for example. Other paths of travel than those specifically shown are contemplated, e.g., an arcuate path.

Third module 800 may include a table mount 806 extending laterally from a side surface thereof in a direction defined by an extension direction G-G of table mount 806 (see FIG. 43), for example. Table mount 806 may facilitate the secure placement of third module 800 such that third module 800 remains fixed in 3D space and/or facilitate the relative motion of third module 800 (and/or modular retractor 500 when coupled thereto) in any direction when moving table mount 70, for example. Third module 800 may be configured to extend arm 805 by activation of actuator 801, e.g., by rotation of actuator 801. Actuator 801 may be securely attached to body portion 803 and include a pinion portion 801*a* (pinion gear and/or spur gear) having teeth that engage with and are meshed with straight rack portion 805d disposed on a side surface of arm 805, for example. Accordingly, rotation of actuator 801 may rotate pinion portion 801a such that teeth of pinion portion 801a cause arm 805 to move forward and/or backward depending on the direction actuator 801 is rotated in the same, similar, and/or substantially the same manner as previously explained. Accordingly, duplicative description will be omitted. Additionally, third module 800 may include a first pawl 804 that may be configured to engage rack portion 805e disposed on a top surface of arm 805, for example. First pawl 804 may be configured to allow pinion portion 801a to rotate in a first direction (counter clockwise direction) and prevent pinion portion 801a from rotating in a second direction (clockwise direction) in the same, similar, and/or substantially the same manner as previously explained. Accordingly, duplicative description will be omitted.

In various embodiments, curved arm portion 811 of arm 805 may be coupled to blade attachment mechanism 805c at a distal most end. The curved arm portion 811 may support blade attachment mechanism 805c such that it faces modular retractor 500 and is aligned with the longitudinal axis A-A of modular retractor 500 (see FIG. 43). In the example embodiment, blade attachment mechanism 805c is fixed and a corresponding blade 35 does not pivot and/or angulate. However in other embodiments, third module 800 may include a first blade actuator (not illustrated) that is configured to adjust the angulation of a corresponding blade and a corresponding pivoting member with the same, substantially the same, and/or similar structural and characteristics as explained herein with respect to other embodiments.

Third module 800 may include a table mount 806 extending in a first lateral direction along axis G-G from arm 805 and a module mount 809 extending in a second lateral direction along axis H-H from arm 805. i.e., in an opposite lateral direction (see FIG. 43). For example, table mount 806 may extend to the left direction and module mount 809 may extend to the right direction. Additionally, straight portion 810 of arm 805 may be supported by body 803 on the left side of the longitudinal axis A-A of modular retractor 500. In this configuration, the module mount 809 may cross over the longitudinal axis A-A, for example. Module mount 809 may support a free hand module 900, as will explained in further detail below.

Figure 45A:
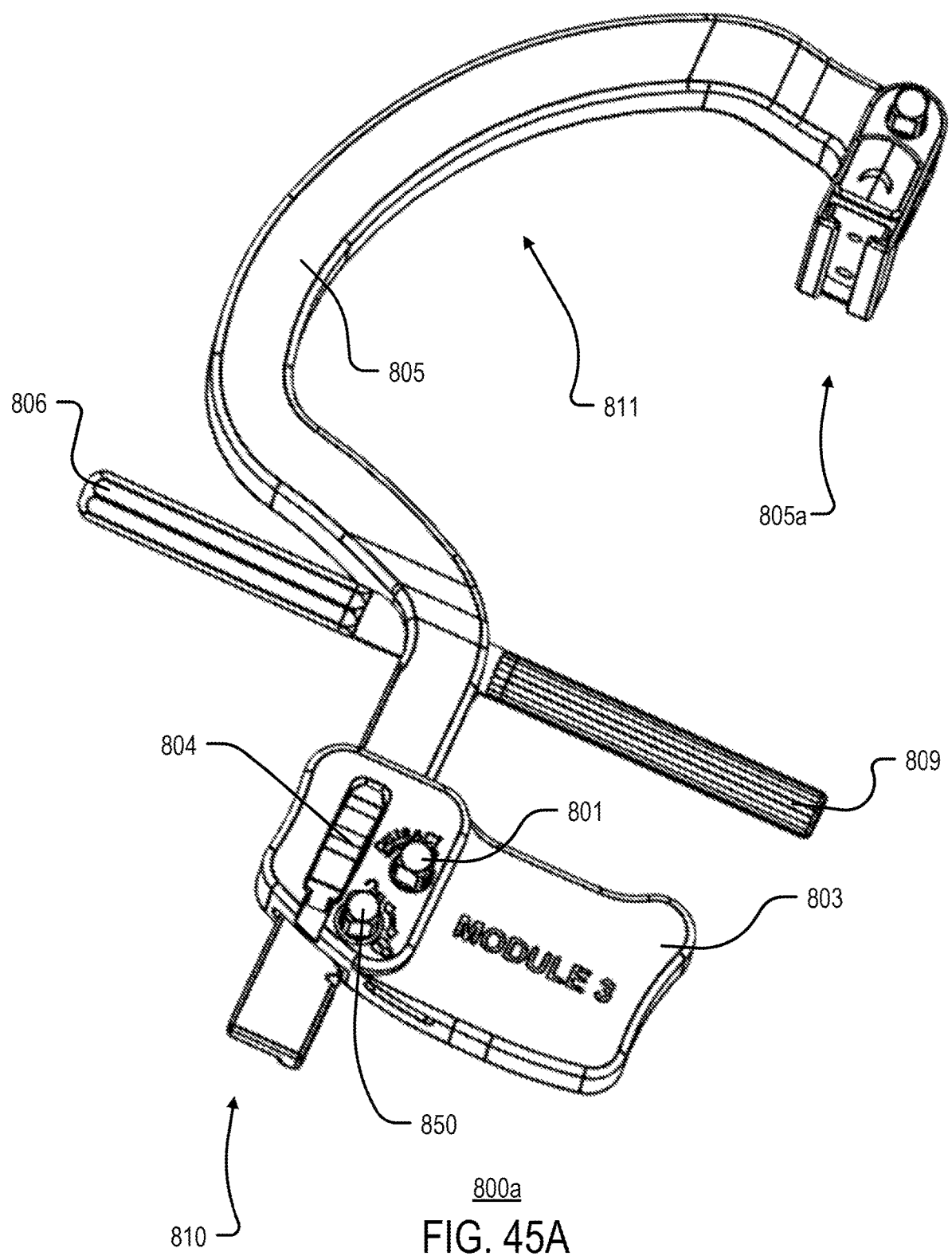
FIG. 45A is a top perspective view of an alternate embodiment of a third module.
Figure 45B:
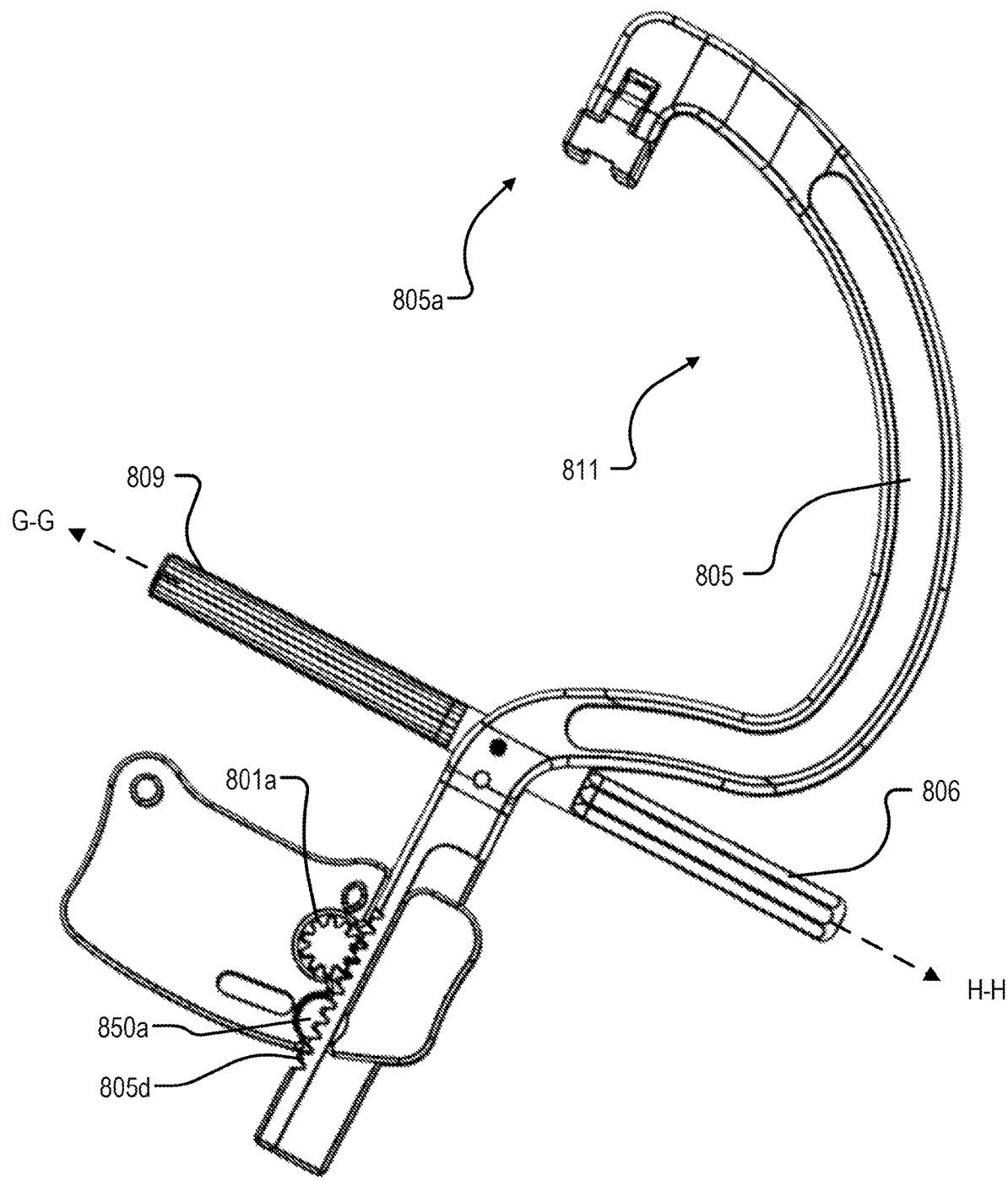
FIG. 45B is a bottom perspective view of an alternate embodiment of a third module.

Referring generally to FIGS. 45A-45B an alternative third module 800a embodiment is disclosed. Third module 800a may include the same, substantially the same, and/or similar components and functionality as third module 800. Accordingly, duplicative description will be omitted. In the example embodiment, third module 800a may be modified such that table mount 806 and module mount 809 are aligned. For example, table mount 806 and module mount 809 each extend from arm 805 in opposite directions and are aligned on the same common extension axis. For example still, axis G-G of table mount 806 and axis H-H of module mount 809 are aligned and extend in opposite directions.

Alternative third module 800a may include a locking actuator 850, for example. Locking actuator 850 may be rotatably secured within body portion 803 and be disposed above straight portion 810 of arm 805, for example. In various embodiments, locking actuator 850 may include an outside thread pattern corresponding to an inside thread pattern of body 803 (not illustrated). In various embodiments, locking actuator 850 may be rotated in a first direction such that locking actuator 850 advances towards straight portion 810 of arm 805. As locking actuator 850 advances, a bottom portion of locking actuator 850 may contact an upper surface of straight portion 810 of arm 805 and apply a downward force to straight portion 810. In this way, locking actuator 850 may provide a frictional force against straight portion 810 of arm 805 thereby preventing and/or suppressing arm 805 from moving forward and backward. For example, the greater the downward force applied to straight portion 810, the greater the frictional force between the underside of locking actuator 850 and the upper surface of straight portion 810. At least one advantage of locking actuator 850 may be that arm 805 may be locking in position such that it is fixed and is prevented from moving forward and backward, for example. In various embodiments, this may assist a surgeon in placement of third module 800 and/or modular retractor 500. For example, a surgeon may lock arm 805 via locking actuator 850 and position modular retractor 500 and third module 800 as desired while arm 805 remains in place. Thereafter, the surgeon may release locking actuator 850 and extend arm 805 to distract patient tissue or retract arm 805. Additionally, in some surgical settings, it may be advantageous to allow third module 800 to remain in a distracted position (while third module 800 is coupled to a table mount via table mount arm 806) and remove modular retractor 500 while the surgical site remains distracted, or at least partially distracted, by third module 800, for example. Additionally, any of the various disclosed modules may include a locking actuator 850 rotatably disposed in a corresponding body portion above a corresponding arm and work in the same, substantially the same, and/or similar manner as explained above.

In other embodiments, locking actuator 850 may be rotated between a locked position and an unlocked position. For example, in various embodiments, locking actuator 850 may include at least one locking tooth (not illustrated) that is disposed within locking cutout 850a of arm 805. For example, at least one locking tooth may jam with rack portion 805d and prevent arm 805 from moving, for example. In other embodiments, locking actuator 850 may include at least one locking tooth that jams with pinion portion 801a, for example. In other embodiments, locking actuator 850 may lock pawl 804 such that pawl 804 is engaged with rack portion 805e and prevented from pivoting up and down relative to rack portion 805e. For example, by locking pawl 804 in place such that pawl 804 is engaged with rack portion 805e, arm 805 may be prevented from moving forward and backward. Moreover, the above described embodiments and functionality of locking actuator 850 are broadly applicable to all of the disclosed embodiments herein. For example, any of the various modules disclosed herein may include a locking actuator 850 having at least one locking tooth that jams with a corresponding rack portion of an arm, and/or a pinion portion of an actuator as explained above.

Figure 46:
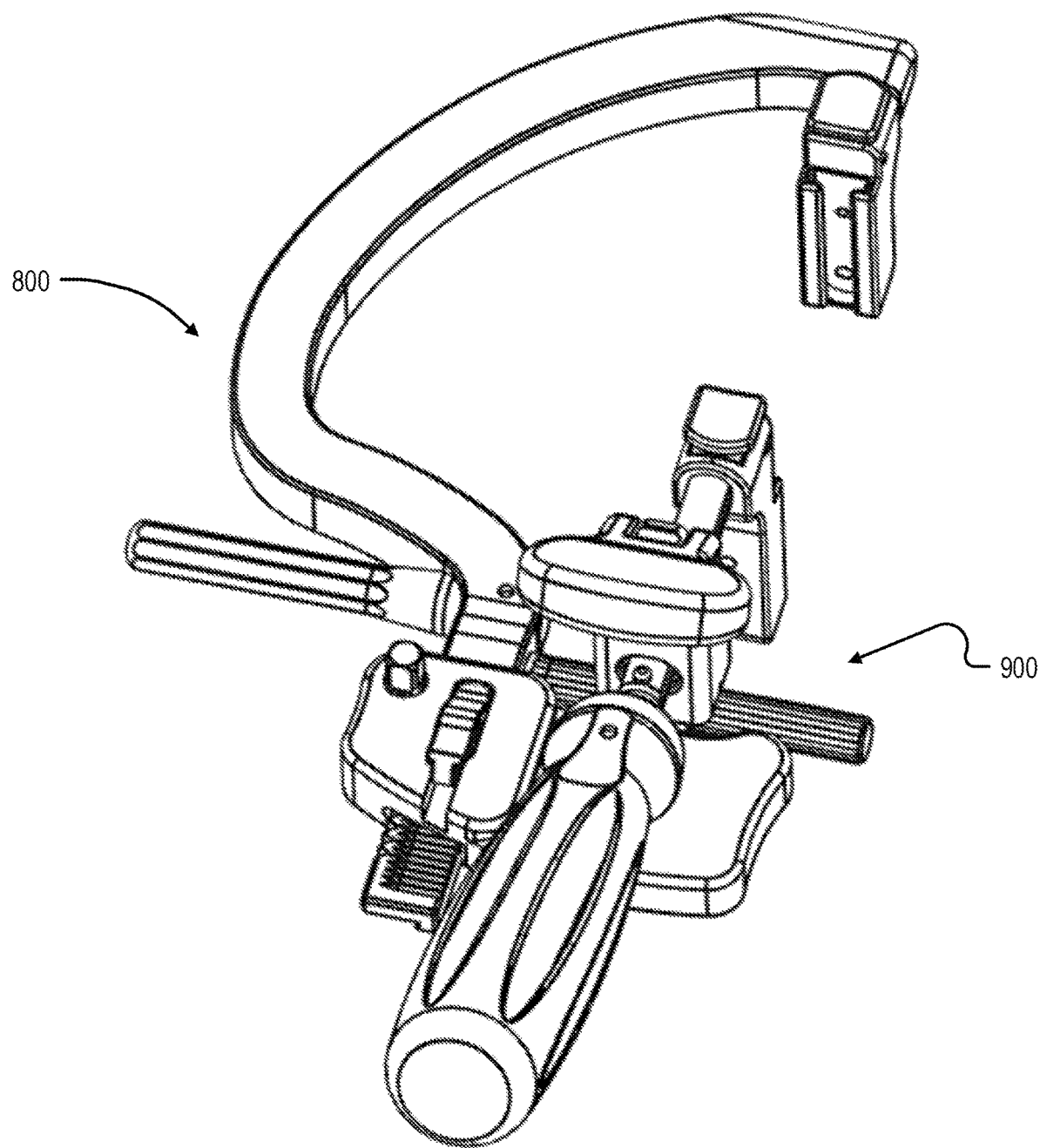
FIG. 46 is a perspective view of a free hand module coupled to a third module for use with disclosed modular retractor embodiments.
Figure 47A:
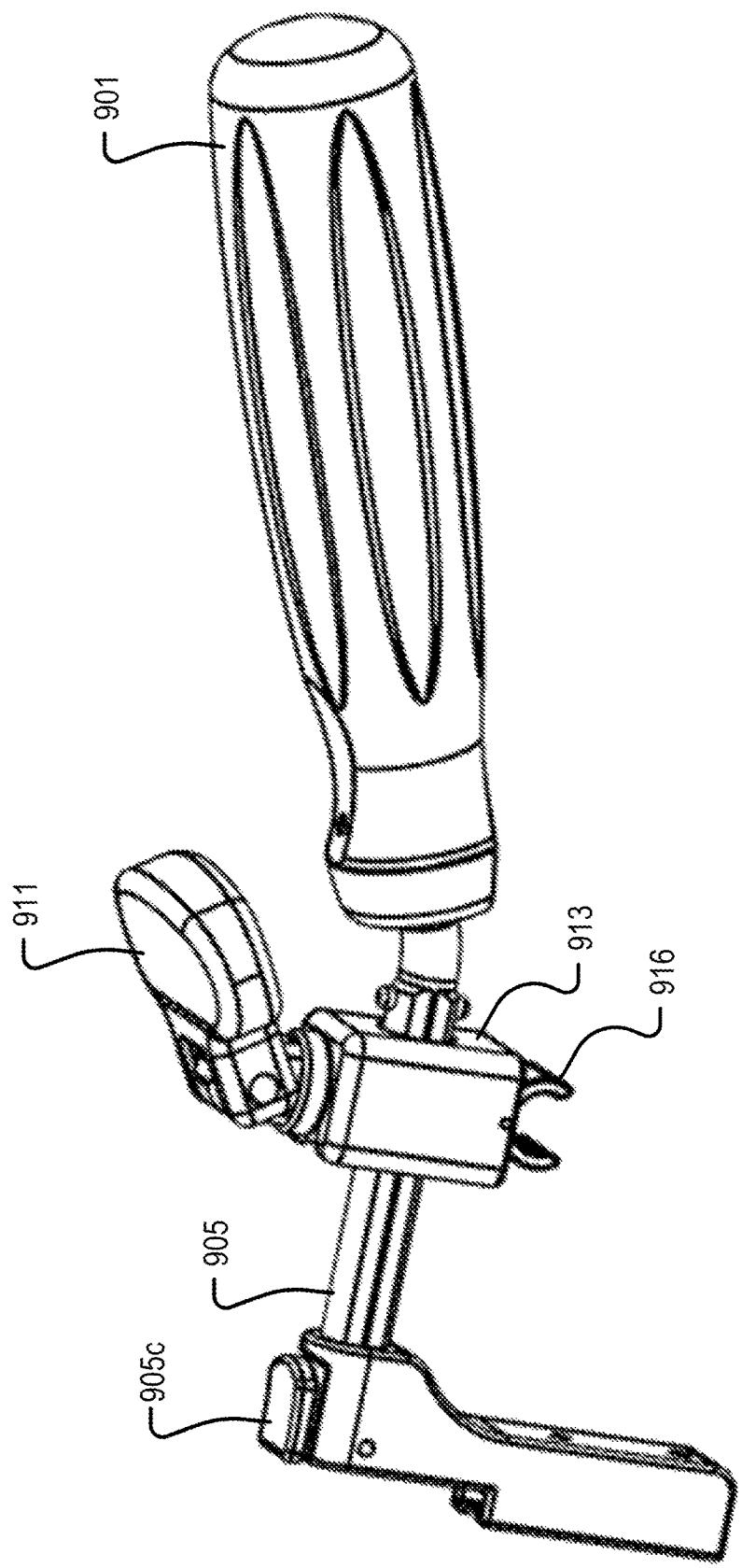
FIG. 47A is a side view of a free hand module for use with disclosed modular retractor embodiments.
Figure 47B:
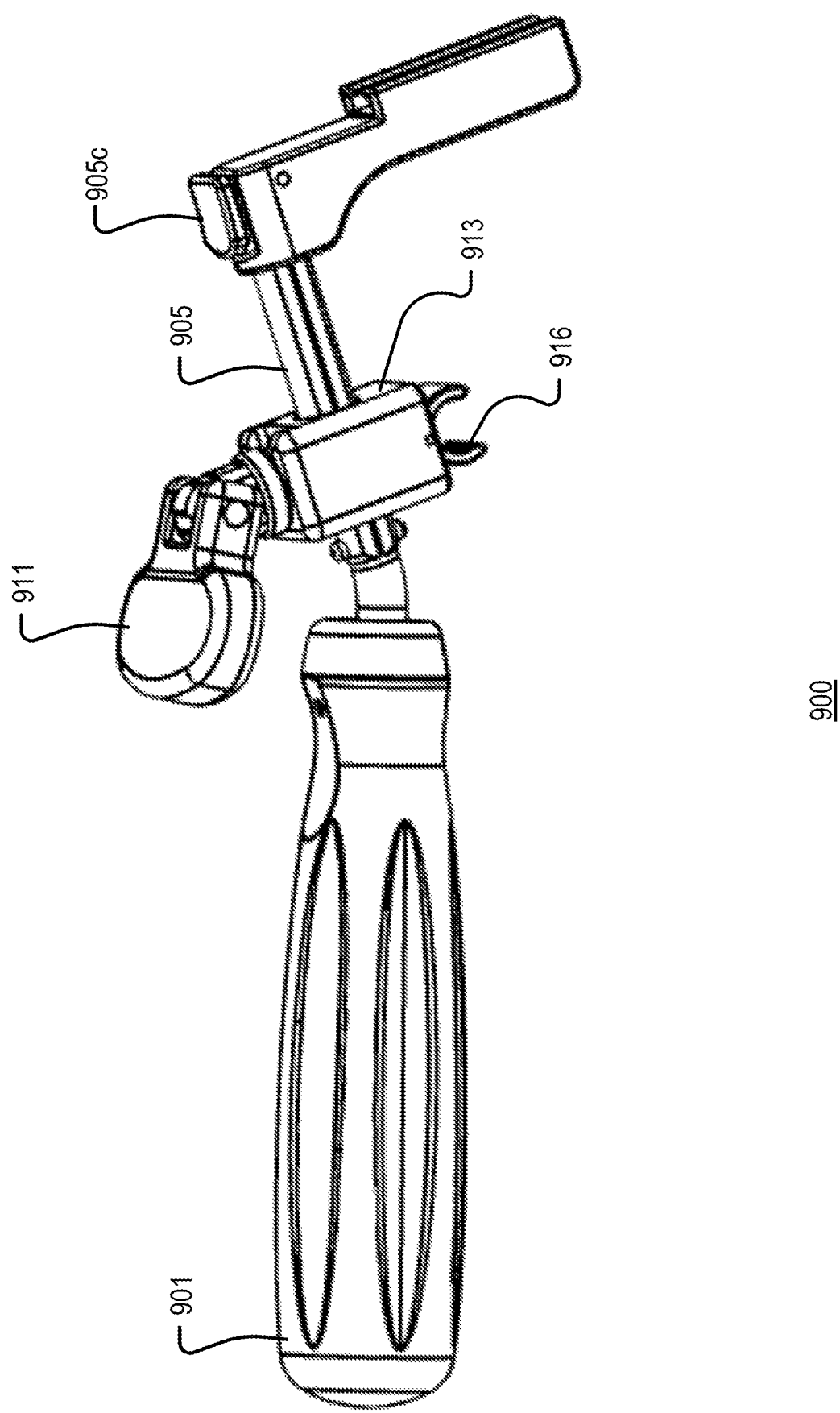
FIG. 47B is a side view of a free hand module for use with disclosed modular retractor embodiments.
Figure 48A:
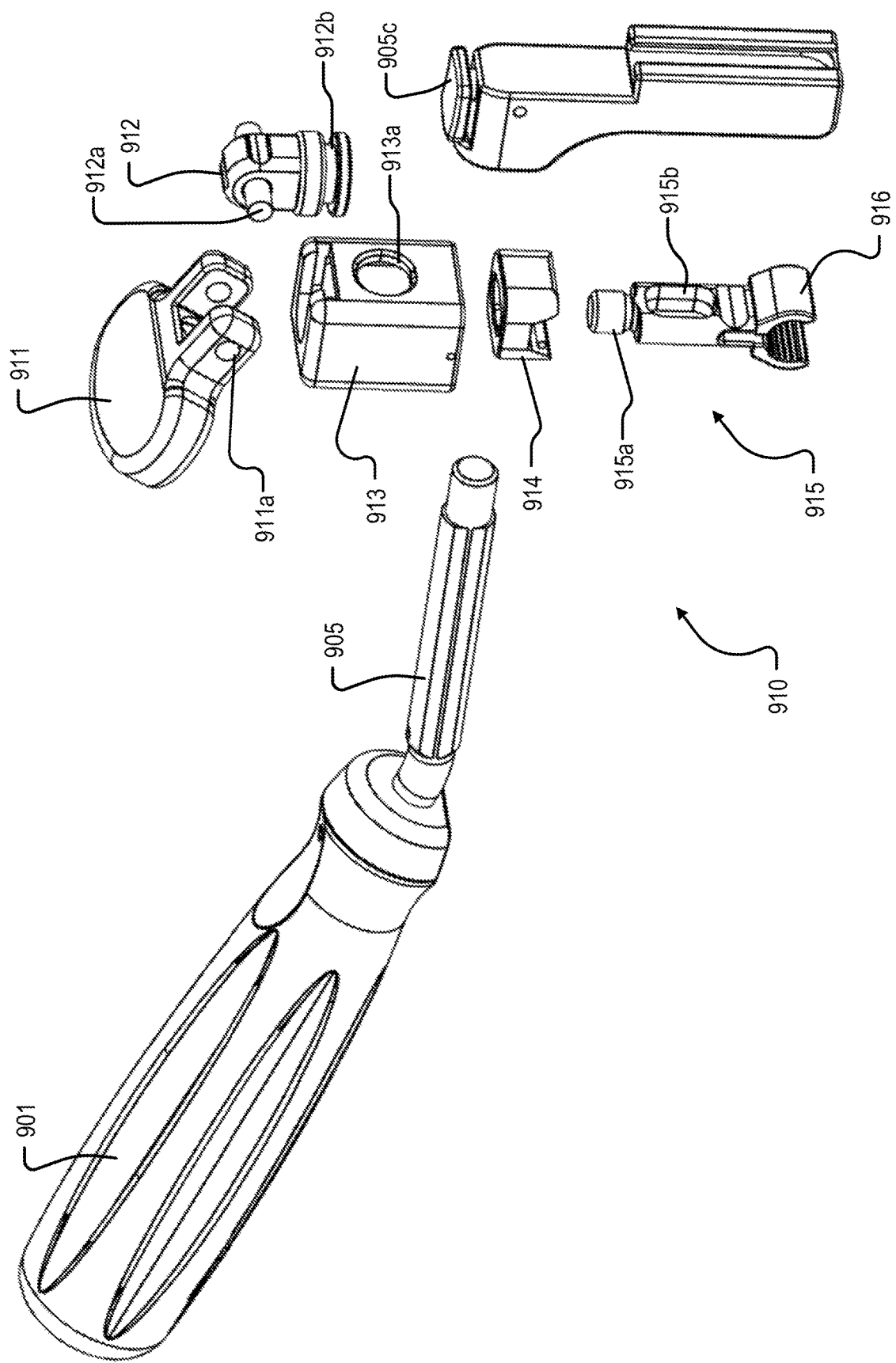
FIG. 48A is an exploded parts view of a free hand module.
Figure 48B:
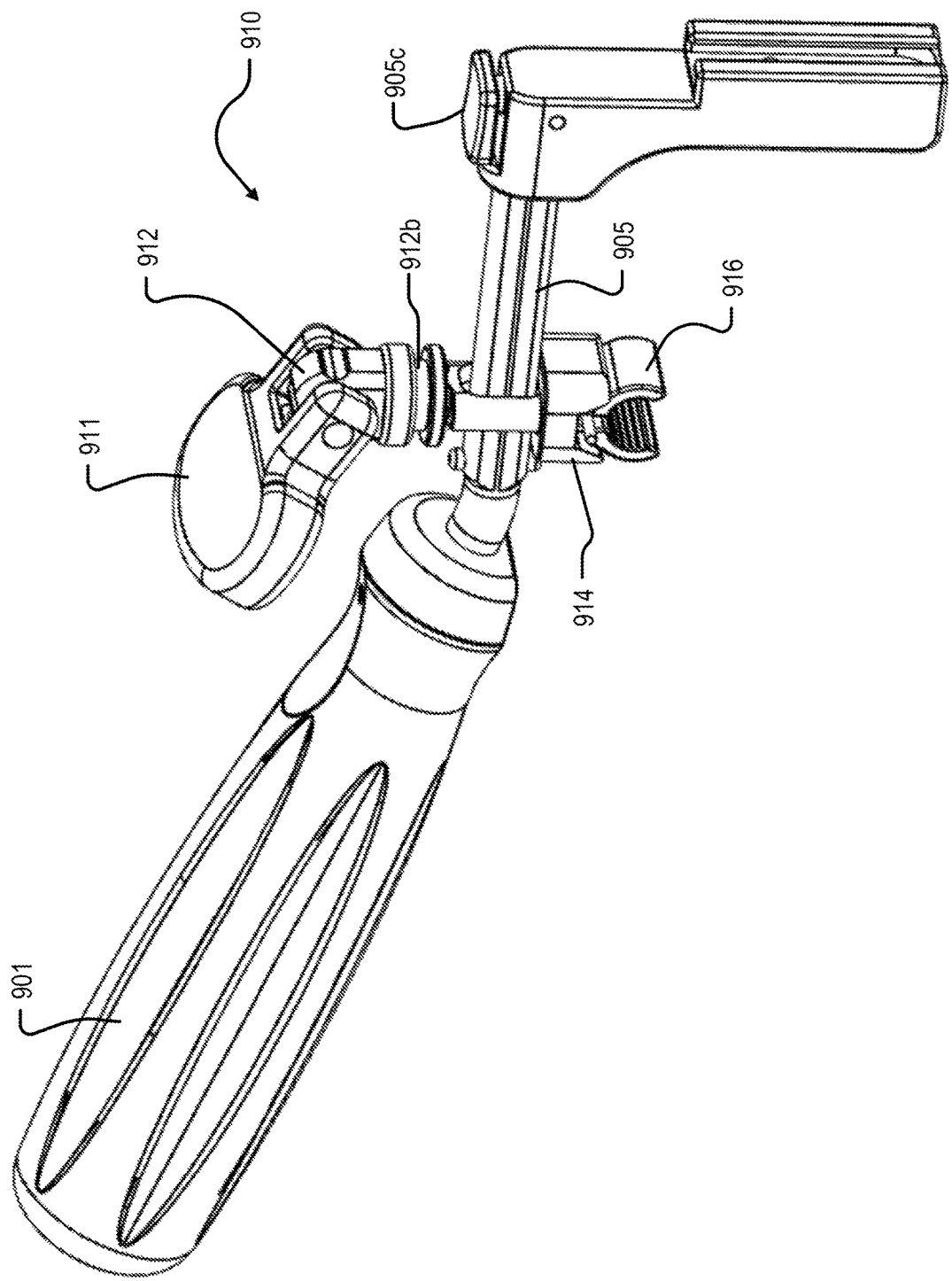
FIG. 48B is a perspective view with partially removed parts of a free hand module.
Figure 49A:
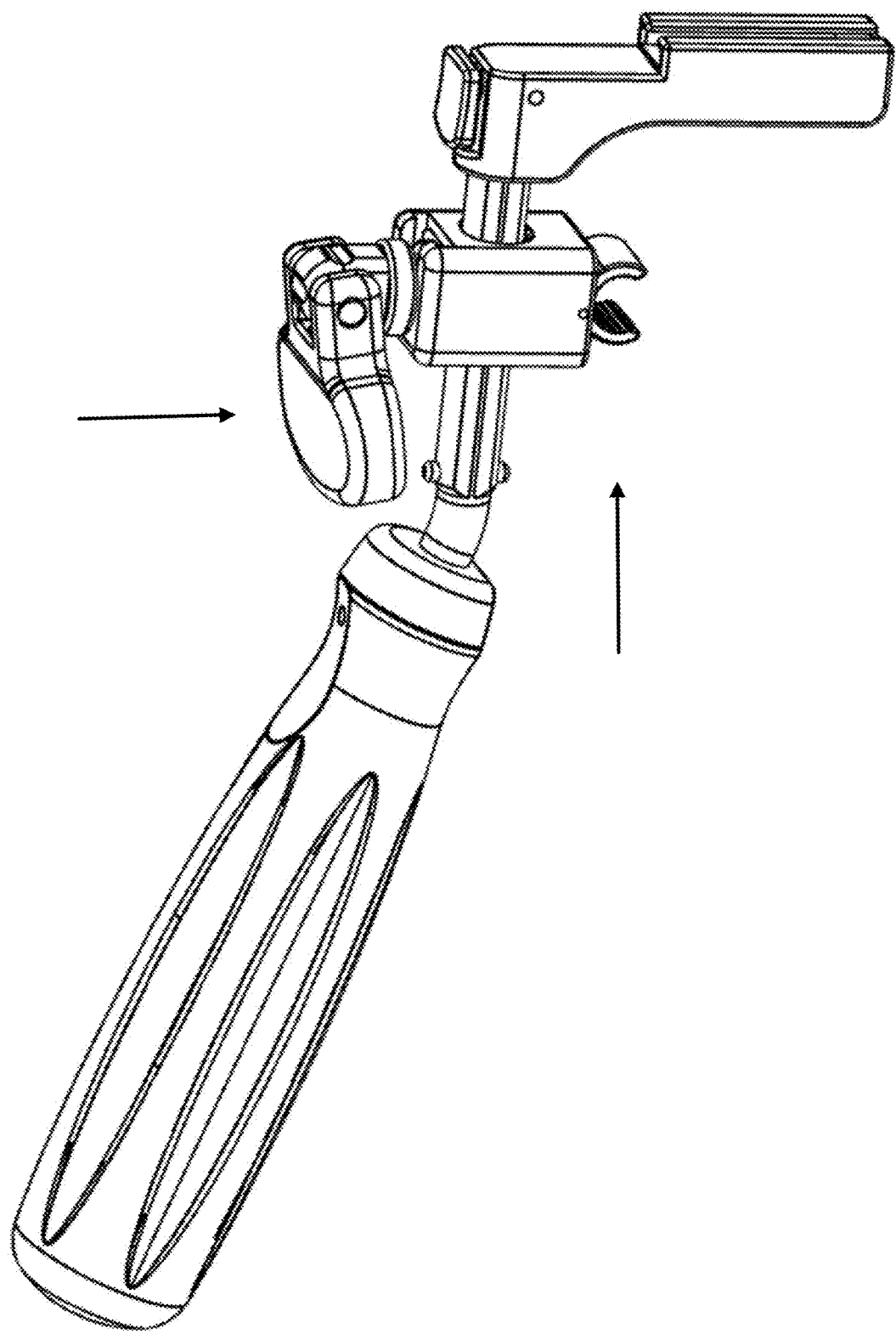
FIG. 49A is a perspective view of a free hand module in a sliding configuration.
Figure 49B:
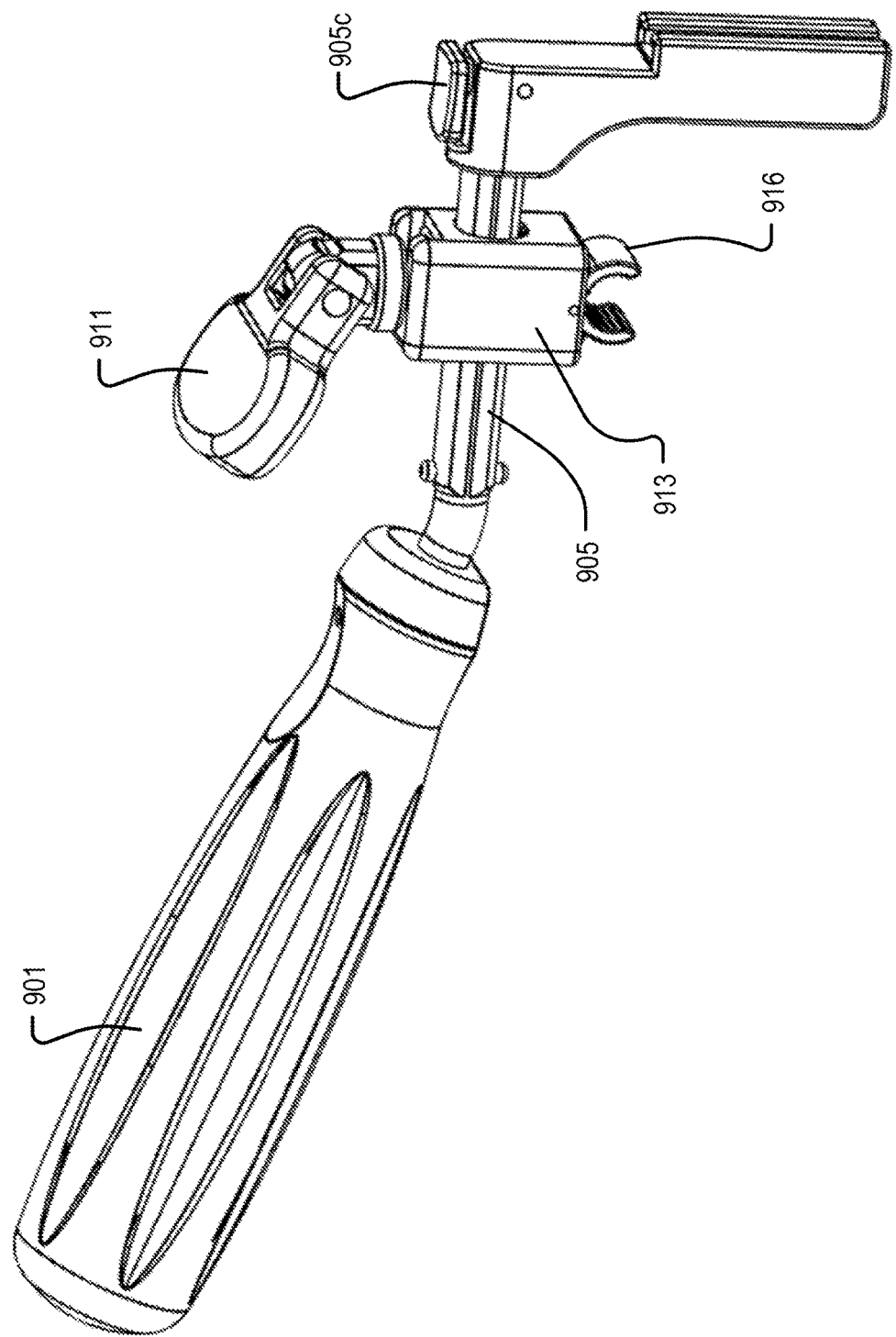
FIG. 49B is a perspective view of a free hand module in a second position.
Figure 50:
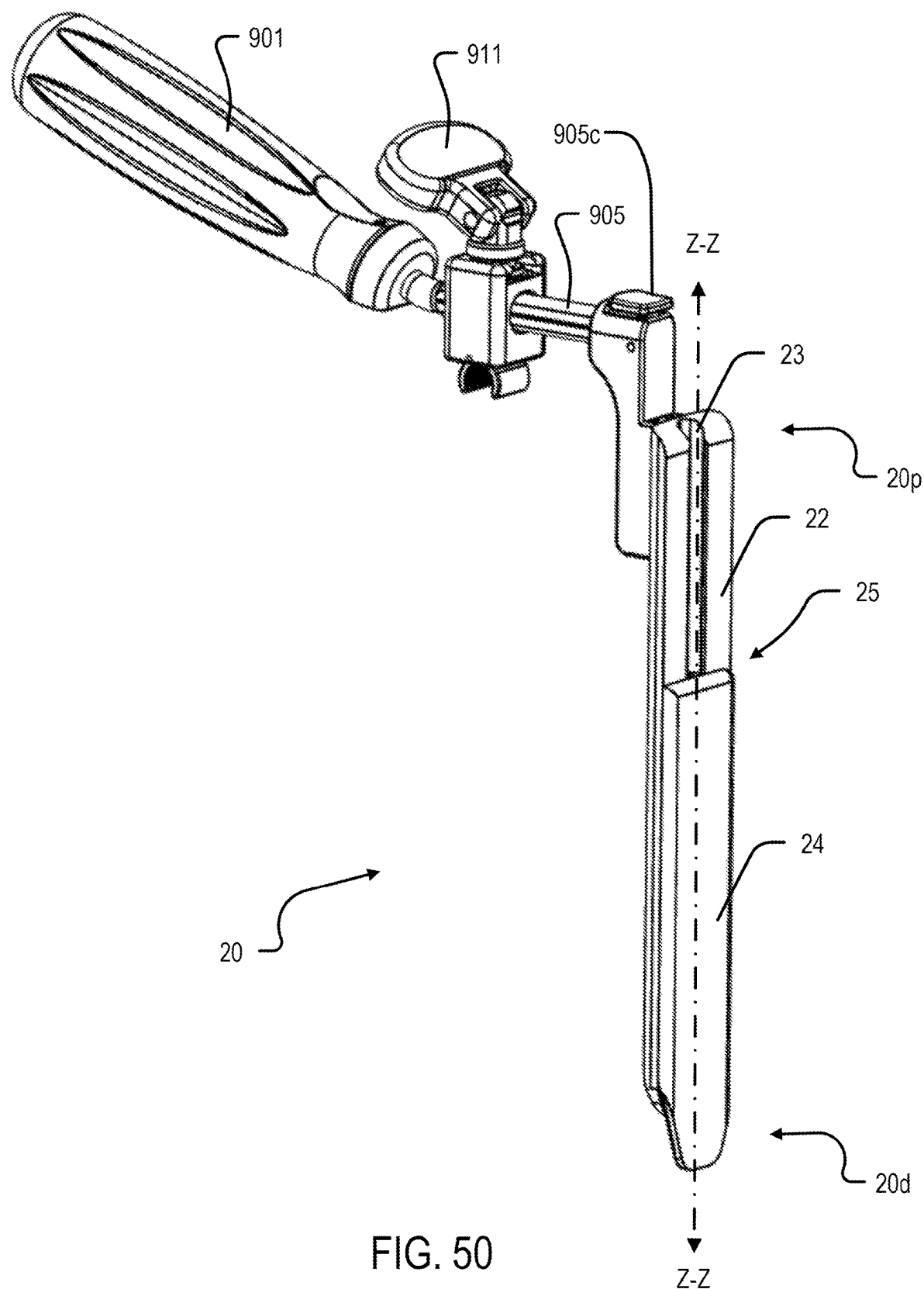
FIG. 50 is a perspective view of a free hand module and an telescoping blade system.
Figure 51:
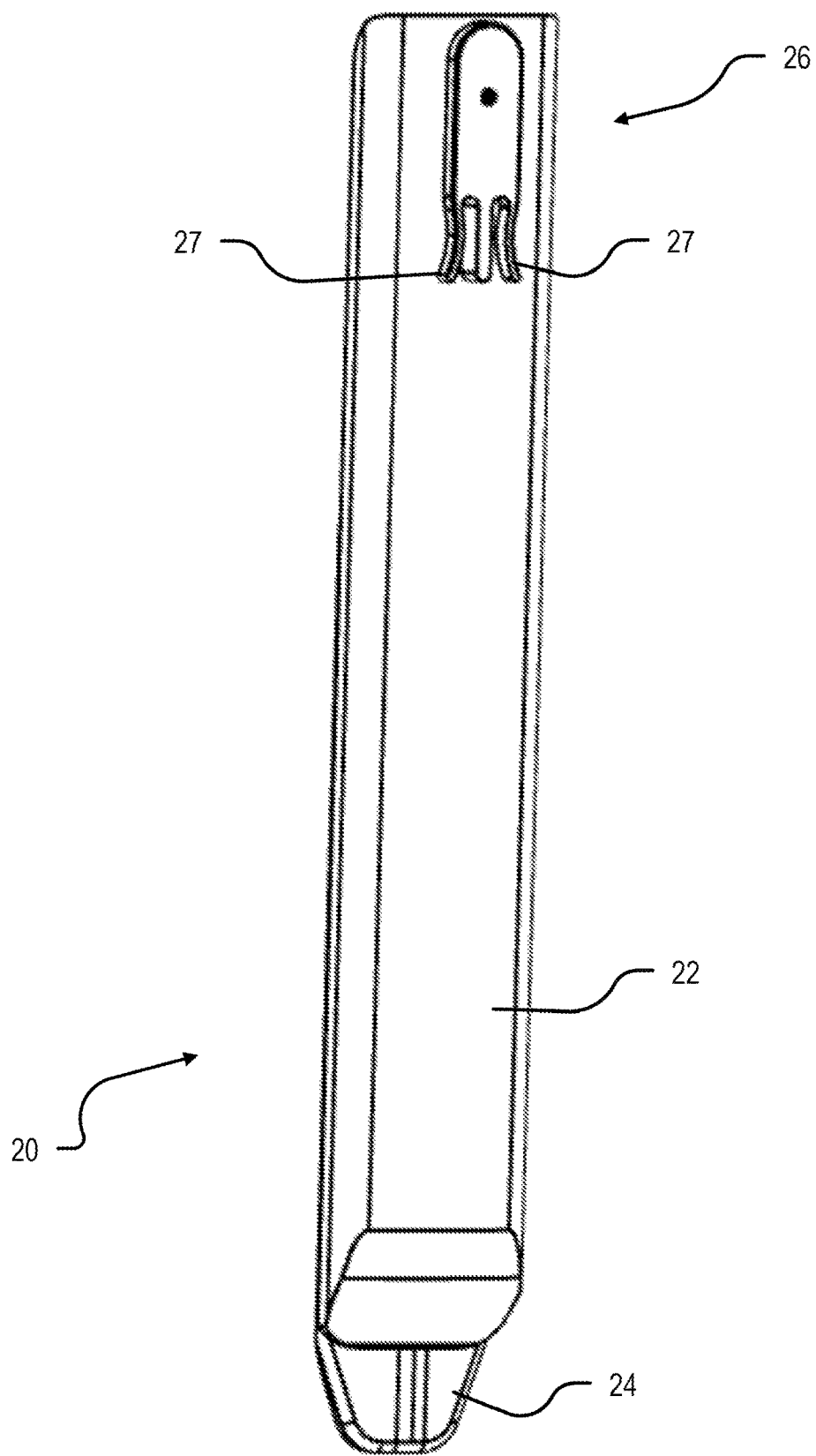
FIG. 51 is a perspective view of an telescoping blade system.
Figure 52:
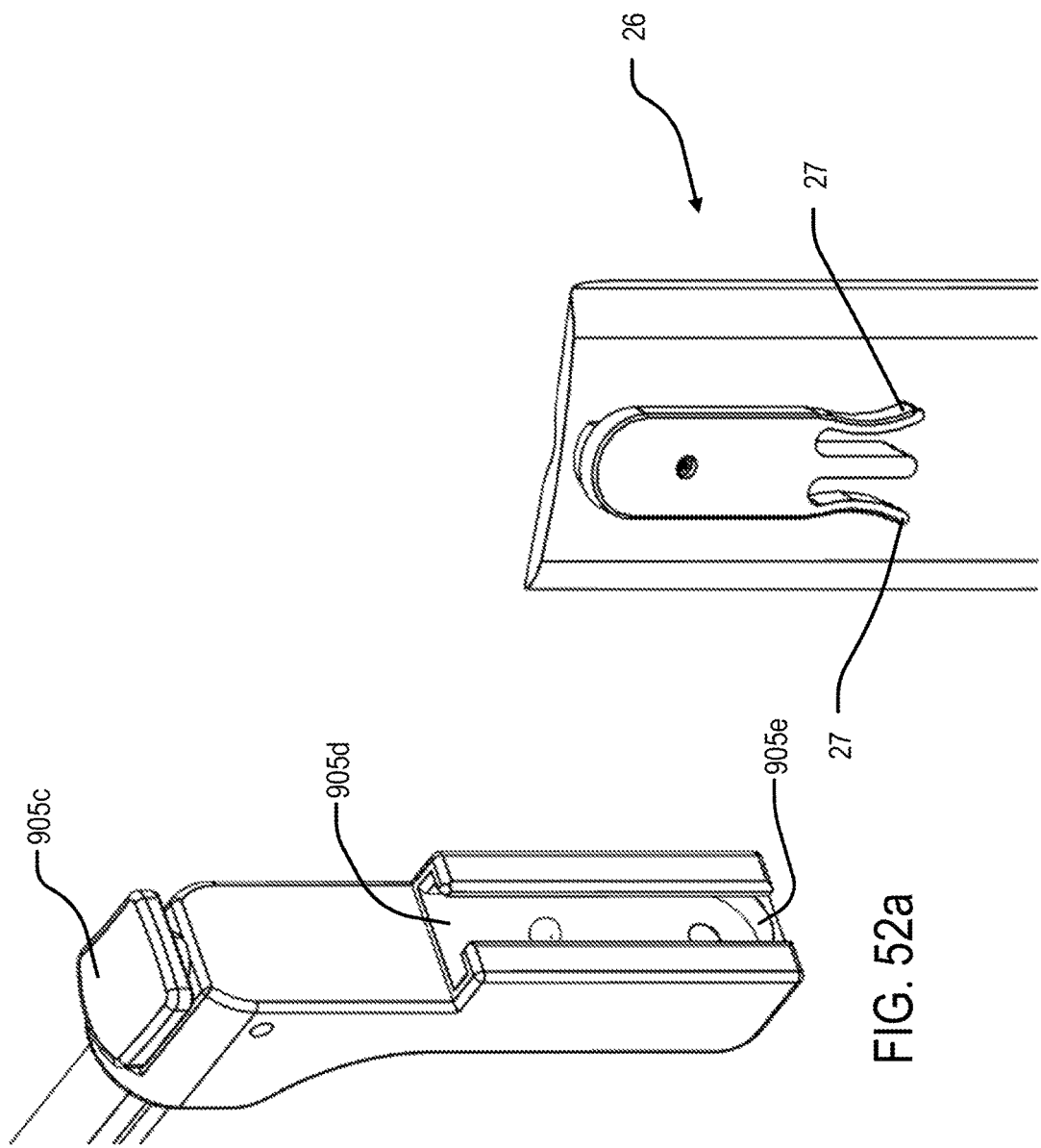
FIG. 52A is a perspective view of a blade connection channel.
FIG. 52B is a perspective view of a blade fastener.

Referring generally to FIGS. 46-54 a free hand module 900 and a telescoping blade 20 for use with the modular retractor 500 and/or free hand module 900 is disclosed. FIG. 46 is a perspective view of a free hand module 900 and FIGS. 47A and 47B are side views of a free hand module 900 for use with disclosed modular retractor 500 embodiments. FIG. 48A is an exploded parts view of a free hand module 900 and FIG. 48B is a removed parts view of free hand module 900. FIGS. 49A-49B are various perspective views of a free hand module 900 in various configurations. FIGS. 50-51 are various perspective views of a free hand module 900 and a telescoping blade system 20. FIG. 52A is a perspective view of a blade connection channel 905d and FIG. 52B is a perspective view of a blade fastener. FIGS.

53-54 are various perspective views of a third module 800 coupled to a modular retractor 500 and a free hand module 900 coupled to the third module 800.

In accordance with disclosed embodiments, free hand module 900 may be configured to couple and uncouple from third module 800 (see FIG. 46). For example, the free hand module 900 may be configured to couple, connect, and/or mate with module mount 809. In the example embodiment, gripping arms 916 may grip onto module mount 809, for example. Additionally, gripping arms 916 may include a plurality of rails and channels extending in the lateral direction on an inside surface thereof. The rails of gripping arms 916 may have a size and shape corresponding to rails and channels of module mount 809, for example. Accordingly, the gripping arms 916 may securely mate with module mount 809 by seating rails of gripping arms 916 in the channels of module mount 809 and seating the rails of module mount 809 in the channels of gripping arms 916. Furthermore, the gripping arms 916 may provide a clamping force against module mount 809 securely coupling the free hand module 900 to third module 800, for example.

In various embodiments, free hand module 900 may be configured to enable a surgeon to freely extend blade 20 forward and backward in the longitudinal direction along longitudinal axis A-A, for example. Free hand module 900 may not include a rack and pinion mechanism to extend the blade 20 and may rely on the manual operability of a surgeon, for example. In some surgical contexts, a free hand module 900 may afford a surgeon greater freedom in installation and facilitate the surgeon in retracting delicate patient tissue by hand. For example, when performing a retraction step with free hand module 900, patient tissue may resist the retraction and/or opening of a surgical access site. The degree of resistance of the patient tissue may be sensed by the surgeon as a form of haptic feedback informing the surgeon how much pressure has been applied to the patient tissue. In this way, the surgeon can sense and or prevent applying to much retraction force to a patient tissue and/or applying just the right amount of retraction force in delicate situations. Similarly, a free hand module 900 may be relatively easier for a surgeon to manipulate than a rack and pinion type of motion. This may allow the surgeon to quickly retract specific patient tissue with greater freedom in operation. Additionally, a length and/or height of telescoping blade 20 may be adjustable. Accordingly, a surgeon can retract various layers of patient tissue that are below (or above) the patient tissue which has been previously retracted by the other blades.

Free hand module 900 may include a handle 901 at a proximal end and a blade attachment mechanism 905c at a distal end, for example. Handle 901 may be rigidly secured to a shaft 905 and shaft 905 may define a longitudinal axis of free hand module 900, for example. Free hand module 900 may include a moving mechanism 910. As illustrated best in FIGS. 48A and 48B, moving mechanism 910 may include various components that enable an end user to toggle a lever 911 to enable the forward and backward movement of handle 901, shaft 905, and blade attachment mechanism 905c relative to moving mechanism 910 and module mount 809, for example. Moving mechanism 809 may include a body portion 913 having an aperture 913 extending therethrough. Shaft 905 may extend through aperture 913a and slotted aperture 915b of gripper body 915, for example. An upper portion of lever support 912 may be disposed above body 913 and be operably coupled to lever 911 while a lower portion including an annular channel 912b may be disposed within body 913. For example, lever support 912 may be securely attached to lever 911 by laterally extending posts 912a that extend through corresponding apertures 911a of lever 911. In this way, lever 911 may be pivotable about posts 912a and when depressed an upper surface of body 913 may act as a support surface such that depressing lever 911 pulls lever support 912 upward. For example, lever support 912 may be pivotable up and down in the vertical direction by depressing and/or rotating lever 911. For example still, pressing down on lever 911 may pull lever support 912 upward relative to body 913. Additionally, the lower portion of lever support 912 disposed within body 913 may prevent the over rotation of lever support 912 due to suitable retaining rails of body 913 being inset within annular ring 912b such that lever support 912 is fixedly retained by body 913, for example.

As shown best in FIGS. 48A-48B, an uppermost coupling portion 915a of gripper body 915 may be secured within a lower cavity of lever support 912. In this way, when lever 911 is actuated and pulls lever support 912 upwards, lever support 912 also pulls gripper body 915 upwards. In various embodiments, a stop block 914 may be disposed within body 913 at a bottom portion thereof. Stop block 914 may be disposed beneath shaft 905, for example. Additionally, stop block 914 may include inclined surfaces that may bias gripping arms 916 inwards (towards one another) to provide a gripping force against module mount 809, for example. In operation, an end user may actuate lever 911 such that gripper body 915 is pulled upwards and gripping arms 916 are biased inwards towards one another to securely couple to module mount 806 via clamping force.

In various embodiments, free hand module 900 via lever 911 may be adjustable and/or fixed in three modes of operation, for example. In a first mode of operation, and when lever 911 is in a first position, shaft 905 is extendable forward and backward through body 913 and gripping arms 916 are in an open position (see FIG. 49A). When gripping arms 916 are in an open position free hand module 900 may be positioned in place around and/or above module mount 809. In the first mode of operation, moving mechanism 910 and gripping arms 916 are both fully open, for example. In a second mode of operation, and when lever 911 is in a second position, shaft 905 is extendable forward and backward through body 913 and gripping arms 916 are in a closed position whereby gripping arms 916 provide a suitable clamping force to module mount 809. In the second mode of operation, moving mechanism 910 is movable in the longitudinal direction and free hand module 900 is securely coupled to module mount 809 due to gripping arms 916 being in the closed position, for example. In a third mode of operation, and when lever 911 is in a third position, shaft 905 is not extendable forward and backward through body 913 and gripping arms 916 are in a closed position (see FIG. 49B). In the third mode of operation, moving mechanism 910 is fixed relative to shaft 905 and free hand module 900 is fixed in 3D space due to gripping arms 916 being in the closed position and securely clamped on to module mount 809 (see FIGS. 53-54).

With reference to FIGS. 50-52B, a telescoping blade 20 is disclosed. Telescoping blade 20 may securely connect to blade attachment mechanism 905c of free blade module 900, for example. Additionally, telescoping blade 20 may securely connect to any of the other blade attachment mechanisms disclosed herein. Telescoping blade 20 may include a first blade 22 and a second blade 24 that is extending along axis Z-Z, for example. First blade 22 may include a channel 23 extending longitudinally down a length thereof from proximal end 20p to about the distal end 20d.

Similarly, second blade 24 may include a rail 25 extending longitudinally down a length thereof from proximal end 20*p* to about distal end 20*d*. In various embodiments, the channel 23 and/or rail 25 may stop and/or terminate before the distal end 20*d* to prevent the second blade 24 from extending too far. In various embodiments, the second blade 24 may slide upward and downward in a proximal-to-distal direction, shown by axis Z-Z in FIG. 50. Additionally, an outside surface of blade 22 may include an engagement feature 26 for securely coupling to blade attachment mechanism 905*c*, for example. Engagement feature 26 may include two spring loaded tabs 27 that are flexible towards one another and naturally biased away from one another, for example. In various embodiments, an end user may slide engagement feature 26 down into channel 905*d* of blade attachment mechanism 905*c* from above and the two spring loaded tabs 27 may push outward against side surfaces of channel 905*d* to frictionally retain engagement feature 26 therein. Additionally, channel 905*d* may include a stop feature 905*e* adjacent a bottom surface thereof. In various embodiments, the stop feature 905*e* may be a curved bottom surface corresponding to the geometry of the spring loaded tabs 27, for example. In other embodiments, the two spring loaded tabs 27 may seat into corresponding channels or indents of blade attachment mechanism 905*c* (not illustrated). Furthermore, in other embodiments the engagement feature 26 may be rotated about 180 degrees such that the blade 20 may be insert into blade engagement mechanism 905*c* from below.

Figure 53:
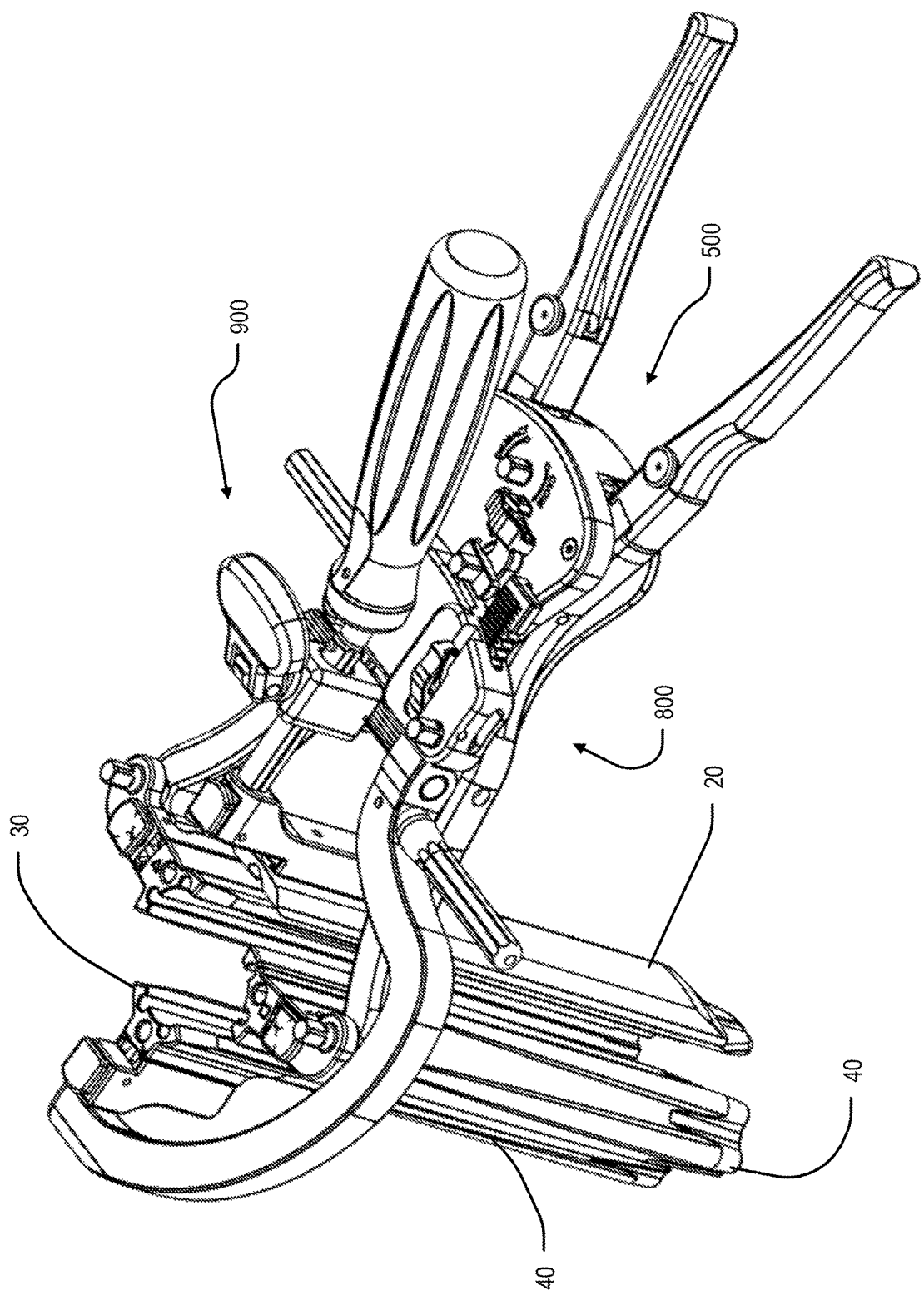
FIG. 53 is a perspective view of a third module coupled to a modular retractor and a free hand module coupled to the third module.
Figure 54:
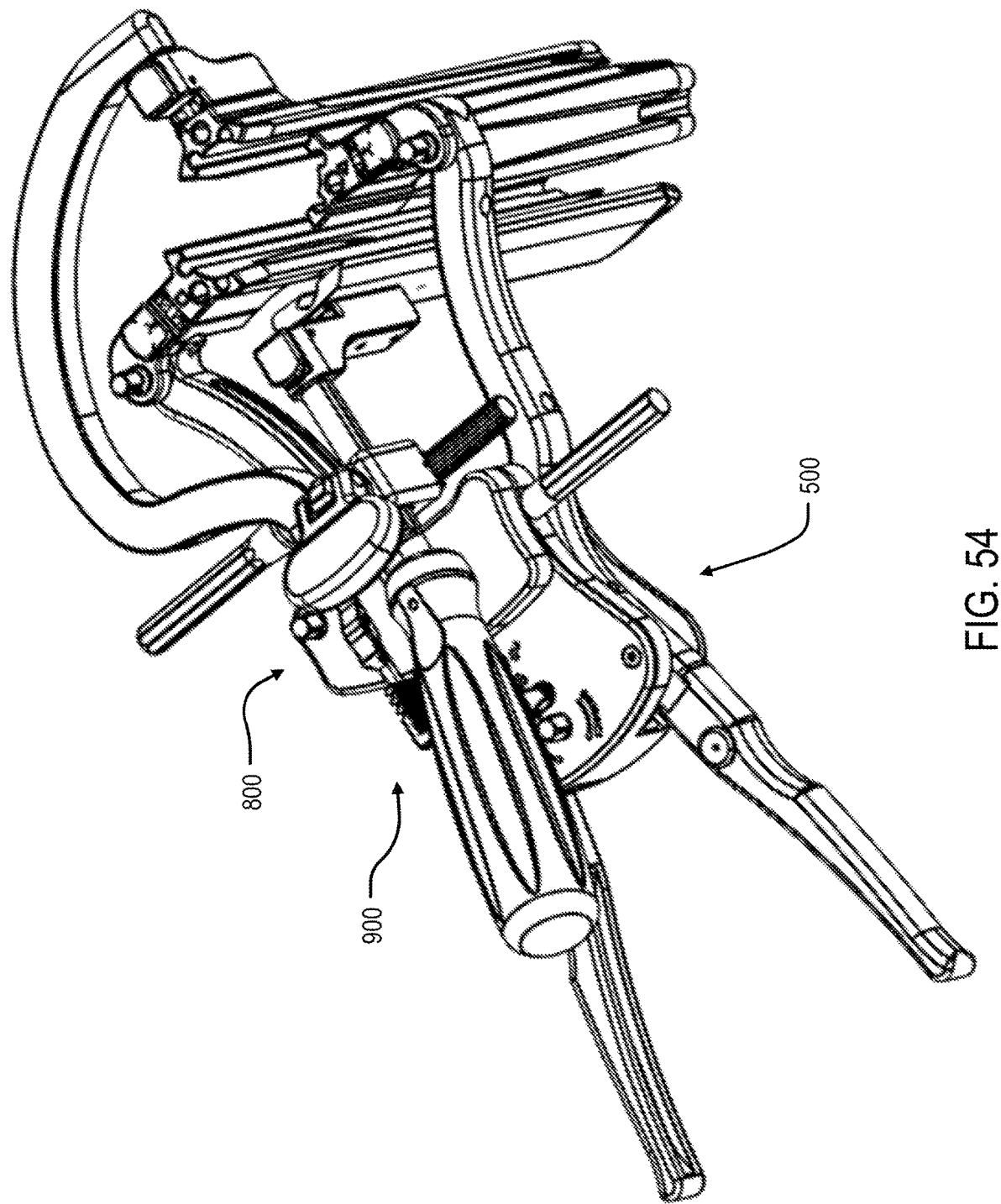
FIG. 54 is a perspective view of a third module coupled to a modular retractor and a free hand module coupled to the third module.

FIGS. 53-54 illustrate a modular retractor 500 with a third module 800 coupled thereto and a free hand module 900 coupled to the third module 800. In the example embodiment, the telescoping blade 20 is attached to a distal end of free hand module 900 and blade 30 is attached to the distal end of third module 800. Additionally, a centerline of telescoping blade 20 and a centerline of blade 30 are aligned with longitudinal axis A-A of modular retractor 500 (see FIG. 22). However, it shall be appreciated that free hand module 900 is slidable along module arm 809 and can be positioned alternately than shown. Furthermore, the curved arm 811 curves out laterally farther than arm 507 of modular retractor 500. As illustrated, blades 30, 40, and 20 form an opening for a surgical access location and/or a surgical access site.

Figure 55:
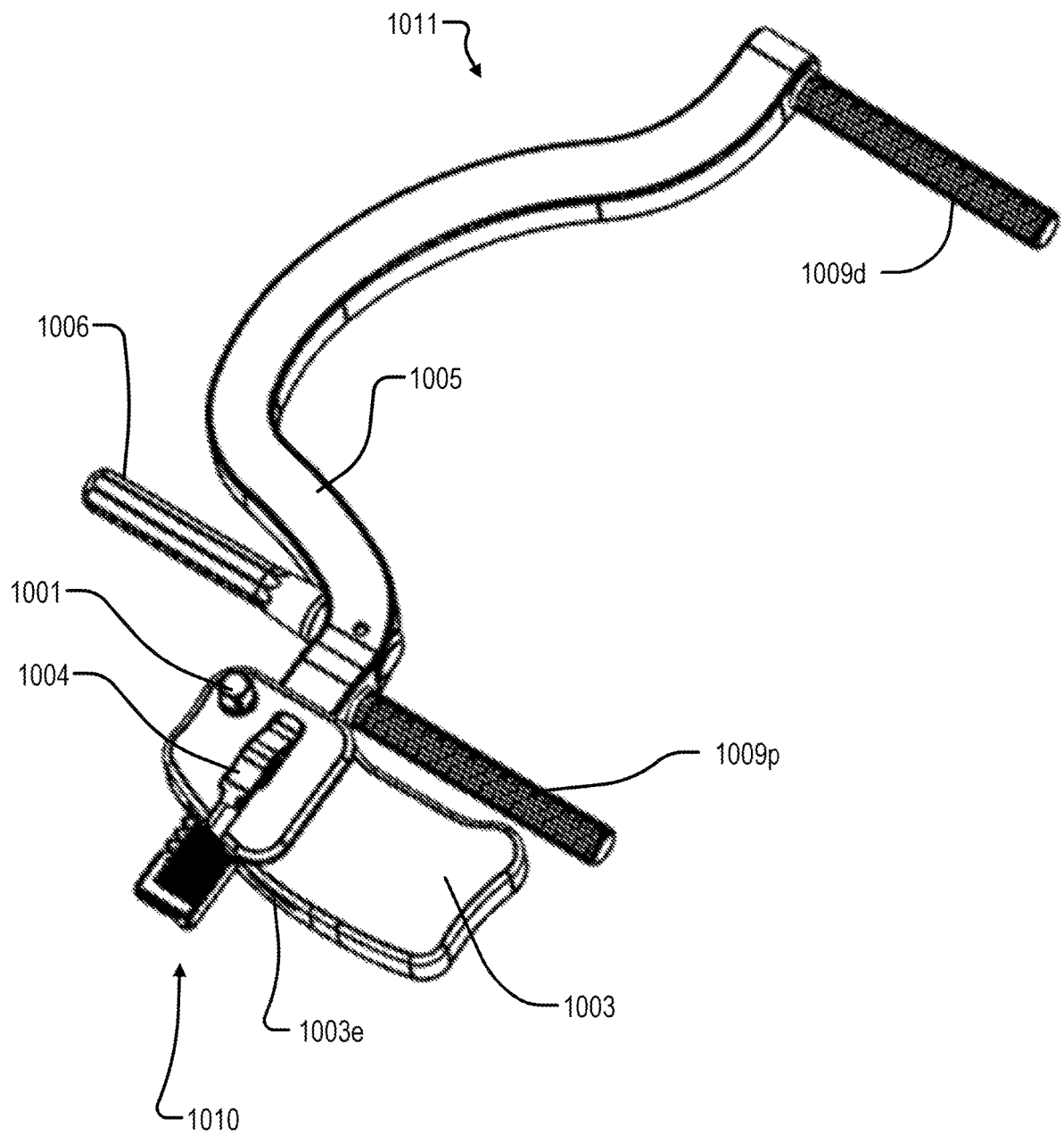
FIG. 55 is a top perspective view of a fourth module for use with disclosed modular retractor embodiments.
Figure 56:
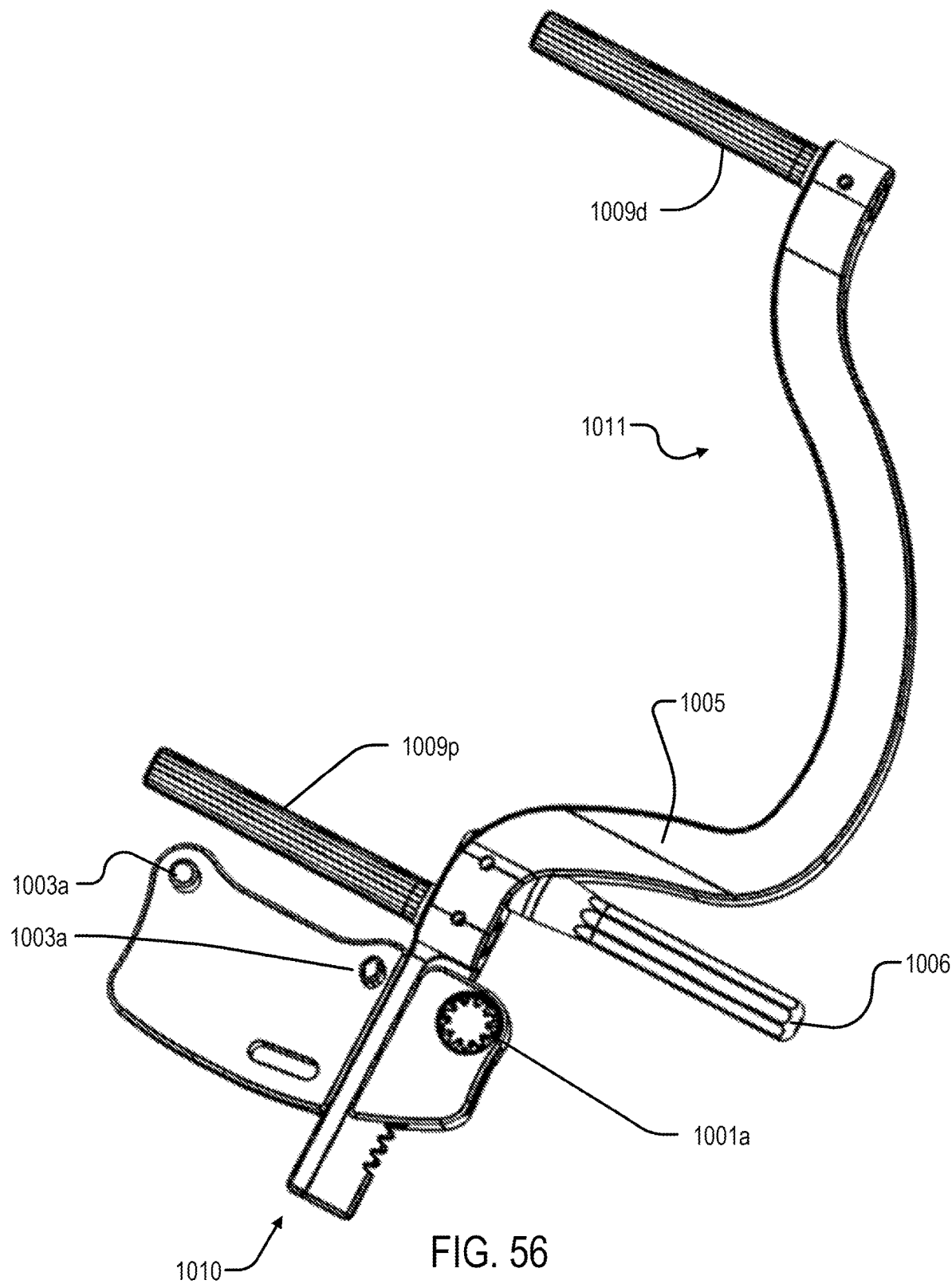
FIG. 56 is a bottom perspective view of a fourth module for use with disclosed modular retractor embodiments.
Figure 57:
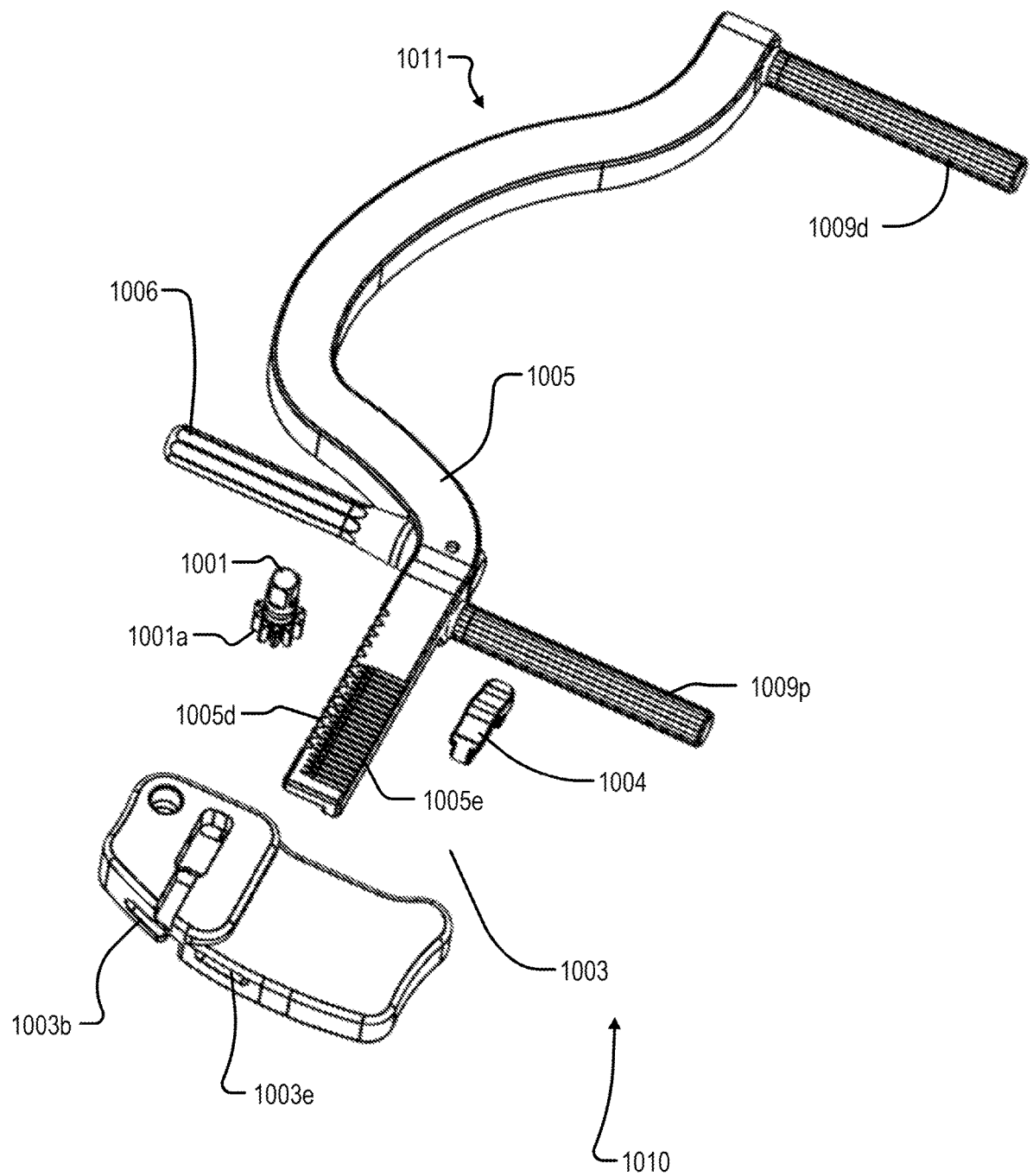
FIG. 57 is an exploded parts view of a fourth module.
Figure 58:
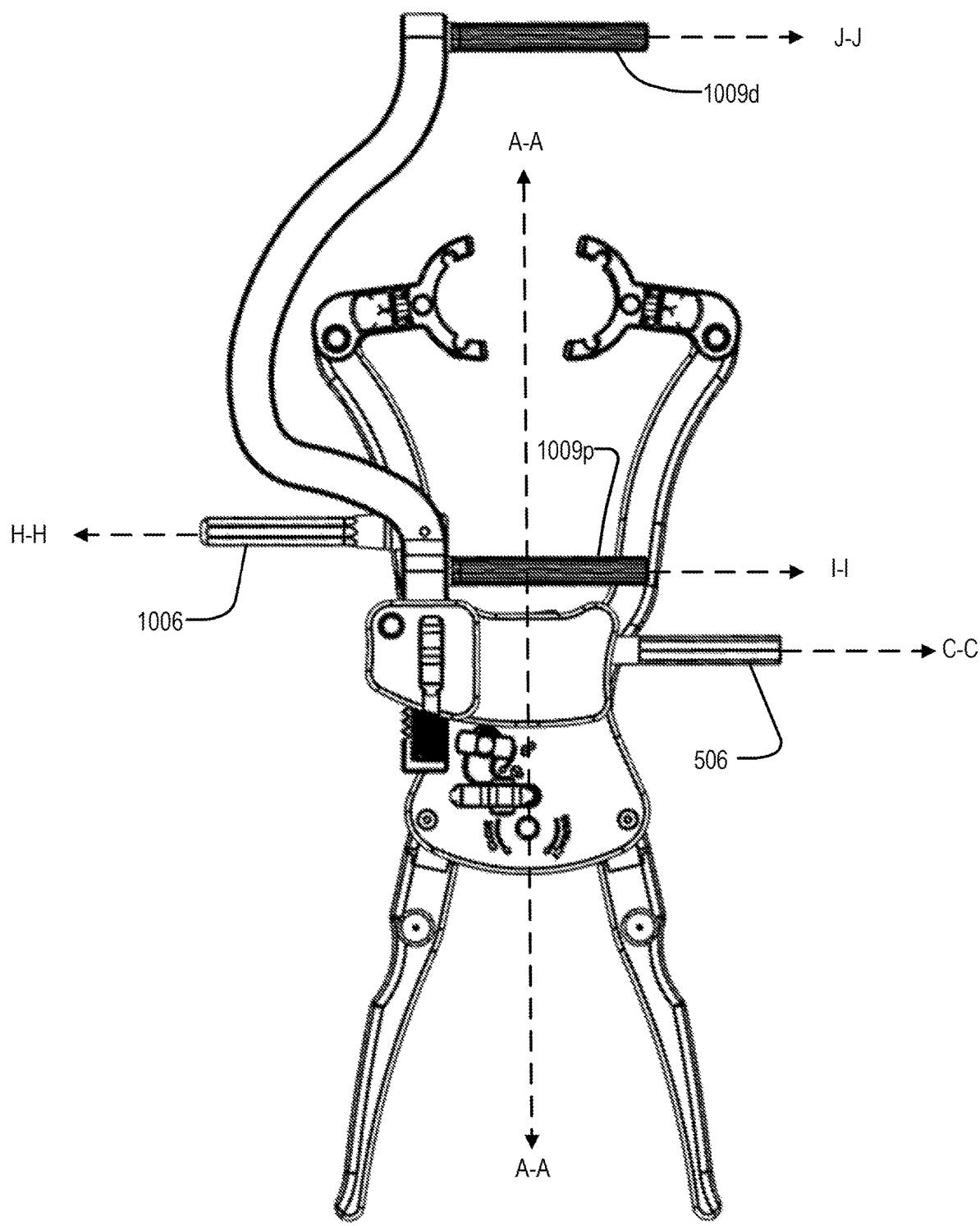
FIG. 58 is a top down view of a fourth module coupled to a modular retractor.
Figure 59:
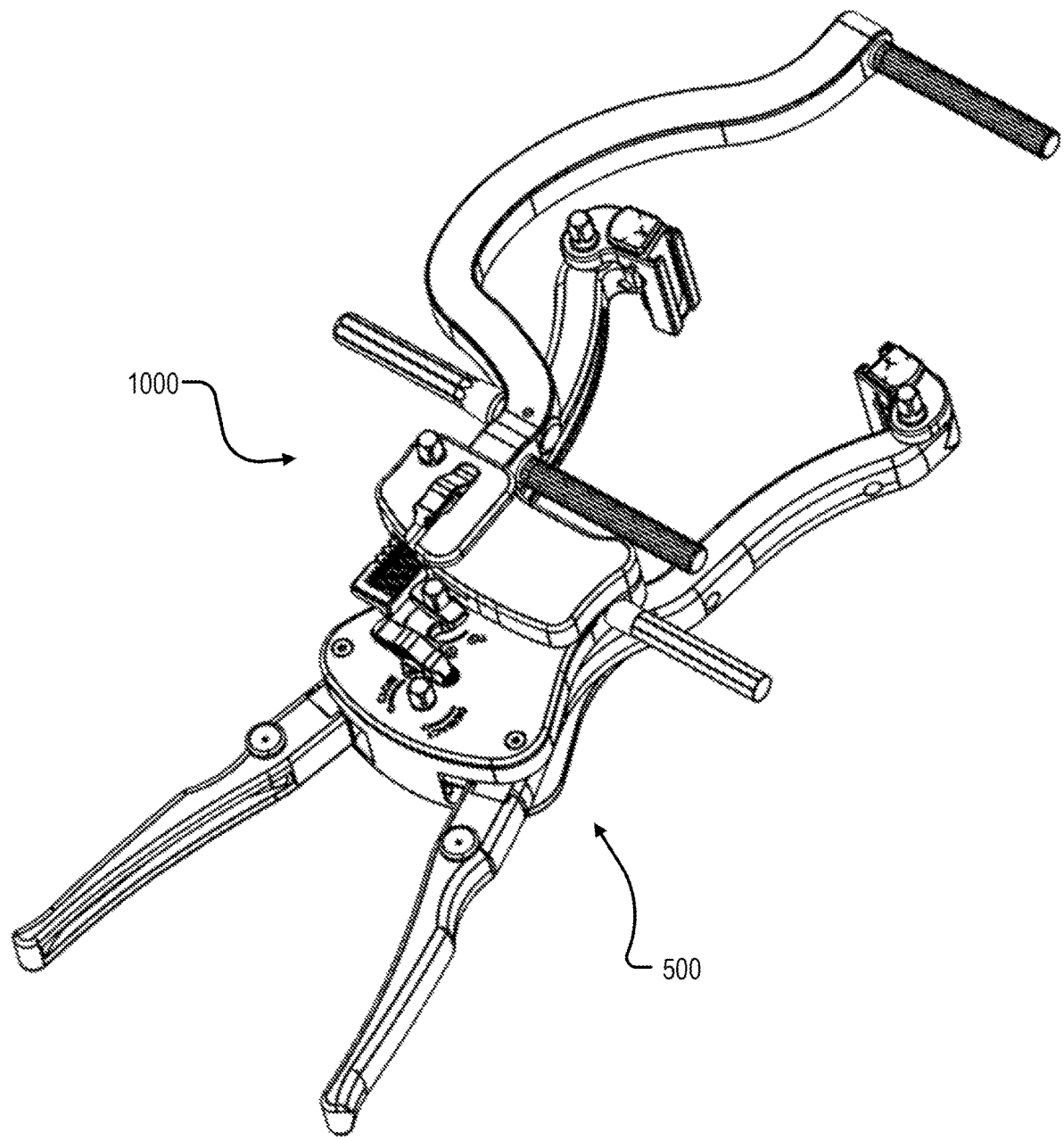
FIG. 59 is a perspective view of a fourth module coupled to a modular retractor.
Figure 60:
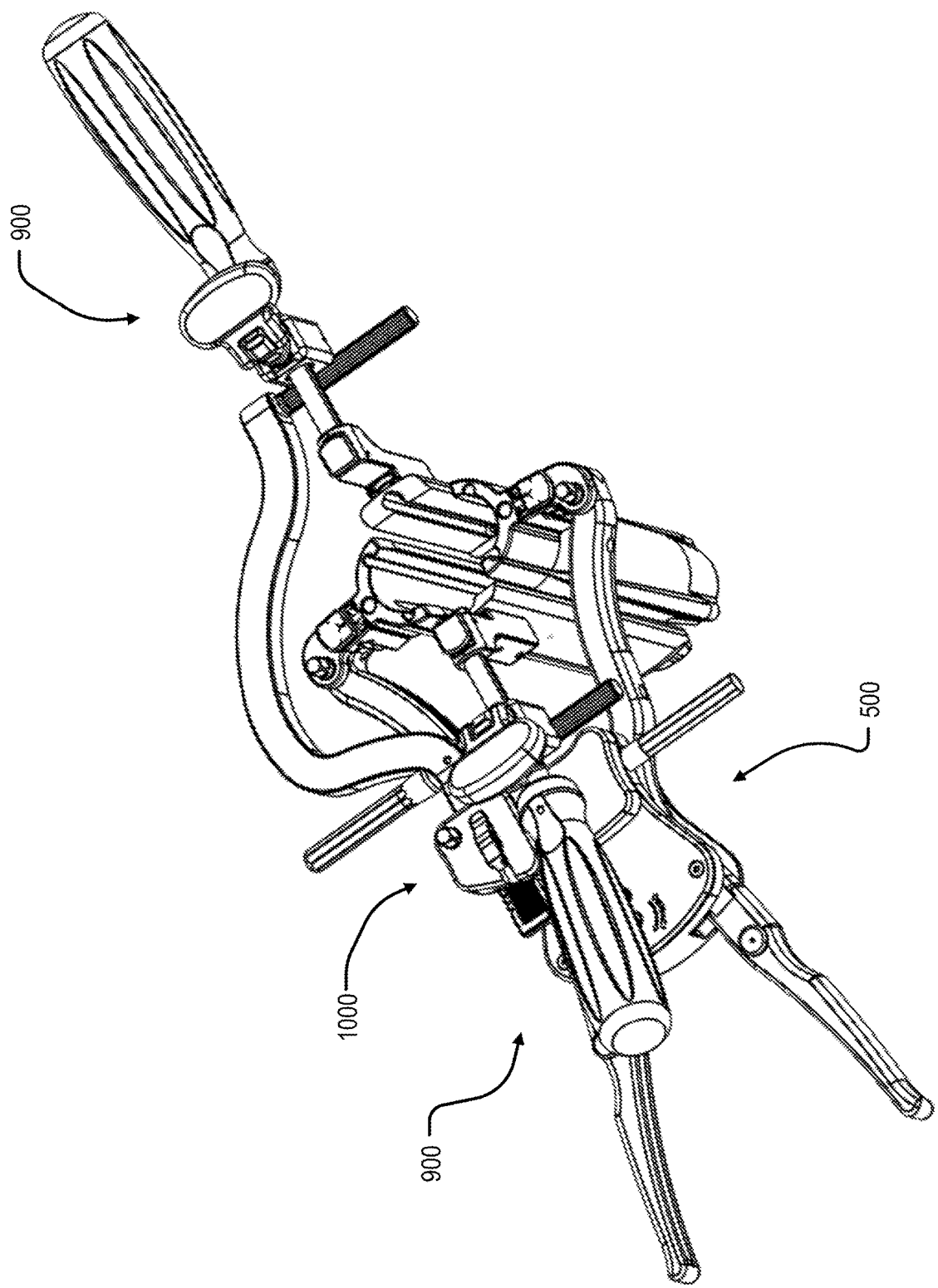
FIG. 60 is a perspective view of a fourth module coupled to a modular retractor and first and second free hand modules coupled to the fourth module.
Figure 61:
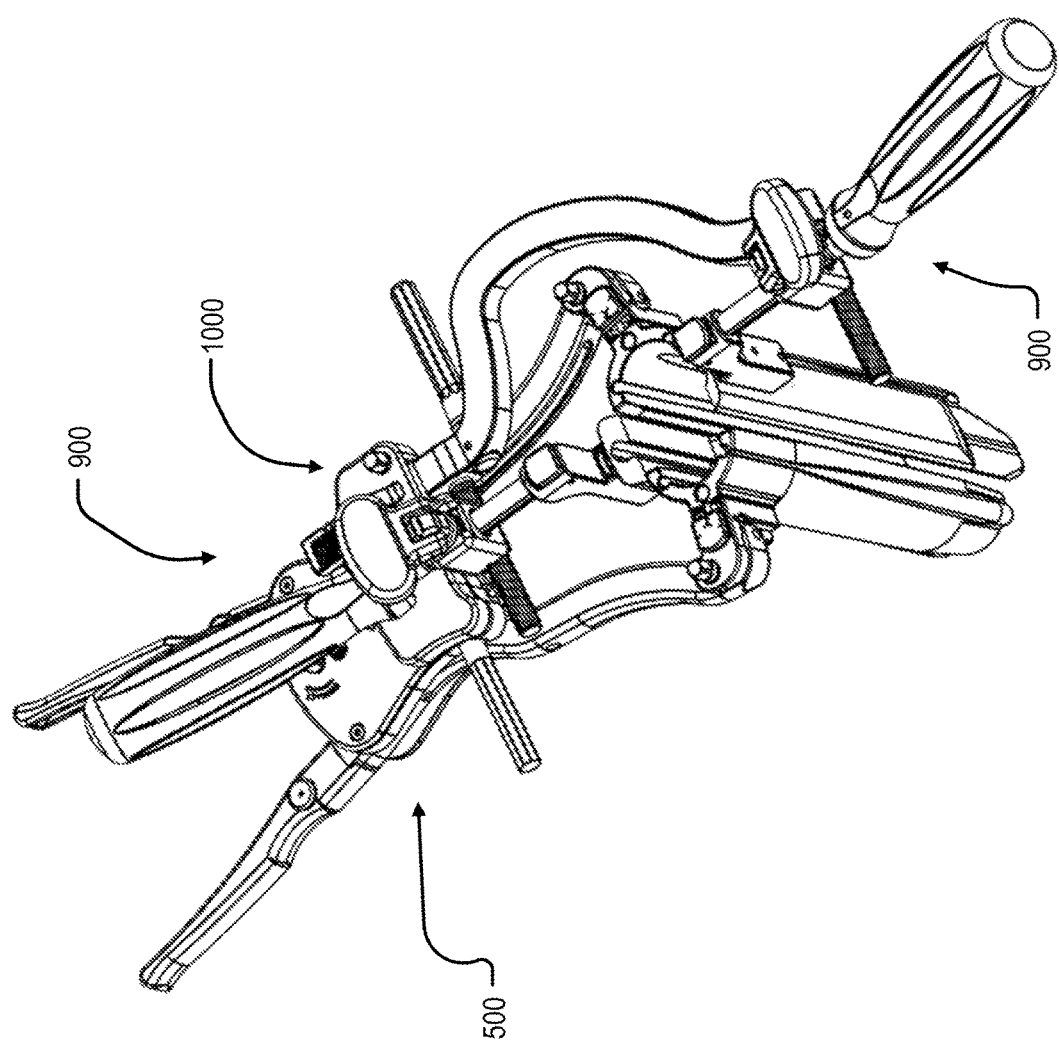
FIG. 61 is a perspective view of a fourth module coupled to a modular retractor and first and second free hand modules coupled to the fourth module.

FIGS. 55-56 are various perspective views of a fourth module 1000 for use with disclosed modular retractor 500 embodiments. FIG. 57 is an exploded parts view of a fourth module 1000. FIGS. 58-59 are various views of a fourth module 1000 coupled to a modular retractor 500 and FIGS. 60-61 are various views of a fourth module 1000 coupled to a first free hand module 900 and a second free hand module 900.

Fourth module 1000 may include the same, substantially the same, and or similar components as third module 800. Accordingly, duplicative disclosure will be omitted and/or minimized. Fourth module 1000 may be configured to couple and uncouple from modular retractor 500 at connection points 503*a*, for example (see FIG. 20). For example, the fourth module 1000 may have at least one corresponding connection point 1003*a* on an underside thereof (see FIG. 56) that is configured to couple, connect, and/or mate with a connection point 503*a* of the modular retractor 500 in the same, substantially the same, and or similar manner as explained above. Additionally, fourth module 1000 may be locked to modular retractor 500 by lock 513 (see FIG. 20). Lock 513 may be pivotable such that in a locked position a flange portion of lock 513 may pivot into a locking aperture 1003*e* of fourth module 1000, in the same, substantially the same, and or similar manner as explained above.

Fourth module 1000 may include an arm 1005 that includes a straight portion 1010 and a C shaped curved portion 1011. Straight portion 1010 of arm 1005 may extend through body 1003 and move forward and backward in a longitudinal direction, for example. As seen best in FIG. 58, when fourth module 1000 is coupled to modular retractor 500 the C shaped curved portion 1011 extends laterally outward in a lateral direction farther than the farthest lateral edge of arm 507 of modular retractor 500. For example, the C shaped curved portion 1011 does not obscure a surgeons viewing area and/or access to a surgical site. The straight portion 1010 of arm 1005 may extend through body 1003 through an L shaped contoured channel 1003*b*, for example. Fourth module 1000 may be configured to extend arm 1005 along a path of travel by a rack and pinion mechanism, for example. The path of travel may be linear path, for example.

Fourth module 1000 may include a table mount 1006 extending laterally from a side surface thereof in a direction defined by an extension direction H-H of table mount 1006 (see FIG. 58), for example. Table mount 1006 may facilitate the secure placement of fourth module 1000 such that fourth module 1000 remains fixed in 3D space and/or facilitate the relative motion of fourth module 1000 (and/or modular retractor 500 when coupled thereto) in any direction when moving table mount 70, for example. Fourth module 1000 may be configured to extend arm 1005 by activation of actuator 1001, e.g., by rotation of actuator 1001. Actuator 1001 may be securely attached to body portion 1003 and include a pinion portion 1001*a* (pinion gear and/or spur gear) having teeth that engage with and are meshed with straight rack portion 1005*d* disposed on a side surface of arm 1005, in the same, substantially the same, and or similar manner as explained above. Additionally, fourth module 1000 may include a first pawl 1004 that may be configured to engage the rack portion 1005*e* disposed on a top surface of arm 1005, for example. First pawl 1004 may be configured to allow pinion portion 1001*a* to rotate in a first direction (counter clockwise direction) and prevent pinion portion 1001*a* from rotating in a second direction (clockwise direction) in the same, substantially the same, and or similar manner as explained above.

Fourth module 1000 may include a table mount 1006 extending in a lateral direction along axis H-H away from arm 1005 and longitudinal axis A-A. Fourth module 1000 may include a proximal module mount 1009 extending along axis I-I in a lateral direction away from arm 1005 towards longitudinal axis A-A. For example, table mount 1006 may extend to the left direction and proximal module mount 1009*p* may extend to the right direction. Additionally, in various embodiments, the C shaped curved portion 1011 may include a distal module mount 1009*d* that extends along axis J-J from a side surface of curved arm portion 1011 such that it crosses over longitudinal axis A-A of modular retractor 500. The distal module mount 1109*d* and proximal module mount 1009*p* may be symmetrically disposed relative to one another with respect to longitudinal axis A-A, for example (see FIG. 58). Additionally, straight portion 1010 of arm 1005 may be supported by body 1003 on the left side of the longitudinal axis A-A of modular retractor 500. In this configuration, module mounts 1009*p*, 1009*d* may cross over the longitudinal axis A-A, for example. Module mounts 1009*p*, 1009*d* may each independently support a free hand module 900, in the same, similar, and/or substantially the same manner as explained previously. For example, as shown in FIGS. 60-61 proximal module mount 1009*p* supports a free hand module 900 in a proximal position and distal module mount 1009d supports a free hand module 900 in a distal position.

Figure 62:
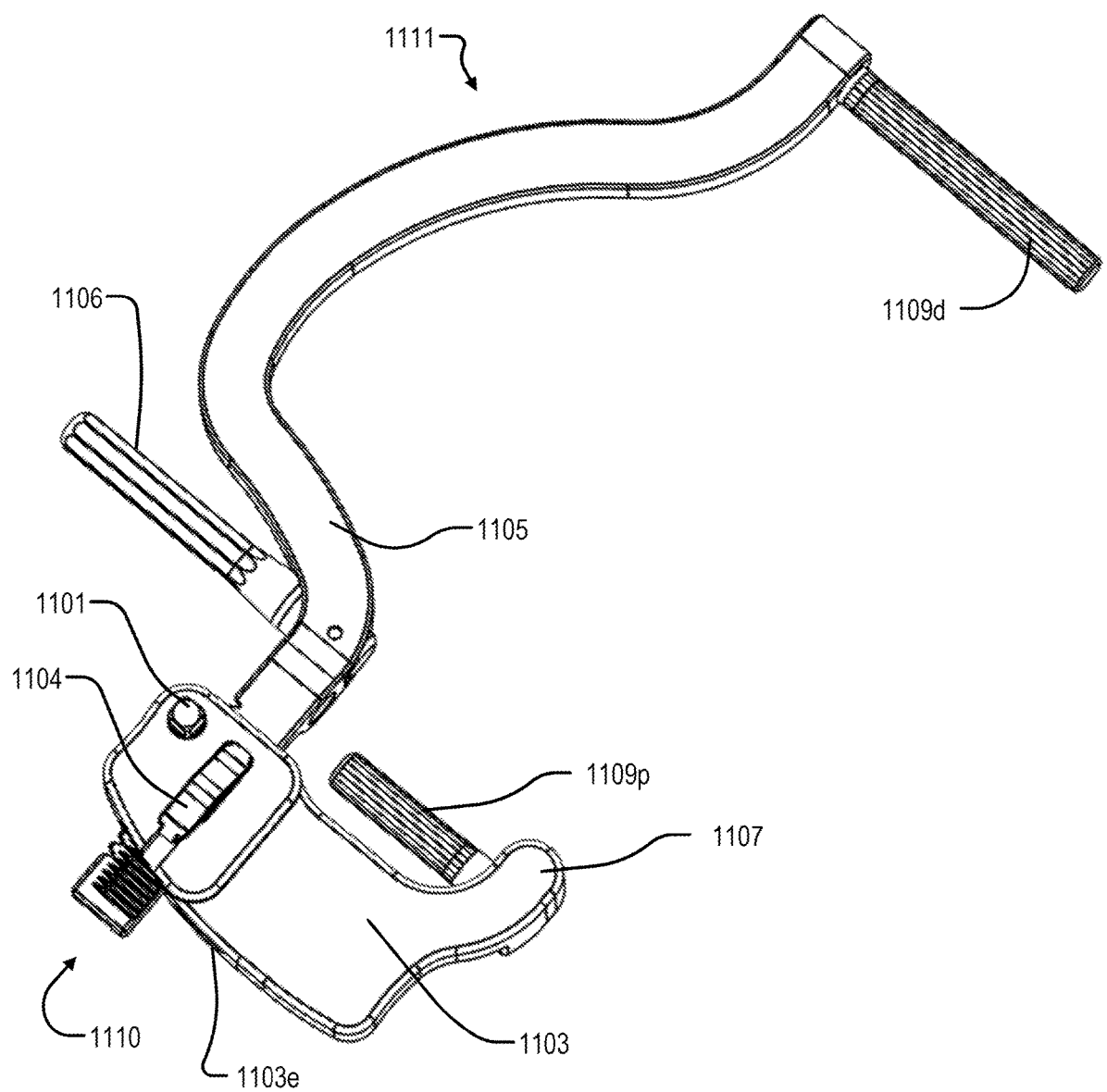
FIG. 62 is a top perspective view of a fifth module for use with disclosed modular retractor embodiments.
Figure 63:
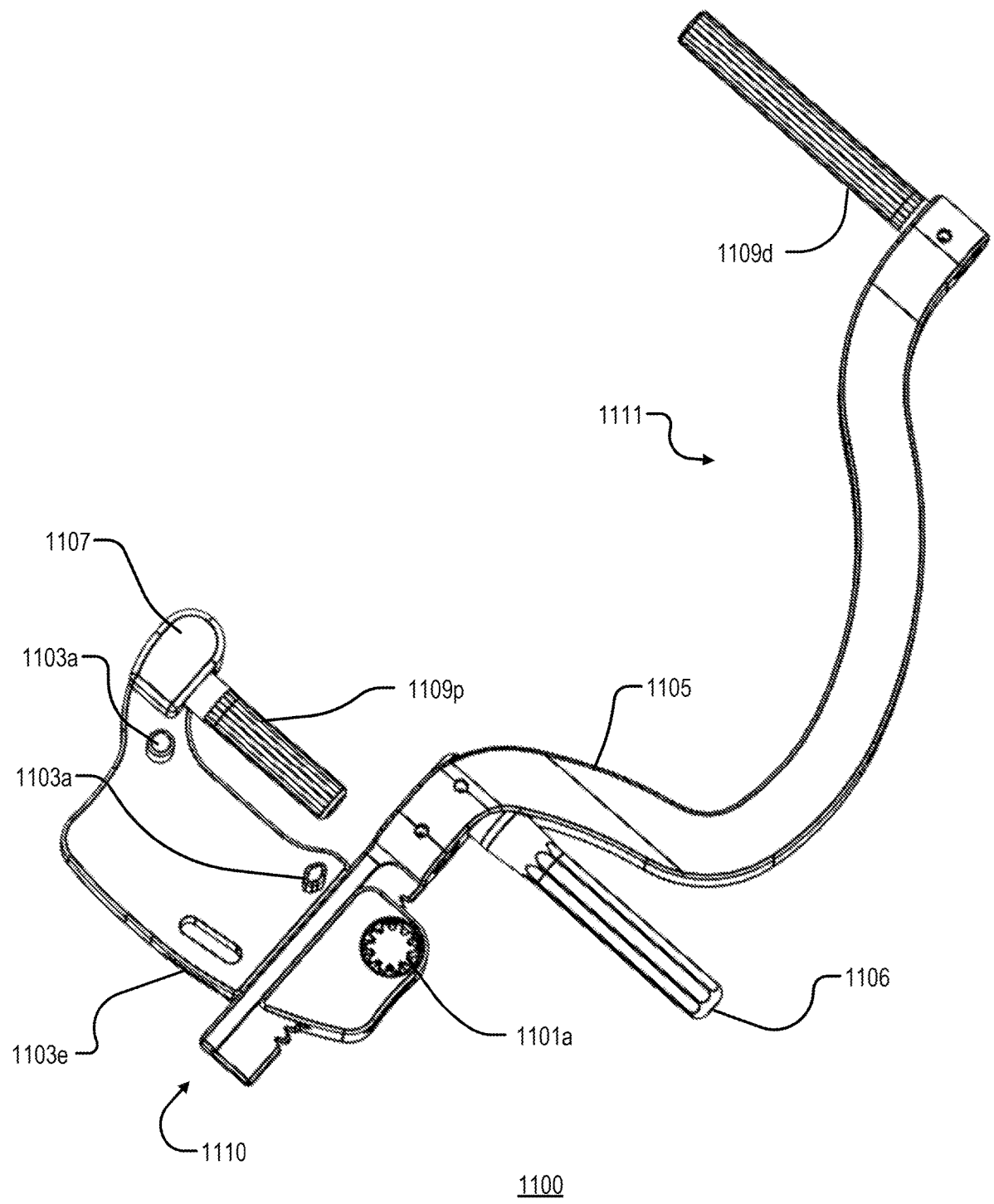
FIG. 63 is a bottom perspective view of a fifth module for use with disclosed modular retractor embodiments.
Figure 64:
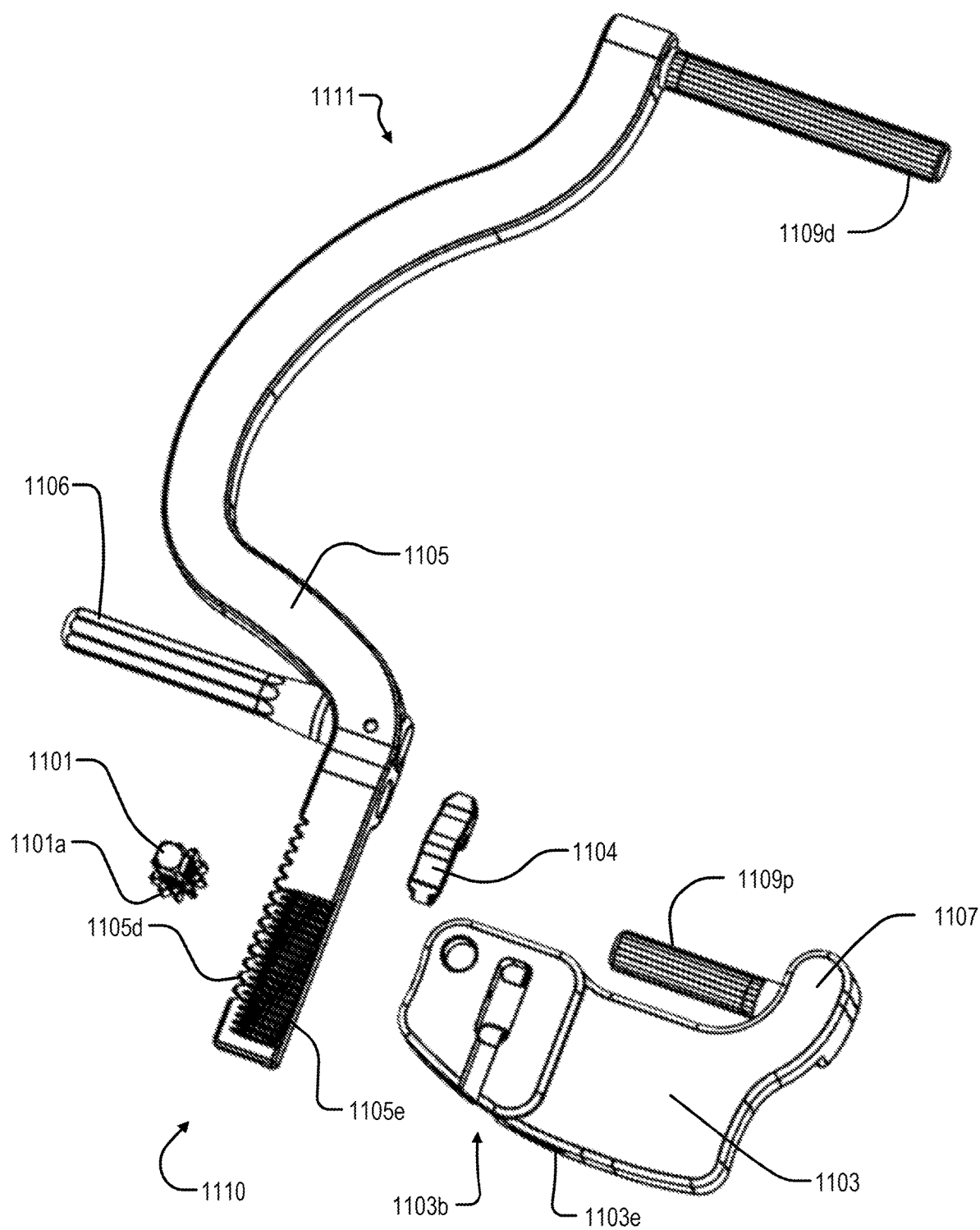
FIG. 64 is an exploded parts view of a fifth module.
Figure 65:
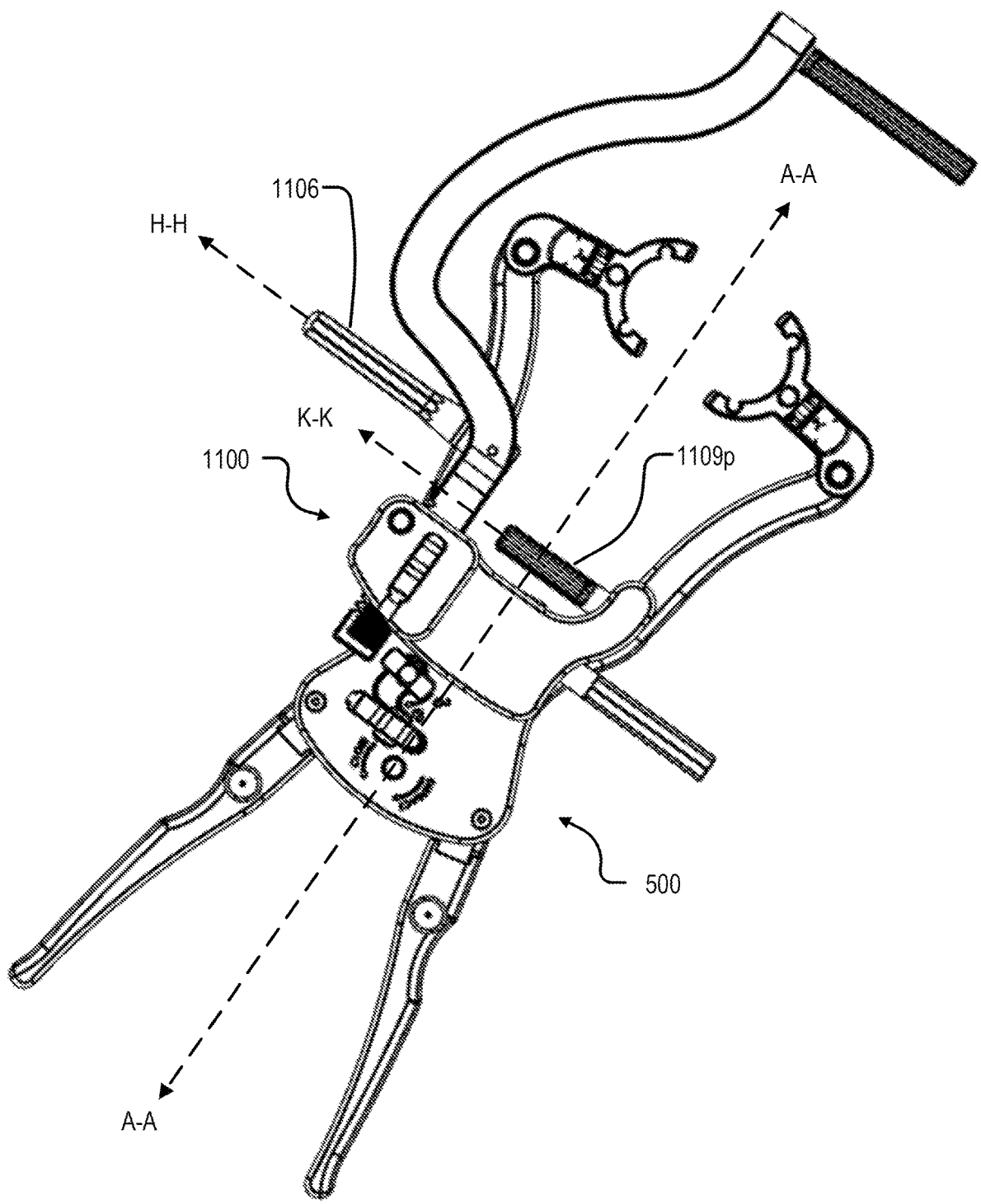
FIG. 65 is a top perspective view of a fifth module.

Referring generally to FIGS. 62-65 a fifth module 1100 for use with the modular retractor 500 is disclosed. FIGS. 62-63 are various perspective views of a fifth module 1100 for use with disclosed modular retractor 500 embodiments. FIG. 64 is an exploded parts view of a fifth module 1100 and FIG. 65 is a top perspective view of a fifth module 1100 coupled to a modular retractor 500.

Fifth module 1100 may include the same, substantially the same, and or similar components as third module 800 and/or fourth module 1000. Accordingly, duplicative disclosure will be omitted and/or minimized. Fifth module 1100 may be configured to couple and uncouple from modular retractor 500 at connection points 503a, for example (see FIG. 20). For example, the fifth module 1100 may have at least one corresponding connection point 1103a on an underside thereof (see FIG. 63) that is configured to couple, connect, and/or mate with a connection point 503a of the modular retractor 500 in the same, substantially the same, and or similar manner as explained above. Additionally, fifth module 1100 may be locked to modular retractor 500 by lock 513 (see FIG. 20). Lock 513 may be pivotable such that in a locked position a flange portion of lock 513 may pivot into a locking aperture 1103e of fifth module 1100, in the same, substantially the same, and or similar manner as explained above. Similarly, in an unlocked position the flange portion of lock 513 may be unseated from aperture 1103e.

Fifth module 1100 may include an arm 1105 that includes a straight portion 1110 and a C shaped curved portion 1111. Straight portion 1110 of arm 1105 may extend through body 1103 and move forward and backward in a longitudinal direction, for example. As seen best in FIG. 65, when fifth module 1100 is coupled to modular retractor 500 the C shaped curved portion 1111 extends laterally outward in a lateral direction farther than the farthest lateral edge of arm 1105. For example, the C shaped curved portion 1111 does not obscure a surgeon's viewing area and/or access to a surgical site. The straight portion 1110 of arm 1105 may extend through body 1103 through an L shaped contoured channel 1103b. Fifth module 1100 may be configured to extend arm 1105 along a path of travel by a rack and pinion mechanism, for example. The path of travel may be linear path, for example.

Fifth module 1100 may include a table mount 1106 extending laterally from a side surface of arm 1105 adjacent a junction of curved portion 1111 and straight portion 1110. Table mount 1106 may extend along axis H-H in a direction defined by an extension direction of table mount 1106 (see FIG. 65), for example. In the example embodiment, table mount 1106 extends in a perpendicular direction to longitudinal axis A-A and/or a dominant extension direction of straight portion 1110. Table mount 1106 may facilitate the secure placement of fifth module 1100 such that fifth module 1100 remains fixed in 3D space and/or facilitate the relative motion of fifth module 1100 (and/or modular retractor 500 when coupled thereto) in any direction when moving table mount 70, for example. Fifth module 1100 may be configured to extend arm 1105 by activation of actuator 1101, e.g., by rotation of actuator 1101. Actuator 1101 may be securely attached to body portion 1103 and include a pinion portion 1101a (pinion gear and/or spur gear) having teeth that engage with and are meshed with straight rack portion 1105d disposed on a side surface of straight portion 1110 of arm 1105, in the same, substantially the same, and or similar manner as explained above. Additionally, fifth module 1100 may include a pawl 1104 that may be configured to engage the rack portion 1105e disposed on a top surface of straight portion 1110 of arm 1105, for example. Pawl 1104 may be configured to allow pinion portion 1101a to rotate in a first direction (counter clockwise direction) and prevent pinion portion 1101a from rotating in a second direction (clockwise direction) in the same, substantially the same, and or similar manner as explained above.

Fifth module 1100 may include a body 1103 having a curved body portion 1107 extending away from longitudinal axis A-A. In the example embodiment, curved body portion 1107 curves away in an opposite direction from arm 1105 and defines the distal most portion of body 1103. Curved body portion 1107 may support and orient proximal modular mount 1109 such that it extends in a lateral direction towards arm 1105, and crosses over longitudinal axis A-A. For example, table mount 1106 may extend to the left direction from a left side of arm 1105 and proximal module mount 1109p may extend along axis K-K to the left direction from a left side of curved body portion 1107 and cross over longitudinal axis A-A. Additionally, in various embodiments, the C shaped curved portion 1111 may include a distal module mount 1109d that extends from a side surface of curved arm portion 1111 such that it crosses over longitudinal axis A-A of modular retractor 500. The distal module mount 1109d and proximal module mount 1109p may be disposed opposite one another and each cross over longitudinal axis A-A, for example. Additionally, straight portion 1110 of arm 1105 may be supported by body 1103 on the left side of the longitudinal axis A-A of modular retractor 500. Module mounts 1109p, 1109d may each independently support a free hand module 900, as explained previously. Furthermore, in various embodiments, module mount 1109p may be relatively shorter than module mount 1109d.

Figure 67:
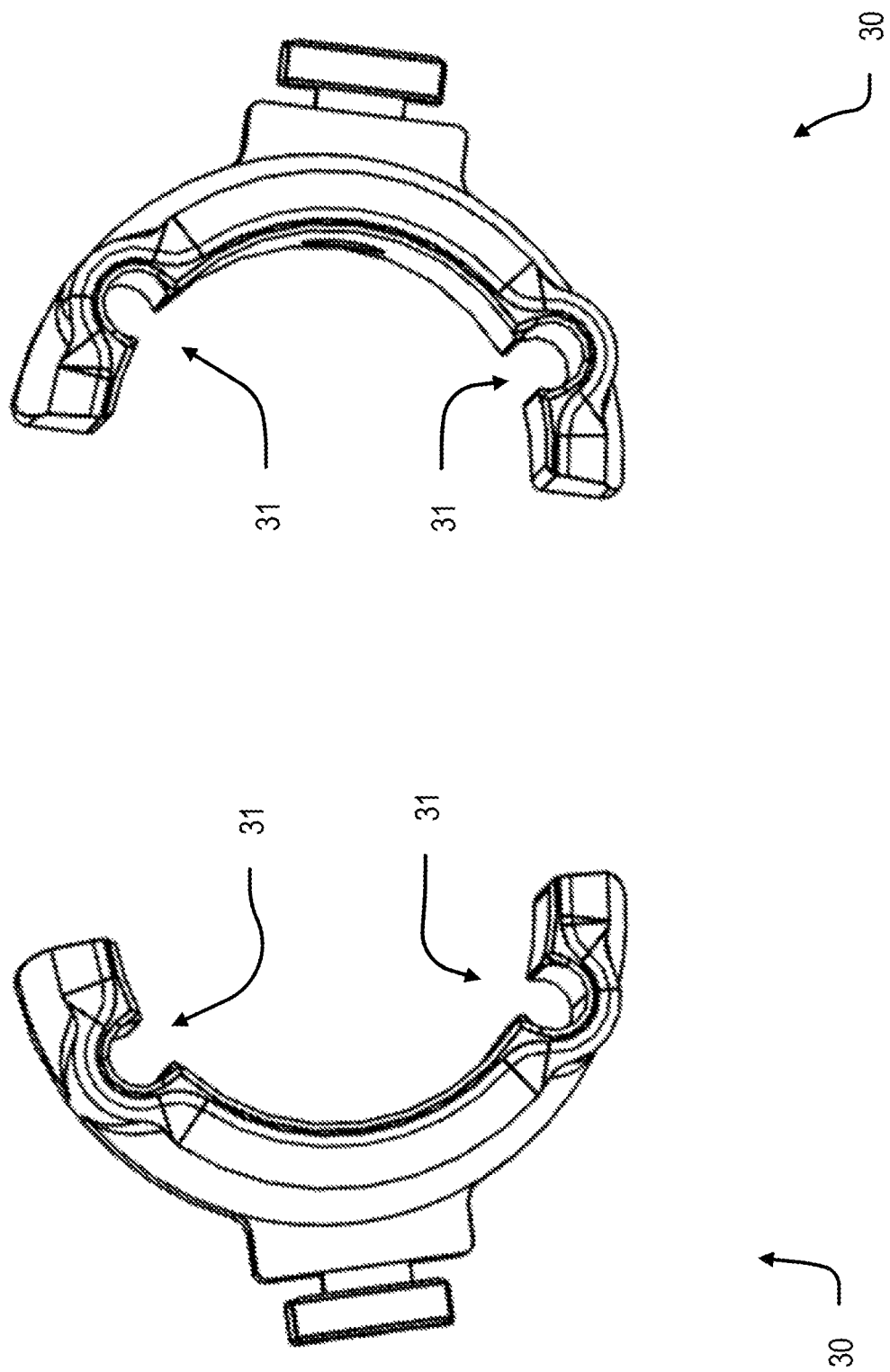
FIG. 67 is a bottom view of a pair of blades for use with disclosed modular retractor embodiments.
Figure 68:
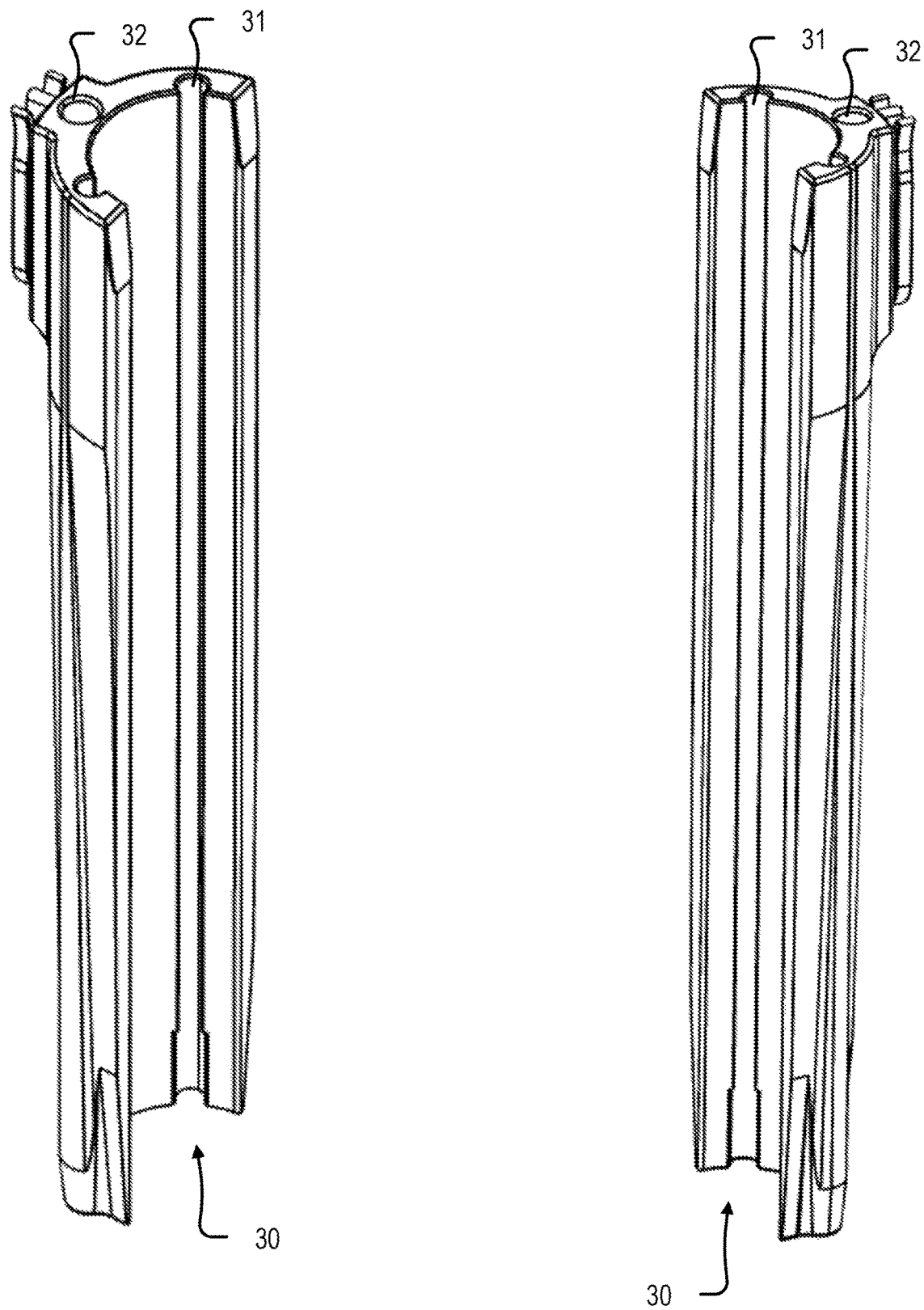
FIG. 68 is a perspective view of a pair of blades for use with disclosed modular retractor embodiments.

Referring generally to FIGS. 66-75 various blades for use with the modular retractor 500 and any of the various modules disclosed herein are disclosed. FIG. 66 is a top view of a pair of blades 30, FIG. 67 is a bottom view of a pair of blades 30, and FIG. 68 is a perspective view of a pair of blades 30 for use with disclosed modular retractor 500 embodiments. Blades 30 may be shaped like a half circle, for example. Accordingly, in various embodiments when blades 30 adjoin one another they may form a common circle in a fully closed position. Additionally, blades 30 may include an arcuate channel 31 extending along an inside surface thereof from a proximal end (see FIG. 66) to a distal end (see FIG. 67), for example. Arcuate channel 31 may have a size and shape corresponding to a size and shape of an arcuate outdent of a dilator, for example arcuate outdent 90a of dilator 90 shown in FIGS. 80A, 80B. Alternatively, arcuate channel 31 may have a size and shape corresponding to a size and shape of an arcuate outdent of a shim (not illustrated). Additionally, blades 30 may include an aperture 32 extending through a top surface of blade 30 at the proximal end and penetrating the inside surface of blade 30 thereby providing access to the surgical access opening created by blades 30, for example. Aperture 32 may provide access for light fixtures and other diagnostic tools such as endoscopes, electrodes, temperature sensors, suction devices, and etc. that may be insert therein and be protected while extending through blade 30, for example.

Figure 69:
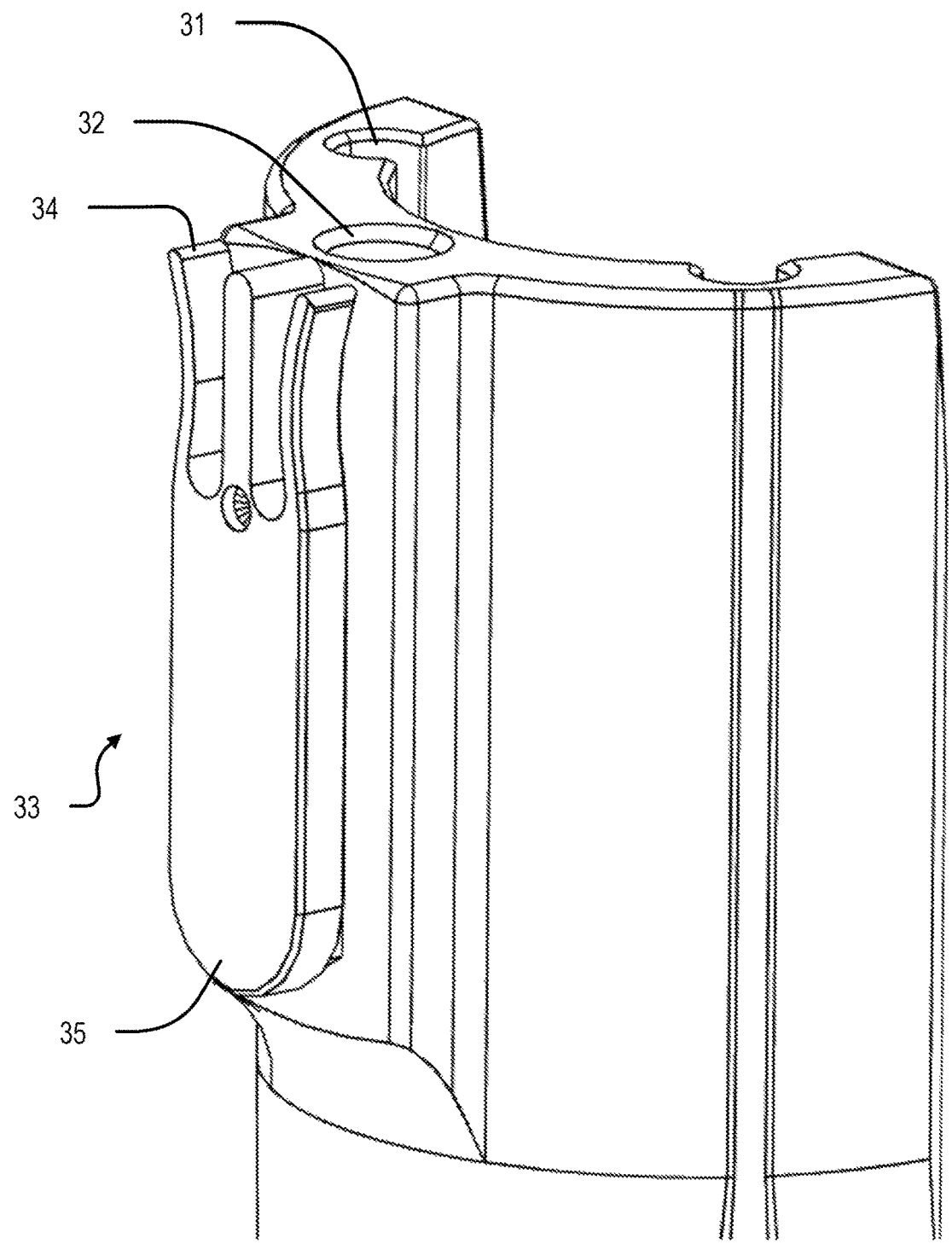
FIG. 69 is an enlarged view of a top portion of a universal blade fastener.

FIG. 69 is an enlarged view of a top portion of a universal blade fastener 33. Universal blade fastener 33 may be similar to blade fastener 26 of telescoping blade 20 (see FIG. 52B) but in reverse. For example, blade fastener 33 may be configured for top loading blade 30 to a blade receiving mechanism. Blade fastener 33 may include a pair of spring loaded tabs 34 adjacent the upper surface of blade 30 and a curved support surface 35 therebelow. For example, spring loaded tabs 34 may be disposed at an upper region of blade fastener 33 and curved support surface 35 may be disposed at a lower portion of blade fastener. In this way, an end user can insert the support surface 35 within a blade receiving mechanism from above and the spring loaded tabs 34 can help retain blade 30 therein by a biasing force applied to sidewalls of a blade receiving mechanism. Furthermore, any other blade disclosed herein may include the same, similar, or substantially the same blade fastener 26.

Figure 70:
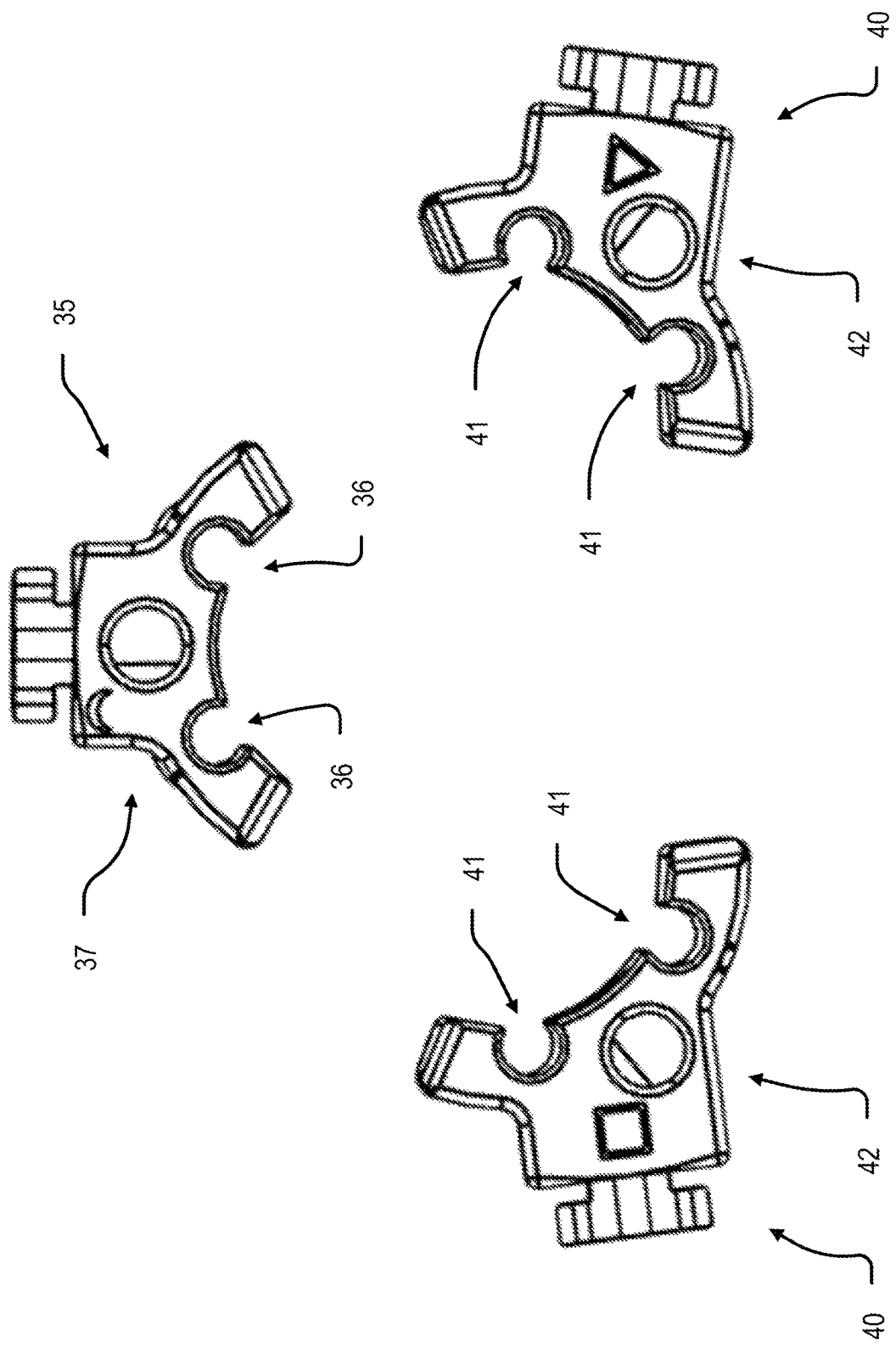
FIG. 70 is a top view of three blades for use with disclosed modular retractor embodiments.
Figure 71:
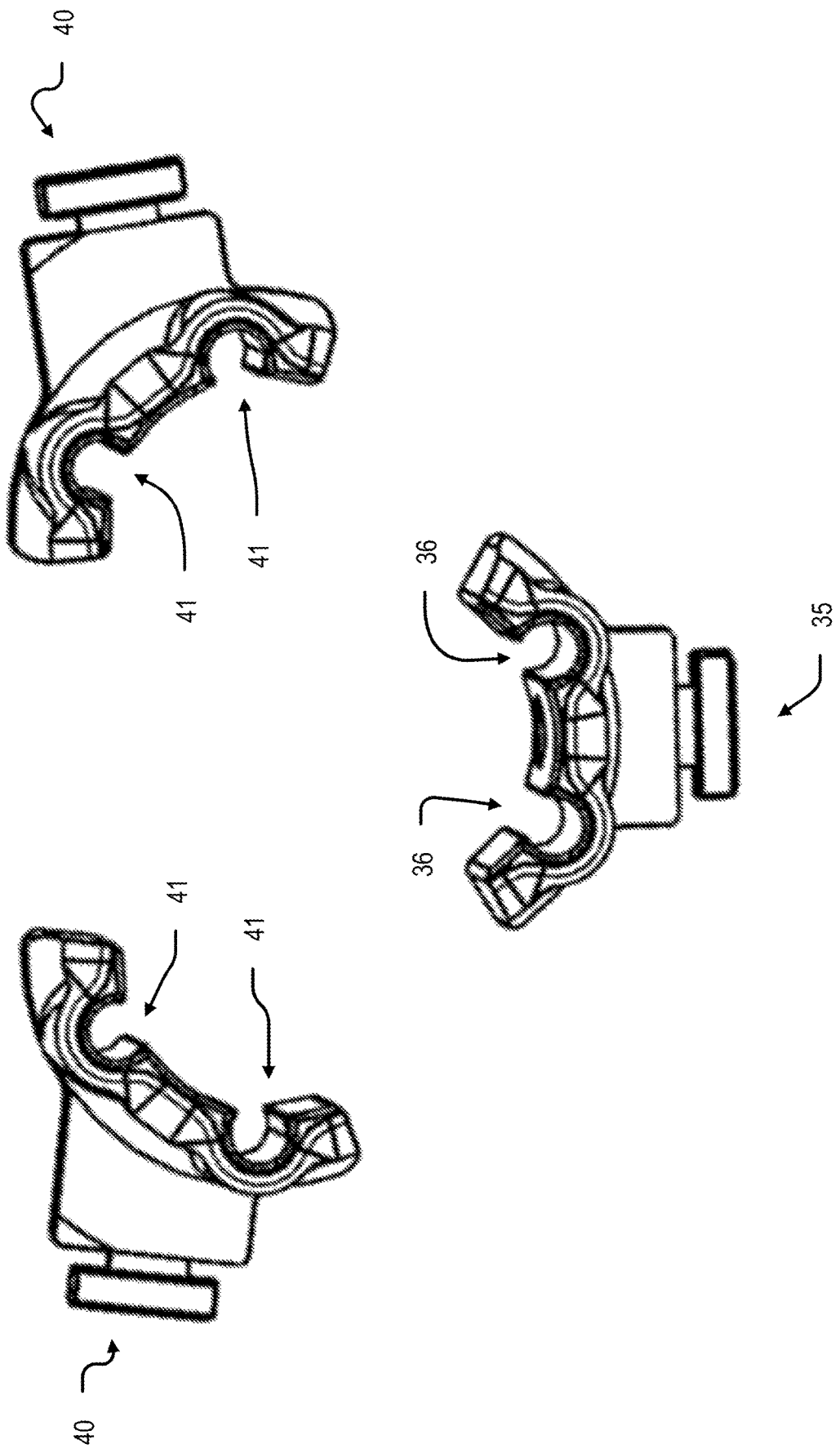
FIG. 71 is a bottom view of three blades for use with disclosed modular retractor embodiments.
Figure 72:
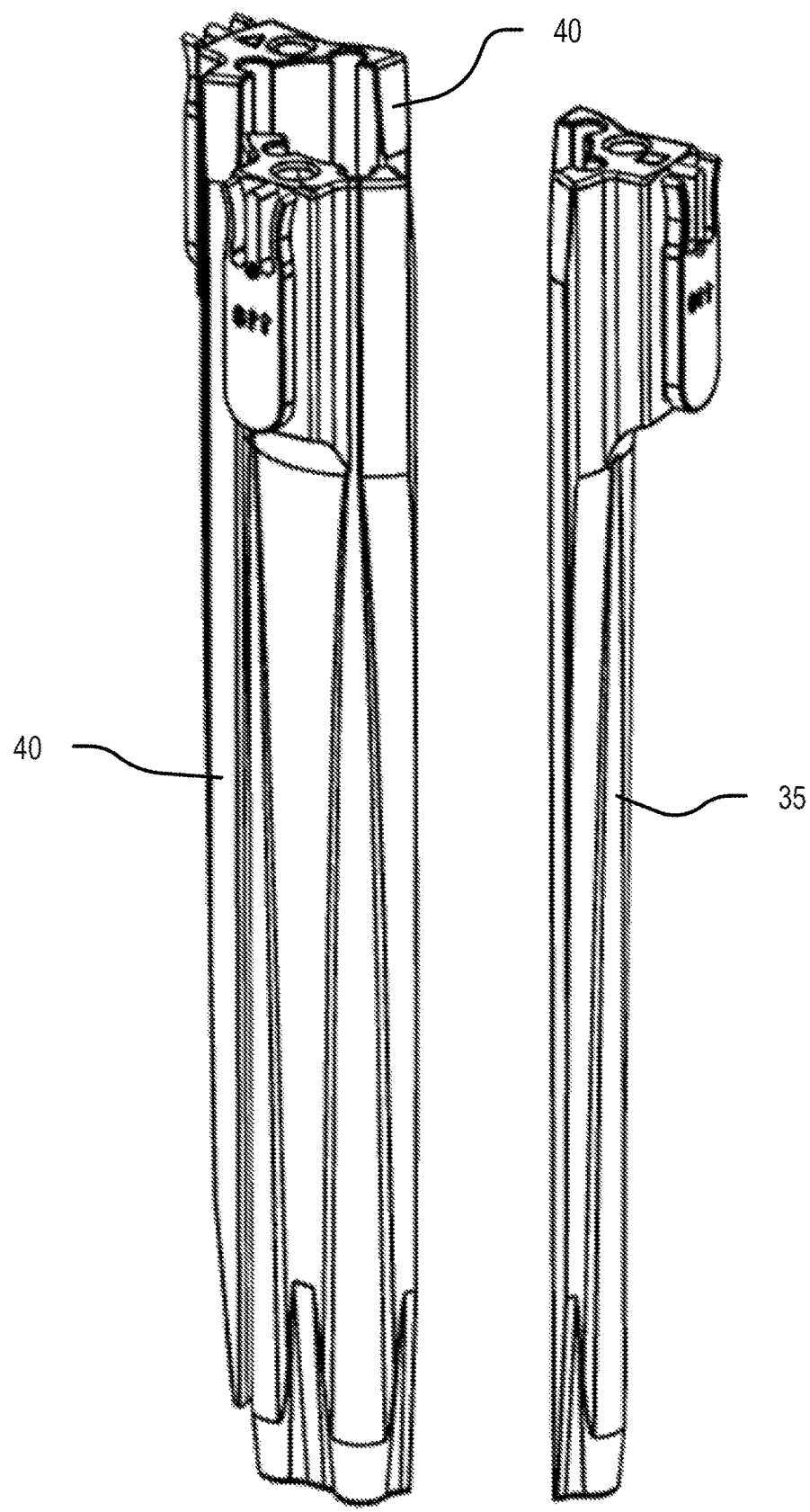
FIG. 72 is a perspective view of three blades for use with disclosed modular retractor embodiments.

FIG. 70 is a top view of various blades 40 and 35 and FIG. 71 is a bottom view of the three blades 40 and 35 for use with disclosed modular retractor 500 embodiments. FIG. 72 is a perspective view of blades 35, 40 for use with disclosed modular retractor 500 embodiments. In the example embodiment, a first blade 40, second blade 40, and a third blade 35 may form an oval shape. For example, when blades 40, 35 are closed together such that they adjoin one another they may form an oval like shape. Blades 40 may include two arcuate channels 41 and an aperture 42. Similarly, blade 35 may include two arcuate channels 36 and an arcuate channel 37. Arcuate channels 41, 37 may have a size and shape corresponding to a size and shape of an arcuate outdent of a dilator, for example arcuate outdent 81 of dilator 81 shown in FIG. 76. Additionally, in the fully closed position where blades 40, 35 adjoin one another, the six arcuate outdents of FIG. 76 may be disposed in a corresponding relative position and have a corresponding size and shape to the six arcuate channels 36, 37 shown in the three blade configuration of FIG. 70.

Furthermore, blades 40 may include an aperture 42 extending through a top surface of blade 40 at the proximal end and penetrating the inside surface of blade 40 and blade 35 may include an aperture 37 extending through a top surface of blade 35 at the proximal end and penetrating the inside surface of blade 35. Apertures 37 and 42 may provide access for light fixtures and other diagnostic tools such as endoscopes, electrodes, temperature sensors, suction devices, and etc. that may be insert therein and be protected while extending through blades 35 and 40, for example.

Figure 73:
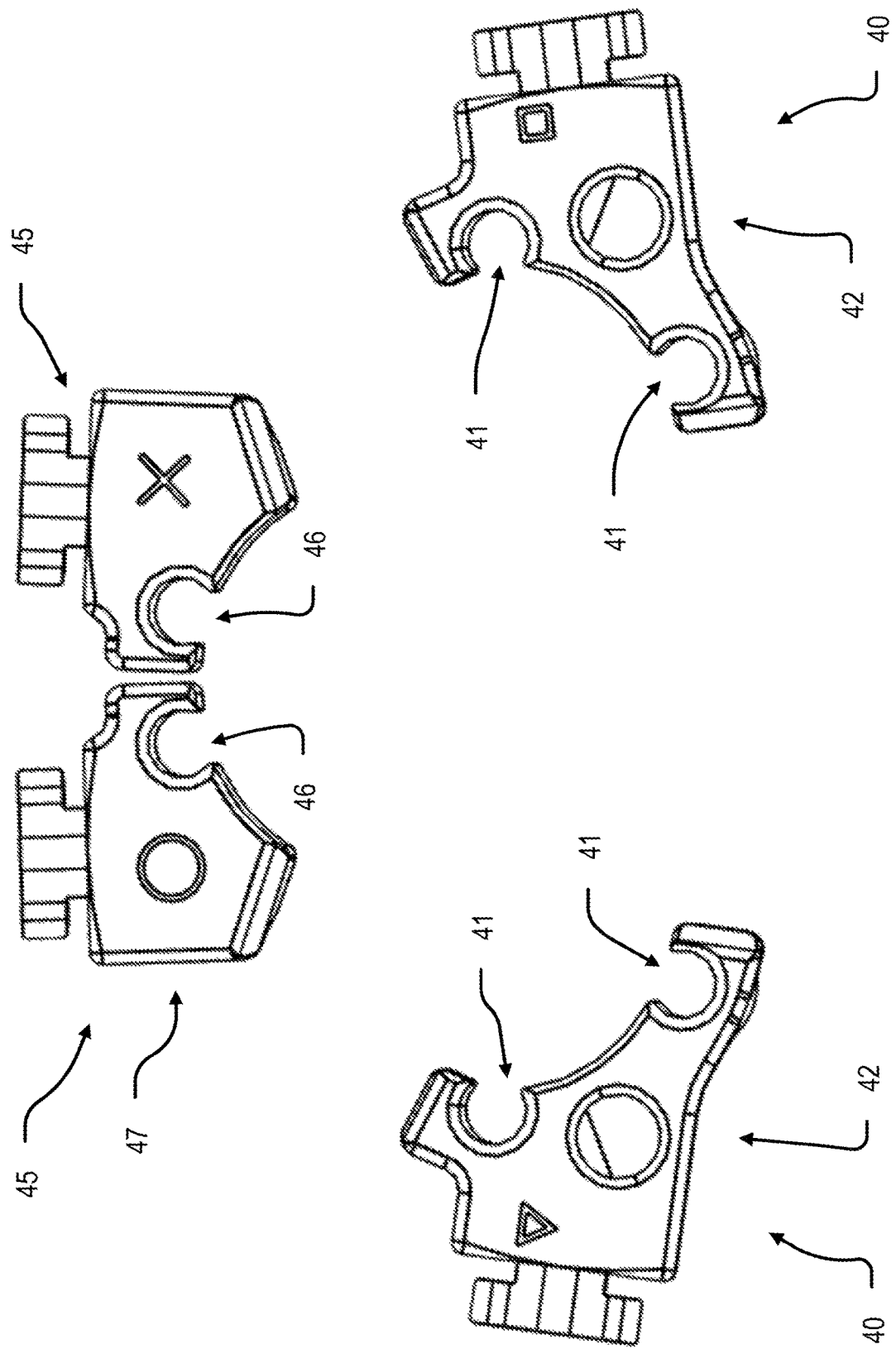
FIG. 73 is a top view of four blades for use with disclosed modular retractor embodiments.
Figure 74:
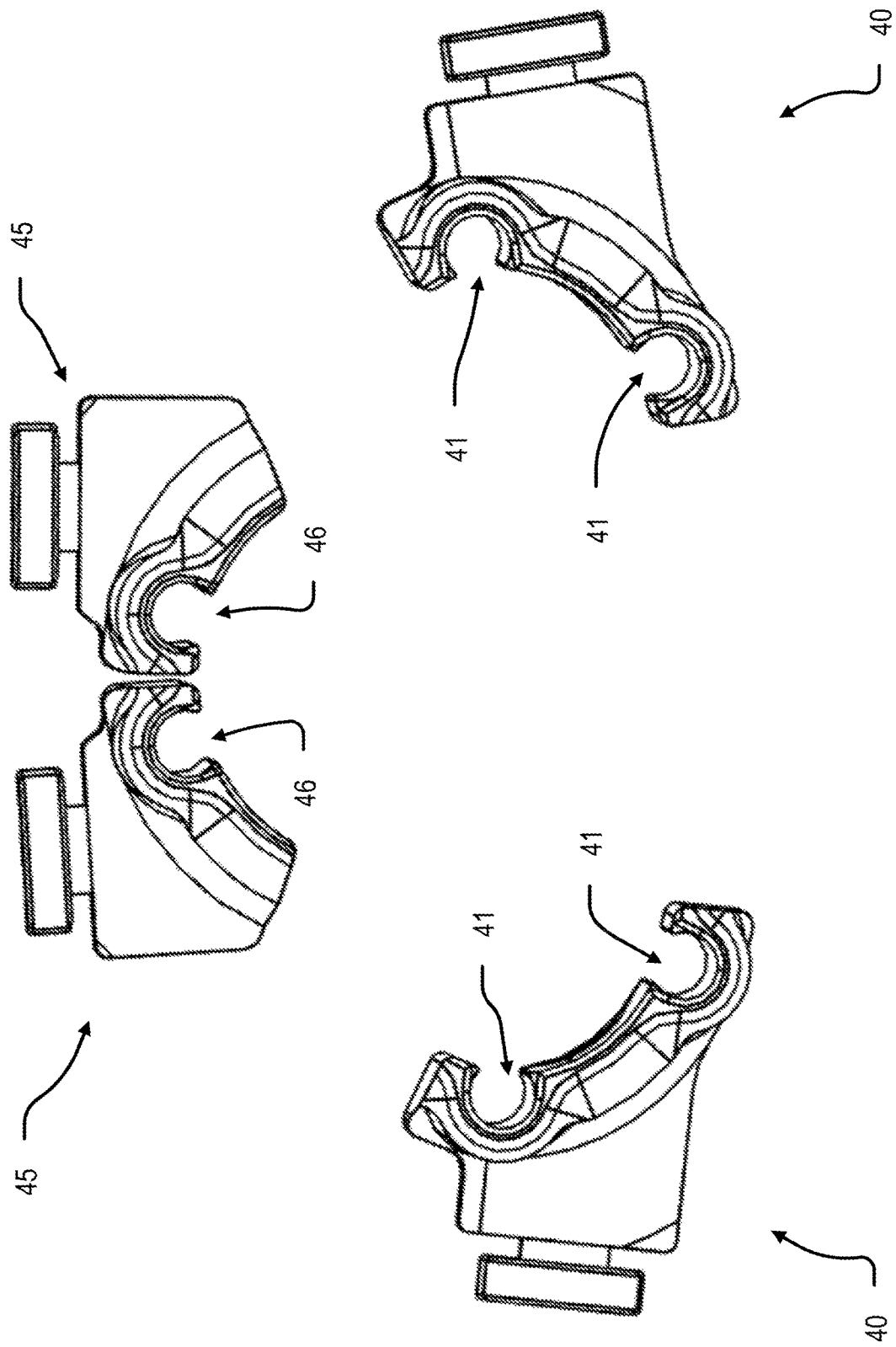
FIG. 74 is a bottom view of four blades for use with disclosed modular retractor embodiments.
Figure 75:
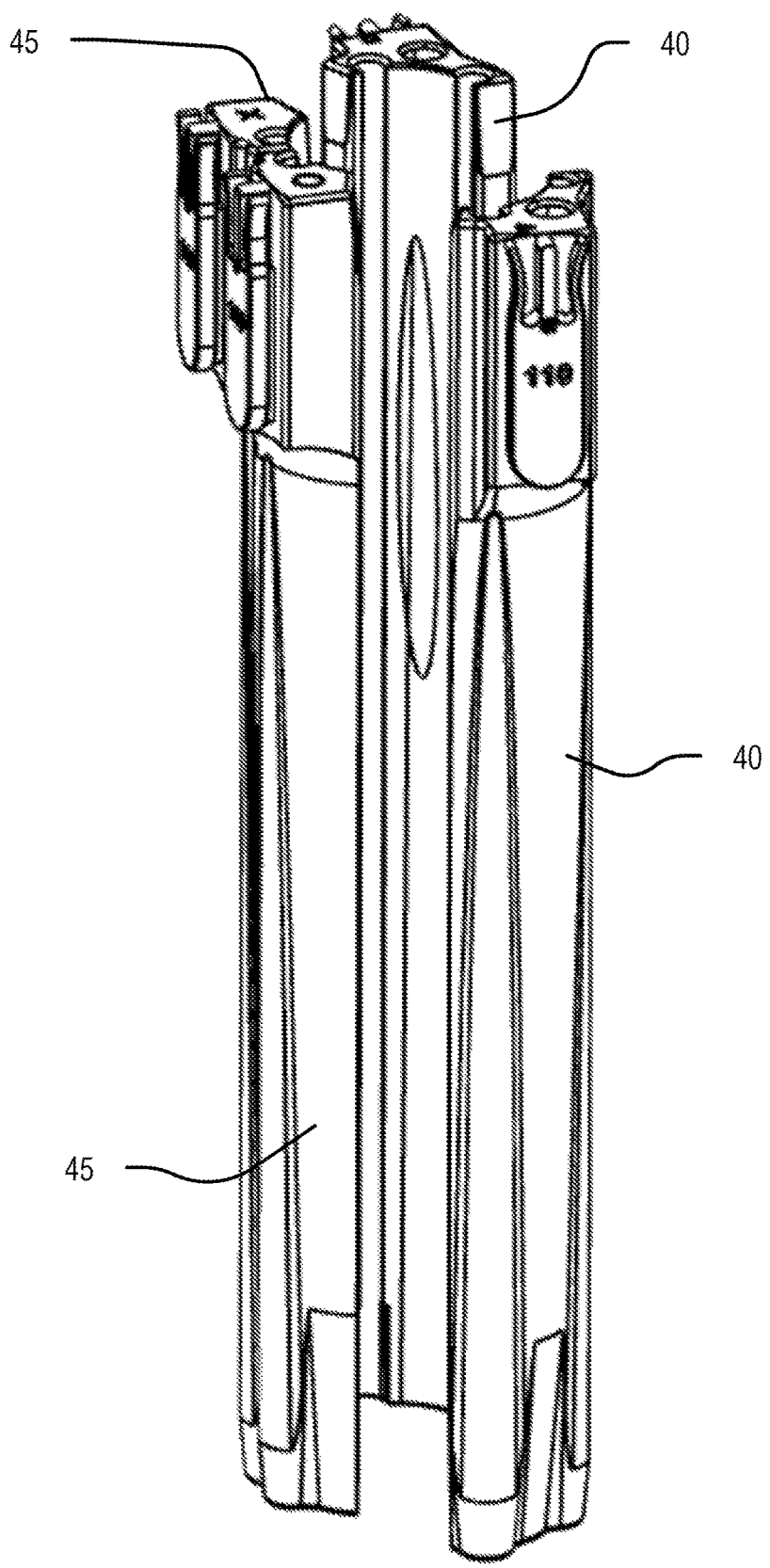
FIG. 75 is a perspective view of four blades for use with disclosed modular retractor embodiments.

FIG. 73 is a top view of four blades 40, 45 and FIG. 74 is a bottom view of the four blades for use with disclosed modular retractor 500 embodiments. FIG. 75 is a perspective view of the four blades 40, 45 for use with disclosed modular retractor 500 embodiments. In the closed position, blades 40, 45 may form an oval like shape. Blade 45 may include an arcuate channel 46 for securing to an arcuate outdent of a dilator having the same, similar, and or substantially the same attributes and purposes as explained above. Additionally blade 45 may include an aperture 47 extending through a top surface of blade 45 at the proximal end and penetrating the inside surface of blade having the same, similar, and or substantially the same attributes and purposes as explained above.

Figure 76:
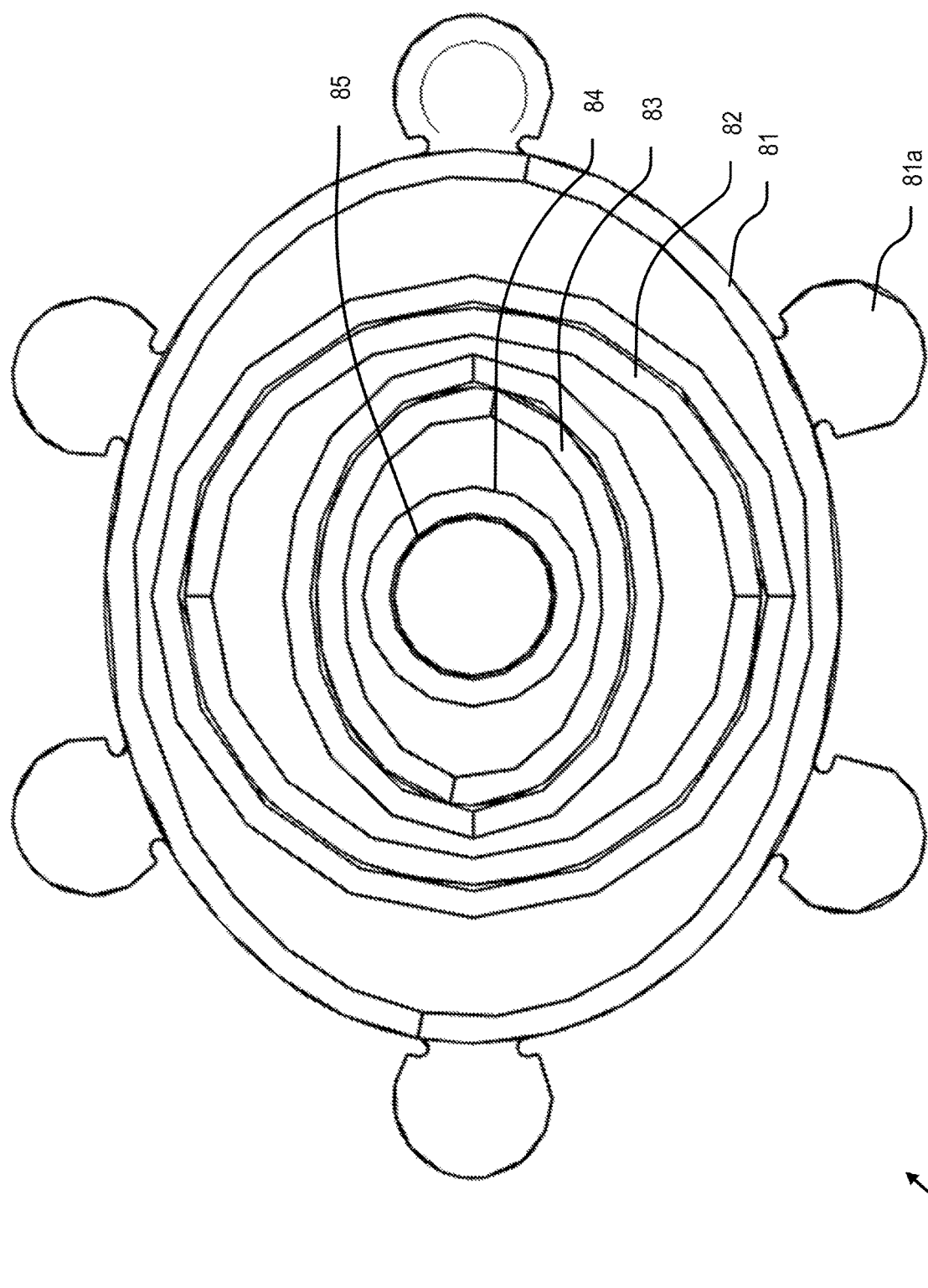
FIG. 76 is a top view of a plurality of nested dilators.
Figure 77A:
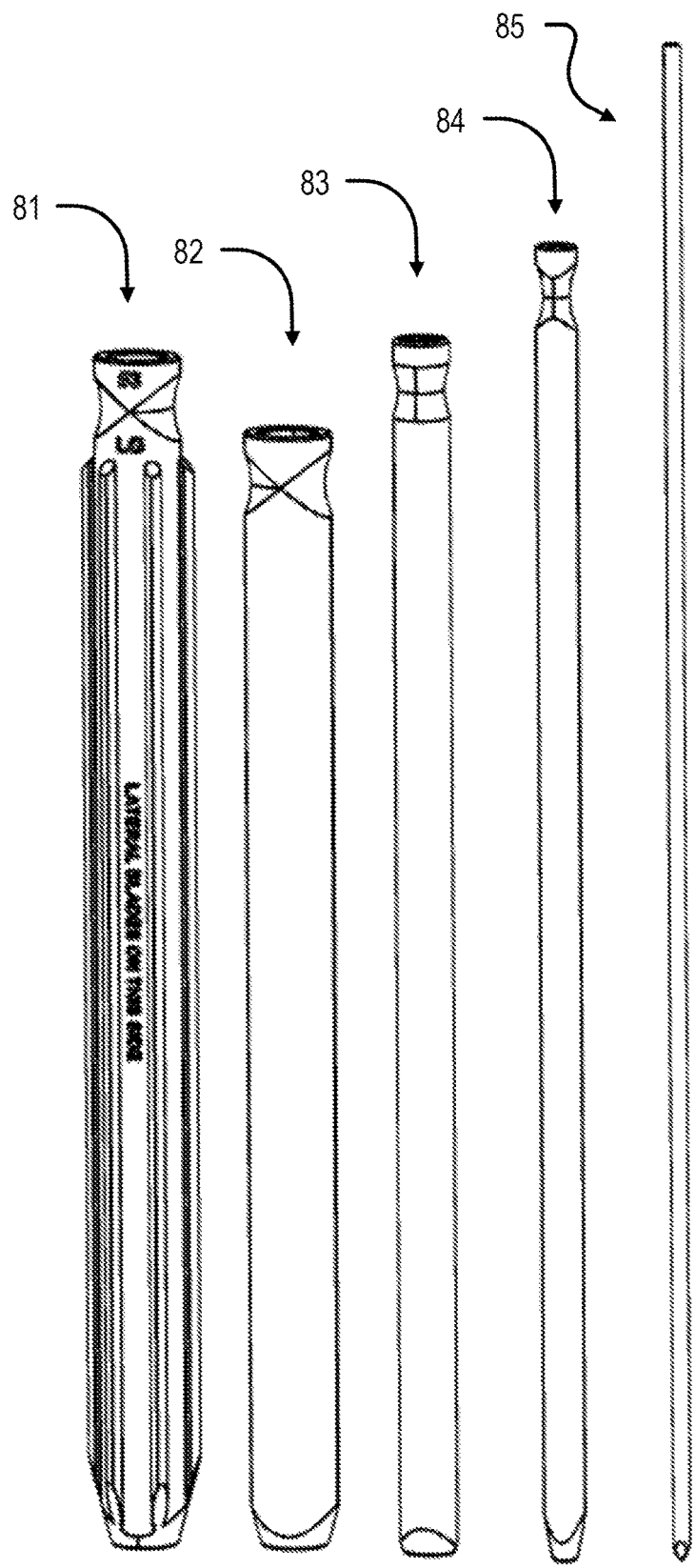
FIG. 77A is a perspective view of a plurality of nesting dilators of FIG. 76 in a non-nested configuration.
Figure 77B:
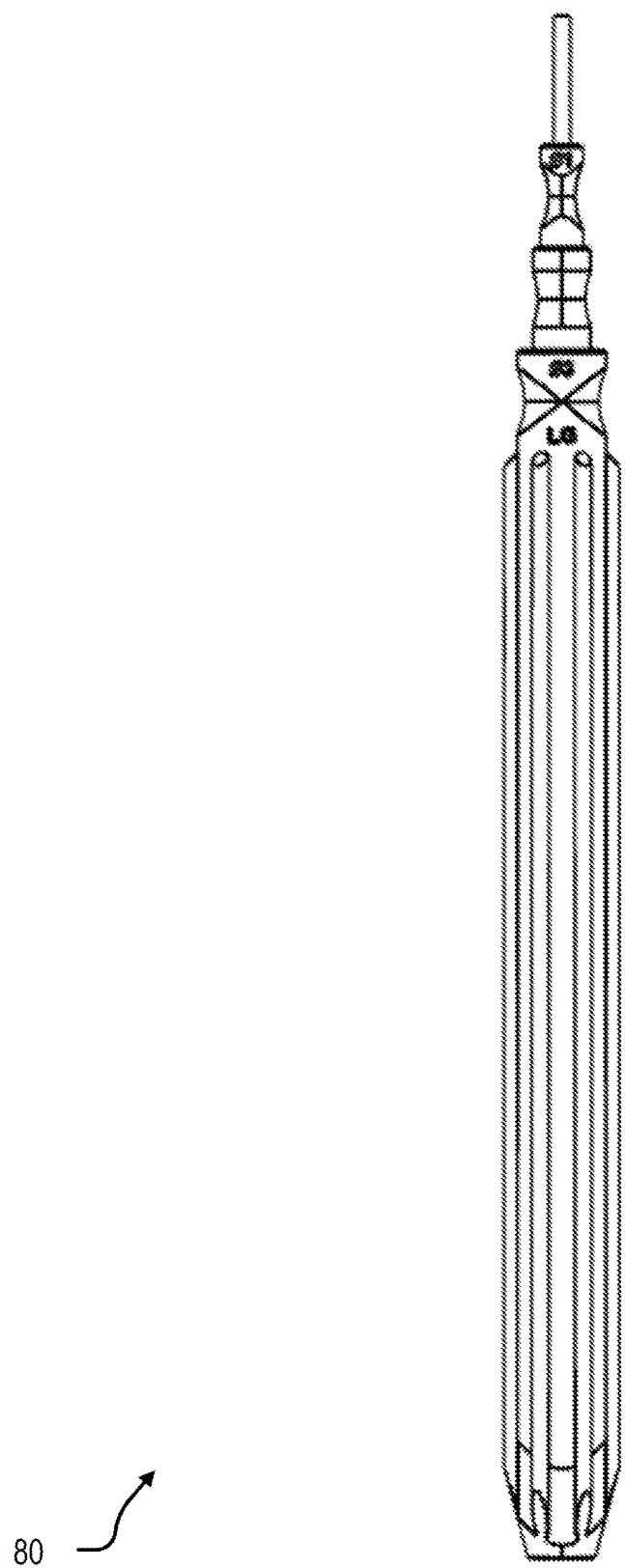
FIG. 77B is a perspective view of a plurality of nesting dilators in a nested configuration.

Referring generally to FIGS. 76-81 various dilators for use with the modular retractor 500 and the various blade embodiments disclosed herein are illustrated. FIG. 76 is a top view of a plurality of nested dilators 80 and FIG. 77A is a perspective view of the plurality of nested dilators 80 in a non-nested configuration and FIG. 77B is a perspective view of the plurality of nested dilators 80 in a nested configuration. In the example embodiment, five dilators are illustrated having progressively increasing sizing. A first dilator 85 may have a circular shape and a relatively narrow diameter for initiating a dilation process. An outside perimeter of the second dilator 84 may have an oval like shape and an inside diameter of dilator 84 may have a circular like shape corresponding to the outer diameter of first dilator 85. An outside perimeter of the third dilator 83 may have an oval like shape and an inside perimeter of the third dilator 83 may have an oval like shape corresponding to the outer perimeter of second dilator 84. Similarly, an outside perimeter of the fourth dilator 82 may have an oval like shape and an inside perimeter of the fourth dilator 82 may have an oval like shape corresponding to the outer perimeter of third dilator 83. Similarly, an outside perimeter of the fifth dilator 81 may have an oval like shape and an inside perimeter of the fifth dilator 81 may have an oval like shape corresponding to the outer perimeter of fourth dilator 82. In various embodiments, the dilators may be successively nested within one another to dilate a patient tissue before use of the various disclosed retractor embodiments. Additionally, fifth dilator 81 may include a plurality of arcuate outdents 81a (e.g., an arcuate rail or the like) extending along an outside surface thereof. The arcuate outdent 81a may mate with an arcuate channel of various blades as disclosed above.

Figure 78:
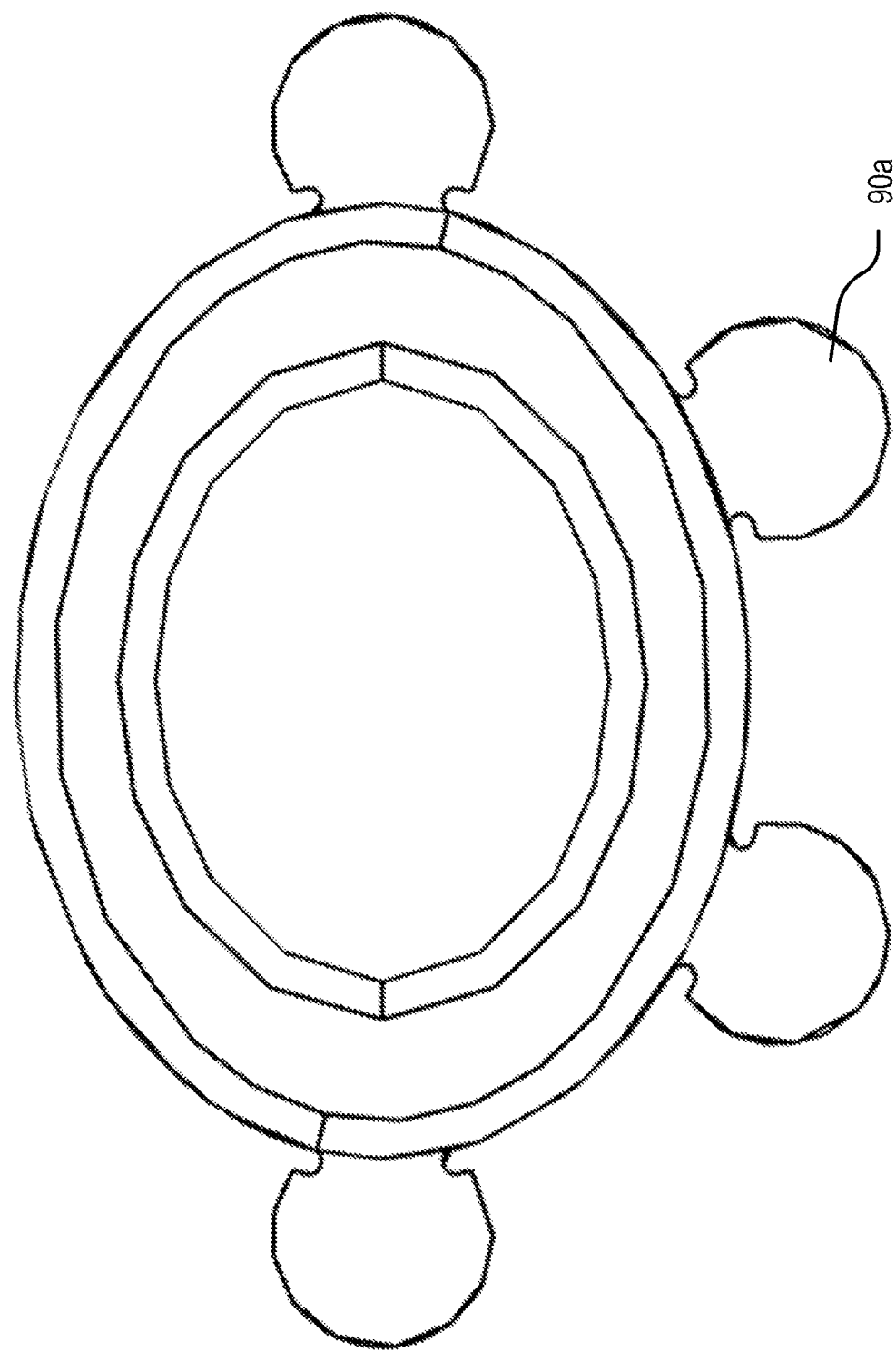
FIG. 78 is a top view of a dilator.
Figure 79:
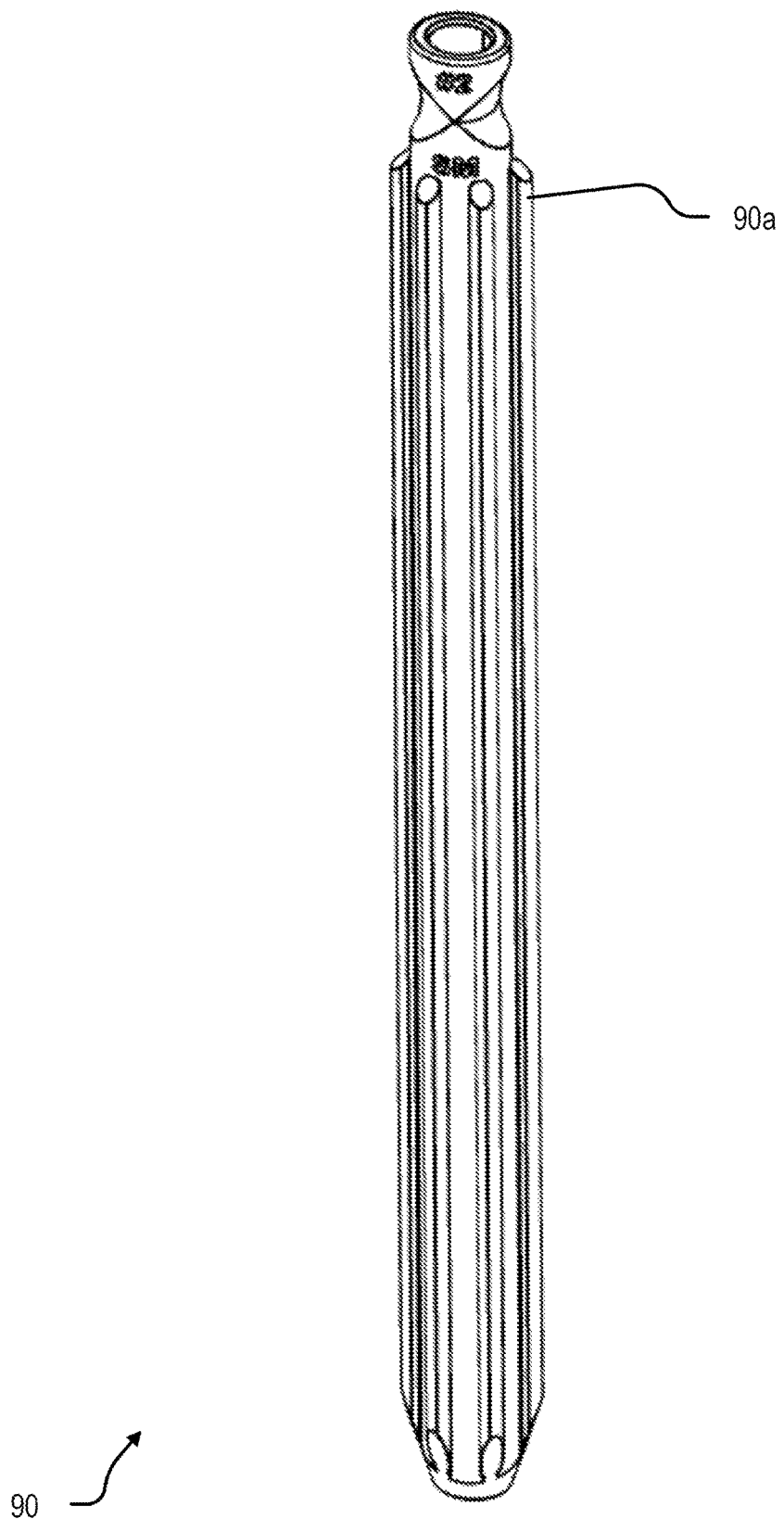
FIG. 79 is a perspective view of the dilator of FIG. 78.
Figure 80A:
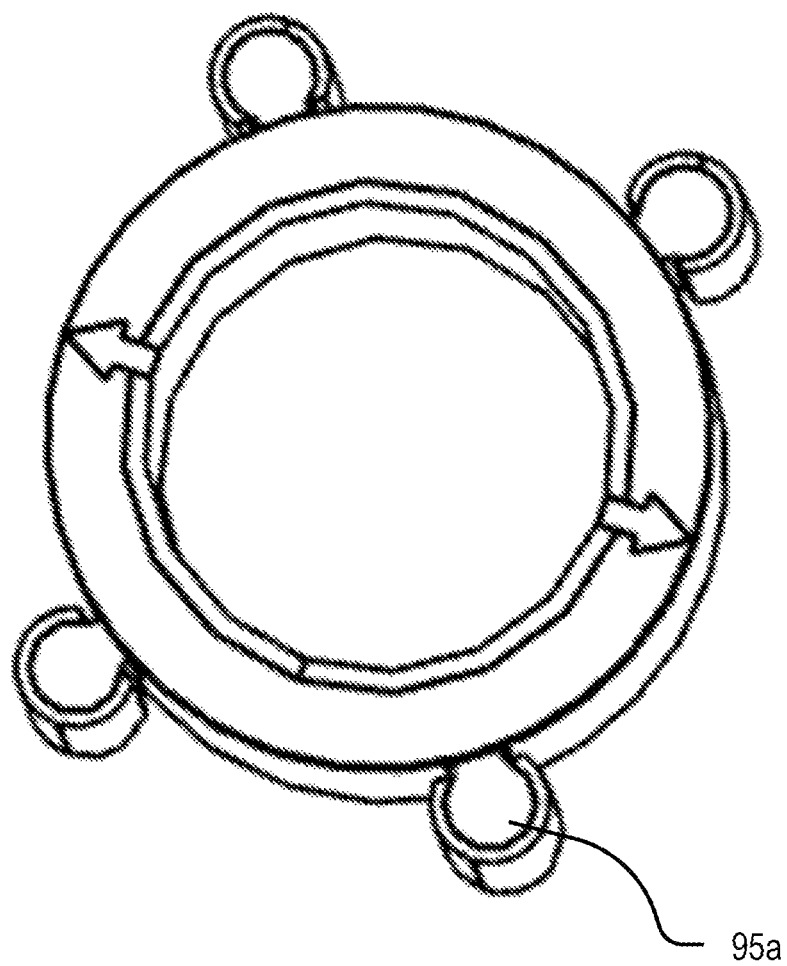
FIG. 80A is a top view of a dilator.
Figure 80B:
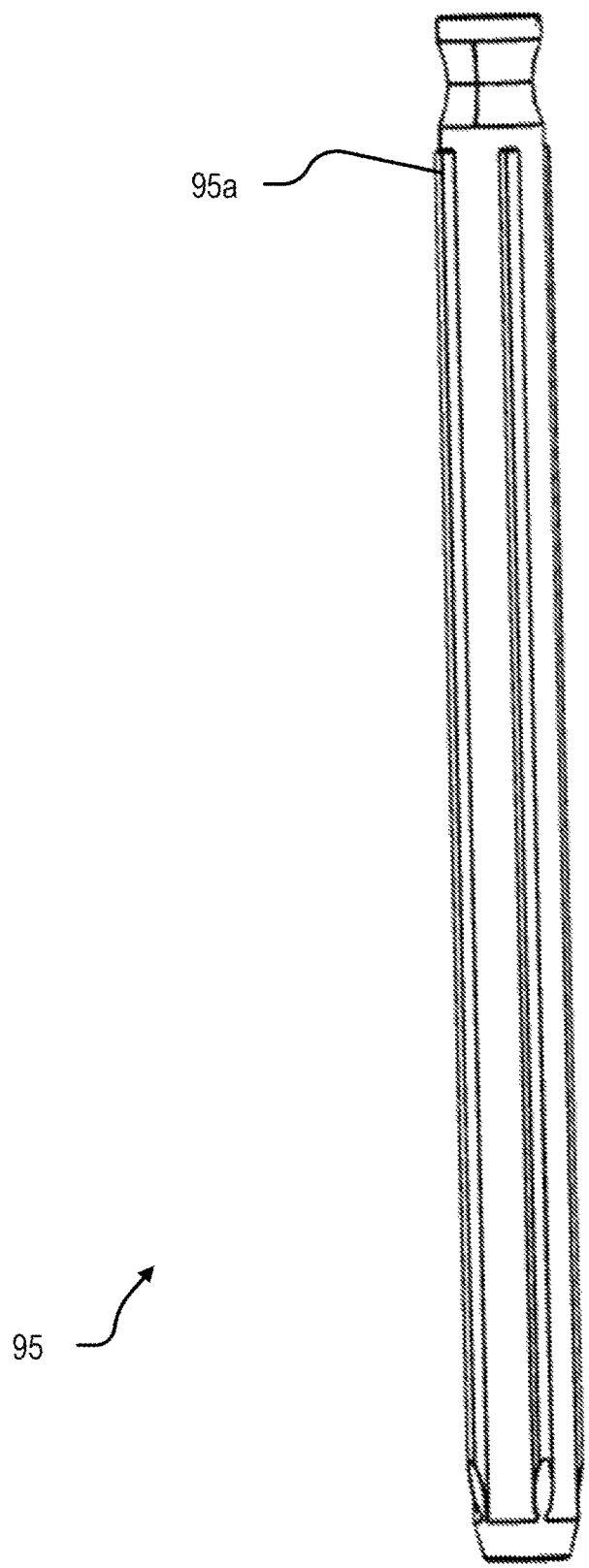
FIG. 80B is a perspective view of the dilator of FIG. 80A.

FIG. 78 is a top view of a dilator 90 having an oval like outer perimeter and an oval like inner perimeter and FIG. 79 is a perspective view of dilator 90. Dilator 90 may include a plurality of arcuate outdents 91a (e.g., an arcuate rail or the like) extending along an outside surface thereof. In the example embodiment, arcuate outdents 91a are disposed along roughly half of the available radial outer surface and extend in a proximal to distal direction, e.g., about half of the available perimeter includes arcuate outdents 91a that extend from the proximal end to distal end. The arcuate outdents 91a may mate with an arcuate channel of various blades in the same, similar, and/or substantially the same manner as explained above. FIG. 80A is a top view of a dilator 95 and FIG. 80B is a perspective view of dilator 95. Dilator 95 may have a circular outer diameter and a circular inner diameter. Dilator 95 may include a plurality of arcuate outdents 95a symmetrically radially disposed along the outer surface. The arcuate outdents 95a may mate with an arcuate channel of various blades as disclosed above.

Figure 80C:
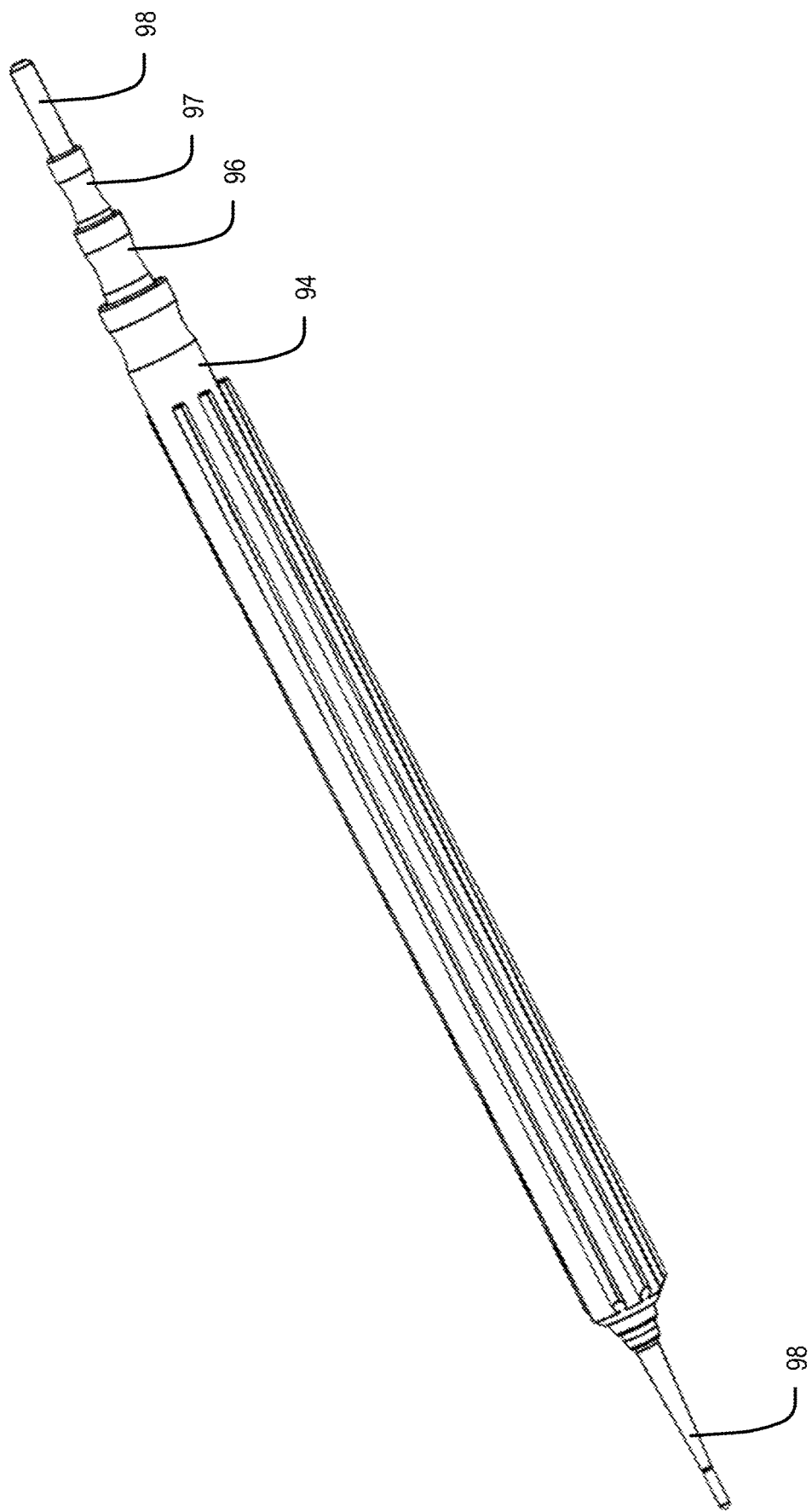
FIG. 80C is a perspective view of a set of nested and cylindrically shaped dilators.
Figure 80D:
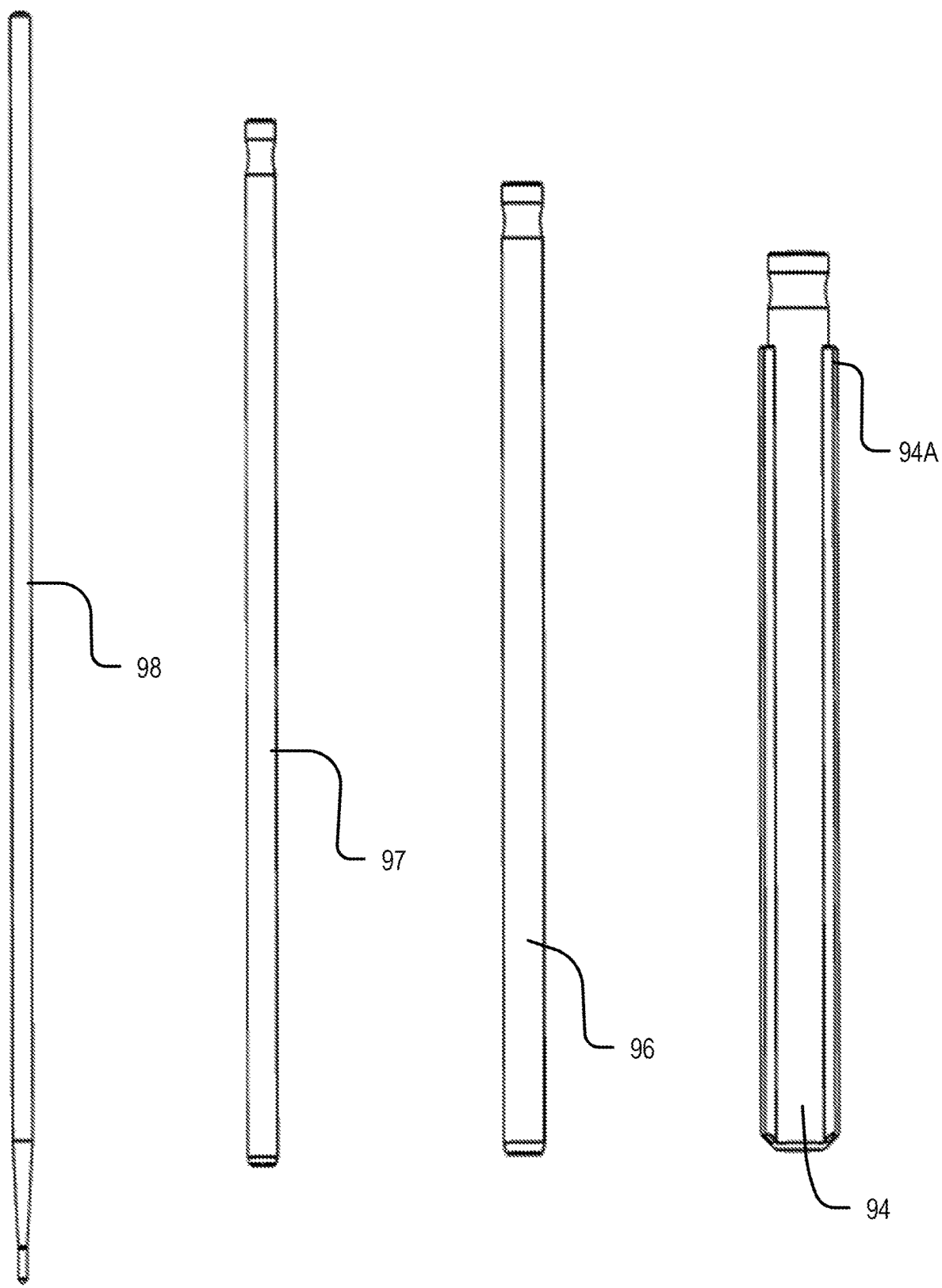
FIG. 80D is an elevation view of the various dilators of embodiment of FIG. 80C.
Figure 80E:
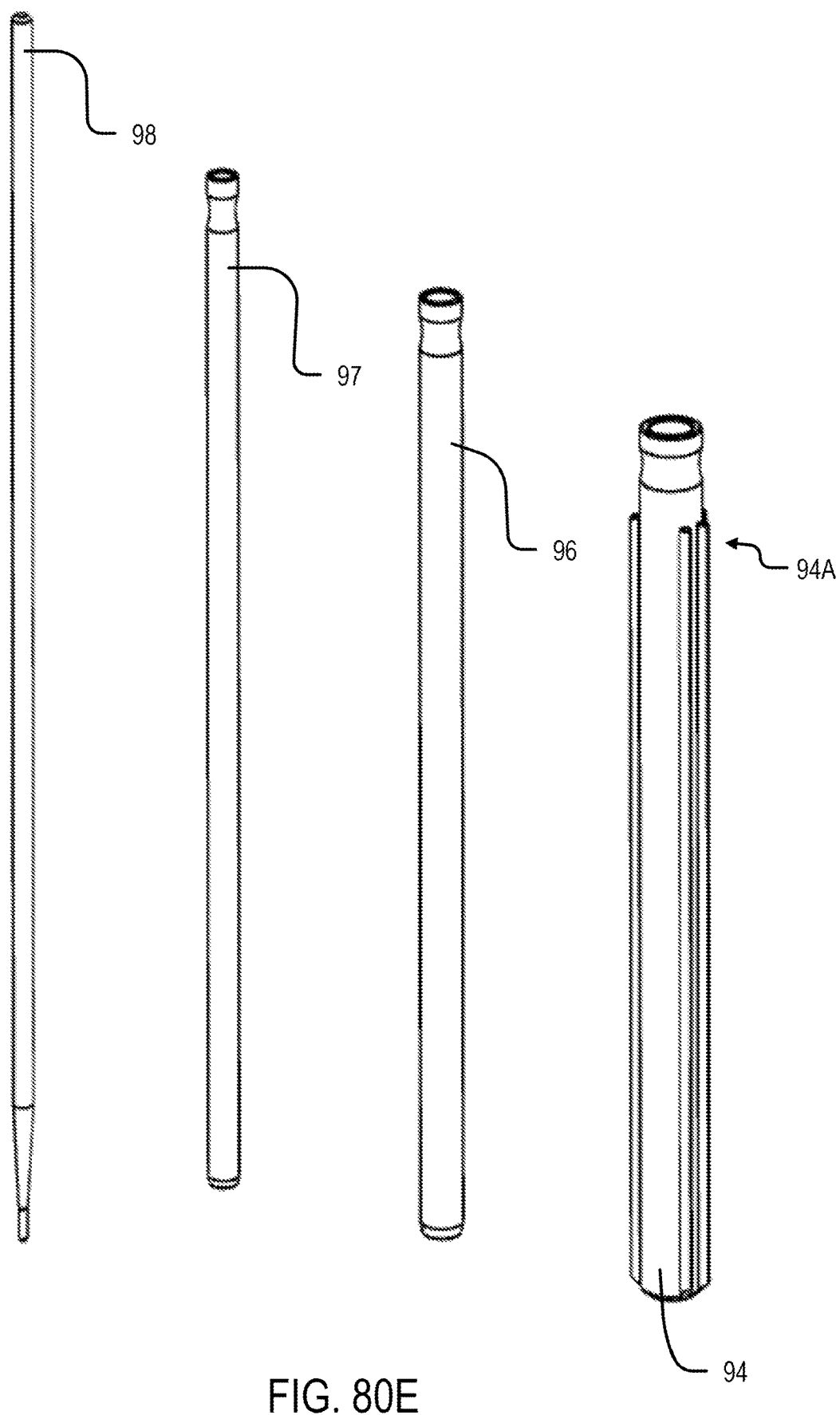
FIG. 80E is a perspective view of the various dilators of embodiment of FIG. 80C.

FIGS. 80C-80E show various perspective and elevation views of a set of nested and cylindrically shaped dilators 99. In the example embodiment, an innermost dilator 98 may be the thinnest and the longest dilator of the set, while the outermost dilator 94 may be the widest and the shortest dilator of the set. Of course the relative length and width of any dilator of the set of dilators 99 may be adjusted consistent with the particular surgery being performed. Additionally, there may be any number and size dilators in between the innermost dilator 98 and outermost dilator 94, for example first inner dilator 97 and second inner dilator 96. With reference to FIGS. 80D and 80E, it is seen that the outside circumferential surface of outermost dilator 94 has a plurality of rail portions 94A that extend down its length in a proximal to distal direction. The rail portions 94A generally have a size and shape corresponding to channel portions of various blades disclosed herein. For example, these rail portions 94A may be disposed in particular locations along the outside circumferential surface of the outermost dilator 94 that takes into account the particular surgical approach employed by the surgeon and the location of the corresponding channel portions of the chosen blades, for example.

As seen best in the top down view of FIG. 81, rail portions 94A may be shaped like circular, oval, or arcuate outdents, for example. Additionally, pairs of adjacent rails 94A may form coupling locations for any of the example blade embodiments disclosed herein. For example, as shown in FIG. 81 blade 1 and blade 2 may couple to respective pairs of rails 94A in a first region (approximately upper half area of FIG. 81) and blade 3 may couple to the remaining respective pair of rails 94A in a second region (approximately lower half area of FIG. 81). The illustrated spacing arrangement of rails 94A takes into account a specific surgical approach chosen by the surgeon and the functionality of disclosed retractor embodiments, e.g., relative movement of retractor arms in a linear, arcuate, ratcheting, and/or pivoting motion, the types of blades and their relative locations, among other things. Further discussion regarding an example method of use of disclosed retractor and retractor module embodiments and surgical approaches utilizing the outer dilator 94 is shown in the top down view of FIG. 130 and the perspective view of FIG. 131, among other places.

Figure 82:
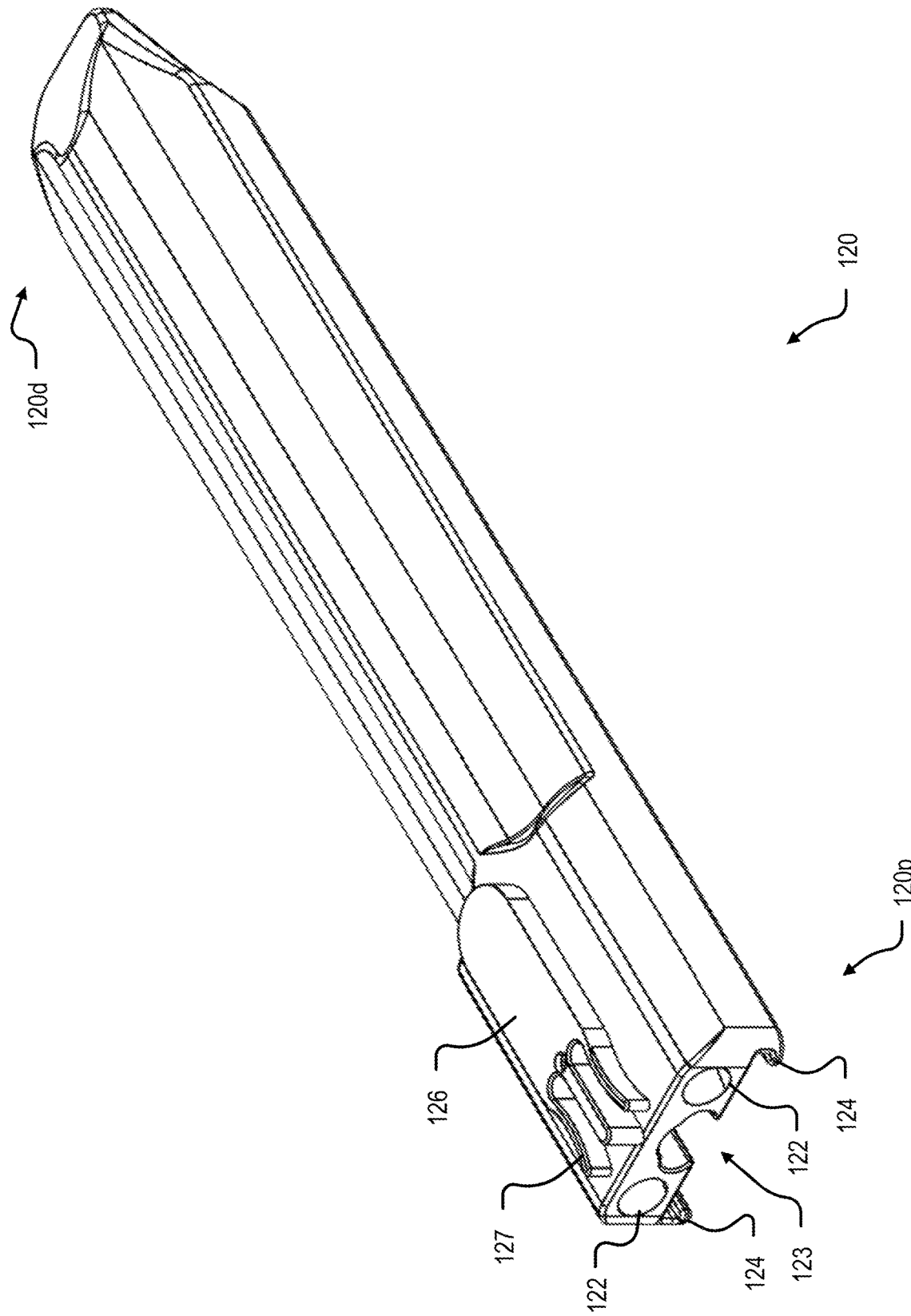
FIG. 82 is a perspective view of a modular blade.
Figure 83:
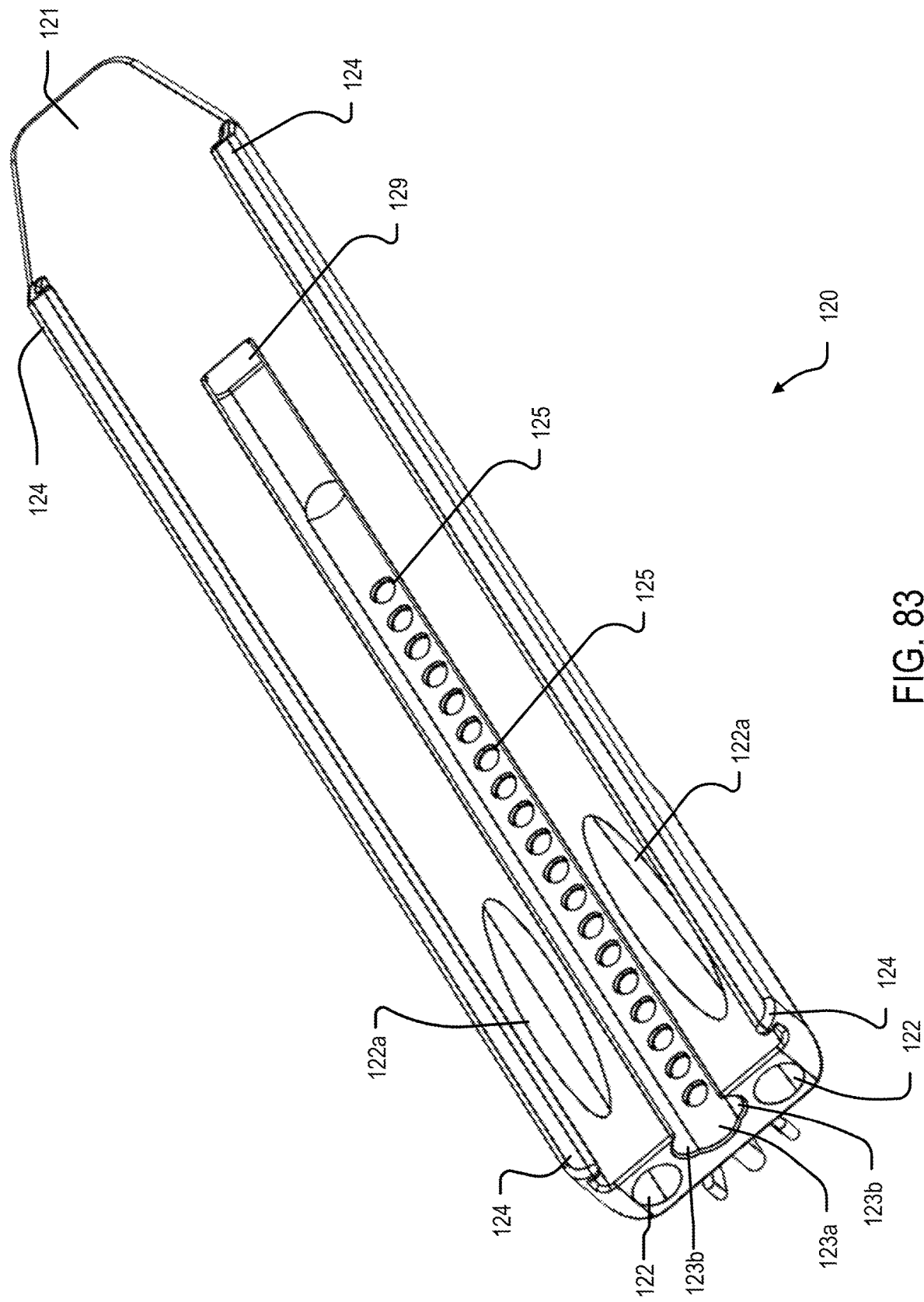
FIG. 83 is a perspective view of a modular blade.
Figure 84:
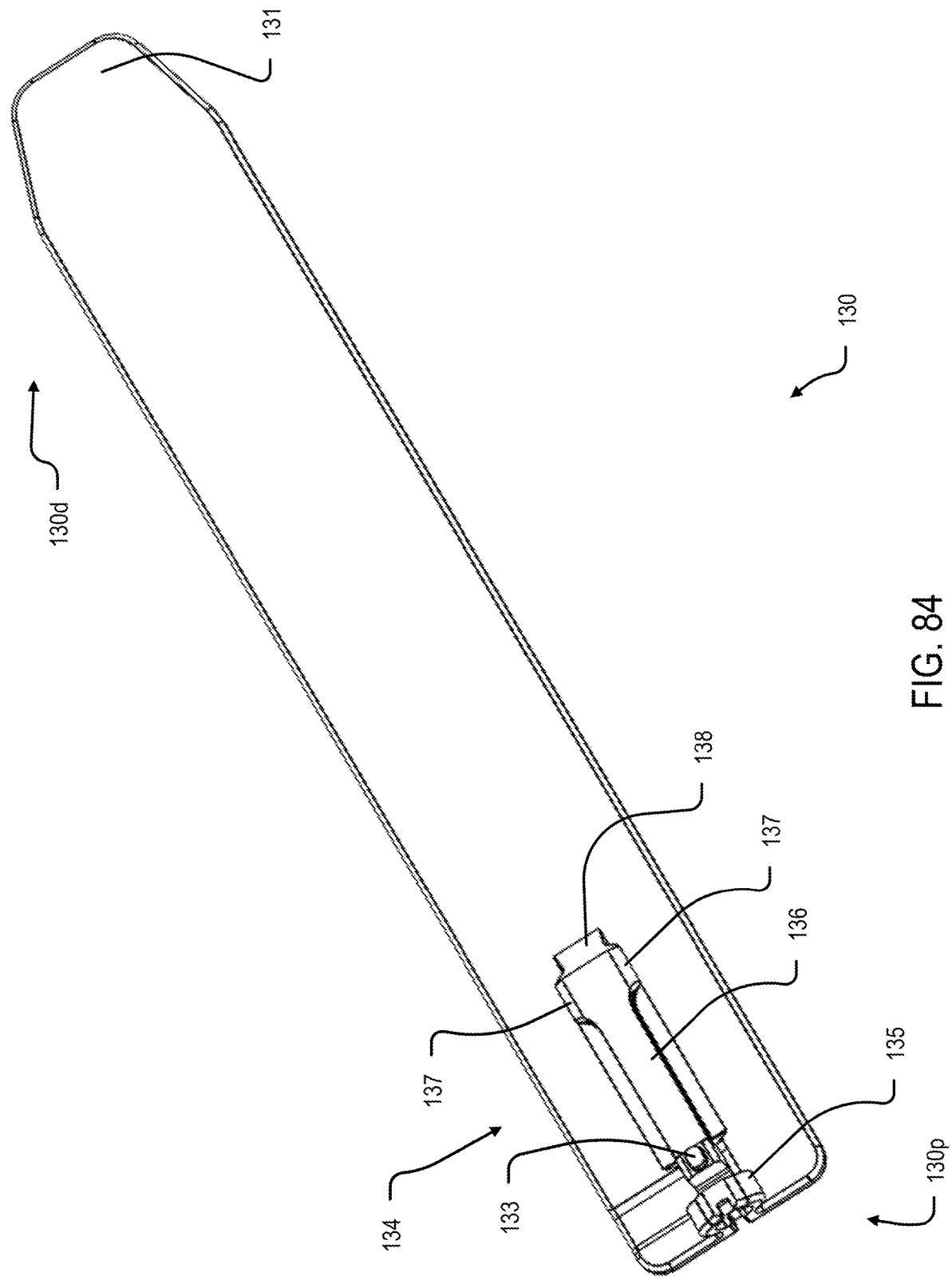
FIG. 84 is a perspective view of an extendable blade for coupling to the modular blade of FIGS. 82-83.
Figure 85:
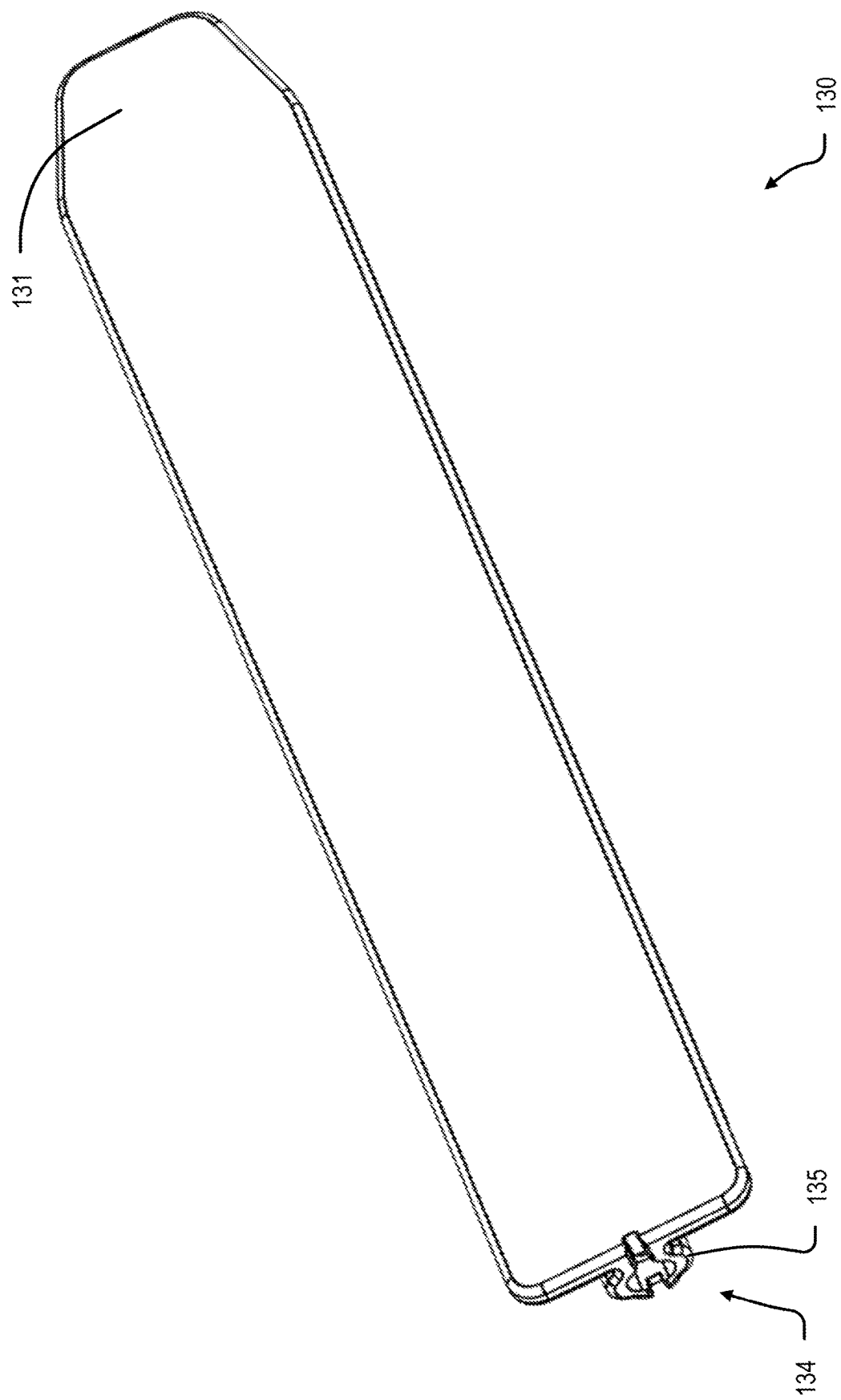
FIG. 85 is a perspective view of an extendable blade for coupling to the modular blade of FIGS. 82-83.
Figure 86:
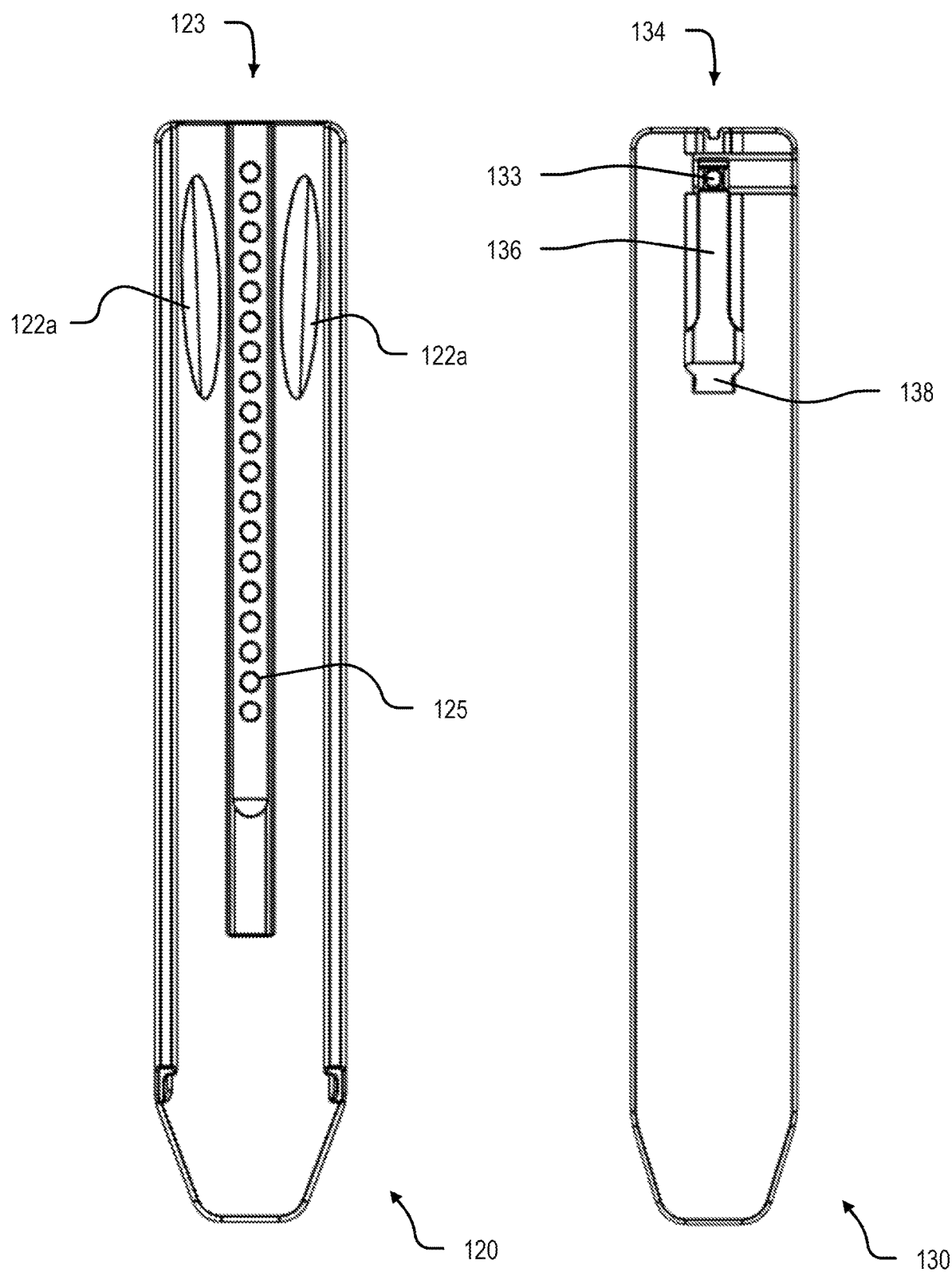
FIG. 86 is a front view of the modular blade of FIGS. 82-83 and the extendable blade of FIGS. 84-85.
Figure 87:
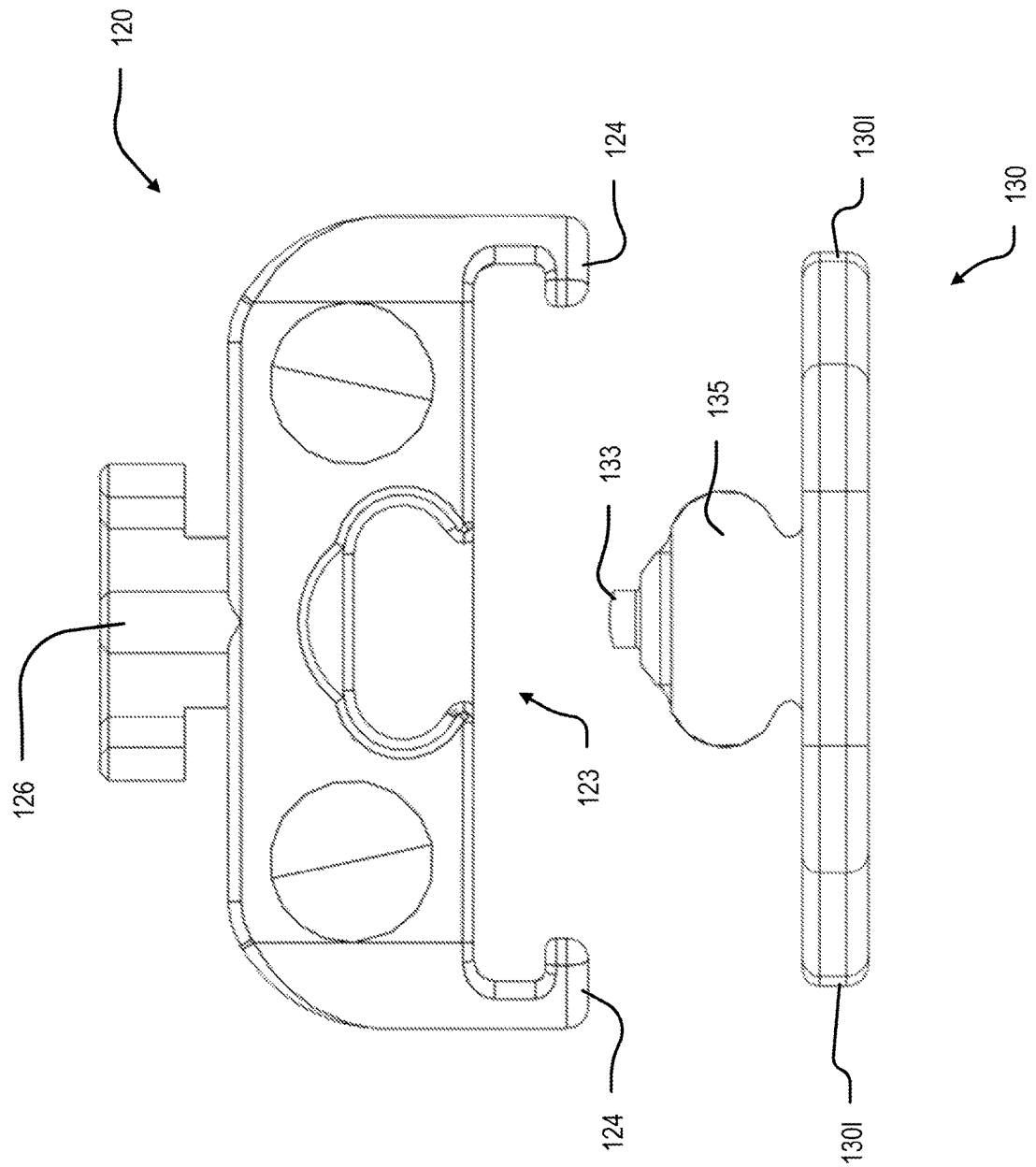
FIG. 87 is a top down view of the modular blade of FIGS. 82-83 and the extendable blade of FIGS. 84-85.

Referring generally to FIGS. 82-87 a modular blade 120 and an extendable blade 130 for coupling to modular blade 120 is disclosed. FIGS. 82 and 83 are various perspective views of a modular blade 120 and FIGS. 84 and 85 are various perspective views of an extendable blade 130 for coupling to modular blade 120. FIG. 86 is a front view of modular blade 120 and extendable blade 130 side by side and FIG. 87 is a top down view of modular blade 120 and extendable blade 130. In various embodiments, the modular blade 120 may be referred to as modular because it may couple to various extendable blades 130 such that extendable blades 130 may extend relative to modular blade 120, e.g., blade 120 and blade 130 may be configured as a telescoping blade system.

Modular blade 120 may extend from a proximal end 120*p* to a distal end 120*d* in a proximal-to-distal direction (may also be referred to as longitudinal direction). The proximal end 120*p* may include an engagement feature 126 having spring loaded tabs 127 for coupling to a blade engagement mechanism in the same, similar, and/or substantially the same way as explained above. The distal end 120*d* may include a tip portion 121. In the example embodiment, tip portion 121 comprises a substantially planar outer surface that tapers towards a centerline of modular blade 120 and terminates as a blunt chisel shaped end having a relatively smaller thickness than the remaining portions of modular blade 120, for example. Modular blade 120 may include a pair of rails 124 that extend from proximal end 120*p* towards distal end 120*d*. For example, a first rail 124 may extend along a first side of blade 120 in the proximal-to-distal direction and a second rail 124, opposite the first rail 124, may extend along a second side of blade 120 in the proximal-to-distal direction. In various embodiments, rails 124 may define a receiving channel for receiving extendable blade 130 as will be explained in further detail below.

Additionally, modular blade 120 may include an aperture 122 extending through a top surface of blade 120 at the proximal end 120*p* and penetrating through the inside surface of blade 120 at oval shaped opening 122*a*, for example. In various embodiments, aperture 122 may comprise a passageway (in a cross section view) that is inclined away from the outside surface of blade 120 and towards the inside surface of blade 120 such that the passageway forms an oval shaped opening 122*a* on the inside surface of blade 120. In cross section, the passageway of aperture 122 may resemble a circle, oval, pentagon, square, rectangle, and/or any combination thereof. Aperture 122 may provide access for light fixtures and other diagnostic tools such as endoscopes, electrodes, temperature sensors, suction devices, and etc. that may be insert therein.

Modular blade 120 may include a contoured channel 123 for connecting with extendable blade 130 and facilitating the forward and backward relative motion of extendable blade 130 in the proximal-to-distal direction, for example. As shown best in FIG. 83, contoured channel 123 may include a relatively large central arcuate channel portion 123*a* having a pair of relatively smaller arcuate channels 123*b* on opposite sides of channel portion 123*a*, for example. Additionally, contoured channel 123 may include a plurality of indentations 125 extending in a proximal-to-distal direction, for example. In various embodiments, indentations 125 may be circular shaped indentations, oval shaped indentations, hexagonal shaped indentations, parallelogram shaped indentations, and/or any combination thereof. A distal end of contoured channel 123 may include a stop feature 129 for preventing extendable blade 130 from extending too far in the proximal-to-distal direction.

Extendable blade 130 may extend from a proximal end 130*p* to a distal end 130*d* in a proximal-to-distal direction (also referred to as a longitudinal direction). The distal end may include a tip portion 131 tapering towards a centerline of extendable blade 130 and terminating as a blunt chisel shaped end having a relatively smaller thickness than the remaining portion of extendable blade 130, for example. In the example embodiment, an outside surface of extendable blade 130 may include an engagement feature 134 for connecting with contoured channel 123, for example. Engagement feature 134 may include a proximal engagement rail 135 having a size and shape generally corresponding to a size and shape of contoured channel 123. For example, proximal engagement rail 135 may have a size and shape generally corresponding to the relatively large central arcuate channel portion 123*a* and the pair of relatively smaller arcuate channels 123*b*, for example. Additionally, engagement feature 134 may include a medial engagement rail 136 having a width approximately corresponding to the relatively large central arcuate channel portion 123*a* of modular blade 120, for example. In various embodiments, an exposed surface of medial engagement rail 136 may be substantially planar although in other embodiments the exposed surface may be arcuately shaped to correspond and/or approximate the geometrical profile of contoured channel 123, for example.

In various embodiments, engagement feature 134 may include at least one protrusion 133 having a size and shape generally corresponding to a size and shape of indentation 125. For example, protrusion 133 may selectively be seated within any one of indentations 125 to secure extendable blade 130 in any one position of the plurality of positions defined by indentations 125. In various embodiments, protrusion 133 may be a circular shaped protrusion, oval shaped protrusion, hexagonal shaped protrusion, parallelogram shaped protrusion, and/or any combination thereof. In various embodiments, protrusion 133 may extend away from extendable blade 130 in a direction perpendicular to the proximal-to-distal direction a distance that is relatively farther out than medial engagement rail 136 and/or proximal engagement rail 135, for example. In some embodiments, protrusion 133 may be spring loaded and/or biased. In other embodiments, protrusion 133 may be a rigid non movable structure.

In various embodiments, engagement feature 134 may include a distal engagement rail 137 having a size and shape generally corresponding to a size and shape of contoured channel 123. For example, distal engagement rail 137 may have a size and shape generally corresponding to the relatively large central arcuate channel portion 123*a* and the pair of relatively smaller arcuate rails 123*b*, for example. Additionally, engagement feature 134 may include a stop feature 138 that may abut against stop feature 129 of modular blade 120 to prevent extendable blade 130 from disengaging with modular blade 120, for example. For example, in a fully extended position, stop feature 138 of extendable blade may directly contact stop feature 129 of modular blade 120 and prevent extendable blade 130 from extending too far that engagement feature 134 becomes unseated from contoured channel 123.

With reference to FIG. 86, the inside surface of modular blade 120 and the outside surface of extendable blade 130 is illustrated. In various embodiments, extendable blade 130 may operably couple to modular blade 120 by inserting engagement feature 134 into channel 123. As explained above, extendable blade 130 may move forward and backward in a proximal-to-distal direction within contoured channel 123. For example, extendable blade 130 may extend forward and backward within contoured channel 123 and protrusion 133 may be seated within any one of indentations 125. For example, when modular blade 120 and extendable blade 130 are coupled together as a system, they may be referred to as a telescoping blade system.

With reference to FIG. 87, a top down view of modular blade 120 and extendable blade 130 is illustrated. In the example embodiment, it is shown that rails 124 define a cavity and/or channel for receiving extendable blade 130. For example, extendable blade 130 has a width in a lateral direction that corresponds to a distance between rails 124 and a thickness of extendable blade 130 corresponds to a depth of the cavity and/or channel between and defined by rails 124. In various embodiments, the outside lateral edges 1301 of extendable blade 130 may be inset within the receiving cavity defined by rails 124 such that they frictionally engage and slide across the interior side surfaces of modular blade 120, for example. In this way, rails 124 may provide a bearing surface for retaining extendable blade 130 therein while also allowing extendable blade 130 to move forward and backward in the proximal-to-distal direction. Additionally, it is shown that engagement feature 134 has a size and shape corresponding to contoured channel 123. For example, the curved surfaces of proximal engagement rail 135 may be inset within (mated within) contoured channel 123 and frictionally engage and slide across the interior surfaces defined by the relatively large central arcuate channel portion 123a and/or pair of relatively smaller arcuate channels 123b on opposite sides of channel portion 123a, for example.

Figure 88:
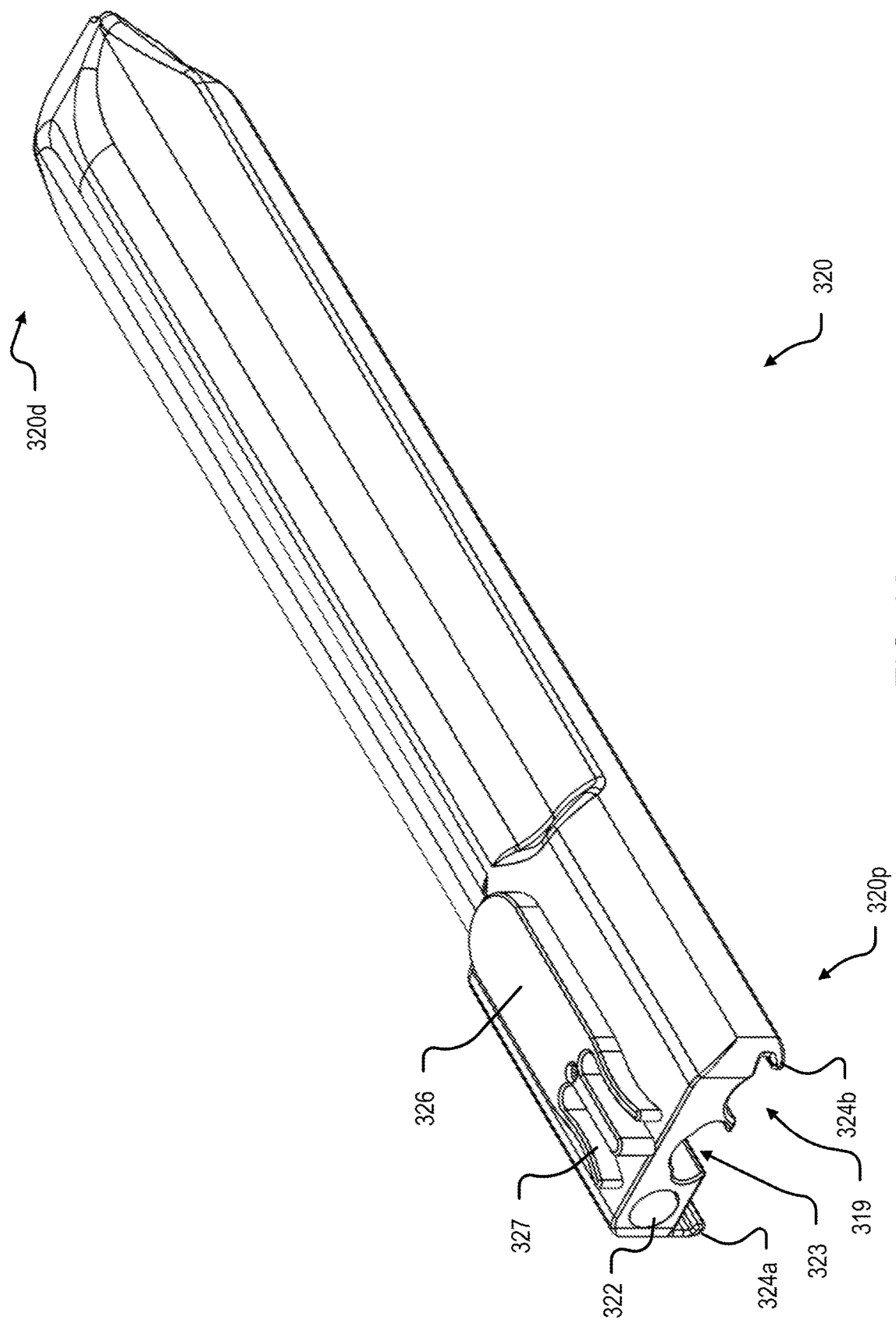
FIG. 88 is a perspective view of a modular blade.
Figure 89:
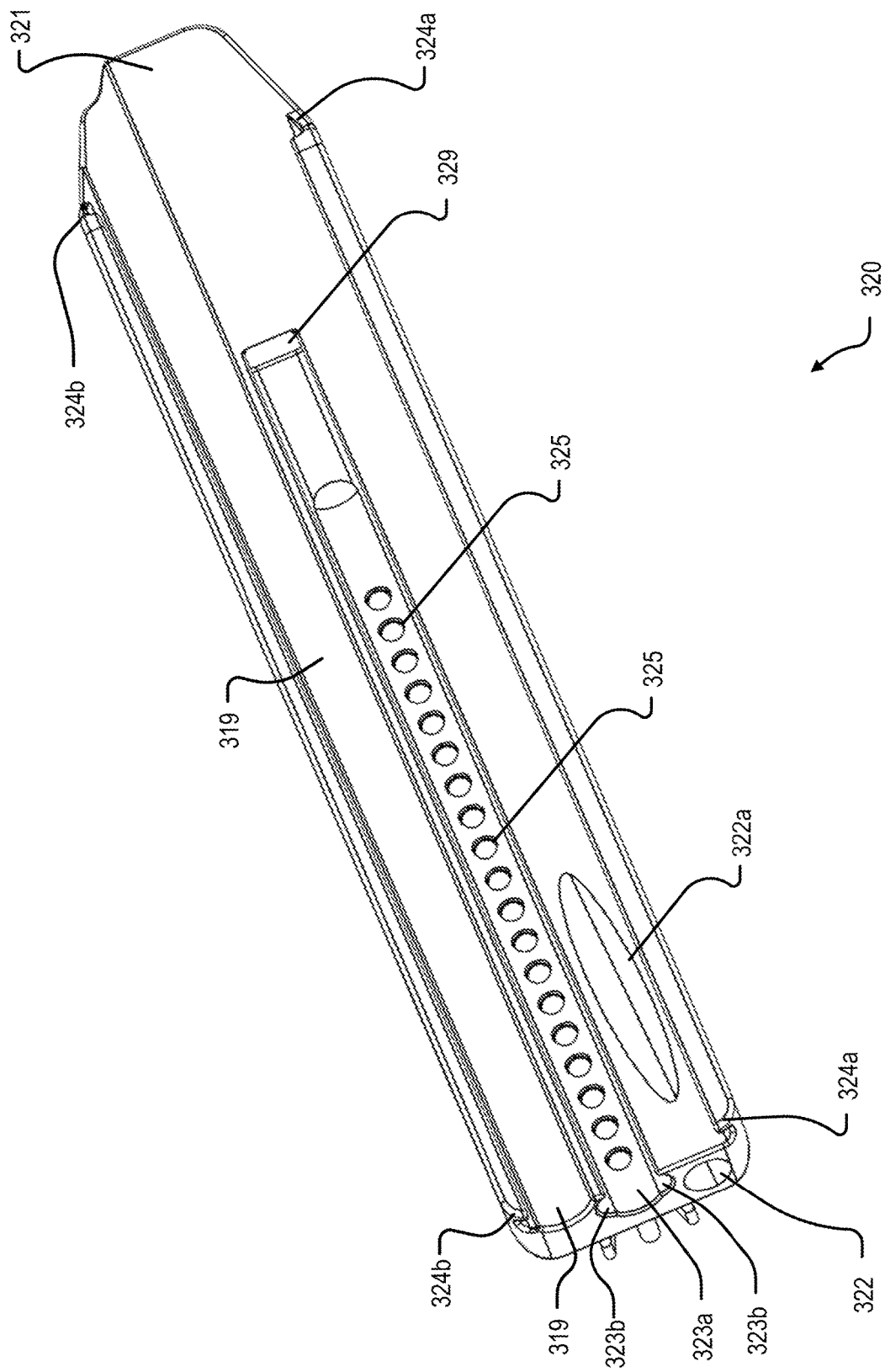
FIG. 89 is a perspective view of a modular blade.
Figure 90:
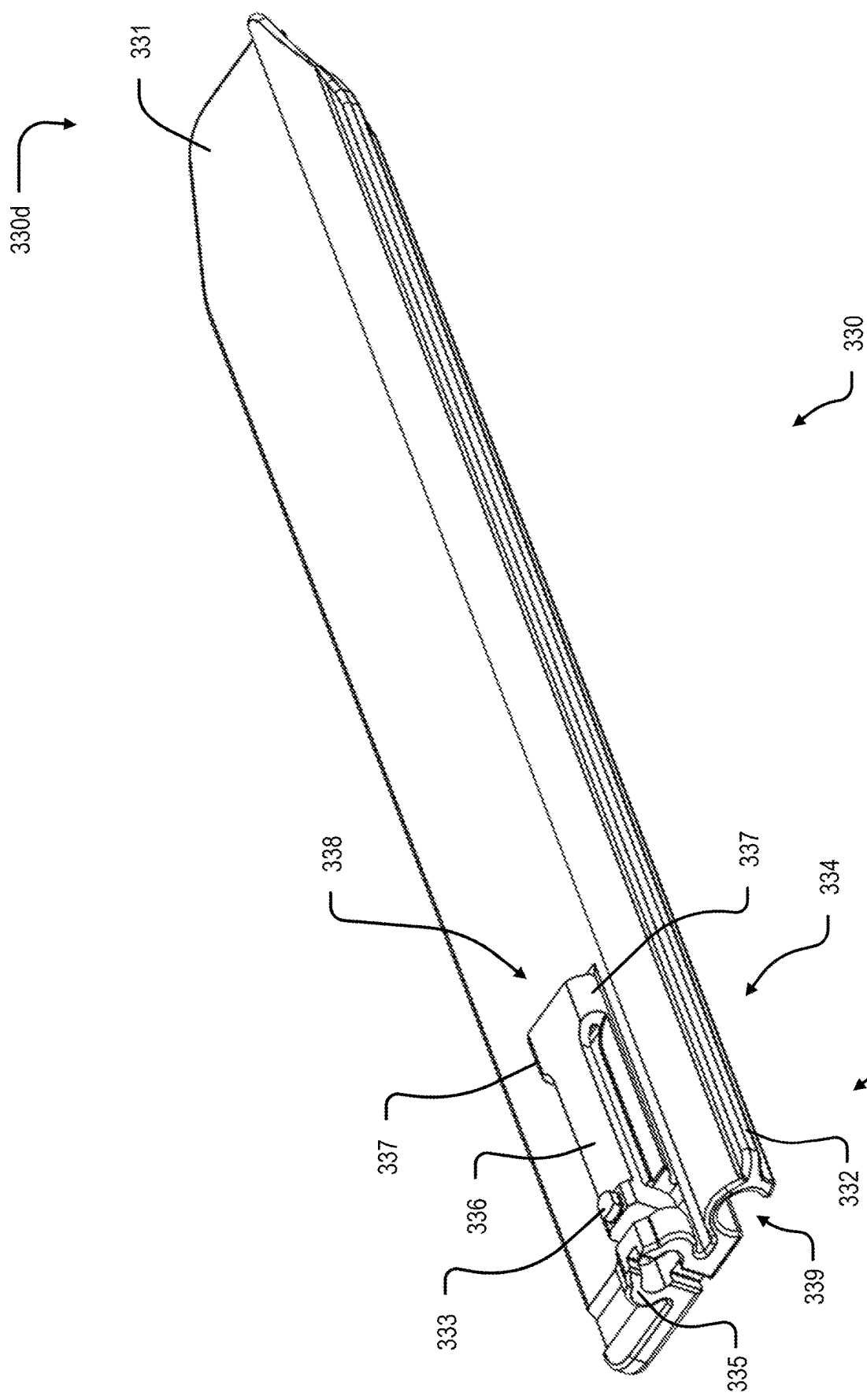
FIG. 90 is a perspective view of an extendable blade for coupling to the modular blade of FIGS. 82-83.
Figure 91:
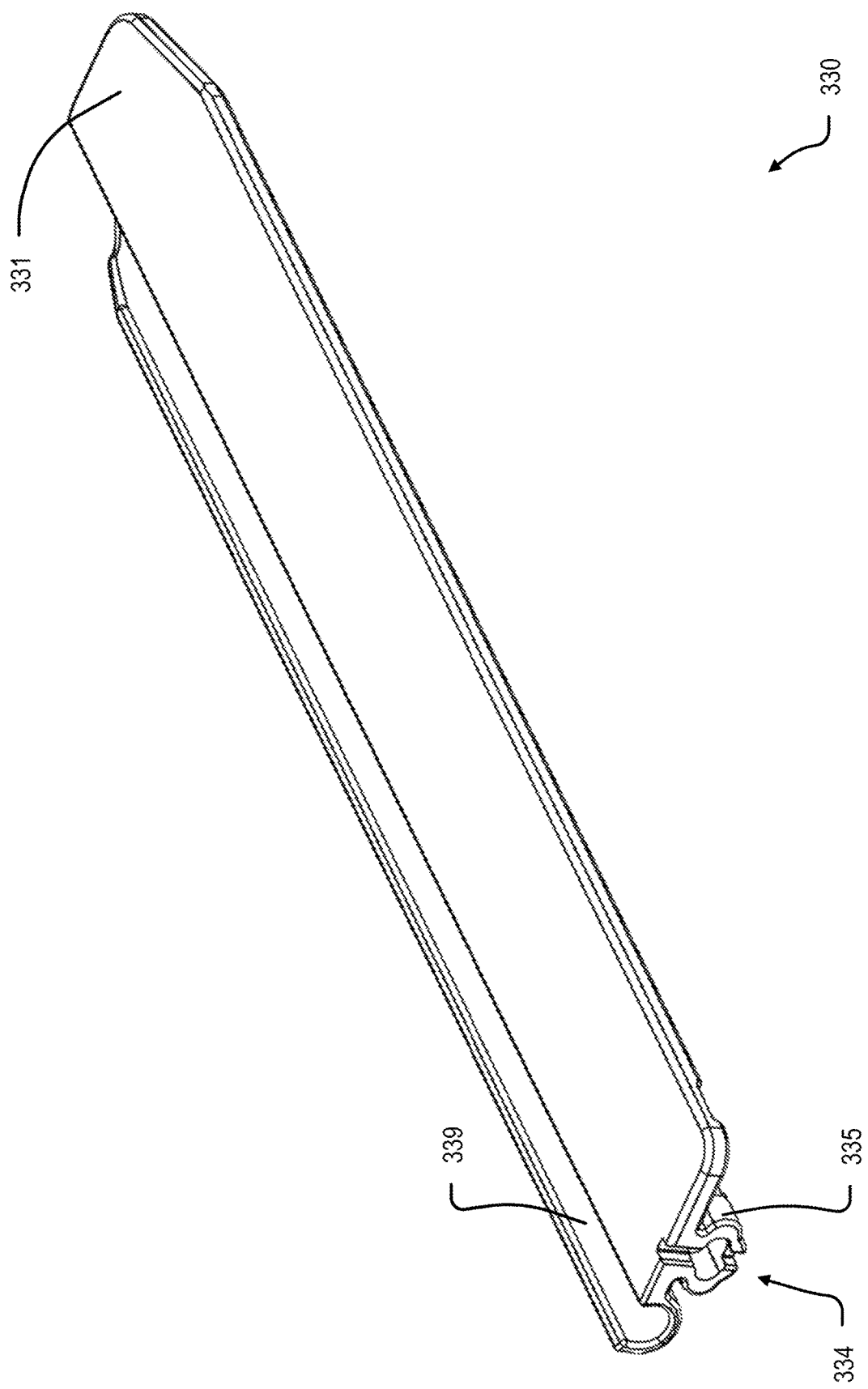
FIG. 91 is a perspective view of an extendable blade for coupling to the modular blade of FIGS. 88-89.
Figure 92:
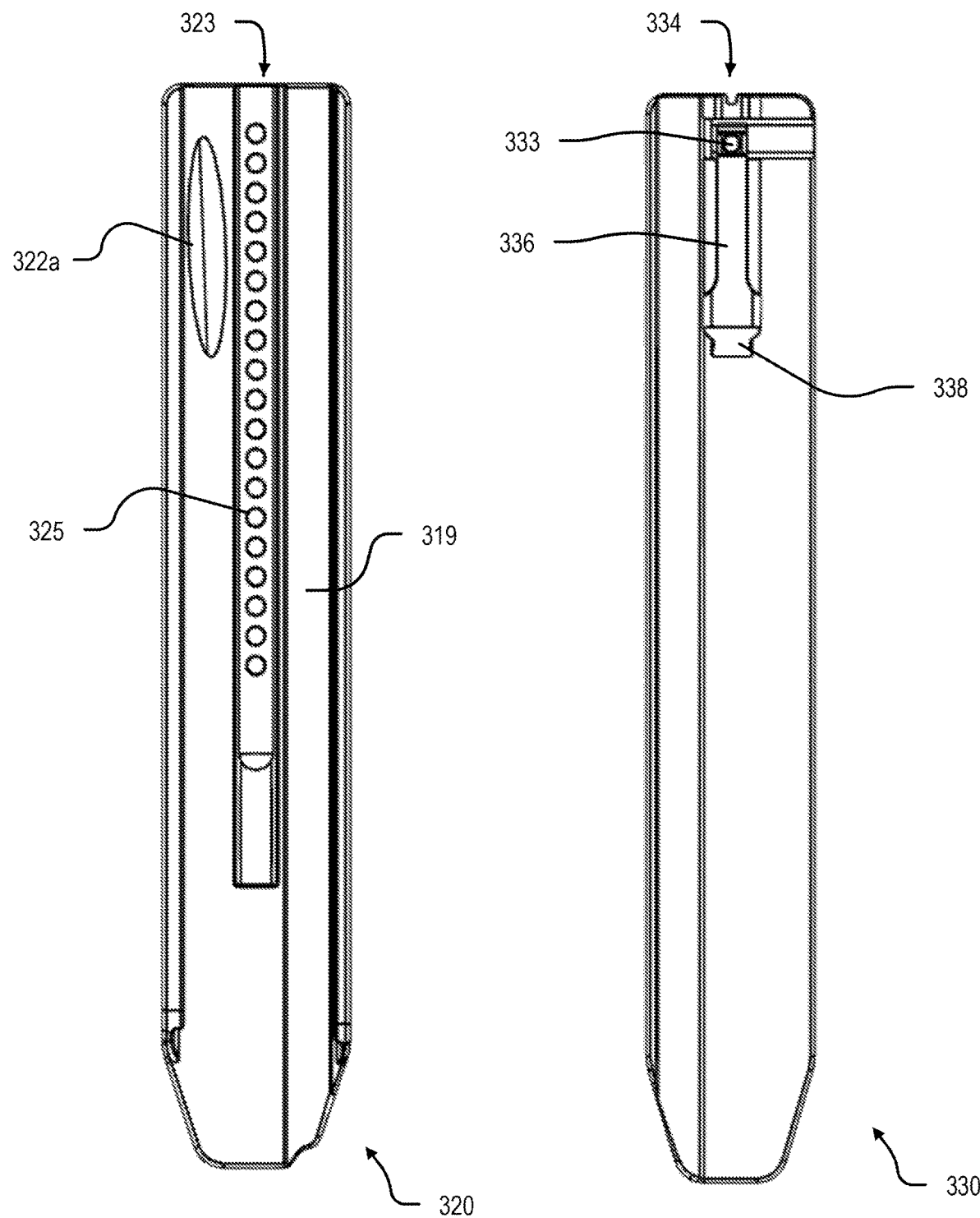
FIG. 92 is a front view of the modular blade of FIGS. 88-89 and the extendable blade of FIGS. 90-91.
Figure 93:
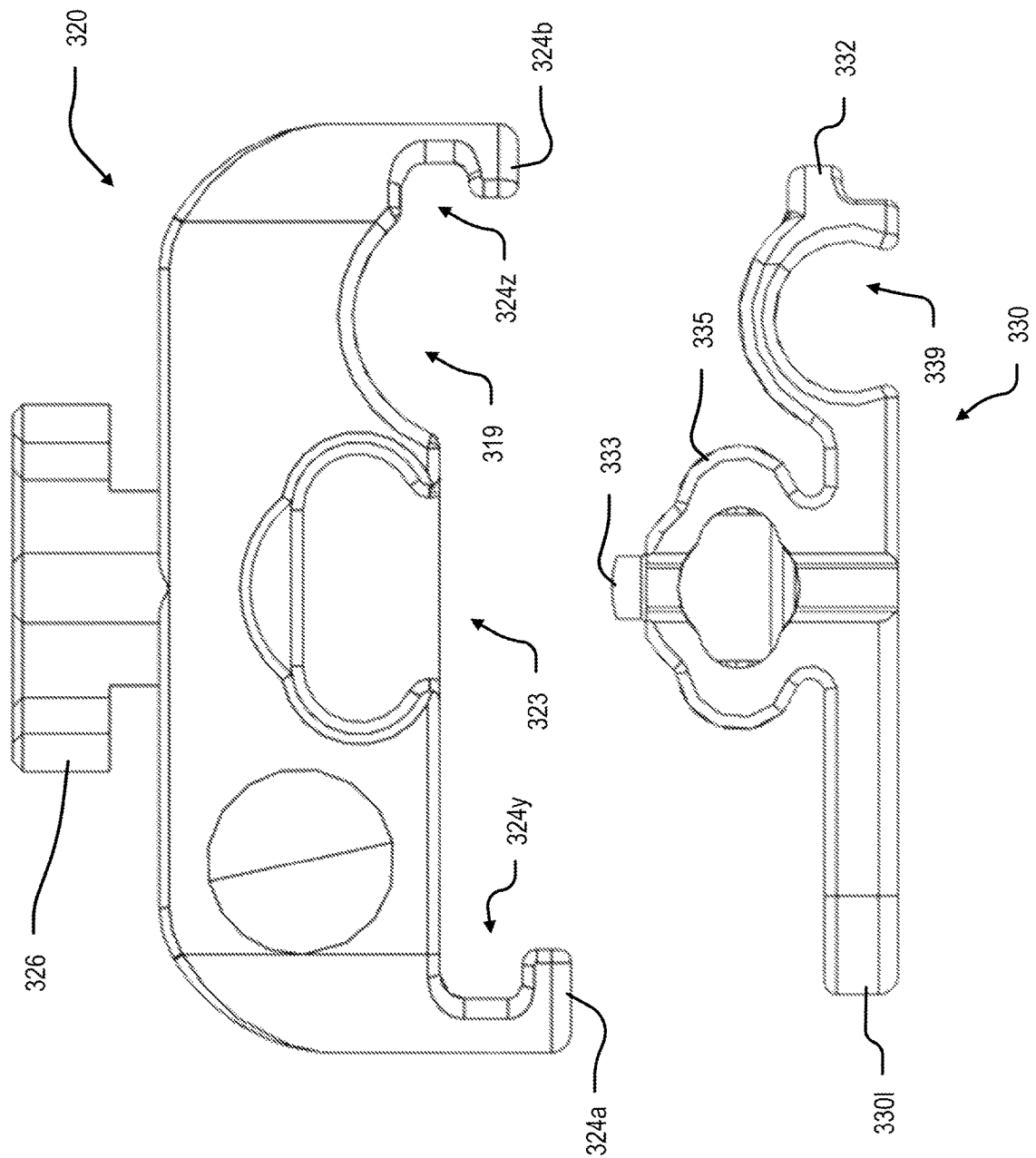
FIG. 93 is a top down view of the modular blade of FIGS. 88-89 and the extendable blade of FIGS. 90-91.

Referring generally to FIGS. 88-93 a modular blade 320 and an extendable blade 330 for coupling to modular blade 320 is disclosed. FIGS. 88 and 89 are various perspective views of a modular blade 320 and FIGS. 90 and 91 are various perspective views of an extendable blade 330 for coupling to modular blade 320. FIG. 92 is a front view of modular blade 320 and extendable blade 330 side by side and FIG. 93 is a top down view of modular blade 320 and extendable blade 330. In various embodiments, modular blade 320 and extendable blade 330 may be configured as a telescoping blade system.

Modular blade 320 may extend from a proximal end 320p to a distal end 320d in a proximal-to-distal direction (may also be referred to as longitudinal direction). The proximal end 320p may include an engagement feature 326 having spring loaded tabs 327 for coupling to a blade engagement mechanism in the same, similar, and/or substantially the same way as explained above. The distal end 320d may include a tip portion 321. In the example embodiment, tip portion 321 comprises a substantially planar outer surface that tapers towards a centerline of modular blade 320 and terminates as a blunt chisel shaped end having a relatively smaller thickness than the remaining portions of modular blade 320, for example. Modular blade 320 may include a pair of rails 324a and 324b that extend from proximal end 320p towards distal end 320d. For example, a first rail 324a may extend along a first lateral side of blade 320 in the proximal-to-distal direction and a second rail 324b, opposite first rail 324a, may extend along a second lateral side of blade 320 in the proximal-to-distal direction. First rail 324a may extend laterally away from extendable blade 320 farther than second rail 324b, for example. For example still, second rail 324b may be inset towards a center of modular blade 320 relative to first rail 324a and 324a may be outset relative to second rail 324b (see FIG. 93). First rail 324a may define a first receiving cavity 324y and second rail 324z may define a second receiving cavity 324z, for example. Additionally, modular blade may include a channel 319 extending along the outside surface of modular blade 320 in the proximal-to-distal direction and/or from a proximal end to a distal end. Channel 319 may have a size and shape generally corresponding to a size and shape of channel 339 of extendable blade 330, for example. In various embodiments, a stability pin may be positioned within channels 319 and 339, for example. In various embodiments, rails 324a, 324b, and channel 319 may define a contoured receiving channel for receiving extendable blade 330, as will be explained in further detail below.

Modular blade 320 may include an aperture 322 extending through a top surface of blade 320 at the proximal end 320p and penetrating through the inside surface of blade 320 at oval shaped opening 322a, for example. Aperture 322 may have the same, similar, and/or substantially the same features and functionality of aperture 122. Accordingly, duplicative description will be omitted. Modular blade 320 may include a contoured channel 323 for connecting with extendable blade 330 and facilitating the forward and backward relative motion of extendable blade 330 in the proximal-to-distal direction, for example. Contoured channel may include a relatively large central arcuate channel portion 323a having a pair of relatively smaller arcuate channels 323b on opposite sides of channel portion 323a, for example. Additionally, contoured channel 323 may include a plurality of indentations 325 extending in a proximal-to-distal direction, for example. In various embodiments, indentations 325 may be circular shaped indentations, oval shaped indentations, hexagonal shaped indentations, parallelogram shaped indentions, and/or any combination thereof. A distal end of contoured channel 323 may include a stop feature 329 for preventing extendable blade 330 from extending too far in the proximal-to-distal direction.

Extendable blade 330 may extend from a proximal end 330p to a distal end 330d in a proximal-to-distal direction (also referred to as a longitudinal direction). The distal end may include a tip portion 331 tapering towards a centerline of extendable blade 330 and terminating as a blunt chisel shaped end having a relatively smaller thickness than the remaining portion of extendable blade 330, for example. In the example embodiment, an outside surface of extendable blade 330 may include an engagement feature 334 for connecting with contoured channel 323, for example. Engagement feature 334 may include a proximal engagement rail 335 having a size and shape generally corresponding to a size and shape of contoured channel 323. For example, proximal engagement rail 335 may have a size and shape generally corresponding to the relatively large central arcuate channel portion 323a and the pair of relatively smaller arcuate channels 323b, for example. Additionally, engagement feature 334 may include a medial engagement rail 336 having a width approximately corresponding to the relatively large central arcuate channel portion 323a of modular blade 320, for example. In various embodiments, an exposed surface of medial engagement rail 336 may be substantially planar although in other embodiments the exposed surface may be arcuately shaped to correspond and/or approximate the geometrical profile of contoured channel 323, for example.

In various embodiments, engagement feature 334 may include at least one protrusion 333 having a size and shape generally corresponding to a size and shape of indentation 325. For example, protrusion 333 may selectively be seated within any one of indentations 325 to secure extendable blade 330 in any one position of the plurality of positions defined by indentations 325. In various embodiments, protrusion 333 may be a circular shaped protrusion, oval shaped protrusion, hexagonal shaped protrusion, parallelogram shaped protrusion, and/or any combination thereof. In various embodiments, protrusion 333 may extend away from extendable blade 330 in a direction perpendicular to the proximal-to-distal direction a distance that is relatively farther out than medial engagement rail 336 and proximal rail 335, for example. In some embodiments, protrusion 333 may be spring loaded and/or biased. In other embodiments, protrusion 333 may be a rigid non movable structure.

In various embodiments, engagement feature 334 may include a distal engagement rail 337 having a size and shape generally corresponding to a size and shape of contoured channel 323. For example, distal engagement rail 337 may have a size and shape generally corresponding to the relatively large central arcuate channel portion 323a and the pair of relatively smaller arcuate rails 323b, for example. Additionally, engagement feature 334 may include a stop feature 338 that may abut against stop feature 329 of modular blade 320 to prevent extendable blade 330 from disengaging with modular blade 320 as explained above, for example.

With reference to FIG. 91, the inside surface of modular blade 320 and the outside surface of extendable blade 330 is illustrated. In various embodiments, extendable blade 330 may operably couple to modular blade 320 by inserting engagement feature 334 into channel 323. As explained above, extendable blade 330 may move forward and backward in a proximal-to-distal direction within contoured channel 323. For example, extendable blade 330 may extend forward and backward within contoured channel 323 and protrusion 333 may be seated within any one of indentations 325. For example, when modular blade 320 and extendable blade 330 are coupled together as a system, they may be referred to as a telescoping blade system.

With reference to FIG. 92, a top down view of modular blade 320 and extendable blade 330 is illustrated. In the example embodiment, it is shown that rails 324a, 324b and channel 319 define a cavity and/or channel for receiving extendable blade 330. For example, extendable blade 330 has a width in a lateral direction that corresponds to a distance between rails 324a, 324b and a thickness of extendable blade 330 corresponds to a depth of the cavity and/or channel between and defined by rails 324a and 324b. In various embodiments, the outside lateral edge 3301 of extendable blade 330 may be mated within the receiving cavity 324y defined by rail 324a and an outside lateral rail 332 of extendable blade 330 may be mated within receiving cavity 324z, for example. In various embodiments, outside lateral rail 332 of extendable blade 330 may extend along the outside lateral edge of extendable blade 330 in the proximal-to-distal direction until about the tip portion 331, for example. Additionally, channel 319 of extendable blade 330 may be mated within channel 319 of modular blade 320. In this way, rails 324a and 324b may provide a bearing surface for retaining extendable blade 330 therein while also allowing extendable blade 330 to move forward and backward in the proximal-to-distal direction. Additionally, it is shown that engagement feature 334 has a size and shape corresponding to contoured channel 323. For example, the curved surfaces of proximal engagement rail 335 may be inset within contoured channel 323 and frictionally engage and slide across the interior surfaces defined by the relatively large central arcuate channel portion 323a and/or pair of relatively smaller arcuate channels 323b on opposite sides of channel portion 323a, for example.

Figure 94:
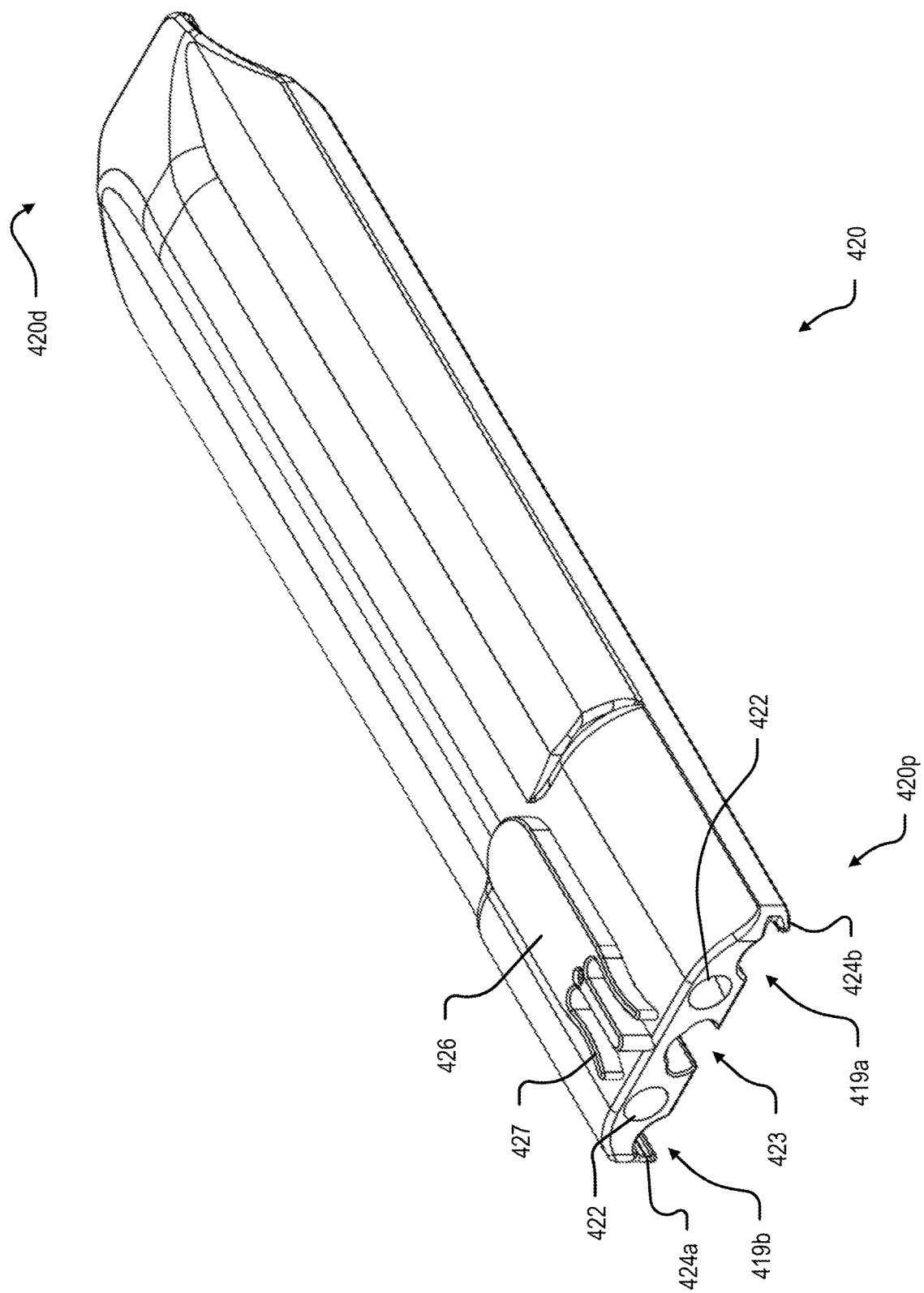
FIG. 94 is a perspective view of a modular blade.
Figure 95:
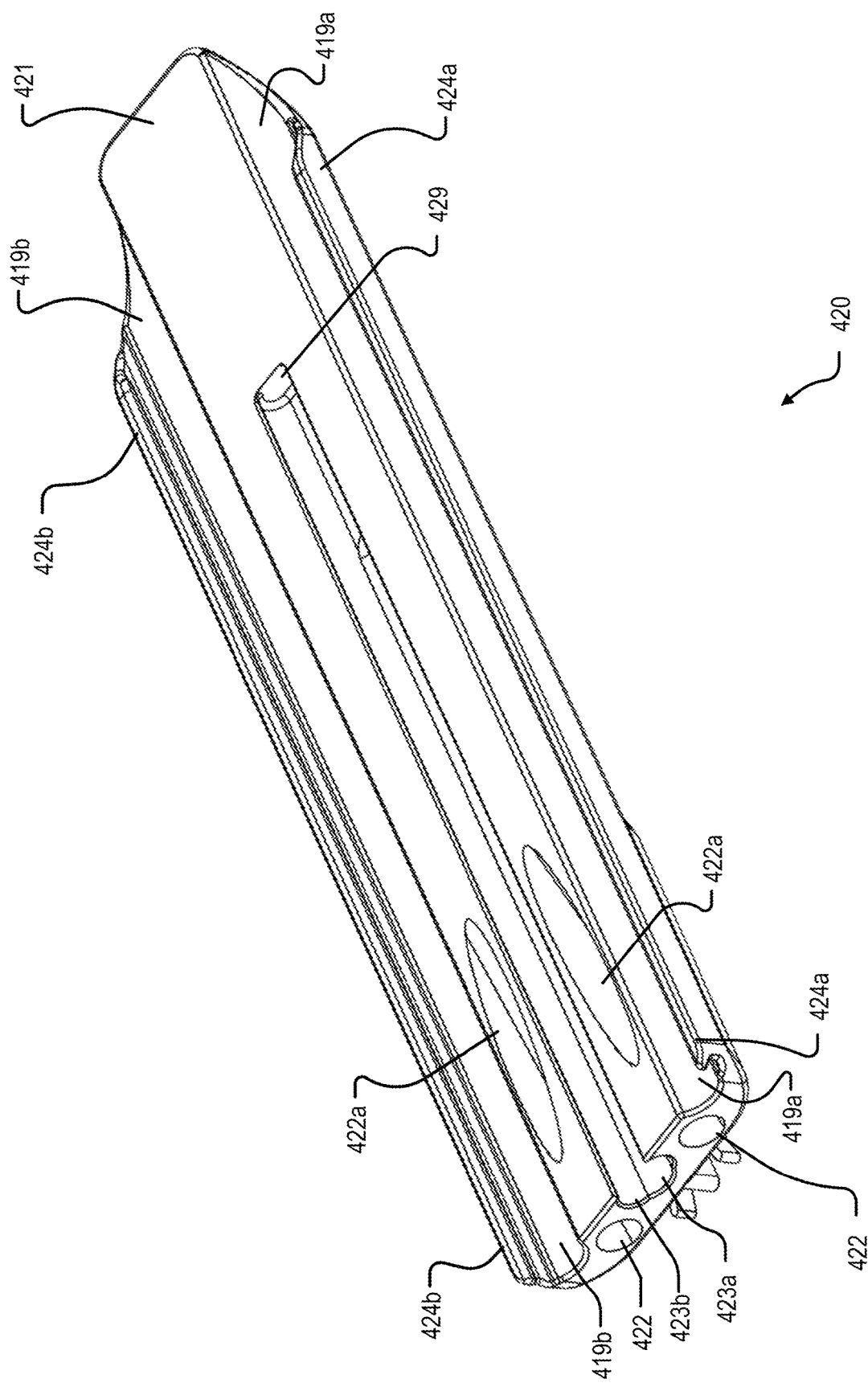
FIG. 95 is a perspective view of a modular blade.
Figure 96:
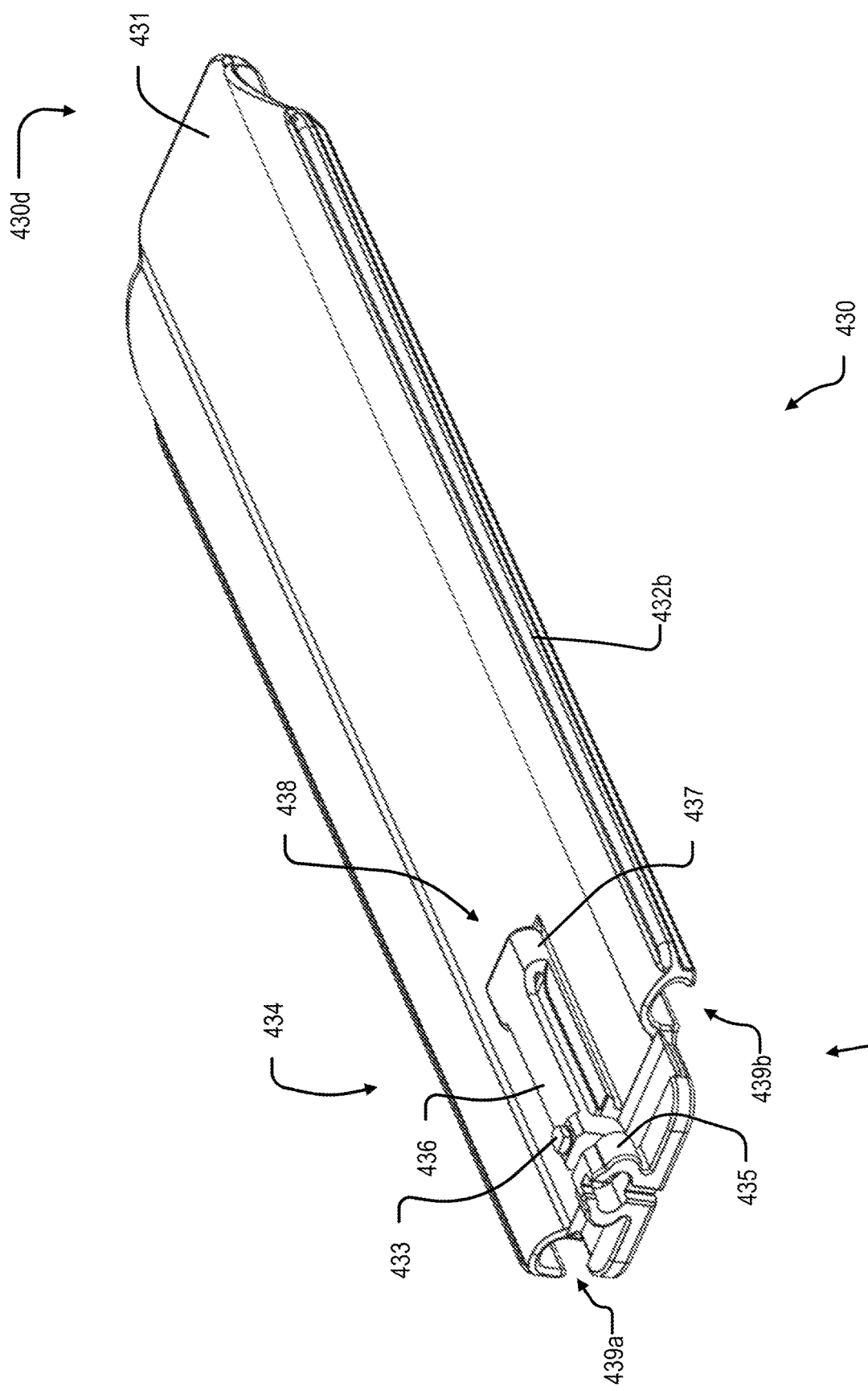
FIG. 96 is a perspective view of an extendable blade for coupling to the modular blade of FIGS. 94-95.
Figure 97:
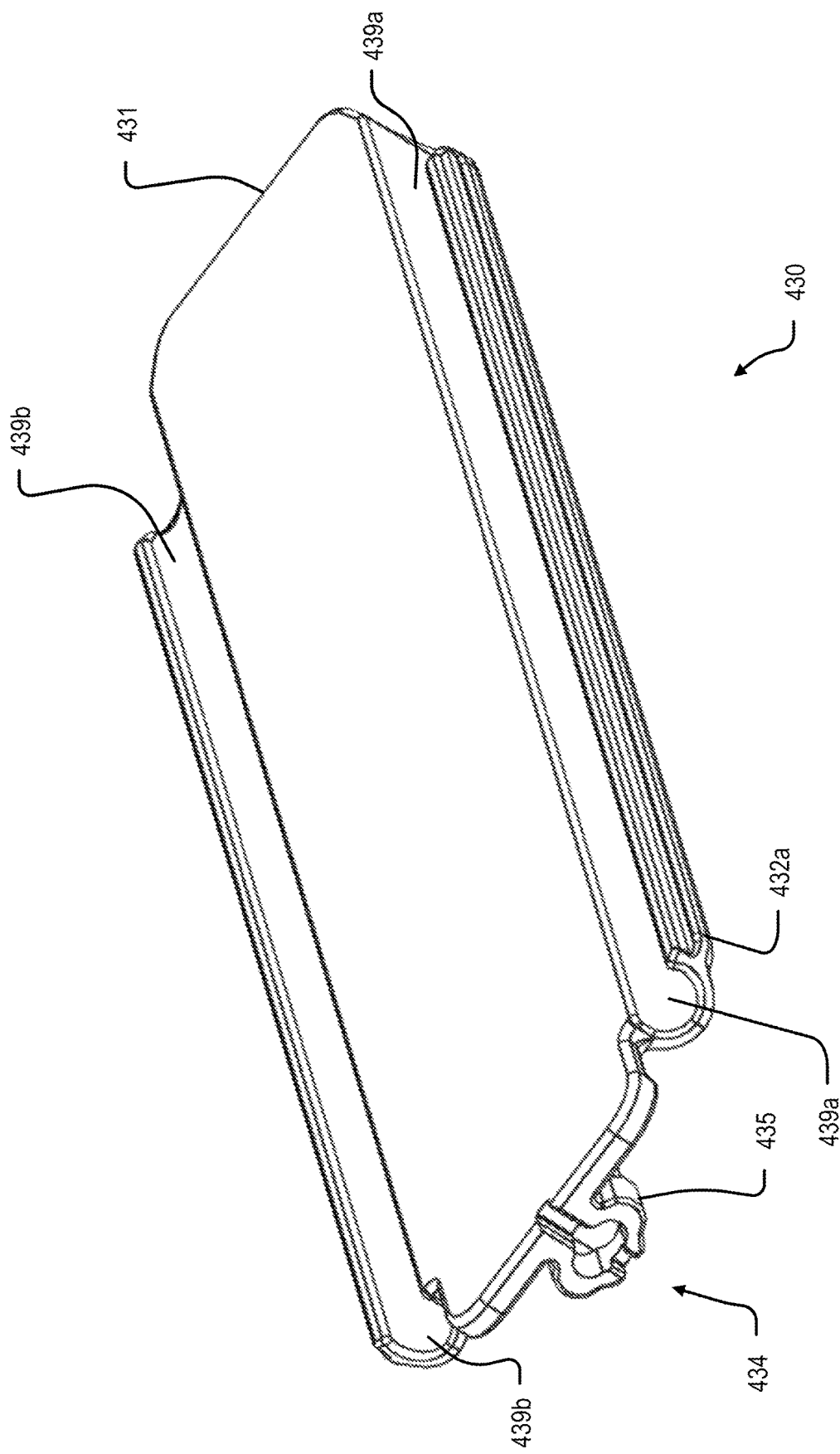
FIG. 97 is a perspective view of an extendable blade for coupling to the modular blade of FIGS. 94-95.
Figure 98:
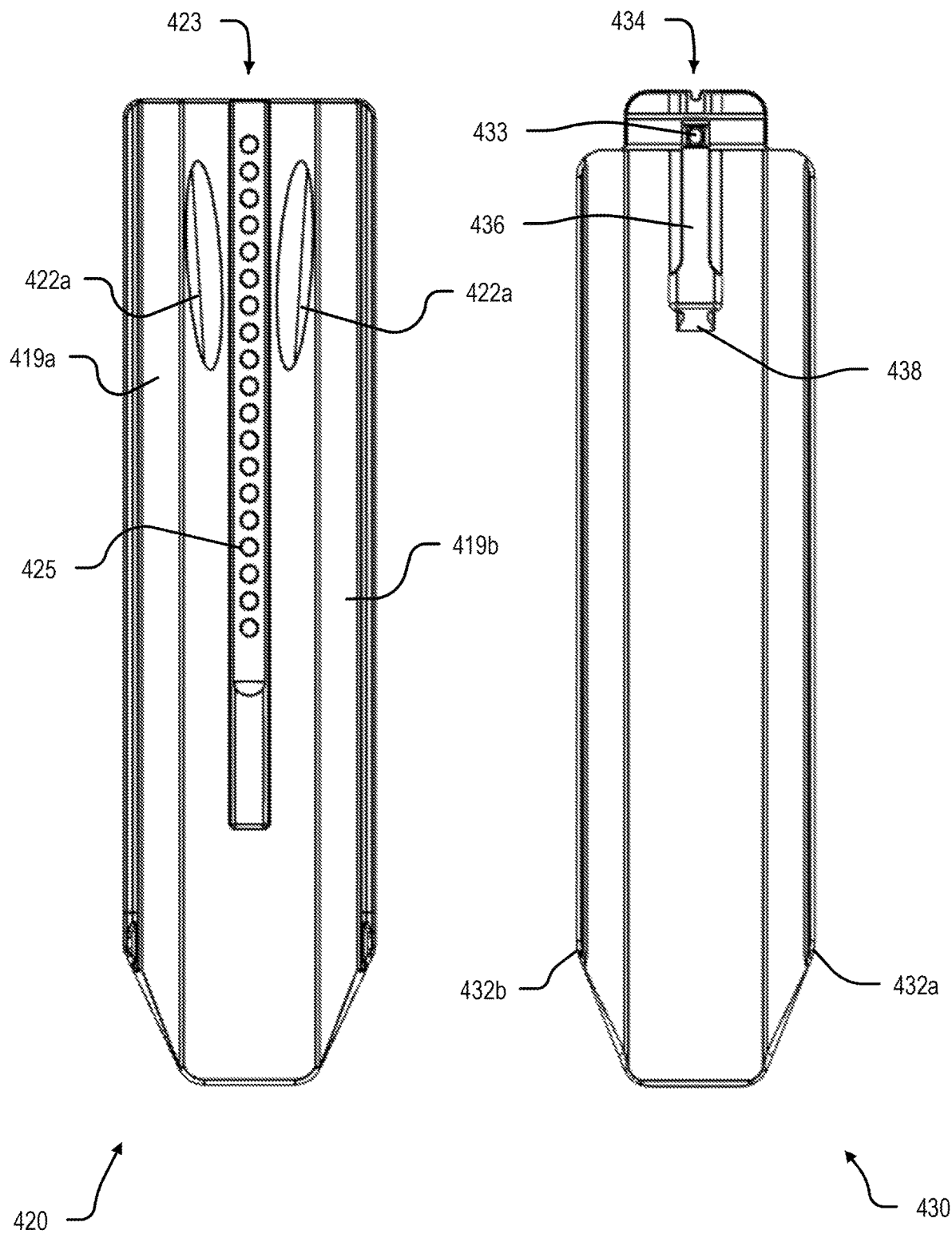
FIG. 98 is a front view of the modular blade of FIGS. 94-95 and the extendable blade of FIGS. 96-97.
Figure 99:
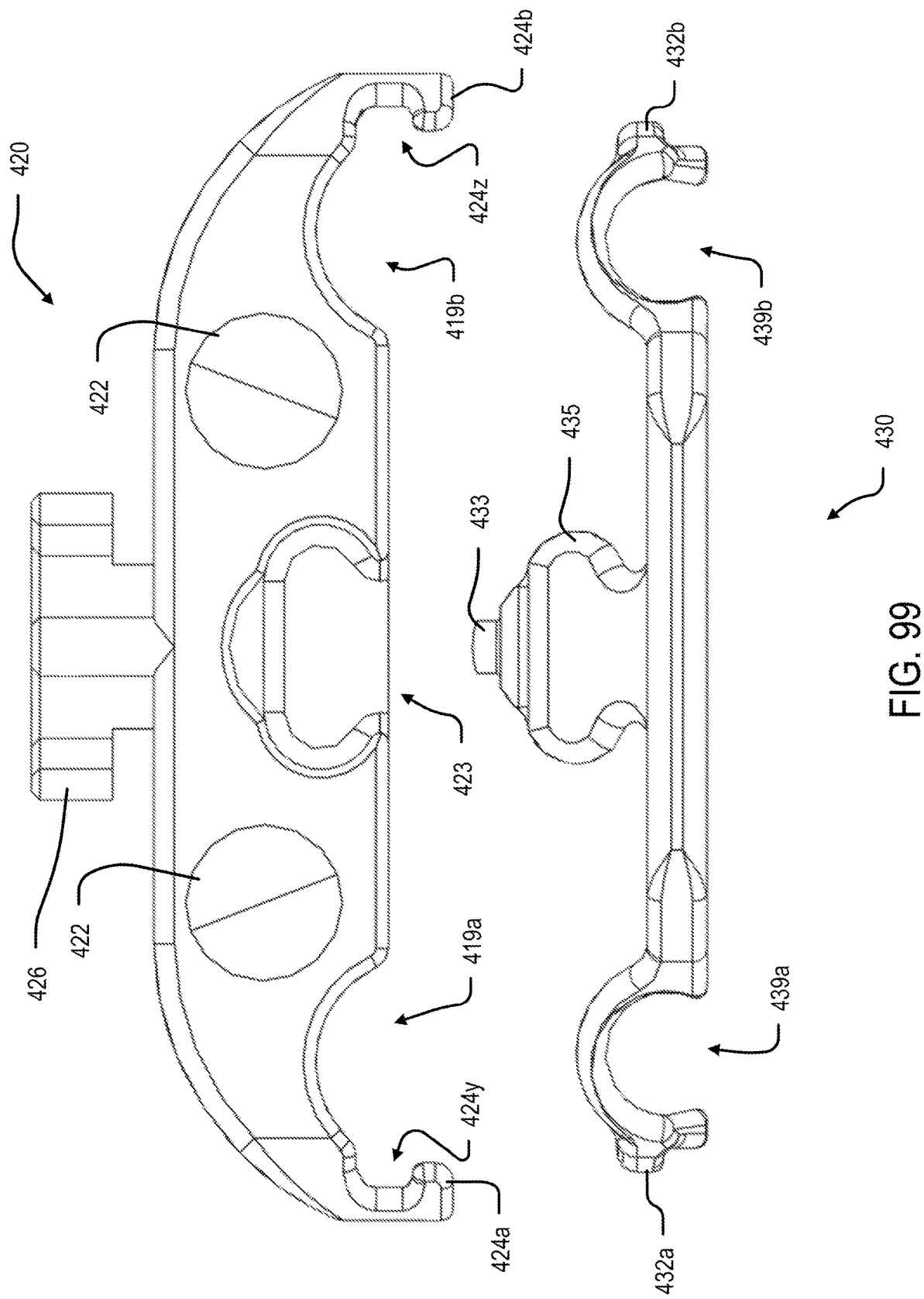
FIG. 99 is a top down view of the modular blade of FIGS. 94-95 and the extendable blade of FIGS. 96-97.

Referring generally to FIGS. 94-99 a modular blade 420 and an extendable blade 430 for coupling to modular blade 420 is disclosed. FIGS. 94 and 95 are various perspective views of a modular blade 420 and FIGS. 96 and 97 are various perspective views of an extendable blade 430 for coupling to modular blade 420. FIG. 98 is a front view of modular blade 420 and extendable blade 430 side by side and FIG. 99 is a top down view of modular blade 420 and extendable blade 430. In various embodiments, modular blade 420 and extendable blade 430 may be configured as a telescoping blade system.

Modular blade 420 may extend from a proximal end 420p to a distal end 420d in a proximal-to-distal direction (may also be referred to as longitudinal direction). The proximal end 420p may include an engagement feature 426 having spring loaded tabs 427 for coupling to a blade engagement mechanism in the same, similar, and/or substantially the same way as explained above. The distal end 420d may include a tip portion 421. In the example embodiment, tip portion 421 comprises a substantially planar outer surface that tapers towards a centerline of modular blade 420 and terminates as a blunt chisel shaped end having a relatively smaller thickness than the remaining portions of modular blade 420, for example. As best seen in FIG. 95, in some embodiments tip portion 421 may curve inward and/or arc inward in various embodiments, for example. Modular blade 420 may include a pair of rails 424a and 424b that extend from proximal end 420p towards distal end 420d. For example, a first rail 424a may extend along a first lateral side of blade 420 in the proximal-to-distal direction and a second rail 424b, opposite first rail 424a, may extend along a second lateral side of blade 420 in the proximal-to-distal direction. In various embodiments, modular blade 420 may be symmetrical on either side of a centerline extending in the proximal-to-distal direction, for example.

In various embodiments, first rail 424a may define a first receiving cavity 424y and second rail 424b may define a second receiving cavity 424z, for example (see FIG. 99). Additionally, modular blade 420 may include a first channel 419a and second channel 419b extending along the inside surface of modular blade 420 in the proximal-to-distal direction and/or from a proximal end to a distal end, for example. Channels 419a, 419b may have a size and shape generally corresponding to a size and shape of channels 439a and 439b of extendable blade 430, for example. In various embodiments, rails 424a, 424b, and channels 419a, 419b may define a contoured receiving channel for receiving extendable blade 430, as will be explained in further detail below.

Modular blade 420 may include at least one aperture 422 extending through a top surface of blade 420 at the proximal end 420p and penetrating through the inside surface of blade 420 at oval shaped opening 422a, for example. Apertures 422 may have the same, similar, and/or substantially the same features and functionality of aperture 122. Accordingly, duplicative description will be omitted. Modular blade 420 may include a contoured channel 423 for connecting with extendable blade 430 and facilitating the forward and backward relative motion of extendable blade 430 in the proximal-to-distal direction, for example. Contoured channel may include a relatively large central arcuate channel portion 423a having a pair of relatively smaller arcuate channels 423b on opposite sides of channel portion 423a, for example. Additionally, contoured channel 423 may include a plurality of indentations 425 extending in a proximal-to-distal direction, for example. In various embodiments, indentations 425 may be circular shaped indentations, oval shaped indentations, hexagonal shaped indentations, parallelogram shaped indentions, and/or any combination thereof. A distal end of contoured channel 423 may include a stop feature 429 for preventing extendable blade 430 from extending too far in the proximal-to-distal direction.

Extendable blade 430 may extend from a proximal end 430p to a distal end 430d in a proximal-to-distal direction (also referred to as a longitudinal direction). The distal end may include a tip portion 431 and extendable blade 430 may be generally shaped like a rectangle (in a plan view). In the example embodiment, an outside surface of extendable blade 430 may include an engagement feature 434 for connecting with contoured channel 423, for example. Engagement feature 434 may include a proximal engagement rail 435 having a size and shape generally corresponding to a size and shape of contoured channel 423. For example, proximal engagement rail 435 may have a size and shape generally corresponding to the relatively large central arcuate channel portion 423a and the pair of relatively smaller arcuate channels 423b, for example. Additionally, engagement feature 434 may include a medial engagement rail 436 having a width approximately corresponding to the relatively large central arcuate channel portion 423a of modular blade 420, for example. In various embodiments, an exposed surface of medial engagement rail 436 may be substantially planar although in other embodiments the exposed surface may be arcuately shaped to correspond and/or approximate the geometrical profile of contoured channel 423, for example.

In various embodiments, engagement feature 434 may include at least one protrusion 433 having a size and shape generally corresponding to a size and shape of indentation 425. For example, protrusion 433 may selectively be seated within any one of indentations 425 to secure extendable blade 430 in any one position of the plurality of positions defined by indentations 425. In various embodiments, protrusion 433 may be a circular shaped protrusion, oval shaped protrusion, hexagonal shaped protrusion, parallelogram shaped protrusion, and/or any combination thereof. In various embodiments, protrusion 433 may extend away from extendable blade 430 in a direction perpendicular to the proximal-to-distal direction a distance that is relatively farther out than medial engagement rail 436 and proximal engagement rail 435, for example. In some embodiments, protrusion 433 may be spring loaded and/or biased. In other embodiments, protrusion 433 may be a rigid non movable structure.

In various embodiments, engagement feature 434 may include a distal engagement rail 437 having a size and shape generally corresponding to a size and shape of contoured channel 423. For example, distal engagement rail 437 may have a size and shape generally corresponding to the relatively large central arcuate channel portion 423a and the pair of relatively smaller arcuate channels 423b, for example. Additionally, engagement feature 434 may include a stop feature 438 that may abut against stop feature 429 of modular blade 420 to prevent extendable blade 430 from disengaging with modular blade 420 as explained above, for example.

With reference to FIG. 98, the inside surface of modular blade 420 and the outside surface of extendable blade 430 is illustrated. In various embodiments, extendable blade 430 may operably couple to modular blade 420 by inserting engagement feature 434 into channel 423. As explained above, extendable blade 430 may move forward and backward in a proximal-to-distal direction within contoured channel 423. For example, extendable blade 430 may extend forward and backward within contoured channel 423 and protrusion 433 may be seated within any one of indentations 425.

With reference to FIG. 99, a top down view of modular blade 420 and extendable blade 430 is illustrated. In the example embodiment, it is shown that rails 424a, 424b and channels 419a, 419b define a cavity and/or channel for receiving extendable blade 430. For example, extendable blade 430 has a width in a lateral direction that corresponds to a distance between rails 424a, 424b and a thickness of extendable blade 430 corresponds to a depth of the cavity and/or channel between and defined by rails 424a and 424b. In various embodiments, the outside lateral rail 432a of extendable blade 430 may be mated within the receiving cavity 424y defined by rail 424a and an outside lateral rail 432b of extendable blade 430 may be mated within receiving cavity 424z, for example. In various embodiments, outside lateral rail 432a, 432b of extendable blade 430 may extend along the outside lateral edge of extendable blade 430 in the proximal-to-distal direction until about the tip portion 431, for example. Additionally, channels 439a, 439b of extendable blade 430 may be mated within channels 419a, 419b of modular blade 420. In this way, rails 424a and 424b may provide a bearing surface for retaining extendable blade 430 therein while also allowing extendable blade 430 to move forward and backward in the proximal-to-distal direction. Additionally, it is shown that engagement feature 434 has a size and shape corresponding to contoured channel 423. For example, the curved surfaces of proximal engagement rail 435 may be inset within contoured channel 423 and frictionally engage and slide across the interior surfaces defined by the relatively large central arcuate channel portion 423a and/or pair of relatively smaller arcuate channels 423b on opposite sides of channel portion 423a, for example.

Figure 100:
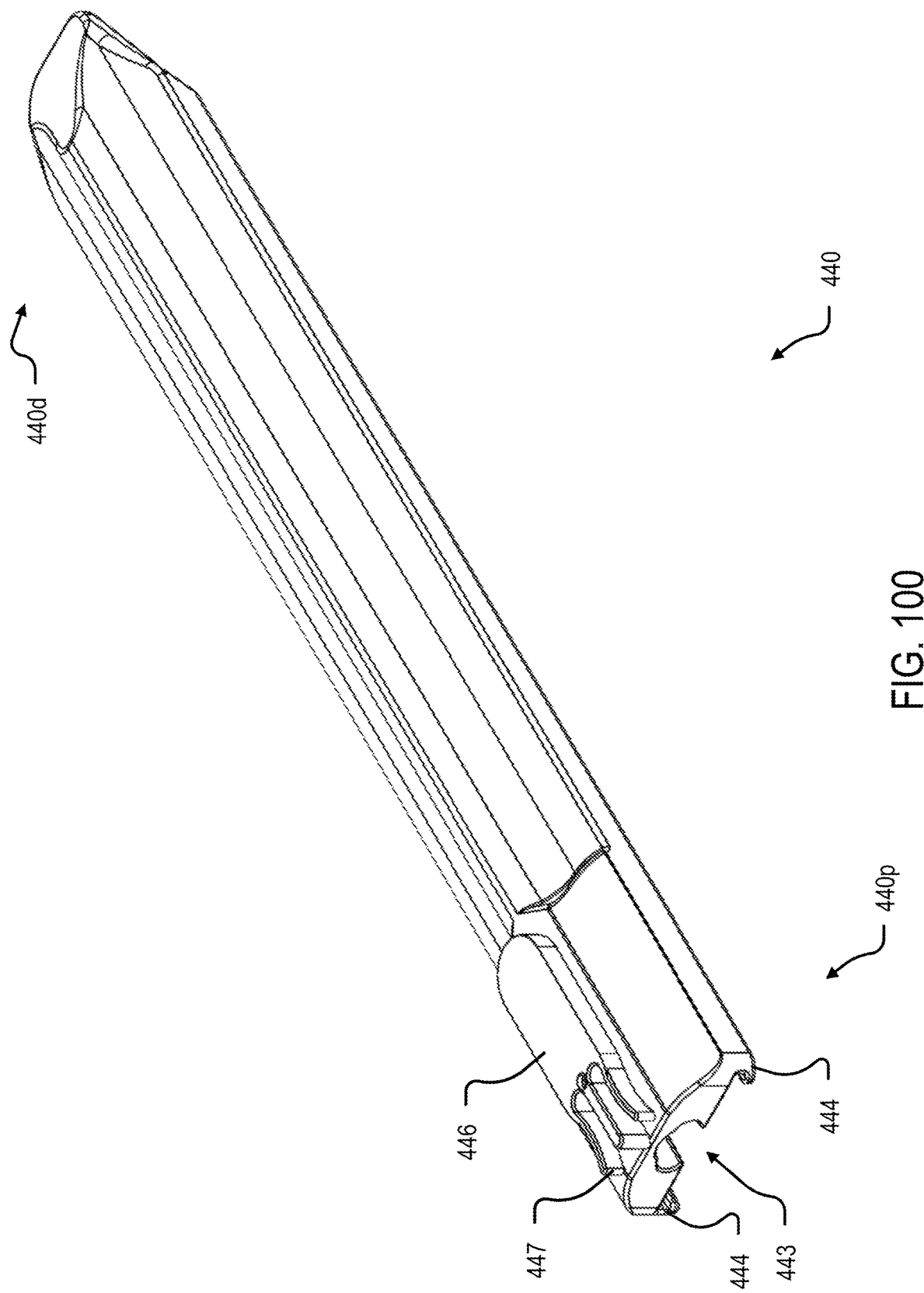
Figure 101:
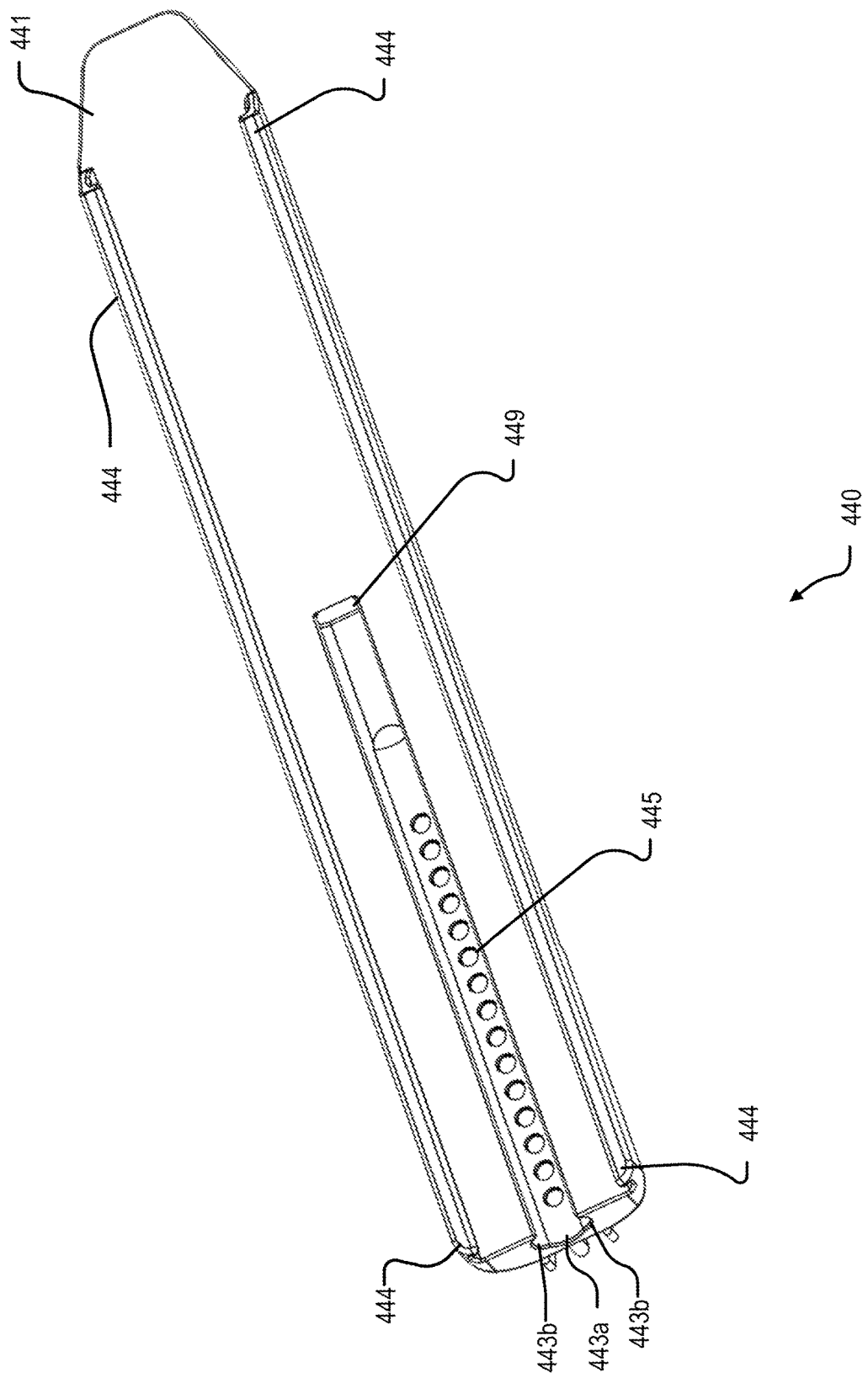
Figure 102:
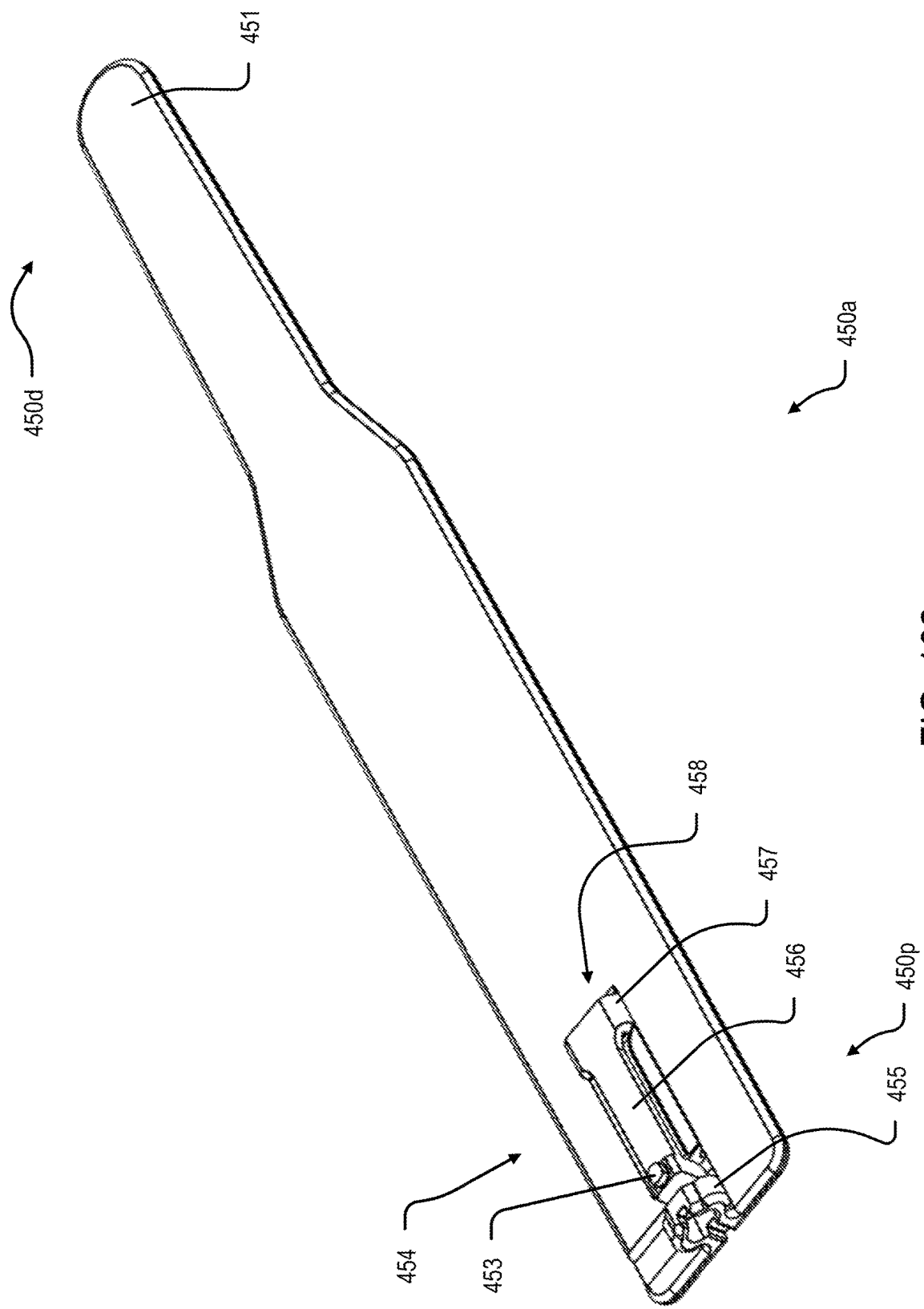
Figure 103:
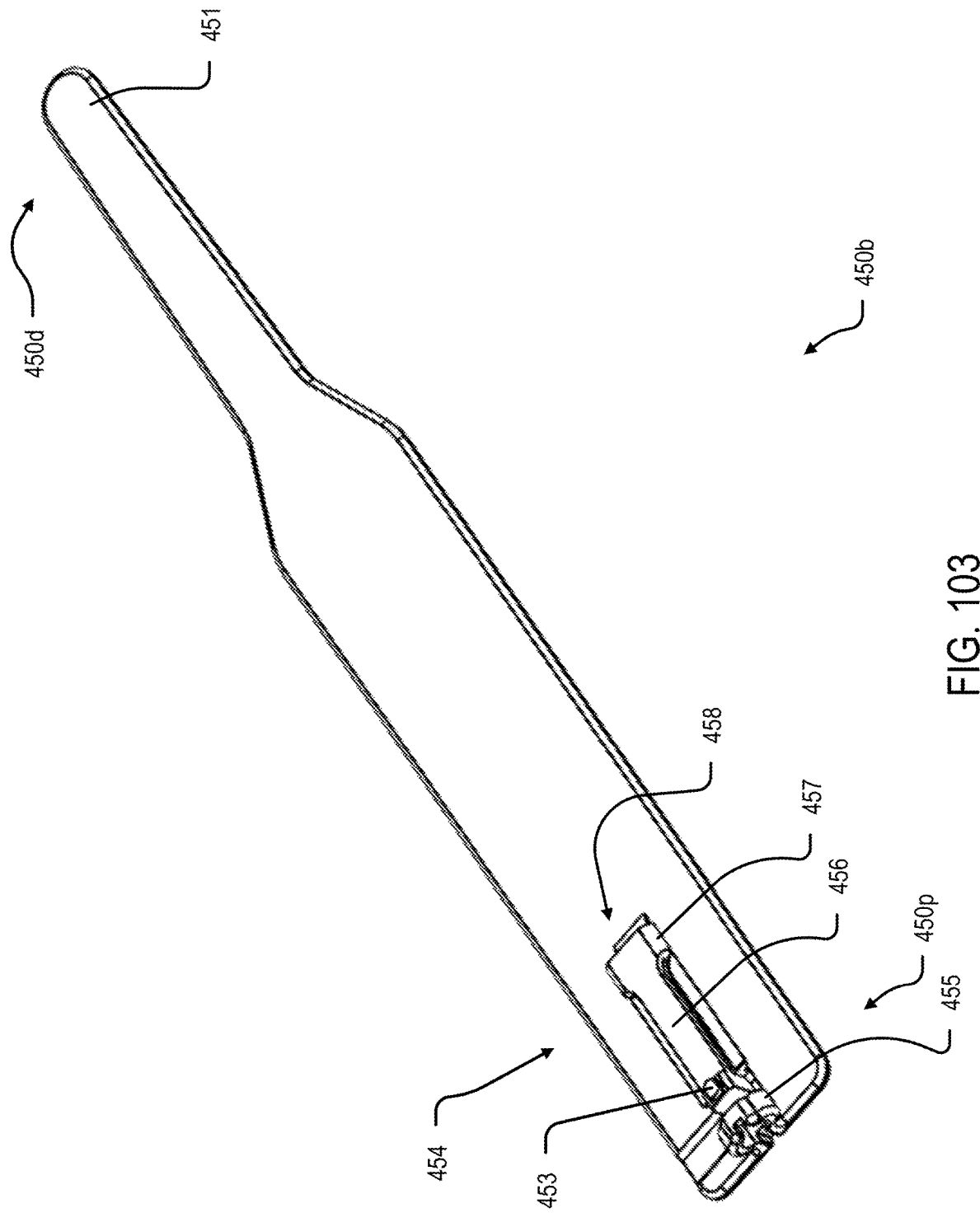
Figure 104:
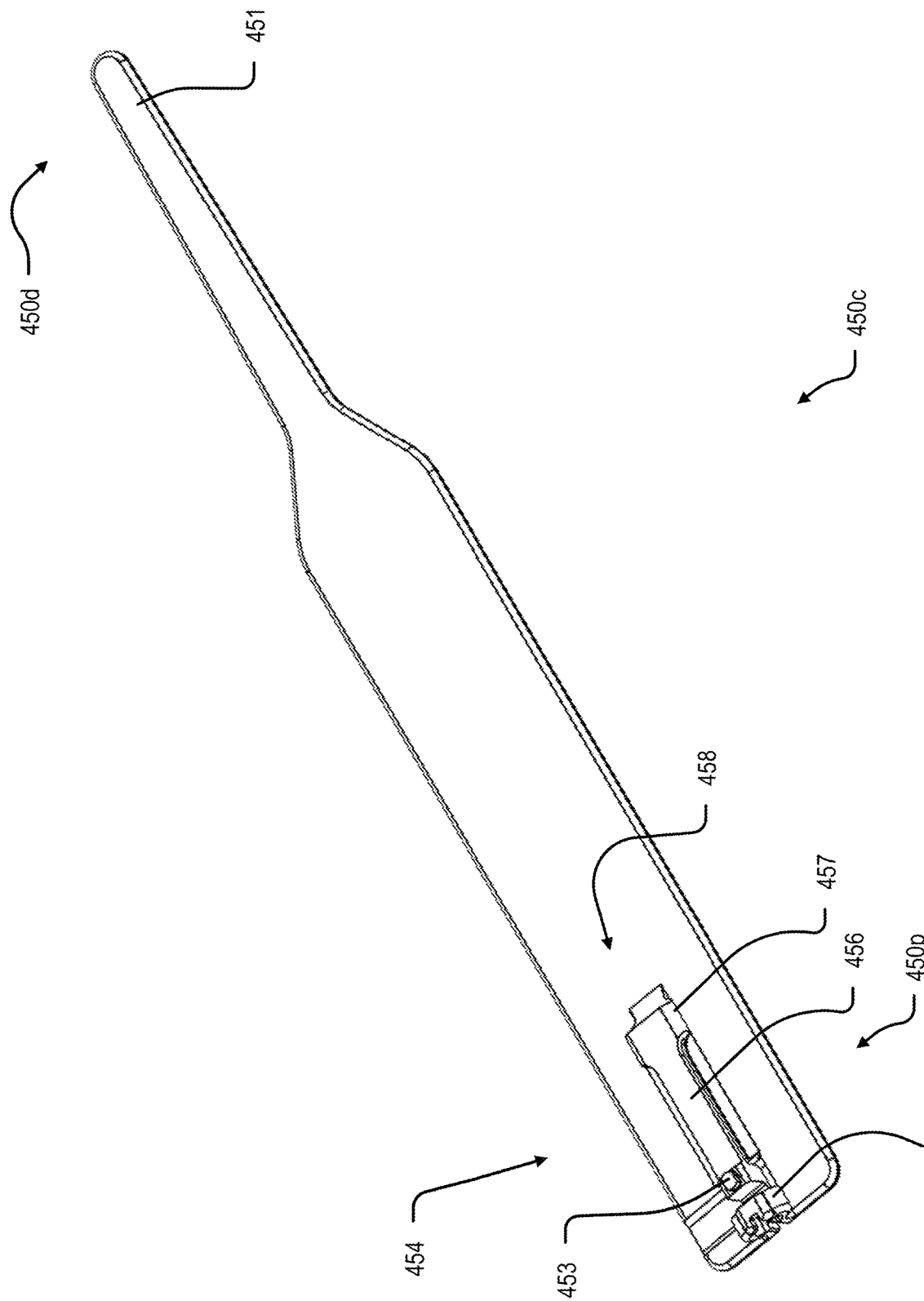
Figure 105:
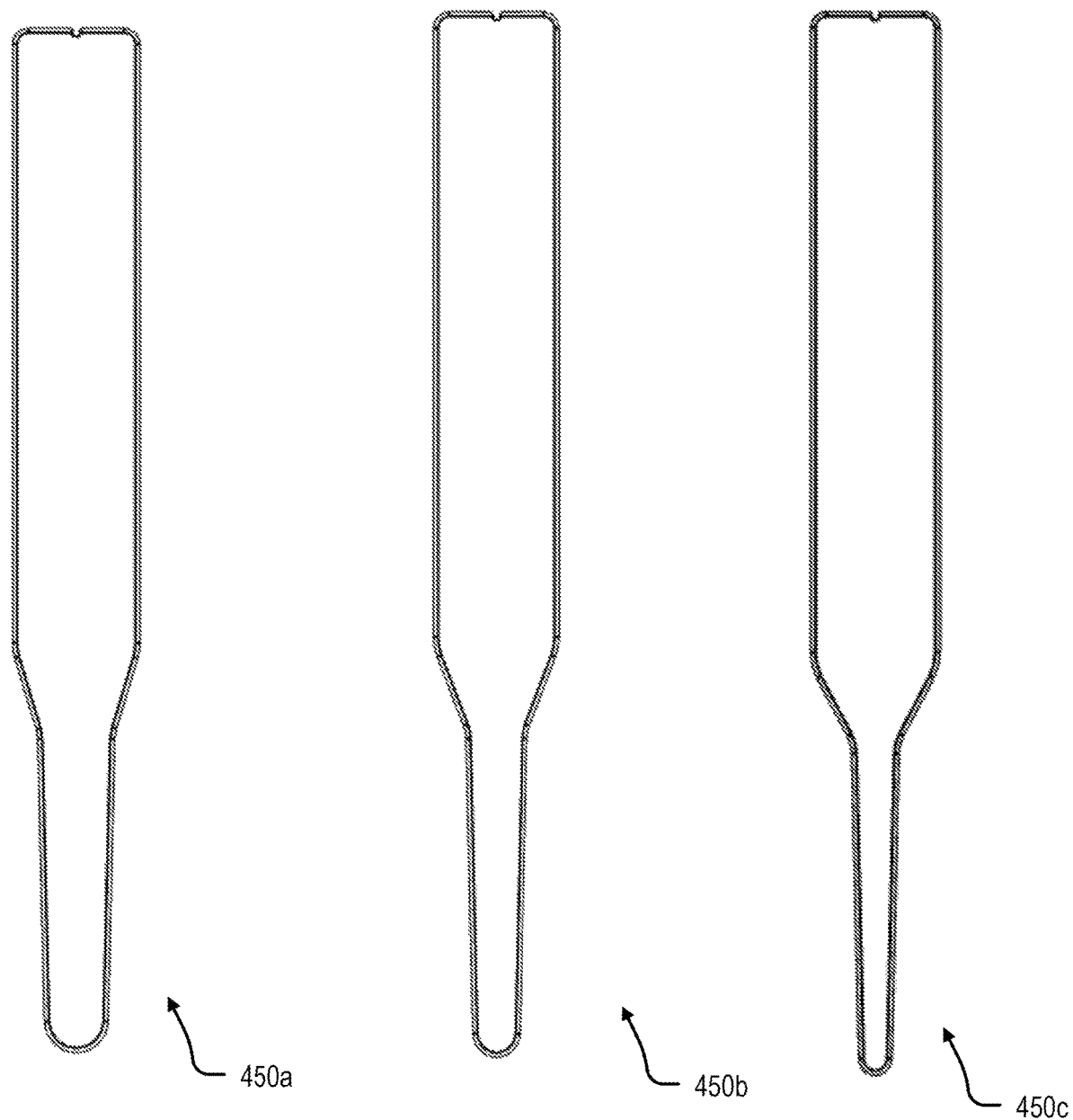

Referring generally to FIGS. 100-105 a modular blade 440 and various extendable blades 450a, 450b, and 450c for coupling to modular blade 440 is disclosed. FIGS. 100-101 are various perspective views of a modular blade 440 and FIGS. 102-104 are various perspective views of extendable blades 450a, 450b, and 450c for coupling to modular blade 440. FIG. 105 is a front view of extendable blades 450a, 450b, and 450c. In various embodiments, modular blade 440 and extendable blades 450a, 450b, and 450c may be configured as a telescoping blade system. In various embodiments, the extendable blades 450a, 450b, and 450c may have a relatively long and narrow tip section that may be advantageous for distracting soft tissues of a patient, for example.

Modular blade 440 may extend from a proximal end 440p to a distal end 440d in a proximal-to-distal direction (may also be referred to as longitudinal direction). The proximal end 440p may include an engagement feature 446 having spring loaded tabs 447 for coupling to a blade engagement mechanism in the same, similar, and/or substantially the same way as explained above. The distal end 440*d* may include a tip portion 441. In the example embodiment, tip portion 441 comprises a substantially planar outer surface that tapers towards a centerline of modular blade 440 and terminates as a blunt chisel shaped end having a relatively smaller thickness than the remaining portions of modular blade 440, for example. Modular blade 440 may include a pair of rails 444 that extend from proximal end 440*p* towards distal end 440*d*. For example, a first rail 444 may extend along a first side of blade 440 in the proximal-to-distal direction and a second rail 444, opposite the first rail 444, may extend along a second side of blade 440 in the proximal-to-distal direction. In various embodiments, rails 444 may define a receiving channel for receiving any one of extendable blades 450*a*, 450*b*, and 450*c*, for example.

Modular blade 440 may include a contoured channel 443 for connecting with extendable blades 450*a*, 450*b*, and 450*c* and facilitating the forward and backward relative motion of extendable blades 450*a*, 450*b*, and 450*c* in the proximal-to-distal direction, for example. As shown best in FIG. 83, contoured channel 443 may include a relatively large central arcuate channel portion 443*a* having a pair of relatively smaller arcuate channels 443*b* on opposite sides of channel portion 443*a*, for example. Additionally, contoured channel 443 may include a plurality of indentations 445 extending in a proximal-to-distal direction, for example. In various embodiments, indentations 445 may be circular shaped indentations, oval shaped indentations, hexagonal shaped indentations, parallelogram shaped indentions, and/or any combination thereof. A distal end of contoured channel 443 may include a stop feature 449 for preventing extendable blades 450*a*, 450*b*, and 450*c* from extending too far in the proximal-to-distal direction.

Extendable blades 450*a*, 450*b*, and 450*c* may extend from a proximal end 450*p* to a distal end 450*d* in a proximal-to-distal direction (also referred to as a longitudinal direction). The distal end may include a relatively long tip portion 451 that tapers near a medial portion of extendable blades 450*a*, 450*b*, and 450*c* and then extends towards distal end 450*d* at the same, similar, and/or substantially the same width. Relatively long tip portion 451 may terminate as an arcuate curved end with chamfered surfaces, for example. As seen best in FIG. 105, extendable blades 450*a*, 450*b*, and 450*c* are similar and have differently sized tip portions 451. For example, extendable blade 450*a* has a relatively wider tip portion 451 than extendable blades 450*b* and 450*c*, for example. Extendable blade 450*b* has a relatively narrower tip portion 451 than extendable blade 450*a* and a relatively wider tip portion 451 than extendable blade 450*c*, for example. Extendable blade 450*c* has a relatively narrow tip portion 451 than extendable blades 450*a* and 450*b*, for example. The other remaining features and components may be the same, substantially the same, and or similar.

In the example embodiment, an outside surface of extendable blades 450*a*, 450*b*, and 450*c* may include an engagement feature 454 for connecting with contoured channel 443, for example. Engagement feature 454 may include a proximal engagement rail 455 having a size and shape generally corresponding to a size and shape of contoured channel 443. For example, proximal engagement rail 455 may have a size and shape generally corresponding to the relatively large central arcuate channel portion 443*a* and the pair of relatively smaller arcuate channels 443*b*, for example. Additionally, engagement feature 454 may include a medial engagement rail 456 having a width approximately corresponding to the relatively large central arcuate channel portion 443*a* of modular blade 440, for example. In various embodiments, an exposed surface of medial engagement rail 456 may be substantially planar although in other embodiments the exposed surface may be arcuately shaped to correspond and/or approximate the geometrical profile of contoured channel 443, for example.

In various embodiments, engagement feature 454 may include at least one protrusion 453 having a size and shape generally corresponding to a size and shape of indentation 445. For example, protrusion 453 may selectively be seated within any one of indentations 445 to secure extendable blades 450*a*, 450*b*, and 450*c* in any one position of the plurality of positions defined by indentations 445. In various embodiments, protrusion 453 may be a circular shaped protrusion, oval shaped protrusion, hexagonal shaped protrusion, parallelogram shaped protrusion, and/or any combination thereof. In various embodiments, protrusion 453 may extend away from extendable blades 450*a*, 450*b*, and 450*c* in a direction perpendicular to the proximal-to-distal direction a distance that is relatively farther out than medial engagement rail 456 and/or proximal engagement rail 455, for example. In some embodiments, protrusion 453 may be spring loaded and/or biased. In other embodiments, protrusion 453 may be a rigid non movable structure.

In various embodiments, engagement feature 454 may include a distal engagement rail 457 having a size and shape generally corresponding to a size and shape of contoured channel 443. For example, distal engagement rail 457 may have a size and shape generally corresponding to the relatively large central arcuate channel portion 443*a* and the pair of relatively smaller arcuate channels 443*b*, for example. Additionally, engagement feature 454 may include a stop feature 458 that may abut against stop feature 449 of modular blade 440 to prevent extendable blades 450*a*, 450*b*, and 450*c* from disengaging with modular blade 440, for example. For example, in a fully extended position, stop feature 449 of extendable blade may directly contact stop feature 458 of extendable blades 450*a*, 450*b*, and 450*c* and prevent extendable blades 450*a*, 450*b*, and 450*c* from extending too far that engagement feature 454 becomes unseated from contoured channel 443.

In various embodiments, extendable blades 450*a*, 450*b*, and 450*c* may operably couple to modular blade 440 by inserting engagement feature 454 into channel 443. As explained above, extendable blades 450*a*, 450*b*, and 450*c* may move forward and backward in a proximal-to-distal direction within contoured channel 443. For example, extendable blades 450*a*, 450*b*, and 450*c* may extend forward and backward within contoured channel 443 and protrusion 453 may be seated within any one of indentations 445. For example, when modular blade 440 and any one of extendable blades 450*a*, 450*b*, and 450*c* are coupled together as a system, they may be referred to as a telescoping blade system and such system may be particularly advantageous for distracting and retracting various soft patient tissue, for example.

In the example embodiment, rails 444 may define a cavity and/or channel for receiving any one of extendable blades 450*a*, 450*b*, and 450*c*. For example, extendable blades 450*a*, 450*b*, and 450*c* may have a width in a lateral direction that corresponds to a distance between rails 444 and a thickness of each extendable blades 450*a*, 450*b*, and 450*c* may correspond to a depth of the cavity and/or channel between and defined by rails 444, for example. In various embodiments, any one corresponding pair of outside lateral edges of extendable blades 450*a*, 450*b*, and 450*c* may be inset within the receiving cavity defined by rails 444 such that a pair of lateral edges frictionally engages and slides across the interior side surfaces of modular blade 440, for example. In this way, rails 444 may provide a bearing surface for retaining any one of extendable blades 450a, 450b, and 450c therein while also allowing any inserted blade to move forward and backward in the proximal-to-distal direction. Additionally, in various embodiments engagement feature 454 has a size and shape corresponding to contoured channel 443. For example, the curved surfaces of proximal engagement rail 455 may be inset within (mated within) contoured channel 443 and frictionally engage and slide across the interior surfaces defined by the relatively large central arcuate channel portion 443a and/or pair of relatively smaller arcuate channels 443b on opposite sides of channel portion 443a, for example.

Additional Retractor Embodiments

Referring generally to FIGS. 106-108D a modular blade 140 and an extendable blade 150 having a pointed end 151 is disclosed. In some embodiments, extendable blade 150 may be referring to as an "impact blade" on account of being configured with a pointed end 151 that may be driven into a disc space, for example. FIG. 106 is a front view of the modular blade 140 and extendable blade 150 slidably coupled together and FIG. 107 is a rear view of the modular blade 140 and extendable blade 150 slidably coupled together. FIGS. 108A and 108B are various exploded parts views of the modular blade 140 and extendable blade 150. FIG. 108C is a perspective view of the modular blade 140 and FIG. 108D is a top down view of the modular blade 140.

In the example embodiment, modular blade 140 may include an engagement feature 146 having similar functional attributes to blade engagement feature 126 explained above with respect to blade 120. However, in this embodiment, the engagement feature 146 of modular blade 140 does not include spring loaded tabs 127, for example. Rather, as best seen in FIGS. 108B, 108C, and 108D, engagement feature 146 comprises a raised rail 146B having an arcuately shaped and/or curved shaped uppermost surface 146A, for example. The raised rail portion 146B may be offset from the outside surface of modular blade 140 by platform 146D. In the example embodiment, a thickness or dimension of platform 146D in a lateral direction is less than a thickness or dimension of raised rail 146B in the lateral direction. In the example embodiment, channel portions 146C are formed on opposite sides of platform 146D and are located between the outside surface of modular blade 140 and the adjacent inside surface of raised rail 146B, for example. In this way, engagement feature 146 may be configured to slidably connect to a corresponding blade coupling portion of an arm of the variously disclosed blade coupling portions having corresponding male/female features. In at least one embodiment, modular blade 140 may be securely coupled to blade coupling portion 535 shown in FIGS. 119-121B by sliding the modular blade 140 from beneath blade coupling portion 535 upwards into blade coupling portion 535. For example, modular blade 140 may be configured for bottom loading as will be explained in further detail below. Additionally, any blade disclosed herein may be configured with the same, similar, or substantially the same type of engagement feature 146. However, consistent with the disclosure herein, modular blade and engagement feature 146 may also be reversed for top loading.

As seen best in FIGS. 108B, 108C, and 108D, modular blade 140 may comprise a pair of channels 143 extending along the interior surface thereof from a proximal end 140P to a distal end 140D. In various embodiments, the interior surface of modular blade 140 may be a curved surface 148. Additionally, the extendable blade 150 may comprise a pair of outdented rail portions 153 extending along the side surfaces thereof from a proximal end 150P to a distal end 150D thereof. In the example embodiment, the blade surface of extendable blade 150 has a curved sidewall surface 158 having a size and shape generally corresponding to the interior curved surface 148 of modular blade 140, for example. In use, the extendable blade 150 may be configured to couple to the modular blade 140 by sliding the outdented rails 153 into the interior channels 143 of modular blade 140, for example. In this way, extendable blade 150 may be configured to slidably couple to modular blade 140 in an operable way, for example. However, it shall be understood that other embodiments may rely on a single rail 153 and a single channel 143 and that channels 143 and rails 153 may take various shapes, for example oblong, square, trapezoidal, dovetail, tongue and groove, etc.

FIG. 108E is a perspective view of a driver 149 for use with the modular blade 140 and extendable blade 150, for example. In some embodiments, driver 149 may be a referred to as an impact driver on account of being suitable for sustaining an impact force to drive extendable blade 150 forward, for example. In the example embodiment, driver 149 may extend in a longitudinal direction from a proximal end to a distal end. For example, driver 149 may include a proximal end comprising a striking end or surface 149A having a relatively flat or smooth top surface and a circumferential side surface 149B having various texturing. In the example embodiment, the texturing of side surface 149B extends in a proximal to distal direction along the outside side surface of the proximal end of driver 149 as raised rails and indented valleys therebetween. The texturing may assist a surgeon in rotating driver 149 within channel 143 and in some embodiments, rotating driver 149 may be used to rotate a threaded pin (not illustrated). In some embodiments, the contouring and/or texturing may correspond to a torx head or a similar driver end, for example. In various embodiments, a shaft 149C may couple to or be integrally formed together with the proximal end and distal end, for example. In the example embodiment, shaft 149C may have a diameter substantially corresponding in size and shape to a diameter of channel 143, for example. Additionally, a distal end of shaft 149C may comprise a blunt distal end 149D. In operation, the blunt end 149D may contact the proximal end of extendable blade 150 for pushing extendable blade 150 forward. Additionally, a first and second driver 149 may be used together to push extendable blade 150 forward within both of channels 143, for example.

FIG. 109 is a perspective view of a rectangular shaped dilator 160. In the example embodiment, dilator 160 extends in a longitudinal direction from a proximal end 160P to a distal end 160D. The proximal end 160P may include a pair of opposing curvilinear indents 165 for gripping dilator 160, for example. In various embodiments, dilator 160 may comprise an aperture 163 or opening extending from proximal end 160P to distal end 160D through dilator 160, for example. In various embodiments, dilator 160 may have planar side surfaces 161 extending in a proximal-to-distal direction. In the example embodiment, dilator 160 may further include a chiseled end or inclined end defining the distal end 160D surfaces. For example, planar side surfaces 161 may terminate into inclined surfaces 162 which may facilitate insertion of dilator 160 into an operative corridor for example. In the example embodiment, dilator 160 is rectangular shaped and in other embodiments dilator 160 may be square shaped. Dilator 160 may be used with any type of blade disclosed herein. Dilator 160 may be particularly advantageous for use with a relatively flat planar blade such as blade 130 shown in FIG. 84 and/or the footed tip blades disclosed below. At least one surgical configuration may comprise the utilization of a four-blade configuration comprising four substantially planar blades that generally surround the rectangular shaped dilator 160, for example.

Referring generally to FIGS. 110-114 various example shims 170, 180 are disclosed. FIG. 110 is a bottom perspective view of a pair of shims 170 for coupling to various blades disclosed herein. FIG. 111 is a perspective view of a relatively short shim 170 having a pointed pin 173 at a distal end thereof and FIG. 112 is a perspective view of a relatively tall shim 170 having a pointed pin 173 at a distal end thereof. FIG. 113 is a perspective view of a relatively tall shim 170 having a blunted distal end. FIG. 114 is a perspective view of a double-sided shim 180 for coupling to various blades disclosed herein. In the example embodiments, shim 170 may extend in a longitudinal direction from a proximal end 170P to a distal end 170D. The proximal end may include a tab 172 for gripping shim 170 and pushing shim 170 downward or pulling shim 170 upward, for example. As seen best in FIG. 110, shim 170 may comprise an arcuate rail 171 having a size and shape generally corresponding to a channel of a blade, for example channel 143 of modular blade 140. Additionally, in various embodiments, tab 172 may comprise a relatively smooth planar upper surface that is strong enough to sustain an impact for driving or tapping of shim 170. For example, a surgeon may provide an impact force to tab 172 by a mallet or hammer which drives shim 170 forward while remaining partially constrained within a corresponding channel of a blade. In striking tab 172, the shim 170 may be thrust forward or in a distal direction thereby inserting pin 173 into patient anatomy such as a bone or disc space, for example. Each shim 170 may have various dimensioned side surfaces for abutting against patient tissue. As seen in FIG. 111, some shim 170 embodiments may include a working surface 175 extending for a relatively short distance in the longitudinal direction and for a relatively great distance in a lateral direction substantially perpendicular to the longitudinal direction of shim 170, for example. As seen in the example embodiment of FIG. 112, some shim 170 embodiments may include a working surface 176 extending for a relatively long distance in a longitudinal direction and for a relatively short distance in a lateral direction substantially perpendicular to the longitudinal direction of shim 170, for example. In the example embodiment of FIG. 112, working surface 176 extends in the longitudinal direction for slightly less than half the length of the shim 170 in the longitudinal direction. As seen in the example embodiment of FIG. 113, some shim 170 embodiments may include a working surface 177 extending for a relatively long distance in a longitudinal direction and for a relatively short distance in a lateral direction substantially perpendicular to the longitudinal direction of shim 170, for example. In the example embodiment of FIG. 113, working surface 177 extends in the longitudinal direction for more than half the length of the shim 170 in the longitudinal direction.

FIG. 114 is an example embodiment of a double-sided shim 180. In this embodiment, shim 180 includes a pair of tabs 182, and a pair of rails 181. In this way, shim 180 may slidably couple to a pair of corresponding channels of a blade, for example channels 143 of modular blade 140. In the example embodiment of FIG. 114, shim 180 comprises a first working surface 184 extending away from shim 180 in a first lateral direction perpendicular to the longitudinal direction and a second working surface 185 extending away from shim 180 in a second lateral direction perpendicular to the longitudinal direction. In this embodiment, working surfaces 184, 185 are disposed on opposite sides of a centerline 189 of shim 180.

Referring generally to FIGS. 115A-116B a blade adjustment and positioning tool 250 is disclosed. FIG. 115A is a perspective view of a blade adjustment and positioning tool 250 and FIG. 115B is an exploded parts view of the blade adjustment and positioning tool 250. FIG. 116A is an outside surface perspective view of the blade adjustment and positioning tool engaged with a modular blade and an extendable blade and FIG. 116B is an inside surface perspective view of the blade adjustment and positioning tool engaged with a modular blade and an extendable blade, for example. In the example embodiment, tool 250 may extend in a longitudinal direction from a proximal end 250P to a longitudinal end 250D, for example. In the example embodiment, the proximal end may be defined by a rotatable turnkey 251 and the distal end may be defined by a tab 256.

In the example embodiment, the first portion 250A may comprise a gripping portion 255 having a plurality of gripping indentations extending along a length thereof, for example. Additionally, the gripping portion may include a centrally disposed shaft extending therethrough in the longitudinal direction between proximal aperture 257A and medial aperture 257B, for example. Additionally, the second portion may include a matting rail 258 having a size and shape that corresponds to a size and shape of a channel of modular blade 120, for example channel 123 shown in FIG. 83. However, it shall be understood that reference to channel 123 is by example only, and that matting rail 258 and the corresponding channel of modular blade 120 does not necessarily need indentations 125 and arcuate channel portions 123B, for example. In various embodiments, the distal end of first portion 250A may be defined by tab 256. In the example embodiment, tab 256 is offset laterally from an extension axis extending through proximal aperture 257A and medial aperture 257B, for example.

Second portion 250B may include a turnkey 251 and/or a knob at a proximal end thereof. Turnkey 251 may be coupled to or monolithically formed with primary shaft 252 and extension shaft 253. In various embodiments, extension shaft 243 may comprise a drive feature or driving head 254 at a distal end thereof. In operation, second portion 250B may be insert inside of first portion 250A by inserting the driving head 254, extension shaft 253, and primary shaft 252 through proximal aperture 257A. Due to the particular design of this embodiment, the primary shaft 252 may be rotatably disposed within the central shaft of the first portion and primary shaft 252 may have a size and shape generally corresponding to a size and shape of the central shaft of the first portion, e.g., substantially the same diameter and a length substantially the same as a distance between proximal aperture 257A and medial aperture 257B. Extension shaft 253 may be partially mated to and/or disposed within an open channel 258C of matting rail 258 such that it may freely rotate and so can driving end 254.

With reference to FIGS. 116A and 116B, tool 250 may couple to a modular blade 120 by inserting matting rail 258 with channel 123. Additionally, as seen best in FIG. 116B, due to the offset nature of tab 256 an inside surface of tab 256 may be directly adjacent to and/or directly contact an inside surface of extendable blade 130. In this way, tool 250 may provide a fulcrum or handle to manipulate the modular blade 120 and extendable blade 130. At least one particularly advantageous use of tool 250 may be when modular blade 120 and extendable blade 130 are coupled to a free hand module, as explained above, which may not have actuators to cause pivoting and/or angulation, e.g., free hand module 900 as shown in FIG. 49B. Additionally, in some embodiments, an end user may initially mate first portion 250A to modular blade 120 and extendable blade 130, then insert second portion into first portion, and slide second portion forward in a distal direction such that it pushes extendable blade 130 forward. In some embodiments, a chiseled end of second portion, e.g., drive feature 254, may unseat a protrusion of extendable blade 130 from a corresponding indentation of modular blade 120, e.g., protrusion 133 and indentations 125 (see FIGS. 83-84). In this way, an end user may utilize tool 250 to extend a position of extendable blade 130 via second portion 250B and may use tool 250 as a fulcrum or handle for applying a mechanical advantage as a fulcrum to modular blade 250 and extendable blade 230, for example. Additionally, in at least some embodiments, because drive end 254 may be rotatable, it may facilitate the unseating of the protrusion of the extendable blade 130 from the corresponding indentation of modular blade 120.

Referring generally to FIGS. 117A-118E, various views of a modular blade 260 and an extendable blade 262 having a footed tip 263, a quick connect handle 270, and a retractor mount coupler 280 are disclosed. FIG. 117A is a perspective view of the inside surfaces of the modular blade 260 and extendable blade 262 and FIG. 117B is a perspective view of the outside surfaces of the modular blade 260 and extendable blade 262. In the example embodiment, the extendable blade 262 has a footed tip 263 and is slidably coupled to the modular blade 260 similarly as explained above. Accordingly, duplicative description is omitted or only briefly described again. In this embodiment, modular blade 260 comprises an attachment rail 264 on the outside surface thereof adjacent the proximal end. Attachment rail 264 may include various surface texturing on the outside surface thereof, e.g., rail like peaks and channel like valleys therebetween extending in a proximal to distal direction around the outside curved surface of attachment rail 264. In at least some embodiments, attachment rail 264 is integrally formed with modular blade 260 and in others it may be removably coupled thereto. In various embodiments, attachment rail 264 may include attachment shaft 265 extending from the proximal end of modular blade 260, for example. The proximal most portion of attachment shaft 265 may comprise a generally cylindrical extension shaft having a planar indent 267, a necked down portion 268, and an end 266 that is wider than the necked down portion 268, for example. In various embodiments, the attachment shaft 265 may quickly couple to and uncouple from a quick connect handle 270, for example.

FIG. 118A is a perspective view of a quick connect handle 270 and FIG. 118B is an exploded parts view of the quick connect handle 270. In the example embodiment, quick connect handle 270 extends in a longitudinal direction from a proximal end 270P to a distal end 270D. The distal end 270D may comprise a coupling aperture 269 for connecting to an attachment shaft 265 of a modular blade 260 when attachment shaft 265 is inserted therein, for example. Quick connect handle 270 may include a main body portion 275 or handle and the distal end 270D may comprise a coupling mechanism having various mating features comprising a size and shape generally corresponding to a size and shape attachment shaft 265, for example. In the example embodiment, the pin 272 and mating features 274 are actuated by actuator 271. Quick connect handle 270 may couple to modular blade 260 by depressing actuator 271 and sliding attachment shaft 265 into aperture 269 such that sliding barrel 276 lockingly engages attachment shaft 265, for example. In various embodiments, barrel 276 may be biased towards the proximal end 270D by set pins 279 and springs 278. In various embodiments, upon activation of actuator 271, e.g., by depressing actuator 271 button, barrel 276 may linearly translate forward to securely couple to modular blade 260.

FIG. 118C is a perspective view of a retractor mount coupler 280. Retractor mount coupler 280 may have many of the same, similar, and/or substantially the same components and functionality as free hand module 900 of FIGS. 47B and 48A, for example. Accordingly, duplicative description will be omitted and/or only briefly described. In this embodiment, retractor mount coupler 280 may include a pair of gripping arms 916 for gripping on to the outside textured surface of rail 264, for example. Additionally, retractor mount coupler 280 may include a lever 911 and a body 913 having an aperture 913A. Lever 911 may function in the same or substantially the same way as previously explained with respect to free hand module 900. As seen best in FIG. 129, retractor mount coupler 280 may couple and couple to a rod, pole, table mount extension, and/or lateral arm 1201 of a secondary module 1200, for example. FIG. 118D is a perspective view of the modular blade 260 and extendable blade 262 of FIGS. 117A-117B coupled to the quick connect handle 270 of FIGS. 118A-118B and the retractor mount coupler 280 of FIG. 118C. FIG. 118E is a perspective view showing the quick connect handle 270 uncoupled from the attachment shaft 265 of modular blade Referring generally to FIGS. 119-122 an additional embodiment of a modular retractor 530 is disclosed. Modular retractor 530 may have the same, similar, and or substantially the same components and functionality as explained above with respect to modular retractor 500 and modular retractor 530 may be used with any of the various add on retractor modules 600, 700, 800, 900, 1000, and 1100 that are disclosed herein and shown in the various views of FIGS. 20-81, for example. Accordingly, significant duplicative description will be omitted although some aspects will be repeated for ease of explanation. FIGS. 119 and 120 are various perspective views of modular retractor 530. FIG. 121A is a top down view of modular retractor 530 and FIG. 121B is a bottom perspective view of a blade attachment mechanism 535. FIG. 122A is an enlarged view of the embodiment of FIGS. 119-121 with the top cover removed for ease of understanding of the internal gear system. FIG. 122B is an enlarged view of the embodiment of FIGS. 119-121 from a bottom perspective showing various structural features of a table mount quick release coupler 533.

In the example embodiment, modular retractor 530 may include handles 501a, 501b and arms 505 and 507. The handles and/or actuator 502 may serve to open the retractor 530 by spreading the arms 505, 507 apart from one another as explained previously. Modular retractor 530 may differ from retractor 500 in a few ways. For example, the blade attachment mechanism 535 may be configured for bottom loading rather than top loading, the blade release actuator 537 may be disposed on a side surface of blade attachment mechanism 535 rather than a top surface, a release mechanism 531 may be relied upon rather than pawl 504, and a table mount quick release connection 533 may be provided rather than table mount arm 506, for example.

As seen best in FIGS. 120 and 121B, blade attachment mechanism 535 may be configured for bottom loading of various blade engagement features, for example blade engagement feature 146 shown in FIGS. 108B, 108C, and 108D. Generally, blade attachment mechanism 535 may have a size and shape generally corresponding to a size and shape of a corresponding blade engagement feature 146. In the example embodiment, blade attachment mechanism 535 includes a channel 535B that is open to the bottom and closed at the top by a curved top surface 535A, for example. The curved top surface may have a curvature generally corresponding to a curvature of the curved uppermost surface 146A and the channel 535B may have a width, length, and height generally corresponding to a width, length, and height of raised rail portion 146B, for example. In some embodiments, the curved top surface 535A may be referred to as a stop surface and/or stopping wall. In various embodiments, channel 535B may be flanked by supports 535C, for example. In use, when blade engagement feature 146 is securely coupled to blade attachment mechanism 535 the side surfaces of platform 146D may contact the side surfaces 535D of supports 535C such that the channel portions 146C are mated with supports 535C, for example. Additionally, in various embodiments the side surfaces 535D may be chamfered and/or inclined, for example as seen best in FIG. 121B. This arrangement may facilitate insertion of a blade thereon, for example. Furthermore, in various embodiments an outside surface of a corresponding blade and/or platform 146D may contact the outermost surface of supports 535C. Further still, blade release mechanism 537 may securely couple and uncouple a blade to blade attachment mechanism 535 when actuated.

As seen best in FIG. 122A, modular retractor 530 may include a distraction mechanism 50. In this embodiment, spur gear 54 includes a plurality of teeth on a side surface thereof but may not include a plurality of teeth on a top surface thereof like the example modular retractor 500 embodiment. Additionally, a release mechanism 531 may include a tooth 531A or tip at an end thereof having a size and shape generally corresponding to a valley between adjacent teeth of spur gear 54. Release mechanism 531 may be biased by a spring tab or leaf spring 531B which naturally urges tooth 531A into a meshed arrangement with the teeth of spur gear 54 such that the spur gear 54 is prevented from rotating in a direction which would cause the arms of modular retractor 530 to collapse or close. Additionally, because release mechanism 531 may pivot in and out of a meshed arrangement with spur gear 54 an end user may cause expansion or distraction between arms 505, 507 of modular retractor 530 without needing to actuate release mechanism 531. In this way, release mechanism 531 functions similarly to a pawl preventing the collapse of arms 505, 507 while simultaneously allowing, for example, an uninhibited expansion of arms 505, 507.

As also seen best in FIGS. 122A and 122B, modular retractor 530 may include a quick connect table mount 533. Quick connect table mount 533 may include an aperture 533Z and a tightening knob 534. Aperture 533Z may have a size and shape corresponding to a square or polygonal driver, for example a drive end of a wrench such as the egg wrench 10 illustrated in FIG. 23. As seen best in FIG. 121A, quick connect table mount 533 may be generally disposed in a central position of the main retractor body and when viewed in a plan view may be aligned along a longitudinal axis bisecting the retractor body. This arrangement may facilitate a symmetrical load distribution, for example. However, it shall be understood that quick connect table mount 533 may be alternately disposed, for example on a side surface on the left side, medial or central area, and/or right side of the retractor body (with respect to plan view of FIG. 121A). Additionally, a plurality of quick connect table mounts 533 may be disposed in any viable region of modular retractor 530 and the various add on modules disclosed herein. As seen best in FIG. 122B, quick connect table mount 533 may be configured to receive a corresponding post 363 and/or rail 362 of a quick connect arm 360 (see FIGS. 124-125). In the example embodiment, quick connect table mount 533 may include a centrally disposed mating aperture 533C accessible from a bottom side of modular retractor 530, for example. In some embodiments, mating aperture 533C is coaxially aligned with aperture 533Z although this is not a requirement. In various embodiments, mating aperture 533C may include a circumferential ring surface having a relatively greater diameter than the central portion of aperture 533C to facilitate seating of post 363 (see FIGS. 124-125) in an arrangement similar to concentric circles of varying depths. Additionally, various counter torque mating features may be disposed around and/or surround aperture 533C, for example. In the example embodiment, a first groove 533A extends in a direction that is substantially parallel with the longitudinal axis of modular retractor 530 and a second groove 533B extends in a direction that is substantially perpendicular with the longitudinal axis of modular retractor 530, e.g. second groove 533B extends in a lateral direction with respect to modular retractor 530. In the example embodiment, the first and second grooves 533A, 533B may resemble a cross shape and/or an X shape. Additionally, the ends of grooves 533A, 533B may be open or closed, for example one side of groove 533B is closed and has an arcuate end surface which ensures proper alignment quick connect arm 360, for example. In various embodiments, the rail 363 of quick connect arm 360 may nest within at least one of grooves 533A, 533B. Accordingly, in this embodiment an orientation of quick connect arm 360 is adjustable between a direct head on orientation type and a side or lateral orientation type, for example. At least one advantage of this configuration may be providing flexibility in orientation to a surgeon depending on different types of procedures being performed and or changes in orientation mid-procedure.

FIG. 123 is a perspective view of a table mount system 340 adapted for use with various retractor components disclosed herein. For example, various armatures of a quick connect table mount system may be used for supporting and manipulating various retractor embodiments disclosed herein. In the example embodiment, table mount system 340 may include a first armature 340A and a second armature 340B. The first armature 340A may be slidably connected to the second armature 340B by armature connection mechanism 345. In at least one embodiment, second armature 340B may include a table mount channel 349 and a table mount clamp 350. In use the second armature 340B may be rigidly and removably secured to an operating table by tightening clamp 350 such that table mount channel 349 is tightened to the table and arm 348 extends in a vertical direction with respect to a horizontal surface or plane of a table (not illustrated). Thereafter, the first armature 340A may be coupled to arm 348 by positioning arm 348 within the aperture of armature connection mechanism 345 and tightening turnkey 346 such that a movable platform 345B clamps down on to armature 348 by closing and/or reducing the size of the aperture, for example. In the example embodiment, movable platform 345B has a channel for seating the curved surfaces of arm 348 and in some embodiments may have grooving or other texturing to facilitate a relatively strong connection.

First armature portion 340A may include a first arm 341A and a second arm 341B that are hingedly connected together by hinge mechanism 342, for example. In various embodiments, hinge mechanism 342 may allow for a full 360 degree rotation, or a subset thereof. At least one embodiment may include corresponding teeth that may mesh together when tightened or clamped together by a tightening knob 342A that urges the corresponding teeth into corresponding valleys, for example. In various embodiments, second arm 341B may be movably coupled to armature connection mechanism 345 by a ball and socket joint 343, for example. Additionally, first armature 341 may be coupled to a snap on connector 347 by a ball and socket joint 343, for example. Consistent with the disclosure herein, it shall be understood that any connection between the various armatures of disclosed table mount systems may be a rotatable hinge like connection, a sliding connection, and/or a ball and joint connection. Additionally, these connection types may be readily swapped and our substituted. For example, post 351 may be inset within a hollow interior of any armature end to change the connection type and/or functionality depending solely on the particular needs of an end user.

FIG. 124 is a first perspective view of a quick connect coupler 360 for connecting various retractor embodiments to various quick connect table mount systems disclosed herein. FIG. 125 is a side view of the quick connect coupler 360. Quick connect coupler 360 may include an arm 361 supporting a post 363 and rail 362 on a first end thereof. In various embodiments, the arm 361 may follow a diagonal, straight, and/or curved profile, for example. On an opposite end, quick connect coupler 360 may include an armature coupler 365, for example. Armature coupler 365 may include a post having an inclined, chamfered, and/or dimpled end 366, for example. Additionally, armature coupler 365 may include a grooved portion 367 to facilitate a rigid and secure engagement with a quick connect coupler of a table mount system, for example connector 347 shown in FIG. 123. Furthermore, a base portion of quick connect coupler 360 may include a counter torque surface 368 for resisting a rotation of quick connect coupler 360, for example surface 368 may directly contact a corresponding counter torque surface 347B of connector 347 (see FIG. 123). It shall be appreciated that armature coupler 365 may take any shape and have any form and type of various indentations, outdents, apertures, posts, slots, and etc. to facilitate attachment to a table mount arm whether in a snap on quick connect style as illustrated in the corresponding FIGS. or by, for example, a clamp on ratcheting style or even a mushroom expansion style.

FIG. 126 is a perspective view of a modular retractor system including the quick connect couplers of FIGS. 124-125. FIG. 127 is a top down view of the system of FIG. 126. Consistent with the disclosure herein, modular retractor 530 is securely coupled to a secondary module, e.g., module 1200. Module 1200 may have the same, similar, and/or substantially the same features and functionality as the various other secondary modules discussed above. However, in this embodiment, secondary module 1200 is capable of linearly extending a centrally disposed first arm and a C shaped second arm, for example. In this embodiment, the C shaped second arm is supporting a free hand module 900 and the first arm is securely connected to a quick connect arm 360 via a table mount quick release coupler 533, for example. Additionally, a body portion of module 1200 includes a table mount quick release coupler 533 and the second C shaped arm includes a table mount quick release coupler 533. Additionally, it is shown that modular retractor 530 is securely connected to a quick connect coupler 360 at the table mount quick release coupler 533. Accordingly, various modular retractor systems may comprise a plurality of quick release couplers 533 whether they be on the primary retractor 530 or secondary module 1200, for example. In this way, a surgeon has maximum flexibility in attaching the modular retractor system to a table mount. FIG. 128 is a perspective view of module 1200 in an uncoupled position with respect to modular retractor 530. FIG. 129 is a perspective view of module 1200 coupled to modular retractor 530. In the example embodiment, retractor mount coupler 280 is secured to attachment rail 264 of the modular blade 260 and extendable blade 262. Additionally, the retractor mount coupler 280 is coupled to lateral arm 1201 of retractor module 1200.

FIG. 130 is a top down view of modular retractor 530 supporting first and second blades and module 1200 supporting a third blade. FIG. 131 is a perspective view of three blades being slidably coupled to a dilator 94. With reference back to the set of dilators 99 disclosed in FIGS. 80C, 80B, 80E, and FIG. 81 an example method of use will be disclosed. In a first step, a surgeon may insert an initial dilator or pin, e.g., innermost dilator 98. In some embodiments, and depending on the particular surgical approach dilator 98 may be insert into a patient from a lateral, anterior, or trans psoas approach, e.g. Once the initial dilator 98 is insert in the patient, a dilator having a relatively wider size may be insert over the initial dilator 98, e.g., dilator 97. After dilator 97 is slipped over innermost dilator 98, a dilator having a relatively wider size than dilator 97 may be slipped over dilator 97, e.g., dilator 96. Any number of successive and iteratively increasing in size dilators may be slipped over one another in this process. Thereafter, an outermost dilator 94 having a plurality of rail portions 94A may be slipped over the immediately prior dilator, e.g., dilator 96.

Next, a surgeon may position modular retractor 530 and retractor module 1200 over the outermost dilator 94. For example, a surgeon may install first and second blades to the first and second arms of modular retractor 530 and a third blade may be installed on the proximal arm of retractor module 1200. The three blades may be collapsed such that edge portions contact one another and a circular void space is formed by the interior surfaces of the three blades. Next, the surgeon may slip the three blades over the outermost dilator 94 such that the corresponding channel portions of the blades slidably couples to the rail portions 94A of the outermost dilator, see FIG. 81. Thereafter, the surgeon may move the modular retractor 530 and retractor module 1200 such that the blades slide down along the length of outermost dilator and into the operative corridor. Once the surgeon has moved the three blades into the operative corridor, and the blades are supporting adjacent tissue, the surgeon may remove the outermost dilator 94. After the outermost dilator 94 has been removed, the surgeon can freely manipulate any one of the three blades in any manner or relative movement as previously explained to enlarge the operative corridor.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

What is claimed is:

1. A retractor system for enabling access to a surgical site, comprising:
    a modular retractor having a longitudinal axis extending in a longitudinal direction and a lateral axis extending from a first lateral end to a second lateral end in a lateral direction, the modular retractor including:
    a first body portion that houses a distraction mechanism;
    a first arm and a second arm pivotally coupled together,
    a first handle coupled to the first arm and a second handle coupled to the second arm;
    a first pivoting member coupled to a distal end of the first arm and a second pivoting member coupled to a distal end of the second arm;
    a first blade attachment mechanism coupled to the first pivoting member and a second blade attachment mechanism coupled to the second pivoting member, the first and second blade attachment mechanisms being configured to couple to first and second blades, respectively;
    a first actuator operably coupled to the distraction mechanism for opening and closing the first arm and the second arm;
    a second actuator for adjusting an angulation of the first pivoting member; and
    a third actuator for adjusting an angulation of the second pivoting member,
    wherein the first body portion comprises at least one table mount quick release coupler.

2. The retractor system of claim 1, wherein the first body portion further comprises a connection point for connecting to at least one retractor module.

3. The retractor system of claim 1, wherein the at least one table mount quick release coupler is disposed on the first body portion such that the longitudinal axis crosses over the at least one table mount quick release coupler.

4. The retractor system of claim 1, wherein the at least one table mount quick release coupler comprises a centrally disposed mating aperture and a tightening knob.

5. The retractor system of claim 1, wherein the first body portion further comprises at least one channel adjacent the at least one table mount quick release coupler.

6. The retractor system of claim 1, wherein the first body portion further comprises a first channel adjacent the at least one table mount quick release coupler and a second channel adjacent the at least one table mount quick release coupler.

7. The retractor system of claim 6, wherein the first channel extends substantially in the longitudinal direction and the second channel extends substantially in the lateral direction.

8. The retractor system of claim 1, further comprising at least one table mount arm configured to releasably couple to the at least one table mount quick release coupler.

9. The retractor system of claim 8, wherein the at least one table mount arm comprises a post.

10. The retractor system of claim 8, wherein the at least one table mount arm comprises at least one rail.

11. The retractor system of claim 1, further comprising at least one table mount arm configured to releasably couple to the at least one table mount quick release coupler,
    wherein the table mount arm comprises a post and a rail.

12. The retractor system of claim 1, further comprising a third blade,
    wherein at least one of the first blade and second blade is a modular blade and the third blade is slidably coupled to the modular blade.

13. The retractor system of claim 1, further comprising an extendable blade,
    wherein the extendable blade comprises at least one rail that is slidably disposed within at least one channel of the first blade.

14. The retractor system of claim 13, wherein the extendable blade comprises a footed tip.

15. The retractor system of claim 14, further comprising a rectangular dilator.

16. The retractor system of claim 14, wherein the first and second blades comprise substantially planar working surfaces.

17. The retractor system of claim 1, further comprising an adjustable armature for supporting the retractor system, wherein:
    the adjustable armature comprises a first armature portion coupled to a second armature portion,
    the first armature portion is configured to couple to an operating table having a horizontal surface, the first armature portion having a first armature extending in a vertical direction substantially opposite a plane defined by the horizontal surface,
    the second armature portion is slidably coupled to the first armature,
    at least one table mount arm is coupled to the second armature, and
    the at least one table mount arm is releasably coupled to the at least one table mount quick release coupler.

18. The retractor system of claim 17, wherein the first armature portion comprises a ball and socket joint.

19. The retractor system of claim 17, wherein the second armature portion comprises a second armature and a third armature that are hingedly connected.

20. The retractor system of claim 17, wherein the at least one table mount arm is coupled to the second armature at a ball and socket joint.

21. A method of forming an operative corridor in a patient, comprising:
    providing a modular retractor and at least one retractor module for coupling to the modular retractor,
    the modular retractor comprising:
        a first body portion that houses a distraction mechanism;
        a first arm and a second arm pivotally coupled together,
        a first handle coupled to the first arm and a second handle coupled to the second arm;
        a first pivoting member coupled to a distal end of the first arm and a second pivoting member coupled to a distal end of the second arm;
        a first blade attachment mechanism coupled to the first pivoting member and a second blade attachment mechanism coupled to the second pivoting member, the first and second blade attachment mechanisms being configured to couple to first and second blades, respectively;
- a first actuator operably coupled to the distraction mechanism for opening and closing the first arm and the second arm;
- a second actuator for adjusting an angulation of the first pivoting member;
- a third actuator for adjusting an angulation of the second pivoting member,
- wherein the first body portion comprises at least one table mount quick release coupler;

the at least one retractor module comprising:
- a third arm supporting a third pivoting member and a third blade attachment mechanism at a distal end thereof, the third blade attachment mechanism being configured to couple to a third blade;
- a fourth actuator operably coupled to the at least one retractor module for extending and contracting the third arm;
- a fifth actuator for for adjusting an angulation of the third pivoting member;

attaching the first blade to the first arm, the second blade to the second arm, and the third blade to the third arm;

sequentially inserting at least two dilators into a patient, the at least two dilators including an outermost dilator and an innermost dilator;

inserting a first dilator into a patient, wherein the outermost dilator forms an operative corridor;

positioning the first blade, second blade, and third blade directly above the outermost dilator;

sliding the first blade, second blade, and third blade over the outermost dilator and into the operative corridor.

22. The method of claim 21, wherein sliding the first blade, second blade, and third blade over the at least one second dilator further comprises mating respective channel portions of the first blade, second blade, and third blade with corresponding rail portions of the outermost dilator.

\* \* \* \* \*